(12) United States Patent
Steer et al.

(10) Patent No.: US 10,329,549 B2
(45) Date of Patent: Jun. 25, 2019

(54) GLUCANASES, NUCLEIC ACIDS ENCODING THEM AND METHODS FOR MAKING AND USING THEM

(71) Applicant: BP Corporation North America Inc., Houston, TX (US)

(72) Inventors: Brian Steer, San Diego, CA (US); Shaun Healey, Carlsbad, CA (US); Alireza Esteghlalian, San Diego, CA (US); Stacy Marie Miles, Chapel Hill, NC (US); Kenneth Barrett, Solana Beach, CA (US); Rene Quadt, Chapel Hill, NC (US)

(73) Assignee: BP Corporation North America Inc., Houston, TX (US)

( * ) Notice: Subject to any disclaimer, the term of this patent is extended or adjusted under 35 U.S.C. 154(b) by 119 days.

(21) Appl. No.: 14/229,633

(22) Filed: Mar. 28, 2014

(65) Prior Publication Data

US 2014/0295523 A1    Oct. 2, 2014

Related U.S. Application Data

(63) Continuation of application No. 12/375,143, filed as application No. PCT/US2007/075226 on Aug. 4, 2007, now abandoned.

(60) Provisional application No. 60/938,410, filed on May 16, 2007, provisional application No. 60/909,365, filed on Mar. 30, 2007, provisional application No. 60/835,734, filed on Aug. 4, 2006.

(51) Int. Cl.
| | | |
|---|---|---|
| C12N 9/42 | (2006.01) |
| C12N 9/24 | (2006.01) |
| C09K 8/035 | (2006.01) |
| C09K 8/52 | (2006.01) |
| C09K 8/68 | (2006.01) |
| C09K 8/74 | (2006.01) |
| C09K 8/80 | (2006.01) |
| C09K 8/90 | (2006.01) |
| C12P 19/02 | (2006.01) |
| C12P 19/14 | (2006.01) |
| E21B 43/26 | (2006.01) |
| A23K 20/147 | (2016.01) |
| A23L 33/18 | (2016.01) |
| G16B 30/00 | (2019.01) |

(52) U.S. Cl.
CPC .......... *C12N 9/2437* (2013.01); *A23K 20/147* (2016.05); *A23L 33/18* (2016.08); *C09K 8/035* (2013.01); *C09K 8/52* (2013.01); *C09K 8/68* (2013.01); *C09K 8/74* (2013.01); *C09K 8/805* (2013.01); *C09K 8/90* (2013.01); *C12N 9/2405* (2013.01); *C12P 19/02* (2013.01); *C12P 19/14* (2013.01); *C12Y 302/01004* (2013.01); *C12Y 302/01006* (2013.01); *C12Y 302/01008* (2013.01); *C12Y 302/01039* (2013.01); *E21B 43/26* (2013.01); *C09K 2208/24* (2013.01); *G16B 30/00* (2019.02); *Y02E 50/17* (2013.01)

(58) Field of Classification Search
CPC .... C12Y 302/01004; C12Y 302/01006; C12Y 302/01008; C12Y 302/01039
See application file for complete search history.

(56) References Cited

U.S. PATENT DOCUMENTS

| | | |
|---|---|---|
| 4,099,583 A | 7/1978 | Maus |
| 4,144,354 A | 3/1979 | Unno |
| 4,725,544 A | 2/1988 | Tan |
| 4,746,517 A | 5/1988 | Ducroo |
| 4,788,066 A | 11/1988 | Witt |
| 4,917,185 A | 4/1990 | Jennings |
| 5,108,765 A | 4/1992 | Maat |
| 5,116,746 A | 5/1992 | Bernier |
| 5,126,051 A | 6/1992 | Shell |
| 5,179,021 A | 1/1993 | Du Manoir |
| 5,202,249 A | 4/1993 | Kluepfel |
| 5,247,995 A | 9/1993 | Tjon-Joe-Pin |

(Continued)

FOREIGN PATENT DOCUMENTS

| WO | WO1981/00857 | 4/1989 |
|---|---|---|
| WO | WO1992/03541 | 3/1992 |

(Continued)

OTHER PUBLICATIONS

Morgan—Xylanases improve wheat and rye diets by reducing chick gut viscosity, Proceedings of the 1st Symposium on Enzymes in Animal Nutrition, Finnfeeds Int'l. Ltd., (1993)—73-77.

(Continued)

*Primary Examiner* — Marsha Tsay
(74) *Attorney, Agent, or Firm* — DLA Piper LLP (US)

(57) ABSTRACT

The invention relates to polypeptides having glucanase, e.g., endoglucanase, mannanase, xylanase activity or a combination of these activities, and polynucleotides encoding them. In one aspect, the glucanase activity is an endoglucanase activity (e.g., endo-1,4-beta-D-glucan 4-glucano hydrolase activity) and comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans or xyloglucans and other plant material containing cellulosic parts. In addition, methods of designing new enzymes and methods of use thereof are also provided. In alternative aspects, the new glucanases e.g., endoglucanases, mannanases, xylanases have increased activity and stability, including thermotolerance or thermostability, at increased or decreased pHs and temperatures.

20 Claims, 14 Drawing Sheets
Specification includes a Sequence Listing.

(56) References Cited

U.S. PATENT DOCUMENTS

| | | |
|---|---|---|
| 5,306,633 A | 4/1994 | Gottschalk |
| 5,405,769 A | 4/1995 | Campbell |
| 5,429,828 A | 7/1995 | Fodge |
| 5,432,074 A | 7/1995 | Evans |
| 5,536,325 A | 7/1996 | Brink |
| 5,582,681 A | 12/1996 | Back |
| 5,591,304 A | 1/1997 | Tolan |
| 5,612,055 A | 3/1997 | Bedford |
| 5,645,686 A | 7/1997 | Troughton |
| 5,661,021 A | 8/1997 | Buchert |
| 5,693,518 A | 12/1997 | Kofod |
| 5,705,369 A | 1/1998 | Torget |
| 5,709,796 A | 1/1998 | Fuqua |
| 5,720,971 A | 2/1998 | Beauchemin |
| 5,725,732 A | 3/1998 | Cooper, III |
| 5,747,320 A | 5/1998 | Saha |
| 5,759,840 A | 6/1998 | Sung |
| 5,760,211 A | 6/1998 | Schleicher |
| 5,770,012 A | 6/1998 | Cooper, III |
| 5,786,316 A | 7/1998 | Baeck |
| 5,795,764 A | 8/1998 | Christgau |
| 5,795,766 A | 8/1998 | Suzuki |
| 5,833,857 A | 11/1998 | Roth |
| 5,834,301 A | 11/1998 | Jeffries |
| 5,874,274 A | 2/1999 | Jakobsen |
| 5,881,813 A | 3/1999 | Brannon |
| 5,881,826 A | 3/1999 | Brookey |
| 5,885,819 A | 3/1999 | Kofod |
| 5,910,467 A | 6/1999 | Bragg |
| 5,925,749 A | 7/1999 | Mathur |
| 5,948,667 A | 9/1999 | Cheng |
| 5,958,758 A | 9/1999 | Miller |
| 5,973,228 A | 10/1999 | Carlson |
| 5,981,233 A | 11/1999 | Ringpfeil |
| 6,022,725 A | 2/2000 | Fowler |
| 6,036,981 A | 3/2000 | Budolfsen |
| 6,066,233 A | 5/2000 | Olsen |
| 6,077,316 A | 6/2000 | Lund |
| 6,083,733 A | 7/2000 | Gronberg |
| 6,087,131 A | 7/2000 | Gunata |
| 6,090,595 A | 7/2000 | Foody |
| 6,099,844 A | 8/2000 | Rohde, Jr. |
| 6,110,875 A | 8/2000 | Tjon-Joe-Pin |
| 6,127,160 A | 10/2000 | Yamanobe |
| 6,132,716 A | 10/2000 | Morgan |
| 6,132,727 A | 10/2000 | Rohde, Jr. |
| 6,138,760 A | 10/2000 | Lopez |
| 6,140,095 A | 10/2000 | Williams |
| 6,156,708 A | 10/2000 | Brookey |
| 6,184,018 B1 | 2/2001 | Li |
| 6,200,797 B1 | 3/2001 | Dunlop |
| 6,241,849 B1 | 6/2001 | Franks |
| 6,245,546 B1 | 6/2001 | Hansen |
| 6,251,643 B1 | 6/2001 | Hansen |
| 6,333,181 B1 | 12/2001 | Ingram |
| 6,346,407 B1 | 2/2002 | DeBuyl |
| 6,376,445 B1 | 4/2002 | Bettiol |
| 6,387,690 B1 | 5/2002 | Schulein |
| 6,399,123 B1 | 6/2002 | Kerley |
| 6,409,841 B1 | 6/2002 | Lombard |
| 6,420,331 B1 | 7/2002 | Bettiol |
| 6,422,326 B1 | 7/2002 | Brookey |
| 6,423,145 B1 | 7/2002 | Nguyen |
| 6,423,524 B1 | 7/2002 | Hagen |
| 6,497,289 B1 | 12/2002 | Cook |
| 6,530,437 B2 | 3/2003 | Maurer |
| 6,566,113 B1 | 5/2003 | Takayama |
| 6,581,687 B2 | 6/2003 | Collins |
| 6,586,209 B1 | 7/2003 | Van Gorcom |
| 6,588,501 B1 | 7/2003 | Boyadjieff |
| 6,602,700 B1 | 8/2003 | Li |
| 6,660,506 B2 | 12/2003 | Nguyen |
| 6,682,923 B1 | 1/2004 | Bentzien |
| 6,702,023 B1 | 3/2004 | Harris |
| 6,712,866 B2 | 3/2004 | Paul |
| 6,763,888 B1 | 7/2004 | Harris |
| 6,818,594 B1 | 11/2004 | Freeman |
| 6,831,044 B2 | 12/2004 | Constien |
| 6,921,655 B1 | 7/2005 | Nakamura |
| 6,979,733 B2 | 12/2005 | Zhao |
| 7,129,069 B2 | 10/2006 | Borchert |
| 7,220,542 B2 | 5/2007 | Van Den Brink |
| 2002/0164730 A1 | 11/2002 | Ballesteros Perdices |
| 2003/0119093 A1 | 6/2003 | Ding |
| 2003/0215812 A1 | 11/2003 | Ma |
| 2003/0233675 A1 | 12/2003 | Cao |
| 2005/0065037 A1 | 3/2005 | Constien |
| 2005/0069998 A1 | 3/2005 | Ballesteros Perdices |
| 2006/0014260 A1 | 1/2006 | Fan |
| 2006/0117958 A1 | 6/2006 | Sakadume |
| 2006/0147581 A1 | 7/2006 | Svendsen |
| 2006/0193897 A1 | 8/2006 | Bedford |
| 2006/0194299 A1 | 8/2006 | Brinch-Pedersen |
| 2006/0257984 A1 | 11/2006 | Borchert |
| 2007/0015678 A1 | 1/2007 | Rodrigues |
| 2007/0027036 A1 | 2/2007 | Polizzotti |
| 2007/0039735 A1 | 2/2007 | Robertson |
| 2007/0054024 A1 | 3/2007 | De Man |
| 2007/0066491 A1 | 3/2007 | Bicerano |
| 2007/0068675 A1 | 3/2007 | Barry |
| 2007/0075706 A1 | 4/2007 | Chen |
| 2007/0081157 A1 | 4/2007 | Csutak |
| 2007/0084638 A1 | 4/2007 | Bohnsack |
| 2007/0089910 A1 | 4/2007 | Hewson |
| 2007/0020744 A1 | 12/2007 | Jolly |

FOREIGN PATENT DOCUMENTS

| | | |
|---|---|---|
| WO | WO1996/13568 | 5/1996 |
| WO | WO1996/23579 | 8/1996 |
| WO | WO1997/01629 | 1/1997 |
| WO | WO1997/32480 | 9/1997 |
| WO | WO1998/40721 | 9/1998 |
| WO | WO1999/46362 | 9/1999 |
| WO | WO2000/43496 | 7/2000 |
| WO | WO 00/73428 | 12/2000 |
| WO | WO2001/30161 | 5/2001 |
| WO | WO2001/64830 | 9/2001 |
| WO | WO 2001/070998 | 9/2001 |
| WO | WO 2002/024882 | 3/2002 |
| WO | WO 02/068597 | 9/2002 |
| WO | WO 2002/099091 | 12/2002 |
| WO | WO 2003/000941 | 1/2003 |
| WO | WO 2003/012109 | 2/2003 |
| WO | WO 2003/093420 | 11/2003 |
| WO | WO 2004/016760 | 2/2004 |
| WO | WO2004/066945 | 8/2004 |
| WO | WO 2004/078919 | 9/2004 |
| WO | WO 2004/081185 | 9/2004 |
| WO | WO 04/091544 | 10/2004 |
| WO | WO 2005/003319 | 1/2005 |
| WO | WO 05/096804 | 10/2005 |
| WO | WO2005/096704 | 10/2005 |
| WO | WO 2006/101584 | 9/2006 |

OTHER PUBLICATIONS

Henrissat—Biochem. J. (1991)—280—309-316.
Henrissat—Biochem. J. (1993)—293—781-788.
Henrissat—Biochem. J. (1996)—316—695-696.
Henrissat—Plant Physiology (2000)—124—1515-1519.
Hoondal—Appl. Microbiol. Biotechnol (2002)—59—409-418.
Kohlmann—Adv. Space Res. (1996)—18—251-256.
Lazaro—Poultry Science (2004)—83—152-160.
Mathlouthi—J. Anim. Sci. (2002)—80—2773-2779.
Perez—Int. Microbiol. (2002)—5—53-63.
Strohmeier—Protein Science (2004)—13—3200-3213.
PCT/US2007/075226—International Search Report & Written Opinion—dated Mar. 2, 2009.
Ngo et al. The Protein Folding Problem and Tertiary Structure Prediction, 1994, Mertz et al (ed). Birkhauser, Boston, MA, pp. 433 and 492-495.

(56) References Cited

OTHER PUBLICATIONS

Skolnick et al. Trends in Biotechnology, 2000 18(1): 34-39.
Rudinger, J. 1976. Peptide Hormones, Edited by Parsons, University Park Press, Baltimore, p. 1-7.
EP07875173—Supplemental EP Search Report—dated Nov. 12, 2009.
UNIPROT Accession No. Q9X273—Endoglucanase—Nov. 1, 1999.
Sakon—Nat. Struc. Biol. (1997)—4—810-818.
MacKenzie—Biochem J. (1998)—335—409-416.
Liebl—Mol. Gen. Genet. (1994)—242—111-115.
Coutinho—The modular structure of cellulases and other carbohydrate-active enzymes: an integrated database approach. In *"Genetics, Biochemistry and Ecology of Cellulose Degradation"* (1999) K. Ohmiya, et al., eds., Uni Publishers Co., Tokyo, pp. 15-23.
Murashima—Jornal of Bacteriology (2005)—187—20—7146-7149.
Pages—Journal of Bacteriology (1996)—178—8—2279-2286.
Kakiuchi—Journal of Bacteriology (1998)—180—16—4303-4308.
Medve—Biotechnology and Bioengineering—(1998)—59—621-634.
Irwin—Journal of Bacteriology (1998)—180—1709-1714.
Baker—Applied Biochemistry and Biotechnology (1994)—45-46—245-256.
Huang—Anal. Biochem. (1976)—2—369-377.
Canevascini—Anal. Biochem. (1985)—2—419-27.
Carder—Anal. Biochem. (1986)—1—75-79.
Shallom—Current Opinion in Microbiology (2003)—6—219-228.
Saha—J. Ind. Microbiol Biotechnol (2003)—30—279-291.
Parry—Archives of Biochemistry and Biophysics (2002)—404—243-253.
Baker—J. Biochem. Biophys Methods (1991)—4—265-273.
DOI—Chemical Record (2001)—1—24-32.
EP06733858—Supplementary EP Search Report—dated Nov. 6, 2009.
GENESEQ Accession No. ADQ79701 (Sep. 9, 2004)—Thermus filiformis tfi beta-gly DNA seqid 5.
UNIPROT Accession No. Q08638 (Oct. 1, 1994)—Beta-glucosidase A.
UNIPROT Accession No. Q82M59 (Jun. 1, 2003)—Putative beta-glucosidase.
Gunnarsson—Protein Engineering Design and Selection (2004)—17(3)—213-221.
Gunnarsson—Glycobiology (2006)—16—1171-1180.
Tomme—FEBS Lett (1989)—243—239-243.
Gilkes—J. Biol. Chem. (1988)—263—10401-10407.
Tomme—Enzymatic Degradation of Insoluble Polysaccharides (1995, Saddler, J.N. & Penner, M., eds.)—142-163.
Henrissat—Curr. Op. Struct. Biol. (1997)—7—637-644.
Coutinho—J. Mol. Biol. (2003)—328—307-317.
Boraston—Biochem. J. (2004)—382—769-781.
Jager—World Journal of Microbiology and Biotechnology—28—5—455-461.
PCT/US2006/046919—ISR & WO—Apr. 8, 2008.
Altschul—Journal of Molecular Biology (1990)—215—403-410.
Lynd—Microbiol. and Molecular Biol. Reviews (2002)—66—506-577.
Kikuchi—Science (2003)—301—376-379.
Sposato—Mol. Plant. Microbe Interact. (1995)—8—602-609.
Charnock—J. Biol. Chem. (1998)—273—32187-32199.
Leibovitz—J. Bacteriol. (1996)—178—3077-3084.
Leibovitz—J. Bacteriol.(1997)—179—2519-2523.
Murashima—Journal of Bacteriology (2003)—185—1518-1524.
Sharrock—J. Biochem. Biophys. Methods (1988)—2—81-105.
CIPO—Jan. 12, 2010—Requisition by Examiner—CA 2,529,403.
Himmel—Curr. Opin. Biotechnol (1999)—10—358-364.
Harjunpaa—Eur. J. Biochem (1996)—240—584-591.
EP06845040—Supplementary EP Search Report—dated Jul. 14, 2009.
EMBL Accession No. AY690482 (Aug. 23, 2004)—Penicillium occitanis cellobiohydrolase I gene.
UNIPROT Accession No. Q68HC2 (Oct. 11, 2004)—Cellobiohydrolase.
GENESEQ Accession No. AAF85588 (Jun. 25, 2001)—Acremonium cellulolyticus cellbiohydrolase1.
GENESEQ Accession No. AAB81926 (Jun. 25, 2001)—Acremonium cellulolyticus cellobiohydrolase1.
Demain—Microbiology and Molecular Biology Reviews (2005)—69—124-154.
Lin—Applied Microbiology and Biotechnology (2006)—69—627-642.
Zhang—Biotechnology and Bioengineering (2004)—88—797-824.
Wood—Methods in Enzymology (1988)—160—87-116.
Klyosov—Biochemistry (1990)—29—10577-10585.
Johnston—Journal of Food Biochemistry (1998)—22—301-319.
Varrot—Biochem J. (1999)—337—297-304.
Irwin—Biotechnology and Bioengineering (1993)—42—1002-1013.
Grabnitz—Eur.J.Biochem (1991)—200—301-309.
Zverlov—Microbiology (2002)—148—247-255.
Lynd—Current Opinion in Biotechnology (2005)—16—577-583.
Poole—Mol Gen Genet 1990—223—217-223.
UnitProtKB Accession No. P23660 (1991)—Ruminococcus albus.
Guttman—Anal. Biochem. (1996)—233—234-242.
PCT/US2004/021492—ISR & WO—Jul. 25, 2008.
EP04777548—Supplementary EP Search Report—dated Apr. 27, 2009.
Coutinho—Recent Advances in Carbohydrate Bioeng. (1999)—3-12.
Database Uniprot [Online] Archive Nov. 7, 2006 Nov. 1, 1999 (Nov. 1, 1999), "SubName: Full=Endoglucanase;", XP002552825, retrieved from EBI accession No. Uniprot: Q9X273 Database accession No. Q9X273.

FIGURE 5

| SEQ ID NOS: | Family | Topt | Tstab[1] | pH | Significant activities | RA[2] 2.6, 4.0, 5.5, 7.0, 8.0, 9.0 | RA[2] 25, 37, 50, 65, 75, 85°C |
|---|---|---|---|---|---|---|---|
| 5, 6 | 5 | >90°C | t1/2 2 min, 90°C | 6 - 8 | BBG[4], Lichenan, Mannan, Locust bean gum, Guar, CMC[4] | [3] 0, 0.007, 0.07, 0.85, 1 | [3] 0.725, 0.91, 1, 0.034 |
| 161, 162 | 16 | [3]85°C | [3]10 min 100°C | 5.5* | BBG | ND | --, 0.042, 0.17, 0.46, 0.78, 1 |
| 59, 60 | 16 | [3]85°C | [3]10 min 100°C | 5.5* | BBG | ND | --, 0.09, 0.27, 0.69, 0.84, 1 |
| 67, 68 | 9 | 75°C | <1 min at 85°C | 5.5 | BBG | 0, 0.05, 1, 0.62, 0.15, 0.09 | --, 0, 0.66, 1, 0.94, 0 |
| 105, 106 | 5 | ND | ND | ND | BBG | ND | ND |
| 81, 82 | 16 | 70°C | <20 min 70°C | 5.0-7.0 | BBG | [3] 0.006, 0.99, 0.96, 1, 0.83 | [3] 0.62, 0.84, 3, 0.019 |
| 175, 176 | 5 | 75°C | <1 min at 85°C | 5.5 | BBG | 0.1, 0.4, 1, 0.76, 0.34, 0.45 | --, 0.03, 0.2, 0.68, 1, 0.88 |
| 107, 108 | 5 | ND | ND | ND | BBG | ND | ND |
| 221, 222 | 5 | 85°C | <1 min at 95°C | 5.5 | BBG | 0.08, 0.36, 1, 0.52, 0.12, 0.08 | 0.003, 0.07, 0.3, 0.74, 0.89, 1 |
| 9, 10 | 5 | 85°C | >2 min at 95°C | 5.5 | BBG | 0.006, 0.17, 1, 0.34, 0.01, 0 | 0, 0.049, 0.21, 0.62, 0.64, 1 |
| 219, 220 | 5 | ND | ND | ND | BBG | ND | ND |
| 103, 104 | 5 | ND | ND | ND | BBG | ND | ND |
| 171, 172 | 16 | 50°C | <1 min at 85°C | 5.5 | BBG | 0.21, 0.26, 1, 0.48, 0.24, 0.34 | --, 0.77, 1, 0.6, 0.36, 0.49 |
| 137, 138 | 5 | 37°C | <1 min at 85°C | 7.0 | BBG | 0, 0, 0.125, 1, 0.25, 0.125 | --, 1, 0.53, 0, 0.06, 0.1 |
| 143, 144 | 5 | ND | ND | ND | BBG | ND | ND |

SEQ ID NO:4:
MRFPSIFTAVLFAASSALAAPVNTTEDETAQIPAEAVIGYSDLEGDFDVAVLP
FSNSTNNGLLFINTTIASIAAKEEGVSLEKRGVDPFERNKILGRGINI....

Cleavage Site

Residue 1:  Ala, Glu, Gly, Ser, Gln, (Asp), (Phe)
Residue 2:  Glu, (Gly), (Ser), (Lys), (Val), (Ile)
Residue 3:  (Asp), (Ala), (Phe)
Residue 4:  Val
Residue 5:  Ser and Lys
Residue 6:  Leu
Residue 7:  Glu
Residue 8:  (Lys)
Residue 9:  (Asp)
Residue 10: (Lys, Arg)

SEQ ID NO:5:
MRFPSIFTAVLFAASSALAAPVNTTTEDETAQIPAEAVIGYSDLEGDFDVAVLPFSNSTNN
GLLFINTTIASIAAKEEGVSLEKREAGVDPFERNKILGRGINI...

Cleavage Site

Native Gene: MGVDPFERNK...

Sequencing: EAGVDPFERN

Figure 14A Glucanase doublet caused by inconsistent signal processing

Figure 14B 37 kDa band excised and sequenced

GLUCANASES, NUCLEIC ACIDS ENCODING THEM AND METHODS FOR MAKING AND USING THEM

CROSS-REFERENCE TO RELATED APPLICATIONS

This application is a continuation application of U.S. application Ser. No. 12/375,146 filed Jan. 11, 2011, now pending; which is a 35 USC § 371 National Stage application of International Application No. PCT/US2007/075226 filed Aug. 4, 2007; which claims the benefit under 35 USC § 119(e) to U.S. Application Ser. No. 60/938,410 filed May 16, 2007, U.S. Application Ser. No. 60/909,365 filed Mar. 30, 2007 and to U.S. Application Ser. No. 60/835,734 filed Aug. 4, 2006, all now expired. The disclosure of each of the prior applications is considered part of and is incorporated by reference in the disclosure of this application.

BACKGROUND OF THE INVENTION

Field of the Invention

This invention relates generally to enzymes used in food and feed compositions; and in alternative aspects provides novel enzymes, polynucleotides encoding these enzymes, and uses of these polynucleotides and polypeptides, and in alternative aspects provides polypeptides (e.g., enzymes, peptides, antibodies) having a glucanase activity, e.g., an endoglucanase, activity, e.g., catalyzing hydrolysis of internal endo-β-1,4- and/or β-1,3-glucanase linkages. In one aspect, the endoglucanase activity (e.g., endo-1,4-beta-D-glucan 4-glucano hydrolase activity) comprises hydrolysis of 1,4- and/or β-1,3-beta-D-glycosidic linkages in cellulose, cellulose derivatives (e.g., carboxy methyl cellulose and hydroxy ethyl cellulose), lichenin, beta-1,4 bonds in mixed beta-1,3 glucans, such as cereal beta-D-glucans or xyloglucans and other plant or organic material containing cellulosic parts. In one aspect, the polypeptides of the invention have a glucanase, xylanase and/or a mannanase activity.

Background Information

Endoglucanases (e.g., endo-beta-1,4-glucanases, EC 3.2.1.4; endo-beta-1,3(1)-glucanases, EC 3.2.1.6; endo-beta-1,3-glucanases, EC 3.2.1.39) hydrolyze internal β-1,4- and/or β-1,3-glucosidic linkages in cellulose and glucan to produce smaller molecular weight glucose and glucose oligomers. Glucans are polysaccharides formed from 1,4-β- and/or 1,3-glycoside-linked D-glucopyranose. Endoglucanases are of considerable commercial value, being used in the food industry, for baking and fruit and vegetable processing, breakdown of agricultural waste, in the manufacture of animal feed, e.g., a monogastric animal feed, such as a swine or poultry (e.g., chicken) feed, in pulp and paper production, textile manufacture and household and industrial cleaning agents. Endoglucanases are produced by fungi and bacteria.

Beta-glucans are major non-starch polysaccharides of cereals. The glucan content can vary significantly depending on variety and growth conditions. The physicochemical properties of this polysaccharide are such that it gives rise to viscous solutions or even gels under oxidative conditions. In addition glucans have high water-binding capacity. All of these characteristics present problems for several industries including brewing, baking, animal nutrition. In brewing applications, the presence of glucan results in wort filterability and haze formation issues. In baking applications (especially for cookies and crackers), glucans can create sticky doughs that are difficult to machine and reduce biscuit size. In addition, this carbohydrate is implicated in rapid rehydration of the baked product resulting in loss of crispiness and reduced shelf-life. For monogastric animal feed applications with cereal diets, beta-glucan is a contributing factor to viscosity of gut contents and thereby adversely affects the digestibility of the feed and animal growth rate. For ruminant animals, these beta-glucans represent substantial components of fiber intake and more complete digestion of glucans would facilitate higher feed conversion efficiencies. It is desirable for animal feed endoglucanases to be active in the animal stomach.

Endoglucanases are also important for the digestion of cellulose, a beta-1,4-linked glucan found in all plant material. Cellulose is the most abundant polysaccharide in nature. Commercial enzymes that digest cellulose have utility in the pulp and paper industry, in textile manufacture and in household and industrial cleaning agents.

The publications discussed herein are provided solely for their disclosure prior to the filing date of the present application. Nothing herein is to be construed as an admission that the invention is not entitled to antedate such disclosure by virtue of prior invention.

SUMMARY OF THE INVENTION

In one aspect the invention provides compositions (e.g., feeds, drugs, dietary supplements, etc.) comprising the polypeptides (e.g., enzymes (e.g., glucanases), peptides, antibodies) and/or polynucleotides of the invention. These compositions can be formulated in a variety of forms, e.g., as liquids, sprays, aerosols, films, micelles, liposomes, powders, foods, feeds, additives, pellets, tablets, pills, gels, hydrogels, implants or encapsulated forms. For example, the invention provides a feed enzyme product comprising an enzyme of the invention, e.g., for use as a monogastric coarse grain feed or food, wherein the monogastric animals include poultry, swine (pigs, boars, hogs), sheep, rabbits, birds, horses, monogastric pets and humans. In one aspect, feeding animals diets comprising enzymes of the invention will increase the dietary value of the enzyme-comprising food or feed. In one aspect, a composition (e.g., feeds, foods, drugs, dietary supplements, etc.) of the invention can comprise one, two, three or more different polynucleotides of the invention; and in one aspect, a composition of the invention can comprise a combination of an enzyme of the invention with another polypeptide (e.g., enzyme, peptide) of the invention or any known enzyme.

In one aspect, the enzyme of the invention is thermotolerant and/or thermostable; for example, an enzyme of the invention can retain at least 75% residual activity (e.g., glucanase activity) after 2 minutes at 95° C.; and in another aspect, retains 100% activity after heating for 30 minutes at 95° C. In one aspect, an enzyme of the invention used in these compositions comprise recombinant polypeptides expressed, e.g., in yeast (e.g., *Pichia* spp., *Saccharomyces* spp.) or bacterial (e.g., *Pseudomonas* spp., *Bacillus* spp.) expression systems, such as *Pichia pastoris, Saccharomyces cerevisiae* or *Pseudomonas fluorescens* expression systems.

The invention provides isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22 and variations (modifications) thereof as described herein (see, e.g., Tables 1 and 2, below), over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues, and the sequence comprises at least one, two, three, four, five, six, seven, eight, nine, ten, eleven (11), twelve (12), 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 57, 58, 59, 60, 61, 62, 63, 64, 65, 66, 67, 68, 69 or 70 or more or all of the following changes based on SEQ ID NO:1:

the nucleotides at positions 4 to 6 are AAT or AAC,
the nucleotides at positions 37 to 39 are AAT or AAC,
the nucleotides at positions 112 to 114 are TAT or TAC,
the nucleotides at positions 169 to 171 are GAT or GAC,
the nucleotides at positions 181 to 183 are CAA or CAG,
the nucleotides at positions 181 to 183 are TCT, TCC, TCA, TCG, AGT or AGC,
the nucleotides at positions 184 to 186 are ACT, ACC, ACA or ACG,
the nucleotides at positions 187 to 189 are CAT or CAC,
the nucleotides at positions 187 to 189 are ACT, ACC, ACA or ACG,
the nucleotides at positions 205 to 207 are GAA or GAG,
the nucleotides at positions 205 to 207 are CAT or CAC,
the nucleotides at positions 205 to 207 are CAA or CAG,
the nucleotides at positions 205 to 207 are TCT, TCC, TCA, TCG, AGT or AGC,
the nucleotides at positions 205 to 207 are TAT or TAC,
the nucleotides at positions 208 to 210 are CCA, CCC, CCG or CCT,
the nucleotides at positions 211 to 213 are GCT, GCC, GCA or GCG,
the nucleotides at positions 211 to 213 are GAA or GAG,
the nucleotides at positions 211 to 213 are CCA, CCC, CCG or CCT,
the nucleotides at positions 211 to 213 are CAA or CAG,
the nucleotides at positions 211 to 213 are TCT, TCC, TCA, TCG, AGT or AGC,
the nucleotides at positions 211 to 213 are ACT, ACC, ACA or ACG,
the nucleotides at positions 220 to 222 are GAA or GAG,
the nucleotides at positions 220 to 222 are TTA, TTG, CTT, CTC, CTA or CTG,
the nucleotides at positions 220 to 222 are ATG,
the nucleotides at positions 280 to 282 are CAA or CAG,
the nucleotides at positions 301 to 303 are TAT or TAC,
the nucleotides at positions 307 to 309 are TGT or TGC,
the nucleotides at positions 307 to 309 are CAA or CAG,
the nucleotides at positions 316 to 318 are GGT, GGC, GGA or GGG,
the nucleotides at positions 325 to 327 are TTA, TTG, CTT, CTC, CTA or CTG,
the nucleotides at positions 346 to 348 are GCT, GCC, GCA or GCG,
the nucleotides at positions 346 to 348 are CGT, CGC, CGA, CGG, AGA or AGG,
the nucleotides at positions 388 to 390 are TAT or TAC,
the nucleotides at positions 391 to 393 are TTA, TTG, CTT, CTC, CTA or CTG,
the nucleotides at positions 442 to 444 are CAT or CAC,
the nucleotides at positions 484 to 486 are CAA or CAG,
the nucleotides at positions 496 to 498 are GCT, GCC, GCA or GCG,
the nucleotides at positions 496 to 498 are GTT, GTC, GTA or GTG,
the nucleotides at positions 547 to 549 are CGT, CGC, CGA, CGG, AGA or AGG,
the nucleotides at positions 547 to 549 are GTT, GTC, GTA or GTG,
the nucleotides at positions 556 to 558 are GCT, GCC, GCA or GCG,
the nucleotides at positions 556 to 558 are GAT or GAC,
the nucleotides at positions 556 to 558 are CCA, CCC, CCG or CCT,
the nucleotides at positions 556 to 558 are TCT, TCC, TCA, TCG, AGT or AGC,
the nucleotides at positions 571 to 573 are GCT, GCC, GCA or GCG,
the nucleotides at positions 571 to 573 are TGT or TGC,
the nucleotides at positions 571 to 573 are TTA, TTG, CTT, CTC, CTA or CTG,
the nucleotides at positions 601 to 603 are ATT, ATC or ATA,
the nucleotides at positions 601 to 603 are CCA, CCC, CCG or CCT,
the nucleotides at positions 601 to 603 are GTT, GTC, GTA or GTG,
the nucleotides at positions 634 to 636 are CCA, CCC, CCG or CCT,
the nucleotides at positions 646 to 648 are GCT, GCC, GCA or GCG,
the nucleotides at positions 688 to 690 are AAA or AAG,
the nucleotides at positions 688 to 690 are CAA or CAG,
the nucleotides at positions 688 to 690 are CGT, CGC, CGA, CGG, AGA or AGG,
the nucleotides at positions 691 to 693 are ATT, ATC or ATA,
the nucleotides at positions 691 to 693 are ATG,
the nucleotides at positions 691 to 693 are GTT, GTC, GTA or GTG,
the nucleotides at positions 700 to 702 are GAT or GAC,
the nucleotides at positions 736 to 738 are CAA or CAG,
the nucleotides at positions 736 to 738 are TCT, TCC, TCA, TCG, AGT or AGC,
the nucleotides at positions 772 to 774 are TCT, TCC, TCA, TCG, AGT or AGC,
the nucleotides at positions 772 to 774 are TAT or TAC,
the nucleotides at positions 784 to 786 are CAT or CAC,
the nucleotides at positions 784 to 786 are ATG,
the nucleotides at positions 784 to 786 are CCA, CCC, CCG or CCT,
the nucleotides at positions 784 to 786 are CAA or CAG,
the nucleotides at positions 808 to 810 are CGT, CGC, CGA, CGG, AGA or AGG,
the nucleotides at positions 811 to 813 are GCT, GCC, GCA or GCG,
the nucleotides at positions 826 to 828 are GCT, GCC, GCA or GCG,
the nucleotides at positions 826 to 828 are TGT or TGC,
the nucleotides at positions 826 to 828 are TCT, TCC, TCA, TCG, AGT or AGC,
the nucleotides at positions 829 to 831 are TCT, TCC, TCA, TCG, AGT or AGC,
the nucleotides at positions 838 to 840 are GGT, GGC, GGA or GGG,
the nucleotides at positions 868 to 870 are GCT, GCC, GCA or GCG, the nucleotides at positions 889 to 891 are GCT, GCC, GCA or GCG,
the nucleotides at positions 889 to 891 are CCA, CCC, CCG or CCT,
the nucleotides at positions 892 to 894 are GCT, GCC, GCA or GCG,
the nucleotides at positions 892 to 894 are AAT or AAC,
the nucleotides at positions 892 to 894 are CGT, CGC, CGA, CGG, AGA or AGG,
the nucleotides at positions 892 to 894 are TCT, TCC, TCA, TCG, AGT or AGC,
the nucleotides at positions 892 to 894 are GTT, GTC, GTA or GTG,
the nucleotides at positions 898 to 900 are GGT, GGC, GGA or GGG,
the nucleotides at positions 901 to 903 are CAA or CAG,
the nucleotides at positions 913 to 915 are CCA, CCC, CCG or CCT,
the nucleotides at positions 934 to 936 are ATT, ATC or ATA, and/or
the nucleotides at positions 943 to 945 are ATT, ATC or ATA.

All of these sequences are exemplary sequences of the invention having specific residue changes to the "parent" SEQ ID NO:1, summarized (in part) in Tables 1 and 2, below (Table 2 is in Example 5).

In one aspect, a nucleic acid of the invention encodes at least one polypeptide or peptide having a glucanase activity, e.g., an endoglucanase activity, a xylanase activity, or a mannanase activity, or a nucleic acid of the invention encodes at least one polypeptide or peptide capable of eliciting an immune response, e.g., epitopes capable of eliciting a humoral (antibody) or cellular immune response specific for an exemplary polypeptide of the invention. In one aspect, the sequence identities are determined by analysis with a sequence comparison algorithm or by a visual inspection.

In one aspect, the invention provides isolated, synthetic or recombinant nucleic acids comprising a nucleic acid sequence modification of SEQ ID NO:1, wherein the modification comprises, or alternatively—consists of, one, two, three, four, five, six, seven, eight, nine, ten, eleven (11), twelve (12), 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 57, 58, 59, 60, 61, 62, 63, 64, 65, 66, 67, 68, 69 or 70 or more or all of the following changes:

the nucleotides at positions 4 to 6 are AAT or AAC,
the nucleotides at positions 37 to 39 are AAT or AAC,
the nucleotides at positions 112 to 114 are TAT or TAC,
the nucleotides at positions 169 to 171 are GAT or GAC,
the nucleotides at positions 181 to 183 are CAA or CAG,
the nucleotides at positions 181 to 183 are TCT, TCC, TCA, TCG, AGT or AGC,
the nucleotides at positions 184 to 186 are ACT, ACC, ACA or ACG,
the nucleotides at positions 187 to 189 are CAT or CAC,
the nucleotides at positions 187 to 189 are ACT, ACC, ACA or ACG,
the nucleotides at positions 205 to 207 are GAA or GAG,
the nucleotides at positions 205 to 207 are CAT or CAC,
the nucleotides at positions 205 to 207 are CAA or CAG,
the nucleotides at positions 205 to 207 are TCT, TCC, TCA, TCG, AGT or AGC,
the nucleotides at positions 205 to 207 are TAT or TAC,
the nucleotides at positions 208 to 210 are CCA, CCC, CCG or CCT,
the nucleotides at positions 211 to 213 are GCT, GCC, GCA or GCG,
the nucleotides at positions 211 to 213 are GAA or GAG,
the nucleotides at positions 211 to 213 are CCA, CCC, CCG or CCT,
the nucleotides at positions 211 to 213 are CAA or CAG,
the nucleotides at positions 211 to 213 are TCT, TCC, TCA, TCG, AGT or AGC,
the nucleotides at positions 211 to 213 are ACT, ACC, ACA or ACG,
the nucleotides at positions 220 to 222 are GAA or GAG,
the nucleotides at positions 220 to 222 are TTA, TTG, CTT, CTC, CTA or CTG,
the nucleotides at positions 220 to 222 are ATG,
the nucleotides at positions 280 to 282 are CAA or CAG,
the nucleotides at positions 301 to 303 are TAT or TAC,
the nucleotides at positions 307 to 309 are TGT or TGC,
the nucleotides at positions 307 to 309 are CAA or CAG,
the nucleotides at positions 316 to 318 are GGT, GGC, GGA or GGG,
the nucleotides at positions 325 to 327 are TTA, TTG, CTT, CTC, CTA or CTG,
the nucleotides at positions 346 to 348 are GCT, GCC, GCA or GCG,
the nucleotides at positions 346 to 348 are CGT, CGC, CGA, CGG, AGA or AGG,
the nucleotides at positions 388 to 390 are TAT or TAC,
the nucleotides at positions 391 to 393 are TTA, TTG, CTT, CTC, CTA or CTG,
the nucleotides at positions 442 to 444 are CAT or CAC,
the nucleotides at positions 484 to 486 are CAA or CAG,
the nucleotides at positions 496 to 498 are GCT, GCC, GCA or GCG,
the nucleotides at positions 496 to 498 are GTT, GTC, GTA or GTG,
the nucleotides at positions 547 to 549 are CGT, CGC, CGA, CGG, AGA or AGG,
the nucleotides at positions 547 to 549 are GTT, GTC, GTA or GTG,
the nucleotides at positions 556 to 558 are GCT, GCC, GCA or GCG,
the nucleotides at positions 556 to 558 are GAT or GAC,
the nucleotides at positions 556 to 558 are CCA, CCC, CCG or CCT,
the nucleotides at positions 556 to 558 are TCT, TCC, TCA, TCG, AGT or AGC,
the nucleotides at positions 571 to 573 are GCT, GCC, GCA or GCG,
the nucleotides at positions 571 to 573 are TGT or TGC,
the nucleotides at positions 571 to 573 are TTA, TTG, CTT, CTC, CTA or CTG,
the nucleotides at positions 601 to 603 are ATT, ATC or ATA,
the nucleotides at positions 601 to 603 are CCA, CCC, CCG or CCT,
the nucleotides at positions 601 to 603 are GTT, GTC, GTA or GTG,
the nucleotides at positions 634 to 636 are CCA, CCC, CCG or CCT,
the nucleotides at positions 646 to 648 are GCT, GCC, GCA or GCG,
the nucleotides at positions 688 to 690 are AAA or AAG,
the nucleotides at positions 688 to 690 are CAA or CAG,
the nucleotides at positions 688 to 690 are CGT, CGC, CGA, CGG, AGA or AGG,
the nucleotides at positions 691 to 693 are ATT, ATC or ATA, the nucleotides at positions 691 to 693 are ATG,
the nucleotides at positions 691 to 693 are GTT, GTC, GTA or GTG,
the nucleotides at positions 700 to 702 are GAT or GAC,
the nucleotides at positions 736 to 738 are CAA or CAG,
the nucleotides at positions 736 to 738 are TCT, TCC, TCA, TCG, AGT or AGC,
the nucleotides at positions 772 to 774 are TCT, TCC, TCA, TCG, AGT or AGC,
the nucleotides at positions 772 to 774 are TAT or TAC,
the nucleotides at positions 784 to 786 are CAT or CAC,
the nucleotides at positions 784 to 786 are ATG,
the nucleotides at positions 784 to 786 are CCA, CCC, CCG or CCT,
the nucleotides at positions 784 to 786 are CAA or CAG,
the nucleotides at positions 808 to 810 are CGT, CGC, CGA, CGG, AGA or AGG,
the nucleotides at positions 811 to 813 are GCT, GCC, GCA or GCG,
the nucleotides at positions 826 to 828 are GCT, GCC, GCA or GCG,
the nucleotides at positions 826 to 828 are TGT or TGC,
the nucleotides at positions 826 to 828 are TCT, TCC, TCA, TCG, AGT or AGC,
the nucleotides at positions 829 to 831 are TCT, TCC, TCA, TCG, AGT or AGC,
the nucleotides at positions 838 to 840 are GGT, GGC, GGA or GGG,
the nucleotides at positions 868 to 870 are GCT, GCC, GCA or GCG,
the nucleotides at positions 889 to 891 are GCT, GCC, GCA or GCG,
the nucleotides at positions 889 to 891 are CCA, CCC, CCG or CCT,
the nucleotides at positions 892 to 894 are GCT, GCC, GCA or GCG,
the nucleotides at positions 892 to 894 are AAT or AAC,
the nucleotides at positions 892 to 894 are CGT, CGC, CGA, CGG, AGA or AGG,
the nucleotides at positions 892 to 894 are TCT, TCC, TCA, TCG, AGT or AGC,
the nucleotides at positions 892 to 894 are GTT, GTC, GTA or GTG,
the nucleotides at positions 898 to 900 are GGT, GGC, GGA or GGG,
the nucleotides at positions 901 to 903 are CAA or CAG,
the nucleotides at positions 913 to 915 are CCA, CCC, CCG or CCT,
the nucleotides at positions 934 to 936 are ATT, ATC or ATA, and/or the nucleotides at positions 943 to 945 are ATT, ATC or ATA.

All of these sequences are exemplary sequences of the invention having specific residue changes to the "parent" SEQ ID NO:1, summarized (in part) in Tables 1 and 2, below (Table 2 is in Example 5).

Exemplary nucleic acids of the invention also include isolated, synthetic or recombinant nucleic acids encoding a polypeptide of the invention, e.g., a polypeptide having a sequence as set forth in SEQ ID NO:2, SEQ ID NO:7, SEQ ID NO:9, SEQ ID NO:11, SEQ ID NO:13, SEQ ID NO:19, SEQ ID NO:21, and SEQ ID NO:23, subsequences thereof and/or variants thereof, e.g., polypeptides encoded by the invention's nucleic acid sequences of the invention, including the nucleic acid sequence modifications of SEQ ID NO:1, SEQ ID NO:6, SEQ ID NO:8, SEQ ID NO:10, SEQ ID NO:12, SEQ ID NO:18, SEQ ID NO:20, and SEQ ID NO:22, as described herein. In one aspect, the polypeptide has a glucanase activity, e.g., endoglucanase activity, e.g., catalyzing hydrolysis of internal endo-β-1,4- and/or 1,3-glucanase linkages, a xylanase activity, and/or a mannanase activity.

In one aspect, the sequence comparison algorithm is a BLAST version 2.2.2 algorithm where a filtering setting is set to blastall -p blastp -d "nr pataa"-F F, and all other options are set to default, or a or FASTA version 3.0t78, with default parameters.

Another aspect of the invention is an isolated, synthetic or recombinant nucleic acid comprising, or consisting of, at least 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more consecutive bases of a nucleic acid sequence of the invention, sequences substantially identical thereto, and the sequences complementary thereto; and in one aspect the nucleic acid encodes a protein or peptide having an glucanase activity. In one aspect, the glucanase activity of a polypeptide or peptide of the invention (which includes a protein or peptide encoded by a nucleic acid of the invention) comprises an endoglucanase activity, e.g., endo-1,4- and/or 1,3-beta-D-glucan 4-glucano hydrolase activity. In one aspect, the endoglucanase activity comprises catalyzing hydrolysis of 1,4-beta-D-glycosidic linkages. In one aspect, the glucanase, e.g., endoglucanase, activity comprises an endo-1,4- and/or 1,3-beta-endoglucanase activity or endo-β-1,4-glucanase activity. In one aspect, the glucanase activity (e.g., endo-1,4-beta-D-glucan 4-glucano hydrolase activity) comprises hydrolysis of 1,4-beta-D-glycosidic linkages in cellulose, cellulose derivatives (e.g., carboxy methyl cellulose and hydroxy ethyl cellulose) lichenin, beta-1,4 bonds in mixed beta-1,3 glucans, such as cereal beta-D-glucans and other plant material containing cellulosic parts.

In one aspect, the glucanase, xylanase, or mannanase activity comprises hydrolyzing a glucan, mannan, arabinoxylan or xylan, or other polysaccharide to produce a smaller molecular weight polysaccharide or oligomer. In one aspect, the glucan comprises a beta-glucan, such as a water soluble beta-glucan. The water soluble beta-glucan can comprise a dough or a bread product.

In one aspect, the glucanase activity comprises hydrolyzing polysaccharides comprising 1,4-β-glycoside-linked D-glucopyranoses. In one aspect, the glucanase activity comprises hydrolyzing cellulose. In one aspect, the glucanase activity comprises hydrolyzing cellulose in a wood or paper pulp or a paper product.

In one aspect, the glucanase, e.g., endoglucanase, activity comprises catalyzing hydrolysis of glucans, mannans, arabinoxylans or xylans, or other polysaccharides in a beverage or a feed, e.g., an animal feed, such as a monogastric animal feed, e.g., a swine or poultry (e.g., chicken) feed, or a food product. The beverage, feed or food product can comprise a cereal-based animal feed, a wort or a beer, a fruit or a vegetable. In one aspect, the invention provides a food, feed (e.g., an animal feed, such as a monogastric animal feed, e.g., for swine or poultry), a liquid, e.g., a beverage (such as a fruit juice or a beer) or a beverage precursor (e.g., a wort), comprising a polypeptide of the invention. The food can be a dough or a bread product. The beverage or a beverage precursor can be a fruit juice, a beer or a wort. In one aspect, the invention provides methods for the clarification of a liquid, e.g., a juice, such as a fruit juice, or a beer, by treating the liquid with an enzyme of the invention.

In one aspect, the invention provides methods of dough conditioning comprising contacting a dough or a bread product with at least one polypeptide of the invention under conditions sufficient for conditioning the dough. In one aspect, the invention provides methods of beverage production comprising administration of at least one polypeptide of the invention to a beverage or a beverage precursor under conditions sufficient for decreasing the viscosity of the beverage.

In one aspect, the glucanase, e.g., endoglucanase, activity comprises catalyzing hydrolysis of glucans, mannans, arabinoxylans or xylans, or other polysaccharides in a cell, e.g., a plant cell or a microbial cell.

In one aspect, the isolated, synthetic or recombinant nucleic acid encodes a polypeptide having a glucanase, e.g., endoglucanase, a xylanase, or a mannanase activity that is thermostable. For example, a polypeptide of the invention, e.g., for example, the variant or evolved enzymes of the invention, e.g., the specific variations to SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, as set forth in Tables 1 and 2 (Table 2 is in Example 5), can be thermostable. The thermostable polypeptide according to the invention can retain binding and/or enzymatic activity, e.g., a glucanase, e.g., endoglucanase, a xylanase, or a mannanase activity, under conditions comprising a temperature range from about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermostable polypeptides according to the invention can retain activity, e.g., a glucanase, e.g., endoglucanase, a xylanase, or a mannanase activity, in temperatures in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermostable polypeptides according to the invention retains activity, e.g., a glucanase, e.g., endoglucanase, a xylanase, or a mannanase activity, at a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more.

In another aspect, the isolated, synthetic or recombinant nucleic acid encodes a polypeptide having a glucanase, e.g., endoglucanase, a xylanase, or a mannanase activity that is thermotolerant. For example, a polypeptide of the invention, e.g., for example, the variant or evolved enzymes of the invention, e.g., the specific variations to SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, as set forth in Tables 1 and 2 (Table 2 is in Example 5), can be thermotolerant or thermoactive. The thermotolerant polypeptides according to the invention can retain binding and/or enzymatic activity, e.g., a glucanase, e.g., endoglucanase, a xylanase, or a mannanase activity, after exposure to conditions comprising a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. The thermotolerant polypeptides according to the invention can retain activity, e.g., a glucanase, e.g., endoglucanase, a xylanase, or a mannanase activity, after exposure to a temperature in the range from about −100° C. to about −80° C., about −80° C. to about −40° C., about −40° C. to about −20° C., about −20° C. to about 0° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C. or more. In some embodiments, the thermotolerant polypeptides according to the invention retains activity, e.g., a glucanase, e.g., endoglucanase, a xylanase, or a mannanase activity, after exposure to a temperature in the ranges described above, at about pH 3.0, about pH 3.5, about pH 4.0, about pH 4.5, about pH 5.0, about pH 5.5, about pH 6.0, about pH 6.5, about pH 7.0, about pH 7.5, about pH 8.0, about pH 8.5, about pH 9.0, about pH 9.5, about pH 10.0, about pH 10.5, about pH 11.0, about pH 11.5, about pH 12.0 or more. In one aspect, the polypeptide retains a glucanase or other activity after exposure to a temperature in the range from greater than 90° C. to about 95° C. at pH 4.5.

The invention provides isolated, synthetic or recombinant nucleic acids comprising a sequence that hybridizes under stringent conditions to a nucleic acid comprising a sequence of the invention, e.g., the sequence of SEQ ID NO:1, SEQ ID NO:3, SEQ ID NO:6, SEQ ID NO:8, SEQ ID NO:10, SEQ ID NO:12, SEQ ID NO:18, SEQ ID NO:20, and SEQ ID NO:22 or fragments or subsequences thereof; and in one aspect this sequence has at least one, or several or all of the sequence modifications to SEQ ID NO:1 (or equivalent modifications), as described herein. In one aspect, the nucleic acid encodes a polypeptide having a glucanase, e.g., endoglucanase, a xylanase, or a mannanase activity. The nucleic acid can be at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200 or more residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying, isolating, cloning, amplifying or sequencing of a nucleic acid encoding a polypeptide having a glucanase, e.g., endoglucanase, activity, a xylanase, or a mannanase, wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof (which includes both strands, sense and antisense, e.g., including sequences fully complementary to SEQ ID NO:1, SEQ ID NO:3, SEQ ID NO:6, SEQ ID NO:8, SEQ ID NO:10, SEQ ID NO:12, SEQ ID NO:18, SEQ ID NO:20, AND SEQ ID NO:22, and the exemplary modifications set forth herein), wherein the probe identifies the nucleic acid by binding or hybridization. The probe can comprise an oligonucleotide comprising between about 10-100 consecutive bases of a sequence in accordance with the invention, or fragments or subsequences thereof, for example, 10, 15, 20, 25, 30, 35, 40, 45, 50, 55, 60, 65, 70, 75, 80, 85, 90, 95 or 100 bases or more, or, any desired length in between.

The invention provides a nucleic acid probe for identifying a nucleic acid encoding a polypeptide having a glucanase, e.g., endoglucanase, a xylanase, or a mannanase activity, wherein the probe comprises, or consists of, a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, AND SEQ ID NO:22, or a nucleic acid comprising a sequence modification of SEQ ID NO:1, as set forth herein (e.g., SEQ ID NO:3), wherein the sequence identities are determined by analysis with a sequence comparison algorithm (e.g., BLAST or FASTA) or by visual inspection. Another aspect of the invention is a polynucleotide probe for isolation or identification of glucanase (or cellulase), e.g., endoglucanase, mannanase, xylanase, amylase, xanthanase and/or glycosidase, e.g., cellobiohydrolase, mannanase and/or beta-glucosidase genes having a sequence which is the same as, or fully complementary to at least a nucleic acid sequence of the invention.

The invention provides an amplification primer pair for amplifying a nucleic acid encoding a polypeptide having a glucanase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 or more consecutive bases of the sequence, or about 10, 11, 12, 13, 14, 15, 16, 17, 18, 19, 20, 21, 22, 23, 24, 25, 26, 27, 28, 29, 30, 31, 32, 33, 34 or 35 or more consecutive bases of the sequence.

The invention provides amplification primer pairs, wherein the primer pair comprises a first member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34 or 35 or more residues of a nucleic acid of the invention, and a second member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34 or 35 or more residues of the complementary strand of the first member.

The invention provides glucanase-, e.g., endoglucanase-encoding, xylanase-encoding, or mannanase-encoding nucleic acids generated by amplification, e.g., polymerase chain reaction (PCR), using an amplification primer pair of the invention. The invention provides glucanases (or cellulases), mannanases, xylanases, amylases, xanthanases and/or glycosidases, e.g., cellobiohydrolases, mannanases and/or beta-glucosidases generated by amplification, e.g., polymerase chain reaction (PCR), using an amplification primer pair of the invention. The invention provides methods of making glucanases (or cellulases), mannanases, xylanases, amylases, xanthanases and/or glycosidases, e.g., cellobiohydrolases, mannanases and/or beta-glucosidases by amplification, e.g., polymerase chain reaction (PCR), using an amplification primer pair of the invention. In one aspect, the amplification primer pair amplifies a nucleic acid from a library, e.g., a gene library, such as an environmental library.

The invention provides methods of amplifying a nucleic acid encoding a polypeptide having a glucanase, e.g., endoglucanase, a mannanase, or a xylanase activity comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. Optionally, the promoter can be a fungal, yeast, viral, bacterial, mammalian, plant, synthetic or hybrid promoter. The promoter can be a constitutive promoter. In another aspect, the promoter can be an inducible promoter. In one aspect, the promoter can be a tissue-specific promoter or an environmentally regulated or a developmentally regulated promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be from any plant, for example plants used for forage and/or feed for any animal, including ruminants, or as a source of feedstock to produce energy or fuel. Plants of particular interest may include crop plants and feedstock plants, for example, maize, alfalfa, sunflower, Brassica, soybean, cotton, safflower, peanut, sorghum, wheat, oat, rye, millet, barley, rice, conifers, grasses, e.g., switch grass and Mis-

*canthus*, legume crops, e.g., pea, bean and soybean, starchy tuber/roots, e.g., potato, sweet potato, cassava, taro, canna and sugar beet and the like.

The invention provides transgenic non-human animals comprising a nucleic acid of the invention or an expression cassette (e.g., a vector) of the invention. In one aspect, the animal is a mouse, a rat, a goat, a rabbit, a sheep, a pig, a cow, or any mammal.

The invention provides transgenic plants comprising a nucleic acid of the invention or an expression cassette (e.g., a vector) of the invention. The transgenic plant can be any plant, but in one embodiment the plant would be used for forage and/or feed for any animal or as a feedstock to produce energy or fuel, such as, maize, alfalfa, sunflower, *Brassica*, soybean, cotton, safflower, peanut, sorghum, wheat, oat, rye, millet, barley, rice, conifers, grasses, e.g., switch grass and *Miscanthus*, legume crops, e.g., pea, bean and soybean, starchy tuber/roots, e.g., potato, sweet potato, cassava, taro, canna and sugar beet and the like.

The invention provides transgenic seeds comprising a nucleic acid of the invention or an expression cassette (e.g., a vector) of the invention. The transgenic seed can from any plant, but in one embodiment the plant would be used for forage and/or feed for any animal or as a feedstock to produce energy or fuel, such as, maize, alfalfa, sunflower, *Brassica*, soybean, cotton, safflower, peanut, sorghum, wheat, oat, rye, millet, barley, rice, conifers, grasses, e.g., switch grass and *Miscanthus*, legume crops, e.g., pea, bean and soybean, starchy tuber/roots, e.g., potato, sweet potato, cassava, taro, canna and sugar beet and the like.

The invention provides an antisense oligonucleotide comprising a nucleic acid sequence complementary to or capable of hybridizing under stringent conditions to a nucleic acid of the invention. The invention provides methods of inhibiting the translation of a glucanase, e.g., endoglucanase, a mannanase, or a xylanase message in a cell comprising administering to the cell or expressing in the cell an antisense oligonucleotide comprising a nucleic acid sequence complementary to or capable of hybridizing under stringent conditions to a nucleic acid of the invention. In one aspect, the antisense oligonucleotide is between about 10 to 50, about 20 to 60, about 30 to 70, about 40 to 80, about 60 to 100, or about 50 to 150 bases in length.

The invention provides methods of inhibiting the translation of a glucanase, e.g., endoglucanase, a mannanase, or a xylanase message in a cell comprising administering to the cell or expressing in the cell an antisense oligonucleotide comprising a nucleic acid sequence complementary to or capable of hybridizing under stringent conditions to a nucleic acid of the invention. The invention provides double-stranded inhibitory RNA (RNAi, or RNA interference) molecules (including small interfering RNA, or siRNAs, for inhibiting transcription, and microRNAs, or miRNAs, for inhibiting translation) comprising a subsequence of a sequence of the invention. In one aspect, the RNAi is about 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100 or more duplex nucleotides in length. The invention provides methods of inhibiting the expression of a polypeptide, enzyme, protein, peptide, e.g., structural or binding protein in a cell comprising administering to the cell or expressing in the cell a double-stranded inhibitory RNA (iRNA, including small interfering RNA, or siRNAs, for inhibiting transcription, and microRNAs, or miRNAs, for inhibiting translation), wherein the RNA comprises a subsequence of a sequence of the invention.

The invention provides isolated, synthetic or recombinant polypeptides comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 25, 50, 75, 100, 125, 150, 175, 200, 225, 250, 275, 300, 325, 350 or more residues, or over the full length of the polypeptide, and the sequence identities are determined by analysis with a sequence comparison algorithm or by a visual inspection. Exemplary polypeptide or peptide sequences of the invention include SEQ ID NO:2, subsequences thereof and variants thereof, wherein in one aspect exemplary polypeptide sequences of the invention comprise, or alternatively—consist of, one, two, three, four, five, six, seven, eight, nine, ten, eleven (11), twelve (12), 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 56, 57, 58, 59, 60, 61, 62, 63, 64, 65, 66, 67, 68, 69 or 70 or more or all of the following amino acid residue changes to SEQ ID NO:2:

the glycine at amino acid position 2 is asparagine,
the glycine at amino acid position 13 is asparagine,
the phenylalanine at amino acid position 38 is tyrosine,
the serine at amino acid position 57 is aspartic acid,
the tyrosine at amino acid position 61 is glutamine,
the tyrosine at amino acid position 61 is serine,
the alanine at amino acid position 62 is threonine,
the phenylalanine at amino acid position 63 is histidine,
the phenylalanine at amino acid position 63 is threonine,
the methionine at amino acid position 69 is glutamic acid,
the methionine at amino acid position 69 is glutamine,
the methionine at amino acid position 69 is histidine,
the methionine at amino acid position 69 is serine,
the methionine at amino acid position 69 is tyrosine,
the aspartic acid at amino acid position 70 is proline,
the arginine at amino acid position 71 is alanine,
the arginine at amino acid position 71 is glutamic acid,
the arginine at amino acid position 71 is glutamine,
the arginine at amino acid position 71 is proline,
the arginine at amino acid position 71 is serine,
the arginine at amino acid position 71 is threonine,
the lysine at amino acid position 74 is glutamic acid,
the lysine at amino acid position 74 is leucine,
the lysine at amino acid position 74 is methionine,
the isoleucine at amino acid position 94 is glutamine,
the methionine at amino acid position 101 is tyrosine,
the aspartic acid at amino acid position 103 is cysteine,
the aspartic acid at amino acid position 103 is glutamine,
the glutamic acid at amino acid position 106 is glycine,
the glutamic acid at amino acid position 109 is leucine,
the lysine at amino acid position 116 is alanine,
the lysine at amino acid position 116 is arginine,
the phenylalanine at amino acid position 130 is tyrosine,
the phenylalanine at amino acid position 131 is leucine,
the glutamic acid at amino acid position 148 is histidine,
the lysine at amino acid position 162 is glutamine,
the isoleucine at amino acid position 166 is alanine,
the isoleucine at amino acid position 166 is valine,
the serine at amino acid position 183 is arginine,
the serine at amino acid position 183 is valine,
the lysine at amino acid position 186 is alanine,
the lysine at amino acid position 186 is aspartic acid,
the lysine at amino acid position 186 is proline, the lysine at amino acid position 186 is serine,
the serine at amino acid position 191 is alanine,
the serine at amino acid position 191 is cysteine,
the serine at amino acid position 191 is leucine,
the phenylalanine at amino acid position 201 is isoleucine,
the phenylalanine at amino acid position 201 is proline,
the phenylalanine at amino acid position 201 is valine,
the glutamic acid at amino acid position 212 is proline,
the lysine at amino acid position 216 is alanine,
the histidine at amino acid position 230 is arginine,
the histidine at amino acid position 230 is glutamine,
the histidine at amino acid position 230 is lysine,
the leucine at amino acid position 231 is isoleucine,
the leucine at amino acid position 231 is methionine,
the leucine at amino acid position 231 is valine,
the glutamic acid at amino acid position 234 is aspartic acid,
the lysine at amino acid position 246 is glutamine,
the lysine at amino acid position 246 is serine,
the arginine at amino acid position 258 is serine,
the arginine at amino acid position 258 is tyrosine,
the leucine at amino acid position 262 is glutamine,
the leucine at amino acid position 262 is histidine,
the leucine at amino acid position 262 is methionine,
the leucine at amino acid position 262 is proline,
the serine at amino acid position 270 is arginine,
the phenylalanine at amino acid position 271 is alanine,
the methionine at amino acid position 276 is alanine,
the methionine at amino acid position 276 is cysteine,
the methionine at amino acid position 276 is serine,
the glutamic acid at amino acid position 277 is serine,
the arginine at amino acid position 280 is glycine,
the serine at amino acid position 290 is alanine,
the threonine at amino acid position 297 is alanine,
the threonine at amino acid position 297 is proline,
the leucine at amino acid position 298 is alanine,
the leucine at amino acid position 298 is arginine,
the leucine at amino acid position 298 is asparagine,
the leucine at amino acid position 298 is serine,
the leucine at amino acid position 298 is valine,
the lysine at amino acid position 300 is glycine,
the threonine at amino acid position 301 is glutamine,
the aspartic acid at amino acid position 305 is proline,
the glycine at amino acid position 312 is isoleucine, and/or
the serine at amino acid position 315 is isoleucine.

All of these sequences are exemplary amino acid sequences of the invention having specific residue changes to the "parent" SEQ ID NO:2, summarized (in part) in Tables 1 and 2, below. Exemplary polypeptides or peptides also include fragments of at least about 10, 15, 20, 25, 30, 35, 40, 45, 50, 75, 100, 150, 200, 250, 300, 350, 400, 450, 500, 550, 600 or more residues in length, or over the full length of an enzyme or antibody. Exemplary polypeptide or peptide sequences of the invention include sequences encoded by a nucleic acid of the invention. Exemplary polypeptide or peptide sequences of the invention include polypeptides or peptides specifically bound by an antibody of the invention, or sequences capable of eliciting an immune response, e.g., epitopes capable of eliciting a humoral (antibody) or cellular immune response specific for an exemplary polypeptide of the invention.

In one aspect, a polypeptide (e.g., an enzyme, antibody or peptide) of the invention has at least one glucanase, e.g., endoglucanase, a mannanase, or a xylanase activity. In one aspect, the endoglucanase activity comprises endo-1,4-beta-D-glucan 4-glucano hydrolase activity. In one aspect, the endoglucanase activity comprises catalyzing hydrolysis of 1,4-beta-D-glycosidic linkages or 1,3-beta-D-glycosidic linkages. In one aspect, the endoglucanase activity comprises an endo-1,4-beta-endoglucanase activity or endo-β-1,4-glucanase activity, endo-1,3-beta-endoglucanase activity or endo-β-1,3-glucanase activity. In one aspect, the glucanase activity (e.g., endo-1,4 and/or 1,3-beta-D-glucan 4-glucano hydrolase activity) comprises hydrolysis of 1,4-beta-D-glycosidic linkages in cellulose, cellulose derivatives (e.g., carboxy methyl cellulose and hydroxy ethyl cellulose) lichenin, beta-1,4- and/or 1,3-bonds in mixed beta-1,3 glucans, such as cereal beta-D-glucans or xyloglucans and other plant material containing cellulosic parts.

Another aspect of the invention provides an isolated, synthetic or recombinant polypeptide or peptide comprise, or consists of, at least 10, 15, 20, 25, 30, 35, 40, 45, 50, 55, 60, 65, 70, 75, 80, 85, 90, 95 or 100 or more consecutive bases of a polypeptide or peptide sequence of the invention, sequences substantially identical thereto (including the exemplary sequences that are modifications of SEQ ID NO:2, as described herein), and the sequences complementary thereto. The peptide can be, e.g., an immunogenic fragment, an epitope, a motif (e.g., a binding site), a signal sequence, a prepro sequence or a catalytic domain (CD) or active site.

The invention provides isolated, synthetic or recombinant nucleic acids comprising a sequence encoding a polypeptide (e.g., an enzyme, antibody or peptide) of the invention, including the exemplary sequences of the invention, having a glucanase activity, e.g., an endoglucanase activity, a mannanase activity, or a xylanase activity with—or without—a signal (leader) sequence, wherein the nucleic acid comprises a sequence of the invention. The signal (leader) sequence can be derived from another glucanase (or cellulase), e.g., endoglucanase, mannanase, xylanase, amylase, xanthanase and/or glycosidase, e.g., cellobiohydrolase, mannanase and/or beta-glucosidase of the invention, or from another glucanase (or cellulase), e.g., endoglucanase, mannanase, xylanase, amylase, xanthanase and/or glycosidase, e.g., cellobiohydrolase, mannanase and/or beta-glucosidase (not of the invention), or a non-glucanase (or cellulase), e.g., endoglucanase, mannanase, xylanase, amylase, xanthanase and/or glycosidase, e.g., cellobiohydrolase, mannanase and/or beta-glucosidase, etc., i.e., a heterologous enzyme. The invention provides isolated, synthetic or recombinant nucleic acids comprising a sequence encoding a polypeptide having a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase activity, wherein the sequence does not contain a signal (leader) sequence and the nucleic acid comprises a sequence of the invention.

In one aspect, the glucanase, e.g., endoglucanase, activity comprises catalyzing hydrolysis of 1,4-beta-D-glycosidic linkages or 1,3-beta-D-glycosidic linkages. In one aspect, the endoglucanase activity comprises an endo-1,4-beta-endoglucanase activity. In one aspect, the endoglucanase activity comprises hydrolyzing a glucan, a mannan, an arabinoxylan or a xylan to produce a smaller molecular weight polysaccharide or oligomer. In one aspect, the glucan comprises a beta-glucan, such as a water soluble beta-glucan. The water soluble beta-glucan can comprise a dough or a bread product. In one aspect, the glucanase activity comprises hydrolyzing polysaccharides comprising 1,4-β-glycoside-linked D-glucopyranoses. In one aspect, the glucanase activity comprises hydrolyzing cellulose. In one aspect, the glucanase activity comprises hydrolyzing cellulose in a wood or paper pulp or a paper product.

In one aspect, the glucanase, xylanase, or mannanase activity comprises catalyzing hydrolysis of a glucan, a mannan, an arabinoxylan or a xylan, or other carbohydrate in a feed (e.g., an animal feed, such as a monogastric animal feed, including swine or poultry (e.g., chicken) feed) or a food product. The feed or food product can comprise a cereal-based animal feed, a wort or a beer, a fruit or a vegetable.

In one aspect, the glucanase, xylanase, or mannanase activity comprises catalyzing hydrolysis of a glucan, a mannan, an arabinoxylan or a xylan, or other carbohydrate in a cell, e.g., a plant cell, a fungal cell, or a microbial (e.g., bacterial) cell.

In one aspect, the isolated, synthetic or recombinant polypeptide can comprise the polypeptide of the invention that lacks all or part of a signal (leader) sequence. In one aspect, the isolated, synthetic or recombinant polypeptide can comprise, or consist of, the polypeptide of the invention comprising, or consisting of, a heterologous signal (leader) sequence, such as a heterologous glucanase, or mannanase, xylanase signal sequence or non-glucanase (or cellulase), e.g., endoglucanase, mannanase, xylanase, amylase, xanthanase and/or glycosidase, e.g., cellobiohydrolase, mannanase and/or beta-glucosidase signal (leader) sequence.

In one aspect, the invention provides chimeric proteins comprising a first domain comprising a signal sequence of the invention and at least a second domain. The protein can be a fusion protein. The second domain can comprise an enzyme. The enzyme can be a glucanase, e.g., endoglucanase, a mannanase, or a xylanase.

The invention provides chimeric polypeptides comprising, or consisting of, at least a first domain comprising signal peptide (SP), a prepro sequence and/or a catalytic domain (CD) of the invention and at least a second domain comprising a heterologous polypeptide or peptide, wherein the heterologous polypeptide or peptide is not naturally associated with the signal peptide (SP), prepro sequence and/or catalytic domain (CD). In one aspect, the heterologous polypeptide or peptide is not a glucanase, a mannanase, or a xylanase. The heterologous polypeptide or peptide can be amino terminal to, carboxy terminal to or on both ends of the signal peptide (SP), prepro sequence and/or catalytic domain (CD).

The invention provides isolated, synthetic or recombinant nucleic acids encoding a chimeric polypeptide, wherein the chimeric polypeptide comprises, or consists of, at least a first domain comprising signal peptide (SP), a prepro domain and/or a catalytic domain (CD) of the invention and at least a second domain comprising a heterologous polypeptide or peptide, wherein the heterologous polypeptide or peptide is not naturally associated with the signal peptide (SP), prepro domain and/or catalytic domain (CD).

The invention provides isolated, synthetic or recombinant signal (leader) sequences (e.g., signal (leader) peptides) consisting of or comprising a sequence as set forth in the (amino terminal) residues 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 40, 1 to 41, 1 to 42, 1 to 43 or 1 to 44, of a polypeptide of the invention, e.g., an exemplary polypeptide of the invention, such as SEQ ID NO:2, SEQ ID NO:7, SEQ ID NO:9, SEQ ID NO:11, SEQ ID NO:13, SEQ ID NO:19, SEQ ID NO:21, AND SEQ ID NO:23 and the exemplary sequence modifications thereof described herein.

In one aspect, the glucanase, e.g., endoglucanase (or cellulase), e.g., endoglucanase, mannanase, xylanase, amylase, xanthanase and/or glycosidase, e.g., cellobiohydrolase, mannanase and/or beta-glucosidase activity comprises a specific activity at about 37° C. in the range from about 1 to about 1200 units per milligram of protein, or, about 100 to about 1000 units per milligram of protein. In another aspect, the glucanase, e.g., endoglucanase, mannanase, xylanase, amylase, xanthanase and/or glycosidase, e.g., cellobiohydrolase, mannanase and/or beta-glucosidase activity comprises a specific activity from about 100 to about 1000 units per milligram of protein, or, from about 500 to about 750 units per milligram of protein. Alternatively, the glucanase, mannanase, xylanase, amylase, xanthanase and/or glycosidase, e.g., cellobiohydrolase, mannanase and/or beta-glucosidase activity comprises a specific activity at 37° C. in the range from about 1 to about 750 units per milligram of protein, or, from about 500 to about 1200 units per milligram of protein. In one aspect, the glucanase, mannanase, xylanase, amylase, xanthanase and/or glycosidase, e.g., cellobiohydrolase, mannanase and/or beta-glucosidase activity comprises a specific activity at 37° C. in the range from about 1 to about 500 units per milligram of protein, or, from about 750 to about 1000 units per milligram of protein. In another aspect, the glucanase, mannanase, xylanase, amylase, xanthanase and/or glycosidase, e.g., cellobiohydrolase, mannanase and/or beta-glucosidase activity comprises a specific activity at 37° C. in the range from about 1 to about 250 units per milligram of protein. Alternatively, the glucanase, e.g., endoglucanase, mannanase, xylanase, amylase, xanthanase and/or glycosidase, e.g., cellobiohydrolase, mannanase and/or beta-glucosidase activity comprises a specific activity at 37° C. in the range from about 1 to about 100 units per milligram of protein. In another aspect, the thermotolerance comprises retention of at least half of the specific activity of the glucanase, mannanase, xylanase, amylase, xanthanase and/or glycosidase, e.g., cellobiohydrolase, mannanase and/or beta-glucosidase at 37° C. after being heated to an elevated temperature, such as a temperature from about 0° C. to about 20° C., about 20° C. to about 37° C., about 37° C. to about 50° C., about 50° C. to about 70° C., about 70° C. to about 75° C., about 75° C. to about 80° C., about 80° C. to about 85° C., about 85° C. to about 90° C., about 90° C. to about 95° C., about 95° C. to about 100° C., about 100° C. to about 110° C., or higher. Alternatively, the thermotolerance can comprise retention of specific activity at 37° C. in the range from about 1 to about 1200 units per milligram of protein, or, from about 500 to about 1000 units per milligram of protein, after being heated to an elevated temperature. In another aspect, the thermotolerance can comprise retention of specific activity at 37° C. in the range from about 1 to about 500 units per milligram of protein after being heated to an elevated temperature, as described above.

The invention provides the isolated, synthetic or recombinant polypeptide of the invention, wherein the polypeptide comprises at least one glycosylation site. In one aspect, glycosylation can be an N-linked glycosylation and/or an O-linked glycosylation. In one aspect, the polypeptide can be glycosylated after being expressed in a yeast cell, e.g., a *P. pastoris* or a *S. pombe*, or in a mammalian, insect, fungal or other host cell.

In one aspect, the polypeptide can retain glucanase, e.g., endoglucanase, mannanase, xylanase, amylase, xanthanase and/or glycosidase, e.g., cellobiohydrolase, mannanase and/ or beta-glucosidase activity under conditions comprising about pH 6.5, pH 6, pH 5.5, pH 5, pH 4.5, pH 4.0, pH 3.5, pH 3.0 or less (more acidic) pH. In another aspect, the polypeptide can retain a glucanase, mannanase, xylanase, amylase, xanthanase and/or glycosidase, e.g., cellobiohydrolase, mannanase and/or beta-glucosidase activity under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH. In one aspect, the polypeptide can retain a glucanase, mannanase, xylanase, amylase, xanthanase and/or glycosidase, e.g., cellobiohydrolase, mannanase and/or beta-glucosidase activity after exposure to conditions comprising about pH 6.5, pH 6, pH 5.5, pH 5, pH 4.5, pH 4.0, pH 3.5, pH 3.0 or less (more acidic) pH. In another aspect, the polypeptide can retain a glucanase, mannanase, xylanase, amylase, xanthanase and/or glycosidase, e.g., cellobiohydrolase, mannanase and/or beta-glucosidase activity after exposure to conditions comprising about pH 7, pH 7.5 pH 8.0, pH 8.5, pH 9, pH 9.5, pH 10, pH 10.5, pH 11.0, pH 11.5, pH 12, pH 12.5 or more (more basic) pH.

The invention provides protein preparations comprising a polypeptide of the invention, wherein the protein preparation comprises a liquid, a solid or a gel.

The invention provides heterodimers comprising a polypeptide of the invention and a second protein or domain. The second member of the heterodimer can be a different glycanase, a different enzyme or another protein. In one aspect, the second domain can be a polypeptide and the heterodimer can be a fusion protein. In one aspect, the second domain can be an epitope or a tag. In one aspect, the invention provides homomultimers, including, but not limited to, homodimers, homotrimers, homotetramers, homopentamers, and homohexamers comprising a polypeptide (e.g., an enzyme, a peptide) of the invention.

The invention provides immobilized polypeptides having glucanase, e.g., endoglucanase, mannanase, xylanase, amylase, xanthanase and/or glycosidase, e.g., cellobiohydrolase, mannanase and/or beta-glucosidase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated, synthetic or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides method of isolating or identifying a polypeptide having glucanase, e.g., endoglucanase, mannanase, xylanase, amylase, xanthanase and/or glycosidase, e.g., cellobiohydrolase, mannanase and/or beta-glucosidase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having an glucanase, mannanase, xylanase, amylase, xanthanase and/or glycosidase, e.g., cellobiohydrolase, mannanase and/or beta-glucosidase activity.

The invention provides methods of making an anti-glucanase, mannanase, xylanase, amylase, xanthanase and/or glycosidase, e.g., cellobiohydrolase, mannanase and/or beta-glucosidase antibody comprising administering to a non-human animal a nucleic acid of the invention or a polypeptide of the invention or subsequences thereof in an amount sufficient to generate a humoral immune response, thereby making an anti-glucanase, mannanase, xylanase, amylase, xanthanase and/or glycosidase, e.g., cellobiohydrolase, mannanase and/or beta-glucosidase antibody. The invention provides methods of making an anti-glucanase, mannanase, xylanase, amylase, xanthanase and/or glycosidase, e.g., cellobiohydrolase, mannanase and/or beta-glucosidase humoral or cellular immune response comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having glucanase, e.g., endoglucanase, mannanase, xylanase, amylase, xanthanase and/or glycosidase, e.g., cellobiohydrolase, mannanase and/or beta-glucosidase activity comprising the following steps: (a) providing a polypeptide of the invention; or a polypeptide encoded by a nucleic acid of the invention; (b) providing glucanase, e.g., endoglucanase, mannanase, xylanase, amylase, xanthanase and/or glycosidase, e.g., cellobiohydrolase, mannanase and/or beta-glucosidase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having a glucanase, mannanase, xylanase, amylase, xanthanase and/or glycosidase, e.g., cellobiohydrolase, mannanase and/or beta-glucosidase activity.

The invention provides methods for identifying glucanase, e.g., endoglucanase, mannanase, xylanase, amylase, xanthanase and/or glycosidase, e.g., cellobiohydrolase, mannanase and/or beta-glucosidase substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an glucanase, mannanase, xylanase, amylase, xanthanase and/or glycosidase, e.g., cellobiohydrolase, mannanase and/or beta-glucosidase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of a glucanase, e.g., endoglucanase, mannanase, xylanase, amylase, xanthanase and/or glycosidase, e.g., cellobiohydrolase, mannanase and/or beta-glucosidase activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the glucanase, mannanase, xylanase, amylase, xanthanase and/or glycosidase, e.g., cellobiohydrolase, mannanase and/or beta-glucosidase wherein a change in the glucanase mannanase, xylanase, amylase, xanthanase and/or glycosidase, e.g., cellobiohydrolase, mannanase and/or beta-glucosidase activity measured in the presence of the test compound compared to the activity in the absence of the test compound provides a determination that the test compound modulates the glucanase, mannanase, xylanase, amylase, xanthanase and/or glycosidase, e.g., cellobiohydrolase, mannanase and/or beta-glucosidase activity. In one aspect, the glucanase, mannanase, xylanase, amylase, xanthanase and/or glycosidase, e.g., cellobiohydrolase, mannanase and/or beta-glucosidase activity can be measured by providing a glucanase, mannanase, xylanase, amylase, xanthanase and/or glycosidase, e.g., cellobiohydrolase, mannanase and/or beta-glucosidase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of glucanase, mannanase, xylanase, amylase, xanthanase and/or glycosidase, e.g., cellobiohydrolase, mannanase and/or beta-glucosidase activity. An increase in the amount of the substrate or a decrease in the amount of the reaction product with the test compound as compared to the amount of substrate or reaction product without the test compound identifies the test compound as an inhibitor of glucanase, mannanase, xylanase, amylase, xanthanase and/or glycosidase, e.g., cellobiohydrolase, mannanase and/or beta-glucosidase activity.

The invention provides computer systems comprising a processor and a data storage device wherein said data storage device has stored thereon a polypeptide sequence or a nucleic acid sequence of the invention (e.g., a polypeptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having a glucanase, mannanase, xylanase, amylase, xanthanase and/or glycosidase, e.g., cellobiohydrolase, mannanase and/or beta-glucosidase activity from a sample, such as an environmental sample, comprising the steps of: (a) providing an amplification primer sequence pair for amplifying a nucleic acid encoding a polypeptide having a glucanase, mannanase, xylanase, amylase, xanthanase and/or glycosidase, e.g., cellobiohydrolase, mannanase and/or beta-glucosidase activity, wherein the primer pair is capable of amplifying a nucleic acid of the invention; (b) isolating a nucleic acid from the sample or treating the sample such that nucleic acid in the sample is accessible for hybridization to the amplification primer pair; and, (c) combining the nucleic acid of step (b) with the amplification primer pair of step (a) and amplifying nucleic acid from the sample, thereby isolating or recovering a nucleic acid encoding a polypeptide having a glucanase, mannanase, xylanase, amylase, xanthanase and/or glycosidase, e.g., cellobiohydrolase, mannanase and/or beta-glucosidase activity from a sample. One or each member of the amplification primer sequence pair can comprise an oligonucleotide comprising at least about 10 to 50 consecutive bases of a sequence of the invention. In one aspect, the amplification primer sequence pair is an amplification pair of the invention. In one embodiment of the invention, the sample is an environmental sample, e.g., comprising a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods for isolating or recovering a nucleic acid encoding a polypeptide having a glucanase, mannanase, xylanase, amylase, xanthanase and/or glycosidase, e.g., cellobiohydrolase, mannanase and/or beta-glucosidase activity from a sample, such as an environmental sample, comprising the steps of: (a) providing a polynucleotide probe comprising a nucleic acid of the invention or a subsequence thereof; (b) isolating a nucleic acid from the sample or treating the sample such that nucleic acid in the sample is accessible for hybridization to a polynucleotide probe of step (a); (c) combining the isolated, synthetic nucleic acid or the treated sample of step (b) with the polynucleotide probe of step (a); and (d) isolating a nucleic acid that specifically hybridizes with the polynucleotide probe of step (a), thereby isolating or recovering a nucleic acid encoding a polypeptide having a glucanase, mannanase, xylanase, amylase, xanthanase and/or glycosidase, e.g., cellobiohydrolase, mannanase and/or beta-glucosidase activity from a sample. In one embodiment of the invention, the sample is an environmental sample, e.g., comprising a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having a glucanase, mannanase, xylanase, amylase, xanthanase and/or glycosidase, e.g., cellobiohydrolase, mannanase and/or beta-glucosidase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant glucanase, mannanase, xylanase, amylase, xanthanase and/or glycosidase, e.g., cellobiohydrolase, mannanase and/or beta-glucosidase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until a glucanase, mannanase, xylanase, amylase, xanthanase and/or glycosidase, e.g., cellobiohydrolase, mannanase and/or beta-glucosidase having an altered or different activity or an altered or different stability from that of a polypeptide encoded by the template nucleic acid is produced. In one aspect, the variant glucanase, mannanase, xylanase, amylase, xanthanase and/or glycosidase, e.g., cellobiohydrolase, mannanase and/or beta-glucosidase polypeptide is thermotolerant, and retains some activity after being exposed to an elevated temperature. In another aspect, the variant glucanase, mannanase, xylanase, amylase, xanthanase and/or glycosidase, e.g., cellobiohydrolase, mannanase and/or beta-glucosidase polypeptide has increased glycosylation as compared to the glucanase, mannanase, xylanase, amylase, xanthanase and/or glycosidase, e.g., cellobiohydrolase, mannanase and/or beta-glucosidase encoded by a template nucleic acid. Alternatively, the variant polypeptide has a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase activity under a high temperature, wherein the enzyme encoded by the template nucleic acid is not active under the high temperature. In one aspect, the method can be iteratively repeated until a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase coding sequence having an altered codon usage from that of the template nucleic acid is produced. In another aspect, the method can be iteratively repeated until a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase gene having higher or lower level of message expression or stability from that of the template nucleic acid is produced.

The invention provides methods for modifying codons in a nucleic acid encoding a polypeptide having a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase activity to increase its expression in a host cell, the method comprising the following steps: (a) providing a nucleic acid of the invention encoding a polypeptide having a glucanase, e.g., an endoglucanase, a (or cellulase), e.g., an endoglucanase, a mannanase, a xylanase, an amylase, a xanthanase and/or a glycosidase, e.g., a cellobiohydrolase, a mannanase and/or a beta-glucosidase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having a glucanase, mannanase, (or cellulase), e.g., endoglucanase, mannanase, xylanase, amylase, xanthanase and/or glycosidase, e.g., cellobiohydrolase, mannanase and/or beta-glucosidase activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding a glucanase, mannanase, (or cellulase), e.g., endoglucanase, mannanase, xylanase, amylase, xanthanase and/or glycosidase, e.g., cellobiohydrolase, mannanase and/or beta-glucosidase.

The invention provides methods for modifying codons in a nucleic acid encoding a polypeptide having a glucanase, mannanase, (or cellulase), e.g., endoglucanase, mannanase, xylanase, amylase, xanthanase and/or glycosidase, e.g., cellobiohydrolase, mannanase and/or beta-glucosidase activity to increase its expression in a host cell, the method comprising the following steps: (a) providing a nucleic acid of the invention encoding a glucanase, mannanase, (or cellulase), e.g., endoglucanase, mannanase, xylanase, amylase, xanthanase and/or glycosidase, e.g., cellobiohydrolase, mannanase and/or beta-glucosidase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having a glucanase, mannanase, (or cellulase), e.g., endoglucanase, mannanase, xylanase, amylase, xanthanase and/or glycosidase, e.g., cellobiohydrolase, mannanase and/or beta-glucosidase activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified glucanase, mannanase, (or cellulase), e.g., endoglucanase, mannanase, xylanase, amylase, xanthanase and/or glycosidase, e.g., cellobiohydrolase, mannanase and/or beta-glucosidase active sites (catalytic domains (CDs)) or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes a glucanase (or cellulase), e.g., endoglucanase, mannanase, xylanase, amylase, xanthanase and/or glycosidase, e.g., cellobiohydrolase, mannanase and/or beta-glucosidase active site or a glucanase (or cellulase), e.g., endoglucanase, mannanase, xylanase, amylase, xanthanase and/or glycosidase, e.g., cellobiohydrolase, mannanase and/or beta-glucosidase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified glucanase (or cellulase), e.g., endoglucanase, mannanase, xylanase, amylase, xanthanase and/or glycosidase, e.g., cellobiohydrolase, mannanase and/or beta-glucosidase active sites or substrate binding sites. In one aspect, the method comprises mutagenizing the first nucleic acid of step (a) by a method comprising an optimized directed evolution system, Gene Site-Saturation Mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises a glucanase (or cellulase), e.g., endoglucanase, mannanase, xylanase, amylase, xanthanase and/or glycosidase, e.g., cellobiohydrolase, mannanase and/or beta-glucosidase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing a glucanase (or cellulase), e.g., endoglucanase, mannanase, xylanase, amylase, xanthanase and/or glycosidase, e.g., cellobiohydrolase, mannanase and/or beta-glucosidase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the glucanase (or cellulase), e.g., endoglucanase, mannanase, xylanase, amylase, xanthanase and/or glycosidase, e.g., cellobiohydrolase, mannanase and/or beta-glucosidase enzyme, thereby modifying a small molecule by a glucanase (or cellulase), e.g., endoglucanase, mannanase, xylanase, amylase, xanthanase and/or glycosidase, e.g., cellobiohydrolase, mannanase and/or beta-glucosidase enzymatic reaction. In one aspect, the method can comprise a plurality of small molecule substrates for the enzyme of step (a), thereby generating a library of modified small molecules produced by at least one enzymatic reaction catalyzed by the glucanase (or cellulase), e.g., endoglucanase, mannanase, xylanase, amylase, xanthanase and/or glycosidase, e.g., cellobiohydrolase, mannanase and/or beta-glucosidase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule that exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of a glucanase (or cellulase), e.g., endoglucanase, mannanase, xylanase, amylase, xanthanase and/or glycosidase, e.g., cellobiohydrolase, mannanase and/or beta-glucosidase enzyme comprising the steps of: (a) providing a glucanase (or cellulase), e.g., endoglucanase, mannanase, xylanase, amylase, xanthanase and/or glycosidase, e.g., cellobiohydrolase, mannanase and/or beta-glucosidase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for a glucanase (or cellulase), e.g., endoglucanase, mannanase, xylanase, amylase, xanthanase and/or glycosidase, e.g., cellobiohydrolase, mannanase and/or beta-glucosidase activity, thereby determining a functional fragment of a glucanase (or cellulase), e.g., endoglucanase, mannanase, xylanase, amylase, xanthanase and/or glycosidase, e.g., cellobiohydrolase, mannanase and/or beta-glucosidase enzyme. In one aspect, the glucanase, mannanase, or xylanase activity is measured by providing a glucanase (or cellulase), e.g., endoglucanase, mannanase, xylanase, amylase, xanthanase and/or glycosidase, e.g., cellobiohydrolase, mannanase and/or beta-glucosidase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods of increasing thermotolerance or thermostability of a glucanase (or cellulase), e.g., endoglucanase, mannanase, xylanase, amylase, xanthanase and/or glycosidase, e.g., cellobiohydrolase, mannanase and/or beta-glucosidase polypeptide, the method comprising glycosylating a glucanase (or cellulase), e.g., endoglucanase, mannanase, xylanase, amylase, xanthanase and/or glycosidase, e.g., cellobiohydrolase, mannanase and/or beta-glucosidase polypeptide, wherein the polypeptide comprises at least 25, 30, 35, 40, 45, 50, 75, 100, 150, 200, 250 or more contiguous amino acids of a polypeptide of the invention; or a polypeptide encoded by a nucleic acid sequence of the invention, thereby increasing the thermotolerance or thermostability of the glucanase (or cellulase), e.g., endoglucanase, mannanase, xylanase, amylase, xanthanase and/or glycosidase, e.g., cellobiohydrolase, mannanase and/or beta-glucosidase polypeptide. In one aspect, the glucanase (or cellulase), e.g., endoglucanase, mannanase, xylanase, amylase, xanthanase and/or glycosidase, e.g., cellobiohydrolase, mannanase and/or beta-glucosidase specific activity can be thermostable or thermotolerant at a temperature in the range from greater than about 37° C. to about 95° C., or 0° C. to about 37° C.

The invention provides methods for overexpressing a recombinant glucanase (or cellulase), e.g., endoglucanase, mannanase, xylanase, amylase, xanthanase and/or glycosidase, e.g., cellobiohydrolase, mannanase and/or beta-glucosidase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell. The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a sequence of the invention; (b) growing the plant under conditions wherein the heterologous nucleic acids sequence is expressed in the plant cell.

The invention provides methods for hydrolyzing, breaking up or disrupting a glucan-comprising composition comprising the following steps: (a) providing a polypeptide of the invention having a glucanase (or cellulase), e.g., endoglucanase, mannanase, xylanase, amylase, xanthanase and/ or glycosidase, e.g., cellobiohydrolase, mannanase and/or beta-glucosidase activity, or a polypeptide encoded by a nucleic acid of the invention; (b) providing a composition comprising a glucan; and (c) contacting the polypeptide of step (a) with the composition of step (b) under conditions wherein the glucanase (or cellulase), e.g., endoglucanase, mannanase, xylanase, amylase, xanthanase and/or glycosidase, e.g., cellobiohydrolase, mannanase and/or beta-glucosidase hydrolyzes, breaks up or disrupts the glucan-comprising composition. In one aspect, the composition comprises a plant cell, a bacterial cell, a yeast cell, an insect cell, or an animal cell.

Thus, the composition can comprise any plant or plant part, any glucan-, mannan-, xyloglucan- or xylan-containing food or feed, a waste product and the like. The invention provides methods for liquefying or removing a glucan-comprising composition comprising the following steps: (a) providing a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a polypeptide encoded by a nucleic acid of the invention; (b) providing a composition comprising a glucan; and (c) contacting the polypeptide of step (a) with the composition of step (b) under conditions wherein the glucanase (or cellulase), e.g., endoglucanase, mannanase, xylanase, amylase, xanthanase and/or glycosidase, e.g., cellobiohydrolase, mannanase and/or beta-glucosidase removes, softens or liquefies the composition.

The invention provides detergent compositions comprising a polypeptide of the invention, or a polypeptide encoded by a nucleic acid of the invention, wherein the polypeptide has a glucanase, e.g., endoglucanase (or cellulase), e.g., endoglucanase, mannanase, xylanase, amylase, xanthanase and/or glycosidase, e.g., cellobiohydrolase, mannanase and/or beta-glucosidase activity. The glucanase can be a non-surface-active glucanase (or cellulase), e.g., endoglucanase, mannanase, xylanase, amylase, xanthanase and/or glycosidase, e.g., cellobiohydrolase, mannanase and/or beta-glucosidase or a surface-active glucanase (or cellulase), e.g., endoglucanase, mannanase, xylanase, amylase, xanthanase and/or glycosidase, e.g., cellobiohydrolase, mannanase and/or beta-glucosidase. The glucanase (or cellulase), e.g., endoglucanase, mannanase, xylanase, amylase, xanthanase and/or glycosidase, e.g., cellobiohydrolase, mannanase and/or beta-glucosidase can be formulated in a non-aqueous liquid composition, a cast solid, a granular form, a particulate form, a compressed tablet, a gel form, a paste or a slurry form. The invention provides methods for washing an object comprising the following steps: (a) providing a composition comprising a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a polypeptide encoded by a nucleic acid of the invention; (b) providing an object; and (c) contacting the polypeptide of step (a) and the object of step (b) under conditions wherein the composition can wash the object.

The invention provides textiles or fabrics, including, e.g., threads, comprising a polypeptide of the invention, or a polypeptide encoded by a nucleic acid of the invention. In one aspect, the textiles or fabrics comprise glucan-containing fibers. The invention provides methods for treating a textile or fabric (e.g., removing a stain from a composition) comprising the following steps: (a) providing a composition comprising a polypeptide of the invention having a glucanase e.g., endoglucanase (or cellulase), e.g., endoglucanase, mannanase, xylanase, amylase, xanthanase and/or glycosidase, e.g., cellobiohydrolase, mannanase and/or beta-glucosidase activity, or a polypeptide encoded by a nucleic acid of the invention; (b) providing a textile or fabric comprising a glucan; and (c) contacting the polypeptide of step (a) and the composition of step (b) under conditions wherein the glucanase (or cellulase), e.g., endoglucanase, mannanase, xylanase, amylase, xanthanase and/or glycosidase, e.g., cellobiohydrolase, mannanase and/or beta-glucosidase can treat the textile or fabric (e.g., remove the stain). The invention provides methods for improving the finish of a fabric comprising the following steps: (a) providing a composition comprising a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a polypeptide encoded by a nucleic acid of the invention; (b) providing a fabric; and (c) contacting the polypeptide of step (a) and the fabric of step (b) under conditions wherein the polypeptide can treat the fabric thereby improving the finish of the fabric. In one aspect, the fabric is a wool or a silk.

The invention provides feeds, including animal feeds for, e.g., monogastric animals, such as a swine or poultry (e.g., chicken) feed, or foods, comprising a polypeptide of the invention, or a polypeptide encoded by a nucleic acid of the invention. The invention provides methods for hydrolyzing a glucan, a mannan, an arabinoxylan or a xylan, or other polysaccharide in a feed or a food prior to consumption by an animal comprising the following steps: (a) obtaining a feed material comprising a glucanase e.g., endoglucanase (or cellulase), e.g., endoglucanase, mannanase, xylanase, amylase, xanthanase and/or glycosidase, e.g., cellobiohydrolase, mannanase and/or beta-glucosidase of the invention, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention; and (b) adding the polypeptide of step (a) to the feed or food material in an amount sufficient for a sufficient time period to cause hydrolysis of a glucan, a mannan, an arabinoxylan or a xylan, or other polysaccharide and formation of a treated food or feed, thereby hydrolyzing a glucan, a mannan, an arabinoxylan or a xylan, or other polysaccharide in the food or the feed prior to consumption by the animal. In one aspect, the invention provides methods for hydrolyzing a glucan, a mannan, an arabinoxylan or a xylan, or other polysaccharide in a feed or a food after consumption by an animal comprising the following steps: (a) obtaining a feed material comprising a glucanase (or cellulase), e.g., endoglucanase, mannanase, xylanase, amylase, xanthanase and/or glycosidase, e.g., cellobiohydrolase, mannanase and/or beta-glucosidase of the invention, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention; (b) adding the polypeptide of step (a) to the feed or food material; and (c) administering the feed or food material to the animal, wherein after consumption, the glucanase (or cellulase), e.g., endoglucanase, mannanase, xylanase, amylase, xanthanase and/or glycosidase, e.g., cellobiohydrolase, mannanase and/or beta-glucosidase causes hydrolysis of a glucan, a mannan, an arabinoxylan or a xylan, or other polysaccharide in the feed or food in the digestive tract of the animal. The food or the feed (e.g., animal feed, including for monogastric animals such as in swine or poultry (e.g., chicken) feed) can be, e.g., a cereal, a grain, a corn and the like.

In another aspect, the invention provides methods for decreasing the viscosity of glucans, mannans, arabinoxylans or xylans, or other polysaccharides in a composition, e.g., in a food or a feed (e.g., an animal feed, e.g., monogastric animal feed, such as a poultry (e.g., chicken) feed), by treating the composition with a glucanase of the invention, or, including a glucanase of the invention in the composition. The food or feed can comprise barley or wheat, e.g., a food for feed for a high-barley or a high-wheat diet, as in a monogastric animal's diet, including its use in a poultry (e.g., chicken) or swine diet. In one aspect, the invention provides methods for minimizing wet droppings by feeding an animal (e.g., a bird, such as any domestic poultry) a food or a feed treated by or comprising a glucanase (or cellulase), e.g., endoglucanase, mannanase, xylanase, amylase, xanthanase and/or glycosidase, e.g., cellobiohydrolase, mannanase and/or beta-glucosidase of the invention. In one aspect, the invention provides methods for increasing growth rate and/or feed conversion by feeding an animal (e.g., a bird, such as a domestic poultry, e.g., a chicken) a food or a feed treated by or comprising a glucanase (or cellulase), e.g., endoglucanase, mannanase, xylanase, amylase, xanthanase and/or glycosidase, e.g., cellobiohydrolase, mannanase and/or beta-glucosidase of the invention. In one aspect, the invention provides methods for decreasing excrement by feeding an animal (e.g., a bird, such as a domestic poultry, e.g., a chicken) a food or a feed treated by or comprising a glucanase (or cellulase), e.g., endoglucanase, mannanase, xylanase, amylase, xanthanase and/or glycosidase, e.g., cellobiohydrolase, mannanase and/or beta-glucosidase of the invention. Foods or feeds of the invention include dietary supplements and dietary additives, whether for animals or humans.

The invention provides food, feed, a dietary addition or supplements and/or nutritional supplements for an animal (e.g., a fowl, such as a chicken), or human, comprising a polypeptide of the invention, e.g., a polypeptide encoded by the nucleic acid of the invention. In one aspect, the polypeptide in the food, feed, dietary additions or supplements and/or nutritional supplements can be glycosylated. The food, feed, dietary additions or supplements and/or nutritional supplements can comprise any edible plant, including any plant material used for forage and/or feed for any animal, including ruminants, such as hay, corn (e.g., silage), rice, millet, soy, wheat, buckwheat, barley, alfalfa, rye, annual grasses (including forage sorghums, sudangrass, veldt grass, buffel grass, etc.) and the like. The food, feed, a dietary addition or supplements and/or nutritional supplements of the invention also can be part of or added to the food, feed or forage material, e.g., for a ruminant animal, including goats, sheep, cattle/cows, bison and llamas and the like. Enzymes of the invention can be added to, mixed into or sprayed onto the forage material, food or feed, see, e.g., U.S. Pat. No. 4,627,338; alternatively the food, feed or forage material of this invention can comprise transgenic plant material that express one or more enzymes of this invention.

The invention provides edible enzyme delivery matrices comprising a polypeptide of the invention, e.g., a polypeptide encoded by the nucleic acid of the invention. In one aspect, the delivery matrix comprises a pellet comprising an enzyme of the invention, e.g., a pellet comprising a thermotolerant or thermostable enzyme of the invention). In one aspect, the polypeptide can be glycosylated (which in one aspect can make the enzyme more thermotolerant or thermostable). In one aspect, the glucanase e.g., endoglucanase (or cellulase), e.g., endoglucanase, mannanase, xylanase, amylase, xanthanase and/or glycosidase, e.g., cellobiohydrolase, mannanase and/or beta-glucosidase activity is thermotolerant. In another aspect, the glucanase (or cellulase), e.g., endoglucanase, mannanase, xylanase, amylase, xanthanase and/or glycosidase, e.g., cellobiohydrolase, mannanase and/or beta-glucosidase activity is thermostable.

The invention provides a food, a feed (e.g., an animal feed, e.g., monogastric animal feed, such as a swine or poultry (e.g., chicken) feed) or a nutritional supplement comprising a polypeptide of the invention. The invention provides methods for utilizing a glucanase (or cellulase), e.g., endoglucanase, mannanase, xylanase, amylase, xanthanase and/or glycosidase, e.g., cellobiohydrolase, mannanase and/or beta-glucosidase as a nutritional supplement in an animal diet, the method comprising: preparing a nutritional supplement containing a glucanase (or cellulase), e.g., endoglucanase, mannanase, xylanase, amylase, xanthanase and/or glycosidase, e.g., cellobiohydrolase, mannanase and/or beta-glucosidase enzyme comprising at least 25, 30, 35, 40, 45, 50, 75, 100, 150, 200, 250 or more contiguous amino acids of a polypeptide of the invention; and administering the nutritional supplement to an animal to increase utilization of a glucan, a mannan, an arabinoxylan or a xylan, or other polysaccharide contained in a feed or a food ingested by the animal. The animal can be a human, a ruminant or a monogastric animal. For example, the animal can be any poultry or bird, e.g., a chicken; or swine, which includes hogs, pigs and the like. The glucanase (or cellulase), e.g., endoglucanase, mannanase, xylanase, amylase, xanthanase and/or glycosidase, e.g., cellobiohydrolase, mannanase and/or beta-glucosidase enzyme can be prepared by expression of a polynucleotide encoding the glucanase in an organism such as a bacterium, a yeast, a plant, an insect, a fungus or an animal. Exemplary organisms for expressing polypeptides of the invention can be S. pombe, S. cerevisiae, Pichia sp., e.g., P. pastoris, E. coli, Streptomyces sp., Bacillus sp. and Lactobacillus sp.

The invention provides edible enzyme delivery matrix comprising a thermostable recombinant glucanase (or cellulase), e.g., endoglucanase, mannanase, xylanase, amylase, xanthanase and/or glycosidase, e.g., cellobiohydrolase, mannanase and/or beta-glucosidase enzyme, e.g., a polypeptide of the invention. The invention provides methods for delivering a glucanase (or cellulase), e.g., endoglucanase, mannanase, xylanase, amylase, xanthanase and/or glycosidase, e.g., cellobiohydrolase, mannanase and/or beta-glucosidase supplement to an animal (a human, a ruminant, a monogastric animal, a bird, e.g., a chicken), the method comprising: preparing an edible enzyme delivery matrix in the form of pellets comprising a granulate edible carrier and a thermostable isolated, synthetic or recombinant glucanase (or cellulase), e.g., endoglucanase, mannanase, xylanase, amylase, xanthanase and/or glycosidase, e.g., cellobiohydrolase, mannanase and/or beta-glucosidase enzyme, wherein the pellets readily disperse the glucanase (or cellulase), e.g., endoglucanase, mannanase, xylanase, amylase, xanthanase and/or glycosidase, e.g., cellobiohydrolase, mannanase and/or beta-glucosidase enzyme contained therein into aqueous media, and administering the edible enzyme delivery matrix to the animal. The recombinant glucanase (or cellulase), e.g., endoglucanase, mannanase, xylanase, amylase, xanthanase and/or glycosidase, e.g., cellobiohydrolase, mannanase and/or beta-glucosidase enzyme can comprise a polypeptide of the invention. The granulate edible carrier can comprise a carrier selected from the group consisting of a grain germ, a grain germ that is spent of oil, a hay, an alfalfa, a timothy, a soy hull, a sunflower seed meal and a wheat midd. The edible carrier can comprise grain germ that is spent of oil. The glucanase (or cellulase), e.g., endoglucanase, mannanase, xylanase, amylase, xanthanase and/or glycosidase, e.g., cellobiohydrolase, mannanase and/or beta-glucosidase enzyme can be glycosylated to provide thermostability at pelletizing conditions. The delivery matrix can be formed by pelletizing a mixture comprising a grain germ and a glucanase (or cellulase), e.g., endoglucanase, mannanase, xylanase, amylase, xanthanase and/or glycosidase, e.g., cellobiohydrolase, mannanase and/or beta-glucosidase. The pelletizing conditions can include application of steam. The pelletizing conditions can comprise application of a temperature in excess of about 80° C. for about 5 minutes and the enzyme retains a specific activity of at least 350 to about 900 units per milligram of enzyme.

The invention provides methods for improving texture and flavor of a dairy product comprising the following steps: (a) providing a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase encoded by a nucleic acid of the invention; (b) providing a dairy product; and (c) contacting the polypeptide of step (a) and the dairy product of step (b) under conditions wherein the glucanase (or cellulase), e.g., endoglucanase, mannanase, xylanase, amylase, xanthanase and/or glycosidase, e.g., cellobiohydrolase, mannanase and/or beta-glucosidase can improve the texture or flavor of the dairy product. In one aspect, the dairy product comprises a cheese or a yogurt. The invention provides dairy products comprising a glucanase (or cellulase), e.g., endoglucanase, mannanase, xylanase, amylase, xanthanase and/or glycosidase, e.g., cellobiohydrolase, mannanase and/or beta-glucosidase of the invention, or is encoded by a nucleic acid of the invention.

The invention provides methods for improving the extraction of oil from an oil-rich plant material comprising the following steps: (a) providing a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention; (b) providing an oil-rich plant material; and (c) contacting the polypeptide of step (a) and the oil-rich plant material. In one aspect, the oil-rich plant material comprises an oil-rich seed. The oil can be a soybean oil, an olive oil, a rapeseed (canola) oil or a sunflower oil and the like.

In one aspect, the invention provides methods using a glucanase (or cellulase), e.g., endoglucanase, mannanase, xylanase, amylase, xanthanase and/or glycosidase, e.g., cellobiohydrolase, mannanase and/or beta-glucosidase of the invention to produce fermentable sugars that can be converted into fuel ethanol. In one aspect, the invention provides fuels comprising one or more polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase encoded by a nucleic acid of the invention. In one aspect, an enzyme of the invention is used to catalyze the hydrolysis of celluloses and hemicelluloses. The degradation of cellulose may be used for the conversion of plant biomass into fuels and chemicals. See, e.g., Kohlmann (1996) *Adv. Space Res.* 18:251-265; Perez (2002) *Int Microbiol.* 5:53-63.

In another aspect, plant material comprising the enzymes described herein can be used in an industrial process to produce fuel or energy. Enzymes expressed in plants can be added to, mixed into or sprayed onto feedstock material. Alternatively, the enzymes could be directly expressed in the feedstock material. In one embodiment, plant material expressing enzymes could be ground, milled, heated or the like, in order to disrupt the physical integrity of the plant cells or organs that contain the enzyme, thereby releasing the enzyme to come in contact with the substrate. Optional—exemplary-sources of plant material include, but are not limited to, maize, alfalfa, sunflower, *Brassica*, soybean, cotton, safflower, peanut, sorghum, wheat, oat, rye, millet, barley, rice, conifers, grasses, e.g., switch grass and *Miscanthus*, legume crops, e.g., pea, bean and soybean, starchy tuber/roots, e.g., potato, sweet potato, cassava, taro, canna and sugar beet and the like.

The invention provides methods for preparing a fruit or vegetable juice, syrup, puree or extract comprising the following steps: (a) providing a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention; (b) providing a composition or a liquid comprising a fruit or vegetable material; and (c) contacting the polypeptide of step (a) and the composition, thereby preparing the fruit or vegetable juice, syrup, puree or extract.

The invention provides papers or paper products or paper pulp comprising a glucanase (or cellulase), e.g., endoglucanase, mannanase, xylanase, amylase, xanthanase and/or glycosidase, e.g., cellobiohydrolase, mannanase and/or beta-glucosidase of the invention, or a polypeptide encoded by a nucleic acid of the invention. The invention provides methods for treating a paper or a paper or wood pulp comprising the following steps: (a) providing a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention; (b) providing a composition comprising a paper or a paper or wood pulp; and (c) contacting the polypeptide of step (a) and the composition of step (b) under conditions wherein the glucanase (or cellulase), e.g., endoglucanase, mannanase, xylanase, amylase, xanthanase and/or glycosidase, e.g., cellobiohydrolase, mannanase and/or beta-glucosidase can treat the paper or paper or wood pulp. In one aspect, the pharmaceutical composition acts as a digestive aid or an anti-microbial (e.g., against *Salmonella*). In one aspect, the treatment is prophylactic. In one aspect, the invention provides oral care products comprising a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention. The oral care product can comprise a toothpaste, a dental cream, a gel or a tooth powder, an odontic, a mouth wash, a pre- or post brushing rinse formulation, a chewing gum, a lozenge or a candy. The invention provides contact lens cleaning compositions comprising a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity, or a glucanase (or cellulase), e.g., endoglucanase, mannanase, xylanase, amylase, xanthanase and/or glycosidase, e.g., cellobiohydrolase, mannanase and/or beta-glucosidase encoded by a nucleic acid of the invention.

In one aspect, the invention provides methods for eliminating or protecting animals from a microorganism comprising a glucan, a mannan, an arabinoxylan or a xylan, or other polysaccharide comprising administering a polypeptide of the invention. The microorganism can be a bacterium comprising a glucan, e.g., *Salmonella*.

Another aspect of the invention is a method of making a polypeptide of the invention. The method includes introducing a nucleic acid encoding the polypeptide into a host cell, wherein the nucleic acid is operably linked to a promoter and culturing the host cell under conditions that allow expression of the nucleic acid. Another aspect of the invention is a method of making a polypeptide having at least 10 amino acids of a sequence as set forth in amino acid sequences of the invention. The method includes introducing a nucleic acid encoding the polypeptide into a host cell, wherein the nucleic acid is operably linked to a promoter and culturing the host cell under conditions that allow expression of the nucleic acid, thereby producing the polypeptide.

Another aspect of the invention is a method of generating a variant including obtaining a nucleic acid having a sequence of the invention, sequences substantially identical thereto, sequences complementary to a sequence of the invention, fragments comprising at least 30 consecutive nucleotides of the foregoing sequences and changing one or more nucleotides in the sequence to another nucleotide, deleting one or more nucleotides in the sequence, or adding one or more nucleotides to the sequence.

Another aspect of the invention is a computer readable medium having stored thereon a nucleic acid or polypeptide sequence of the invention. Another aspect of the invention is a computer system including a processor and a data storage device wherein the data storage device has stored thereon a nucleic acid or polypeptide sequence of the invention. Another aspect of the invention is a method for comparing a first sequence to a reference sequence wherein the first sequence is a nucleic acid or polypeptide sequence of the invention. The method includes reading the first sequence and the reference sequence through use of a computer program that compares sequences; and determining differences between the first sequence and the reference sequence with the computer program. Another aspect of the invention is a method for identifying a feature in a nucleic acid or polypeptide sequence of the invention, including reading the sequence through the use of a computer program which identifies features in sequences; and identifying features in the sequence with the computer program.

Yet another aspect of the invention is a method of catalyzing the breakdown of glycan or a derivative thereof, comprising the step of contacting a sample containing a glucan, a mannan, an arabinoxylan or a xylan, or other polysaccharide or a derivative thereof with a polypeptide of the invention under conditions which facilitate the breakdown of a glucan.

Another aspect of the invention is an assay for identifying fragments or variants of a polypeptide of the invention, which retain the enzymatic function (e.g., a glucanase activity) of a polypeptide (e.g., enzyme or antibody) of the invention, including exemplary sequences of the invention. The assay includes contacting a polypeptide of the invention with a substrate molecule under conditions which allow the polypeptide fragment or variant to function and detecting either a decrease in the level of substrate or an increase in the level of the specific reaction product of the reaction between the polypeptide and substrate thereby identifying a fragment or variant of such sequences.

In still another aspect, the invention provides a protein preparation comprising a polypeptide having an amino acid sequence of the invention wherein the protein preparation is a liquid. Still another aspect of the invention provides a protein preparation comprising a polypeptide having an amino acid sequence of the invention wherein the polypeptide is a solid.

Yet another aspect of the invention provides a method for modifying small molecules, comprising the step of mixing at least one polypeptide of the invention with at least one small molecule, to produce at least one modified small molecule via at least one biocatalytic reaction, where the at least one polypeptide has glucanase (or cellulase), e.g., endoglucanase, mannanase, xylanase, amylase, xanthanase and/or glycosidase, e.g., cellobiohydrolase, mannanase and/or beta-glucosidase activity.

Another aspect of the invention is a cloning vector of a sequence that encodes a polypeptide of the invention having a glucanase (or cellulase), e.g., endoglucanase, mannanase, xylanase, amylase, xanthanase and/or glycosidase, e.g., cellobiohydrolase, mannanase and/or beta-glucosidase activity. Another aspect of the invention is a host cell comprising a sequence that encodes a polypeptide of the invention. In yet another aspect, the invention provides an expression vector capable of replicating in a host cell comprising a nucleic acid of the invention or a nucleic acid encoding a polynucleotide of the invention.

In another aspect, the invention provides a method of dough conditioning comprising contacting dough with at least one polypeptide of the invention under conditions sufficient for conditioning the dough. Another aspect of the invention is a method of beverage production comprising administration of at least one polypeptide of the invention under conditions sufficient for decreasing the viscosity of wort or beer, or, increasing the clarity (e.g., clarification) of the beverage.

The glucanases (or cellulases), e.g., endoglucanases, mannanases, xylanases, amylases, xanthanases and/or glycosidases, e.g., cellobiohydrolases, mannanases and/or beta-glucosidases of the invention are used to break down the high molecular weight glucans, mannans, arabinoxylans or xylans, or other polysaccharides in animal feed (e.g., a feed for a human, a ruminant, a monogastric animal, a bird, e.g., a chicken). Adding enzymes of the invention stimulates growth rates by improving digestibility, which also improves the quality of the animal litter. Glucanase functions through the gastro-intestinal tract to reduce intestinal viscosity and increase diffusion of pancreatic enzymes. Additionally, the enzymes of the invention may be used in the treatment of endosperm cell walls of feed grains and vegetable proteins. In one aspect of the invention, the novel enzymes of the invention are administered to an animal in order to increase the utilization of a glucan, a mannan, an arabinoxylan or a xylan, or other polysaccharide in the food. This activity of the enzymes of the invention may be used to break down insoluble cell wall material, liberating nutrients in the cell walls, which then become available to the animal. It also changes hemicellulose to nutritive sugars so that nutrients formerly trapped within the cell walls are released. Glucanase (or cellulase), e.g., endoglucanase, mannanase, xylanase, amylase, xanthanase and/or glycosidase, e.g., cellobiohydrolase, mannanase and/or beta-glucosidase enzymes of the invention can produce compounds that may be a nutritive source for the ruminal microflora.

Another aspect of the invention provides a method for utilizing glucanase (or cellulase), e.g., endoglucanase, mannanase, xylanase, amylase, xanthanase and/or glycosidase, e.g., cellobiohydrolase, mannanase and/or beta-glucosidase as a food or feed additive or a nutritional supplement in the diets of animals, comprising preparation of a nutritional supplement containing a recombinant glucanase (or cellulase), e.g., endoglucanase, mannanase, xylanase, amylase, xanthanase and/or glycosidase, e.g., cellobiohydrolase, mannanase and/or beta-glucosidase enzyme of the invention, or an enzymatically active subsequence thereof, e.g., a subsequence comprising at least thirty, 40, 50, 60, 70, 80, 90 or 100 or more contiguous amino acids of an amino acid sequence of the invention, and administering the food or feed additive or nutritional supplement to an animal to increase the utilization of a glucan, a mannan, an arabinoxylan or a xylan, or other polysaccharide contained in food ingested by the animal.

In another aspect of the invention, a method for delivering a glucanase (or cellulase), e.g., endoglucanase, mannanase, xylanase, amylase, xanthanase and/or glycosidase, e.g., cellobiohydrolase, mannanase and/or beta-glucosidase supplement to an animal is provided, where the method comprises preparing an edible enzyme delivery matrix in the form of pellets comprising a granulate edible carrier and a thermostable recombinant or synthetic glucanase (or cellulase), e.g., endoglucanase, mannanase, xylanase, amylase, xanthanase and/or glycosidase, e.g., cellobiohydrolase, mannanase and/or beta-glucosidase enzyme, wherein the particles readily disperse the glucanase (or cellulase), e.g., endoglucanase, mannanase, xylanase, amylase, xanthanase and/or glycosidase, e.g., cellobiohydrolase, mannanase and/or beta-glucosidase enzyme contained therein into aqueous media, and administering the edible enzyme delivery matrix to the animal. The granulate edible carrier may comprise a carrier selected from the group consisting of grain germ that is spent of oil, hay, alfalfa, timothy, soy hull, sunflower seed meal and wheat midd. The glucanase (or cellulase), e.g., endoglucanase, mannanase, xylanase, amylase, xanthanase and/or glycosidase, e.g., cellobiohydrolase, mannanase and/or beta-glucosidase enzyme may have an amino acid sequence of the invention.

The invention provides isolated, synthetic or recombinant nucleic acids, wherein the nucleic acid encodes at least one polypeptide having a glucanase activity, or encodes a polypeptide or peptide capable of generating an antibody that binds specifically to a polypeptide having the sequence of SEQ ID NO:2, and the sequence comprises the following changes based on SEQ ID NO:1:

(A) the nucleotides at positions 112 to 114 are TAT or TAC, the nucleotides at positions 181 to 183 are CAA or CAG, the nucleotides at positions 205 to 207 are GAA or GAG, the nucleotides at positions 280 to 282 are CAA or CAG, the nucleotides at positions 547 to 549 are CGT, CGC, CGA, CGG, AGA or AGG, the nucleotides at positions 571 to 573 are GCT, GCC, GCA or GCG, and the nucleotides at positions 826 to 828 are GCT, GCC, GCA or GCG;

(B) the nucleotides at positions 112 to 114 are TAT or TAC, the nucleotides at positions 181 to 183 are CAA or CAG, the nucleotides at positions 205 to 207 are GAA or GAG, the nucleotides at positions 280 to 282 are CAA or CAG, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 826 to 828 are GCT, GCC, GCA or GCG, and the nucleotides at positions 838 to 840 are GGT, GGC, GGA or GGG;

(C) the nucleotides at positions 112 to 114 are TAT or TAC, the nucleotides at positions 181 to 183 are CAA or CAG, the nucleotides at positions 205 to 207 are GAA or GAG, the nucleotides at positions 280 to 282 are CAA or CAG, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 826 to 828 are GCT, GCC, GCA or GCG, the nucleotides at positions 838 to 840 are GGT, GGC, GGA or GGG, and the nucleotides at positions 889 to 891 are CCA, CCC, CCG or CCT;

(D) the nucleotides at positions 181 to 183 are CAA or CAG, the nucleotides at positions 205 to 207 are GAA or GAG, the nucleotides at positions 280 to 282 are CAA or CAG, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 826 to 828 are GCT, GCC, GCA or GCG, the nucleotides at positions 838 to 840 are GGT, GGC, GGA or GGG, the nucleotides at positions 889 to 891 are CCA, CCC, CCG or CCT, and the nucleotides at positions 901 to 903 are CAA or CAG;

(E) the nucleotides at positions 181 to 183 are CAA or CAG, the nucleotides at positions 205 to 207 are GAA or GAG, the nucleotides at positions 211 to 213 are TCT, TCC, TCA, TCG, AGT or AGC, the nucleotides at positions 280 to 282 are CAA or CAG, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 826 to 828 are GCT, GCC, GCA or GCG, the nucleotides at positions 838 to 840 are GGT, GGC, GGA or GGG, the nucleotides at positions 889 to 891 are CCA, CCC, CCG or CCT, and the nucleotides at positions 901 to 903 are CAA or CAG;

(F) the nucleotides at positions 181 to 183 are CAA or CAG, the nucleotides at positions 205 to 207 are GAA or GAG, the nucleotides at positions 208 to 210 are CCA, CCC, CCG or CCT, the nucleotides at positions 211 to 213 are TCT, TCC, TCA, TCG, AGT or AGC, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 826 to 828 are GCT, GCC, GCA or GCG, the nucleotides at positions 838 to 840 are GGT, GGC, GGA or GGG, the nucleotides at positions 889 to 891 are CCA, CCC, CCG or CCT, and the nucleotides at positions 901 to 903 are CAA or CAG;

(G) the nucleotides at positions 112 to 114 are TAT or TAC, the nucleotides at positions 181 to 183 are CAA or CAG, the nucleotides at positions 205 to 207 are GAA or GAG, the nucleotides at positions 211 to 213 are TCT, TCC, TCA, TCG, AGT or AGC, the nucleotides at positions 496 to 498 are GTT, GTC, GTA or GTG, the nucleotides at positions 547 to 549 are CGT, CGC, CGA, CGG, AGA or AGG, the nucleotides at positions 571 to 573 are GCT, GCC, GCA or GCG, the nucleotides at positions 634 to 636 are CCA, CCC, CCG or CCT, the nucleotides at positions 691 to 693 are ATT, ATC or ATA, the nucleotides at positions 826 to 828 are GCT, GCC, GCA or GCG, the nucleotides at positions 838 to 840 are GGT, GGC, GGA or GGG, the nucleotides at positions 889 to 891 are CCA, CCC, CCG or CCT, and the nucleotides at positions 901 to 903 are CAA or CAG;

(H) the nucleotides at the equivalent of positions 112 to 114 of SEQ ID NO:1 are changed to TAT or TAC, the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 280 to 282 of SEQ ID NO:1 are changed to CAA or CAG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, and the nucleotides at the equivalent of positions 826 to 828 of SEQ ID NO:1 are changed to GCT, GCC, GCA or GCG;

(I) the nucleotides at the equivalent of positions 112 to 114 of SEQ ID NO:1 are changed to TAT or TAC, the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 280 to 282 of SEQ ID NO:1 are changed to CAA or CAG, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 826 to 828 of SEQ ID NO:1 are changed to GCT, GCC, GCA or GCG, and the nucleotides at the equivalent of positions 838 to 840 of SEQ ID NO:1 are changed to GGT, GGC, GGA or GGG;

(J) the nucleotides at the equivalent of positions 112 to 114 of SEQ ID NO:1 are changed to TAT or TAC, the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 280 to 282 of SEQ ID NO:1 are changed to CAA or CAG, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 826 to 828 of SEQ ID NO:1 are changed to GCT, GCC, GCA or GCG, the nucleotides at the equivalent of positions 838 to 840 of SEQ ID NO:1 are changed to GGT, GGC, GGA or GGG, and the nucleotides at the equivalent of positions 889 to 891 of SEQ ID NO:1 are changed to CCA, CCC, CCG or CCT;

(K) the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 280 to 282 of SEQ ID NO:1 are changed to CAA or CAG, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 826 to 828 of SEQ ID NO:1 are changed to GCT, GCC, GCA or GCG, the nucleotides at the equivalent of positions 838 to 840 of SEQ ID NO:1 are changed to GGT, GGC, GGA or GGG, the nucleotides at the equivalent of positions 889 to 891 of SEQ ID NO:1 are changed to CCA, CCC, CCG or CCT, and the nucleotides at the equivalent of positions 901 to 903 of SEQ ID NO:1 are changed to CAA or CAG;

(L) the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 211 to 213 of SEQ ID NO:1 are changed to TCT, TCC, TCA, TCG, AGT or AGC, the nucleotides at the equivalent of positions 280 to 282 of SEQ ID NO:1 are changed to CAA or CAG, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 826 to 828 of SEQ ID NO:1 are changed to GCT, GCC, GCA or GCG, the nucleotides at the equivalent of positions 838 to 840 of SEQ ID NO:1 are changed to GGT, GGC, GGA or GGG, the nucleotides at the equivalent of positions 889 to 891 of SEQ ID NO:1 are changed to CCA, CCC, CCG or CCT, and the nucleotides at the equivalent of positions 901 to 903 of SEQ ID NO:1 are changed to CAA or CAG;

(M) the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 208 to 210 of SEQ ID NO:1 are changed to CCA, CCC, CCG or CCT, the nucleotides at the equivalent of positions 211 to 213 of SEQ ID NO:1 are changed to TCT, TCC, TCA, TCG, AGT or AGC, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 826 to 828 of SEQ ID NO:1 are changed to GCT, GCC, GCA or GCG, the nucleotides at the equivalent of positions 838 to 840 of SEQ ID NO:1 are changed to GGT, GGC, GGA or GGG, the nucleotides at the equivalent of positions 889 to 891 of SEQ ID NO:1 are changed to CCA, CCC, CCG or CCT, and the nucleotides at the equivalent of positions 901 to 903 of SEQ ID NO:1 are changed to CAA or CAG; or, (N) the nucleotides at the equivalent of positions 112 to 114 of SEQ ID NO:1 are changed to TAT or TAC, the nucleotides at the equivalent of positions 181 to 183 of SEQ ID NO:1 are changed to CAA or CAG, the nucleotides at the equivalent of positions 205 to 207 of SEQ ID NO:1 are changed to GAA or GAG, the nucleotides at the equivalent of positions 211 to 213 of SEQ ID NO:1 are changed to TCT, TCC, TCA, TCG, AGT or AGC, the nucleotides at the equivalent of positions 496 to 498 of SEQ ID NO:1 are changed to GTT, GTC, GTA or GTG, the nucleotides at the equivalent of positions 547 to 549 of SEQ ID NO:1 are changed to CGT, CGC, CGA, CGG, AGA or AGG, the nucleotides at the equivalent of positions 571 to 573 of SEQ ID NO:1 are changed to GCT, GCC, GCA or GCG, the nucleotides at the equivalent of positions 634 to 636 of SEQ ID NO:1 are changed to CCA, CCC, CCG or CCT, the nucleotides at the equivalent of positions 691 to 693 of SEQ ID NO:1 are changed to ATT, ATC or ATA, the nucleotides at the equivalent of positions 826 to 828 of SEQ ID NO:1 are changed to GCT, GCC, GCA or GCG, the nucleotides at the equivalent of positions 838 to 840 of SEQ ID NO:1 are changed to GGT, GGC, GGA or GGG, the nucleotides at the equivalent of positions 889 to 891 of SEQ ID NO:1 are changed to CCA, CCC, CCG or CCT, and the nucleotides at the equivalent of positions 901 to 903 of SEQ ID NO:1 are changed to CAA or CAG;

The invention provides isolated, synthetic or recombinant polypeptides having a glucanase activity or polypeptides or peptides capable of generating an antibody that binds specifically to a polypeptide having the sequence of SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, and the sequence comprises the following changes based on SEQ ID NO:2:

(A) the phenylalanine at amino acid position 38 is tyrosine, the tyrosine at amino acid position 61 is glutamine, the methionine at amino acid position 69 is glutamic acid, the isoleucine at amino acid position 94 is glutamine, the serine at amino acid position 183 is arginine, the serine at amino acid position 191 is alanine, and the methionine at amino acid position 276 is alanine;

(B) the phenylalanine at amino acid position 38 is tyrosine, the tyrosine at amino acid position 61 is glutamine, the methionine at amino acid position 69 is glutamic acid, the isoleucine at amino acid position 94 is glutamine, the isoleucine at amino acid position 166 is valine, the serine at amino acid position 183 is arginine, the serine at amino acid position 191 is alanine, the glutamic acid at amino acid position 212 is proline, the methionine at amino acid position 276 is alanine, and the arginine at amino acid position 280 is glycine;

(C) the phenylalanine at amino acid position 38 is tyrosine, the tyrosine at amino acid position 61 is glutamine, the methionine at amino acid position 69 is glutamic acid, the isoleucine at amino acid position 94 is glutamine, the isoleucine at amino acid position 166 is valine, the serine at amino acid position 183 is arginine, the serine at amino acid position 191 is alanine, the glutamic acid at amino acid position 212 is proline, the methionine at amino acid position 276 is alanine, the arginine at amino acid position 280 is glycine, and the threonine at amino acid position 297 is proline;

(D) the tyrosine at amino acid position 61 is glutamine, the methionine at amino acid position 69 is glutamic acid, the isoleucine at amino acid position 94 is glutamine, the isoleucine at amino acid position 166 is valine, the serine at amino acid position 183 is arginine, the serine at amino acid position 191 is alanine, the glutamic acid at amino acid position 212 is proline, the methionine at amino acid position 276 is alanine, the arginine at amino acid position 280 is glycine, the threonine at amino acid position 297 is proline, and the threonine at amino acid position 301 is glutamine;

(E) the tyrosine at amino acid position 61 is glutamine, the methionine at amino acid position 69 is glutamic acid, the arginine at amino acid position 71 is serine, the isoleucine at amino acid position 94 is glutamine, the isoleucine at amino acid position 166 is valine, the serine at amino acid position 183 is arginine, the serine at amino acid position 191 is alanine, the glutamic acid at amino acid position 212 is proline, the methionine at amino acid position 276 is alanine, the arginine at amino acid position 280 is glycine, the threonine at amino acid position 297 is proline, and the threonine at amino acid position 301 is glutamine;

(F) the tyrosine at amino acid position 61 is glutamine, the methionine at amino acid position 69 is glutamic acid, the aspartic acid at amino acid position 70 is proline, the arginine at amino acid position 71 is serine, the isoleucine at amino acid position 166 is valine, the serine at amino acid position 183 is arginine, the serine at amino acid position 191 is alanine, the glutamic acid at amino acid position 212 is proline, the methionine at amino acid position 276 is alanine, the arginine at amino acid position 280 is glycine, the threonine at amino acid position 297 is proline, and the threonine at amino acid position 301 is glutamine;

(G) the phenylalanine at amino acid position 38 is tyrosine, the tyrosine at amino acid position 61 is glutamine, the methionine at amino acid position 69 is glutamic acid, the arginine at amino acid position 71 is serine, the isoleucine at amino acid position 166 is valine, the serine at amino acid position 183 is arginine, the serine at amino acid position 191 is alanine, the glutamic acid at amino acid position 212 is proline, the leucine at amino acid position 231 is valine, the methionine at amino acid position 276 is alanine, the arginine at amino acid position 280 is glycine, the threonine at amino acid position 297 is proline, and the threonine at amino acid position 301 is glutamine;

(H) the amino acid at the equivalent of the phenylalanine at amino acid position 38 of SEQ ID NO:2 is changed to a tyrosine, the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the isoleucine at amino acid position 94 of SEQ ID NO:2 is changed to a glutamine, the amino acid at the equivalent of the serine at amino acid position 183 of SEQ ID NO:2 is changed to a arginine, the amino acid at the equivalent of the serine at amino acid position 191 of SEQ ID NO:2 is changed to an alanine, and the amino acid at the equivalent of the methionine at amino acid position 276 of SEQ ID NO:2 is changed to an alanine;

(J) the amino acid at the equivalent of the phenylalanine at amino acid position 38 of SEQ ID NO:2 is changed to a tyrosine, the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the isoleucine at amino acid position 94 of SEQ ID NO:2 is changed to a glutamine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the methionine at amino acid position 276 of SEQ ID NO:2 is changed to an alanine, and the amino acid at the equivalent of the arginine at amino acid position 280 of SEQ ID NO:2 is changed to a glycine;

(K) the amino acid at the equivalent of the phenylalanine at amino acid position 38 of SEQ ID NO:2 is changed to a tyrosine, the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the isoleucine at amino acid position 94 of SEQ ID NO:2 is changed to a glutamine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the methionine at amino acid position 276 of SEQ ID NO:2 is changed to an alanine, the amino acid at the equivalent of the arginine at amino acid position 280 of SEQ ID NO:2 is changed to a glycine, and the amino acid at the equivalent of the threonine at amino acid position 297 of SEQ ID NO:2 is changed to a proline;

(L) the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the isoleucine at amino acid position 94 of SEQ ID NO:2 is changed to a glutamine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the methionine at amino acid position 276 of SEQ ID NO:2 is changed to an alanine, the amino acid at the equivalent of the arginine at amino acid position 280 of SEQ ID NO:2 is changed to a glycine, the amino acid at the equivalent of the threonine at amino acid position 297 of SEQ ID NO:2 is changed to a proline, and the amino acid at the equivalent of the threonine at amino acid position 301 of SEQ ID NO:2 is changed to a glutamine;

(M) the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the arginine at amino acid position 71 of SEQ ID NO:2 is changed to a serine, the amino acid at the equivalent of the isoleucine at amino acid position 94 of SEQ ID NO:2 is changed to a glutamine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the methionine at amino acid position 276 of SEQ ID NO:2 is changed to an alanine, the amino acid at the equivalent of the arginine at amino acid position 280 of SEQ ID NO:2 is changed to a glycine, the amino acid at the equivalent of the threonine at amino acid position 297 of SEQ ID NO:2 is changed to a proline, and the amino acid at the equivalent of the threonine at amino acid position 301 of SEQ ID NO:2 is changed to a glutamine;

(N) the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the aspartic acid at amino acid position 70 of SEQ ID NO:2 is changed to a proline, the amino acid at the equivalent of the arginine at amino acid position 71 of SEQ ID NO:2 is changed to a serine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the methionine at amino acid position 276 of SEQ ID NO:2 is changed to an alanine, the amino acid at the equivalent of the arginine at amino acid position 280 of SEQ ID NO:2 is changed to a glycine, the amino acid at the equivalent of the threonine at amino acid position 297 of SEQ ID NO:2 is changed to a proline, and the amino acid at the equivalent of the threonine at amino acid position 301 of SEQ ID NO:2 is changed to a glutamine;

(O) the amino acid at the equivalent of the phenylalanine at amino acid position 38 of SEQ ID NO:2 is changed to a tyrosine, the amino acid at the equivalent of the tyrosine at amino acid position 61 of SEQ ID NO:2 is changed to a glutamine, the amino acid at the equivalent of the methionine at amino acid position 69 of SEQ ID NO:2 is changed to a glutamic acid, the amino acid at the equivalent of the arginine at amino acid position 71 of SEQ ID NO:2 is changed to a serine, the amino acid at the equivalent of the isoleucine at amino acid position 166 of SEQ ID NO:2 is changed to a valine, the amino acid at the equivalent of the serine at amino acid position 183 of SEQ ID NO:2 is changed to an arginine, the amino acid at the equivalent of the serine at amino acid position 191 of SEQ ID NO:2 is changed to an alanine, the amino acid at the equivalent of the glutamic acid at amino acid position 212 of SEQ ID NO:2 is changed to a proline, the amino acid at the equivalent of the leucine at amino acid position 231 of SEQ ID NO:2 is changed to a valine, the amino acid at the equivalent of the methionine at amino acid position 276 of SEQ ID NO:2 is changed to an alanine, the amino acid at the equivalent of the arginine at amino acid position 280 of SEQ ID NO:2 is changed to a glycine, the amino acid at the equivalent of the threonine at amino acid position 297 of SEQ ID NO:2 is changed to a proline, and the amino acid at the equivalent of the threonine at amino acid position 301 of SEQ ID NO:2 is changed to a glutamine.

The invention provides isolated, synthetic or recombinant nucleic acids of the invention (including the glucanase-encoding nucleic acids of the invention), wherein nucleotide residues in a cryptic transcriptional start site are modified to eliminate most or all of the production of a truncated transcript. In one aspect, the nucleotide residue modifications in the cryptic transcriptional start site comprise an alteration in a ribosome binding site (RBS), e.g., the nucleotide residue modifications in the cryptic transcriptional start site comprise the following modifications in residues 77 to 106 of SEQ ID NO:3:

ATGAGGGCGACTGGGGAGTCGTGATAAAAG, or equivalent.

The invention provides isolated, synthetic or recombinant polypeptides of the invention, wherein the polypeptide further comprises additional amino acid residues between the signal sequence (leader peptide) and the enzyme; and in one aspect, the additional amino acid residues comprise Glu-Ala, e.g., the additional amino acid residues Glu-Ala are added between residue XX and YY in SEQ ID NO:2, for example, the additional amino acid residues Glu-Ala are added between residue K-R of SEQ ID NO:2 as illustrated:

```
                                   (from SEQ ID NO: 2)
MRFPSIFTAVLFAASSALAAPVNTTTEDETAQIPAEAVIGYSDLEGDF

DVAVLPFSNSTNNGLLFINTTIASIAAKEEGVSLEKRGVDPFERNKIL

GRGINI.
```

Using Polymer-Degrading Enzymes in Drilling and Industrial Processes

The invention provides compositions for and methods of using polymer-degrading enzymes, such as polysaccharide-degrading enzymes, in oil, gas and related drilling processes and oil and gas well washing and/or fracturing processes.

The invention provides compositions and methods of using polymer-degrading enzymes to modify the rheological properties of polysaccharide thickeners (e.g., guar gums), e.g., as enzymes to modify polysaccharides in gels and flocculates, binders, lubricants, to serve as modifiers of film properties, and have a function as adjusters of rheological parameters in these compositions.

In one aspect, polymer-degrading enzymes, e.g., polysaccharide- (e.g., starch-) degrading enzymes, used to practice this invention, including any amylase, glucanase, xanthanase, glycosidase and/or cellulase, which include using "cocktails" of enzymes as described herein, and/or other enzymes. In one aspect, the polymers degraded by the compositions (including the mixtures of enzymes) and methods of this invention include lignin, starch, cellulose, cellulose derivatives (e.g., carboxymethyl cellulose and hydroxyethyl cellulose, guar gum, derivatized guar gum, carob gum, beta-glucan and beta glucan derivatives, xanthan gum, hydroxyalkyl guar, carboxyalkyl guar, or xanthan polymers or derivatives thereof, such as guar borate, and/or combinations thereof.

In one embodiment, the invention provide methods comprising use of mixtures ("cocktails") of enzymes comprising at least one, two, three, four, five, six, seven, eight, nine, ten, 11, 12, 13, 14, 15, 16, 17, 18, 19, 20, 21, 22, 23, 24 or 25 or more or all of the enzymes selected from the group consisting of a lignin degrading enzyme, alpha amylase, beta amylase, glucoamylase, dextrinase, cellulase, cellobiohydrolase, avicelase, carboxymethylcellulase, beta-glucanase, glucosidase, xylanase, mannanase, arabinofuranosidase, laccase, lignin peroxidase, pectinase, pectate lyase, xanthanase, xanthan lyase, xanthan depolymerase, pullulanase, lichenase, pachymanase, lipase, protease, proteinase, phytase, peptidase and catalase.

For example, in one embodiment, methods of the invention using mixtures ("cocktails") of enzymes are used to degrade a guar, hydroxyalkyl guar, carboxyalkyl guar, guar gum, a guar gum powder, a lignified coat of guar seeds or a solidified guar gum; and in one aspect, the method comprises providing a mixture of polymer-degrading enzymes, wherein at least one of the enzymes is a polymer-degrading enzyme, and optionally the polymer-degrading enzyme is a lignin degrading enzyme, a lignin peroxidase, a polysaccharide-degrading enzyme, a protein-degrading enzyme, an amylase, a xanthanase, a glucanase, a protease, a glycosidase and/or a cellulase; and adding the polymer-degrading mixture of enzymes to the guar gum, guar gum powder, lignified coat of guar seeds or solidified guar gum in an amount sufficient to degrade the guar gum, guar gum powder, lignified coat of guar seeds or solidified guar gum.

In another embodiment, the invention provides methods for drilling or oil and gas well washing and/or a fracturing method using mixtures ("cocktails") of enzymes; and in one aspect, the mixture ("cocktail") comprises polymer-degrading enzymes, and optionally at least one polymer-degrading enzyme is a lignin degrading enzyme, a lignin peroxidase, a polysaccharide-degrading enzyme, a protein-degrading enzyme, an amylase, a xanthanase, a glucanase, a protease, a glycosidase and/or a cellulase; and adding the polymer-degrading mixture of enzymes to the guar, hydroxyalkyl guar, carboxyalkyl guar, guar gum, guar gum powder, lignified coat of guar seeds or solidified guar gum in an amount sufficient to degrade the guar gum, guar gum powder, lignified coat of guar seeds or solidified guar gum. In one aspect, the polymers degraded comprise lignin, starch, cellulose, guar, hydroxyalkyl guar, carboxyalkyl guar, or xanthan polymers or derivatives thereof, such as guar borate, and/or combinations thereof.

In one aspect, the composition and methods of the invention are used to degrade "mud cake" (also known as "filter cake") that accumulates on a wellbore wall in an oil and/or gas well, by entraining polymer-degrading enzymes, such as polysaccharide (e.g., starch) degrading enzymes in oil well drilling fluids and oil and gas well washing and/or fracturing processes, and triggering their action by pH adjustment. In one aspect, the polymers degraded comprise lignin, starch, cellulose, guar or xanthan.

In one embodiment, the invention provides for the entraining of a polymer-degrading enzyme (see below) in the drilling fluid used in the oil and gas drilling operations and/or oil and gas well washing and/or fracturing fluids. In one aspect, the activity of the polymer-degrading enzyme is triggered by treating the solid residues deposited in the formation (mud cake or filter cake) with an acid solution.

In alternative embodiments, advantages of practicing the compositions and methods of the invention can be: a) providing better distribution of the enzyme(s) within the mud cake (also known as "filter cake") that will result in more uniform and effective mud cake removal, b) simplifying the operations by eliminating a separate enzyme delivery step (enzyme is included in the drilling fluid formulation, and/or in the fluids for oil and gas well washing and/or fracturing), and c) eliminating the need for buffering salts as the enzyme is not formulated with an acidic fluid.

In alternative embodiments, polymer-degrading enzymes, including amylases, glucanases, xanthanases, glycosidases, any starch degrading enzyme, any cellulase and/or protease, e.g., as described herein, are added to a drilling fluid and/or an oil and gas well washing and/or fracturing fluid that is used during an oil and gas well drilling operations or oil and gas well washing and/or fracturing processes. These fluids can contain starch as a viscosifier and can be formulated at relatively high alkalinity (pH=9-9.5). Because of the alkalinity of the fluid (in this embodiment), an acidic-to-neutral enzyme will remain dormant in the fluid and in the mud cake ("filter cake") that is formed after the loss of water from the fluid onto the formation surface. In order to activate the enzyme, the mud cake can be washed with an acid solution. The acid will neutralize the alkalinity of the mud cake and will provide an acidic environment which will trigger the enzyme activity and hydrolytic function toward starch or other polymers. In this alternative embodiment, the "acid wash" is a necessary step, and can be applied during the well drilling operations and/or the well cleaning operations (including oil and gas well washing and/or fracturing processes) in order to remove calcium carbonate deposits from the formation. Once activated (by an acid environment), the enzyme will degrade the starch or other polymers, and will remove the mud cake from the well bore.

In one operation, this "washing" of the well bore is the final step in the drilling operation, and/or oil and gas well washing and/or fracturing operation, and a complete degradation of the mud cake ("filter cake") by practicing the compositions and methods of the invention enables optimal productivity of the well.

In one aspect, a polymer-degrading enzyme used to practice this invention includes any amylase, xanthanase, glycosidase, glucanase, protease and/or cellulase, which include using mixtures or "cocktails" of these and other enzymes.

The compositions and methods of the invention comprise use of isolated, synthetic or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid used to practice the invention, including SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, and the exemplary variants of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and SEQ ID NO:22, over a region of at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2200, 2250, 2300, 2350, 2400, 2450, 2500, or more residues; where these nucleic acids encode at least one polypeptide having an amylase activity (in particular, the genus based on the exemplary SEQ ID NO:14), and/or a glycosidase or a cellulase activity, e.g., endoglucanase, cellobiohydrolase, xylanase, mannanase and/or beta-glucosidase activity (in particular, the genus based on the exemplary SEQ ID NO:1, the described variants of SEQ ID NO:1 (including SEQ ID NO:3), and/or SEQ ID NO:6, SEQ ID NO:8, SEQ ID NO:10 SEQ ID NO:12, SEQ ID NO:16 SEQ ID NO:18, SEQ ID NO:20, and SEQ ID NO:22), and/or a xanthanase activity. In one aspect, the sequence identities are determined by analysis with a sequence comparison algorithm or by a visual inspection.

The nucleic acids used to practice the compositions and methods of the invention can encode a polypeptide having the amino acid sequence of SEQ ID NO:1, SEQ ID NO:2, SEQ ID NO:7, SEQ ID NO:9, SEQ ID NO:11, SEQ ID NO:13, SEQ ID NO:19, SEQ ID NO:21, and/or SEQ ID NO:23; and the exemplary nucleic acids variants of SEQ ID NO:1, e.g., SEQ ID NO:3, the exemplary amino acid variants of SEQ ID NO:2, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and SEQ ID NO:23, respectively). In one aspect, these polypeptide have an amylase activity (in particular, the genus based on the exemplary SEQ ID NO:14 and SEQ ID NO:15), and/or a glycosidase or a cellulase activity, e.g., endoglucanase, cellobiohydrolase, mannanase and/or beta-glucosidase activity (in particular, the genus based on the exemplary SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:17 (encoded by SEQ ID NO:16), SEQ ID NO:19 (encoded by SEQ ID NO:18), SEQ ID NO:21 (encoded by SEQ ID NO:20), and SEQ ID NO:23 (encoded by SEQ ID NO:22), and/or a xanthanase activity.

The compositions and methods of the invention comprise use of isolated, synthetic or recombinant polypeptides having an amylase activity (in particular, the genus based on the exemplary SEQ ID NO:14 and SEQ ID NO:15), and/or a glycosidase or a cellulase activity, e.g., endoglucanase, cellobiohydrolase, mannanase and/or beta-glucosidase activity (in particular, the genus based on the exemplary SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:17 (encoded by SEQ ID NO:16), SEQ ID NO:19 (encoded by SEQ ID NO:18), SEQ ID NO:21 (encoded by SEQ ID NO:20), and SEQ ID NO:23 (encoded by SEQ ID NO:22), and/or a xanthanase activity.

In one embodiment, a polypeptide used to practice this invention, whether alone or with a "cocktail" of the invention, includes amylases that can catalyze the hydrolysis of polysaccharides comprising glucose monomers, such as starch (a polymer of glucose monomers joined by 1,4-alpha or 1,6-alpha linkages). In one aspect, the polypeptide has an amylase activity, e.g., an alpha amylase activity, endoamylase activity, or a glucoamylase activity; and the term "amylase" as used herein also includes enzyme activity which catalyzes the hydrolysis of a polysaccharide, e.g., a starch. Amylases used to practice the invention include polypeptides having an α-amylase activity, a β-amylase activity, a glucoamylase activity, a 1,4-α-D-glucan glucohydrolase activity, an exoamylase activity, a glucan α-maltotetrahydrolase activity, a maltase activity, an isomaltase activity, a glucan 1, 4, α-glucosidase activity, an α-glucosidase activity, a sucrase activity or an agarase activity (e.g., a β-agarase activity). For example, an amylase used to practice includes polypeptides having α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. An amylase used to practice includes polypeptides having glucoamylase activity, such as the ability to hydrolase glucose polymers linked by α-1,4- and α-1,6-glucosidic bonds. In one aspect, amylase used to practice includes polypeptides having glucoamylase activity, hydrolyzing internal α-1,4-glucosidic linkages to yield smaller molecular weight malto-dextrins. An amylase used to practice includes polypeptides having glucan 1,4-α-glucosidase activity, or, 1,4-α-D-glucan glucohydrolase, commonly called glucoamylase but also called amyloglucosidase and γ-amylase that, in one aspect, releases β-D-glucose from 1,4-α-, 1,6-α- and 1,3-α-linked glucans. An amylase used to practice includes polypeptides having exo-amylase activity.

The enzyme-comprising compositions of the invention can comprise one polysaccharide-degrading enzyme as described herein, or can comprise a mixture (a "cocktail" of) one two, three, four or more of any of the polysaccharide-degrading polypeptides described herein, including the genuses based on SEQ ID NO:2, the exemplary variants of SEQ ID NO:2, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and/or SEQ ID NO:23. A composition used to practice the invention can comprise one, two, three or more polypeptides described herein, including the genuses based on SEQ ID NO:2, the exemplary variants of SEQ ID NO:2, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and/or SEQ ID NO:23, and any combination of other enzymes, such as tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1, 3(4)-laccases, cutinases, peroxidases, amylases, xanthanases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

The invention provides methods for modifying or adjusting the rheological properties of: a polysaccharide thickener; a polysaccharide thickener in a gel, a flocculate, a binder or a lubricant; or, a polysaccharide in a film to modify a property of the film, the method comprising
(I) providing at least one polymer-degrading ("polymer breaking") enzyme comprising
(a) a polypeptide encoded by a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or complete sequence identity to SEQ ID NO:1, SEQ ID NO:3, SEQ ID NO:6, SEQ ID NO:8, SEQ ID NO:10, SEQ ID NO:12, SEQ ID NO:18, SEQ ID NO:20, OR SEQ ID NO:22, and/or the exemplary variants of SEQ ID NO:1, SEQ ID NO:6, SEQ ID NO:8, SEQ ID NO:10, SEQ ID NO:12, SEQ ID NO:14, SEQ ID NO:16, SEQ ID NO:18, SEQ ID NO:20, and/or SEQ ID NO:22, over a region of at least about 20, 30, 40, 50, 75, 100, 150, 200, 250, 300, 350, 400, 450, 500, 550, 600, 650, 700, 750, 800, 850, 900, 950, 1000, 1050, 1100, 1150 or more residues, wherein the nucleic acid encodes at least one polypeptide having a polymer-degrading activity, or an amylase, xanthanase, glucanase, protease and/or a glycosidase or cellulase activity,
and optionally the sequence identities are determined by analysis with a sequence comparison algorithm or by a visual inspection; or
(b) a polypeptide encoded by a nucleic acid sequence that hybridizes under stringent conditions to a nucleic acid comprising SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, and/or the exemplary variants of SEQ ID NO:1, wherein the nucleic acid encodes a polypeptide having a polymer-degrading activity, or an amylase, xanthanase, glucanase, protease and/or a glycosidase or a cellulase activity, and the stringent conditions include a wash step comprising a wash in 0.2×SSC at a temperature of about 65° C. for about 15 minutes,
and optionally the nucleic acid is at least about 20, 30, 40, 50, 60, 75, 100, 150, 200, 300, 400, 500, 600, 700, 800, 900, 1000 or more residues in length or the full length of the gene or transcript;
(c) a polypeptide having a sequence of SEQ ID NO:2, SEQ ID NO:7, SEQ ID NO:9, SEQ ID NO:11, SEQ ID NO:13, SEQ ID NO:19, SEQ ID NO:21, OR SEQ ID NO:23, the exemplary variants of SEQ ID NO:2, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and/or SEQ ID NO:23; or
(d) an isolated, synthetic or recombinant polypeptide having a polymer-degrading activity, or an amylase, xanthanase, glucanase, protease and/or a glycosidase or a cellulase activity and having an amino acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or 100% sequence identity to SEQ ID NO:2, SEQ ID NO:7, SEQ ID NO:9, SEQ ID NO:11, SEQ ID NO:13, SEQ ID NO:19, SEQ ID NO:21, OR SEQ ID NO:23, the exemplary variants of SEQ ID NO:2, SEQ ID NO:7, SEQ ID NO:9, SEQ ID NO:11, SEQ ID NO:13, SEQ ID NO:15, SEQ ID NO:17, SEQ ID NO:19, SEQ ID NO:21, and/or SEQ ID NO:23, over a region of at least about 20, 25, 30, 35, 40, 45, 50, 55, 60, 75, 100, 150, 200, 250, 300 or more residues,
wherein optionally the sequence identities are determined by analysis with a sequence comparison algorithm or by a visual inspection, and optionally the sequence comparison algorithm is a BLAST version 2.2.2 algorithm where a filtering setting is set to blastall-p blastp-d "nr pataa"-F F, and all other options are set to default.
  (e) a polypeptide having an amino acid sequence of (a) to (d), and retaining enzyme activity and comprising at least one amino acid residue conservative substitution,
    wherein optionally conservative substitution comprises replacement of an aliphatic amino acid with another aliphatic amino acid; replacement of a serine with a threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof,
    and optionally the aliphatic residue comprises Alanine, Valine, Leucine, Isoleucine or a synthetic equivalent thereof; the acidic residue comprises Aspartic acid, Glutamic acid or a synthetic equivalent thereof; the residue comprising an amide group comprises Aspartic acid, Glutamic acid or a synthetic equivalent thereof; the basic residue comprises Lysine, Arginine or a synthetic equivalent thereof; or, the aromatic residue comprises Phenylalanine, Tyrosine or a synthetic equivalent thereof; and
  (II) adding the enzyme to the polysaccharide thickener; the polysaccharide thickener in a gel, a flocculate, a binder or a lubricant; or, the polysaccharide in a film, thereby adjusting or modifying the properties of the gel, flocculate, binder, lubricant or film.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

FIG. 5 is a table summarizing the relative activities of several exemplary enzymes of the invention under various conditions.

FIG. 14A illustrates an radiograph of an SDS-PAGE gel showing a glucanase doublet caused by inconsistent signal processing; and FIG. 14B illustrates an radiograph of an SDS-PAGE gel showing a protein as represented by an SDS-PAGE gel 37 kDa band, which was excised and sequenced, as discussed in Example 9, below.

Like reference symbols in the various drawings indicate like elements.

DETAILED DESCRIPTION OF THE INVENTION

Figure 1:
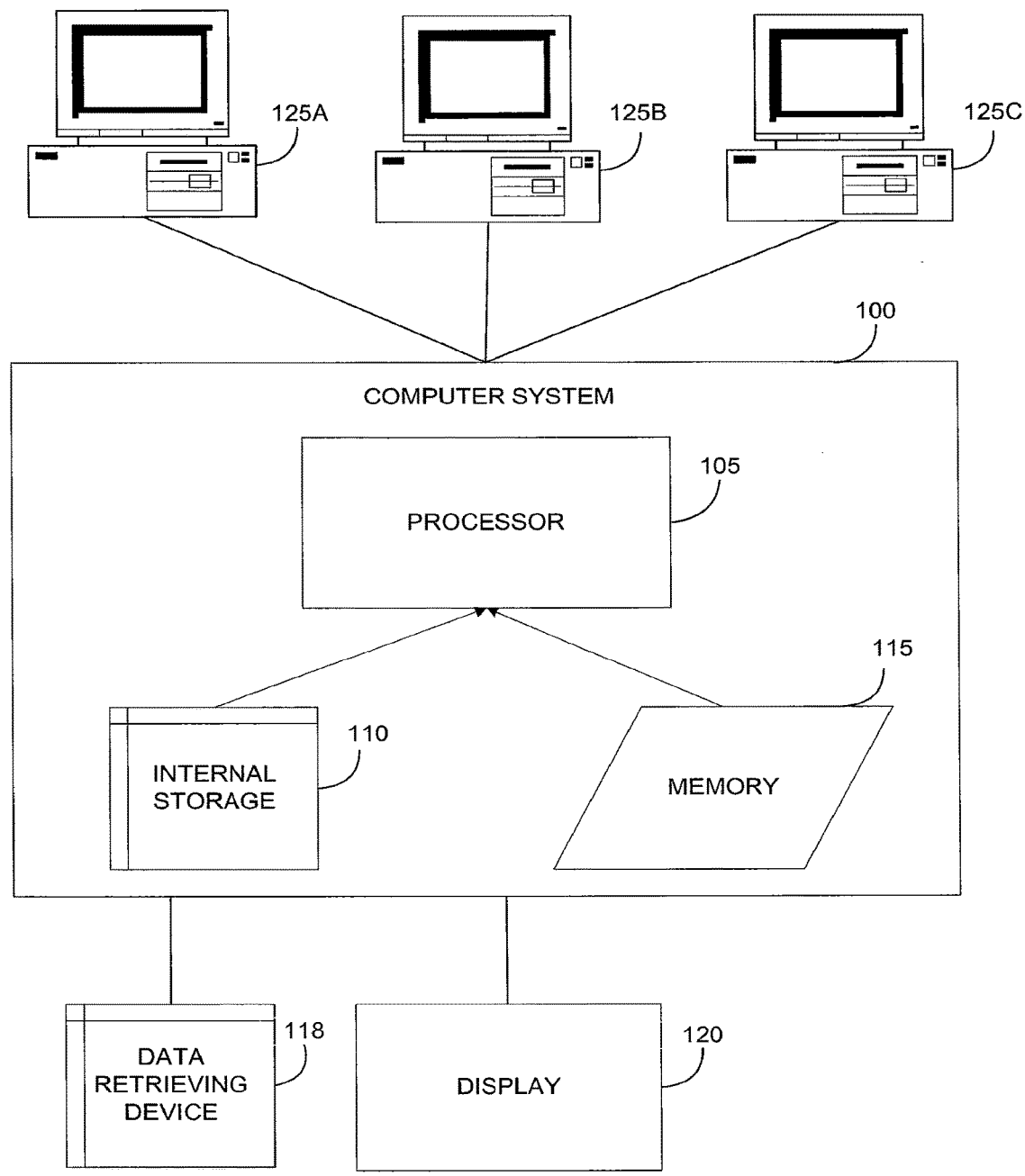
FIG. 1 is a block diagram of a computer system.

The invention provides polypeptides and polynucleotides encoding them and methods of making and using them, including SEQ ID NO:2, encoded, e.g., by SEQ ID NO:1, SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), and the specific modifications to SEQ ID NO:1 and SEQ ID NO:2 described herein. Enzyme activity of the polypeptides of the invention encompasses polypeptides having a hydrolase activity, e.g., a glucanase activity, for example, polypeptides capable of hydrolyzing glycosidic linkages present in a glucan, e.g., catalyzing hydrolysis of internal β-1,4-glucosidic linkages. Enzyme activity of the polypeptides and peptides of the invention (including enzymes and antibodies) encompasses polypeptides having a glucanase, a xylanase, and/or a mannanase activity. The polypeptides and peptides (including enzymes and antibodies) can be used to make and/or process foods, feeds (e.g., for a human, a ruminant, a monogastric animal, a bird, e.g., a chicken), beverages, nutritional supplements, textiles, detergents and the like. The polypeptides and peptides (including enzymes and antibodies) of the invention can be used in pharmaceutical compositions and dietary aids. Glucanases (or cellulases), e.g., endoglucanases, mannanases, xylanases, amylases, xanthanases and/or glycosidases, e.g., cellobiohydrolases, mannanases and/or beta-glucosidases of the invention are useful in food processing, baking, animal feeds or foods, beverages, detergents, pulp processing and paper processes.

Generating and Manipulating Nucleic Acids

The invention provides isolated, recombinant and synthetic nucleic acids, including the exemplary nucleic acids of the invention, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22 and sequences having the specific modifications described herein, and sequences having a sequence identity to an exemplary nucleic acid; nucleic acids encoding polypeptides of the invention, e.g., the exemplary amino acid sequences as set forth in SEQ ID NO:2, SEQ ID NO:7, SEQ ID NO:9, SEQ ID NO:11, SEQ ID NO:13, SEQ ID NO:19, SEQ ID NO:21, and/or SEQ ID NO:23, and sequences having the specific modifications described herein.

Exemplary nucleic acids of the invention include the polypeptides that are sequence variations of SEQ ID NO:2, as set forth (summarized) in Table 1, below (and in Table 2, see Example 5). In this Table 1, "original codon" refers to the codon as in the "parent" sequence SEQ ID NO:1, and "original amino acid" refers to the amino acid residue as in the "parent" polypeptide SEQ ID NO:2:

TABLE 1

|   | Original Codon | Codon Changed To | All Possible Codons For the Mutated Amino Acid | Nucleotide Positions of Changed Codon in SEQ ID NO: 1 | Original Amino Acid | Amino Acid Changed To | Codon Mutation Location |
|---|---|---|---|---|---|---|---|
| 1 | GGT | AAT | AAT, AAC | 4-6 | G | N | 2 |
| 2 | GGA | AAT | AAT, AAC | 37-39 | G | N | 13 |
| 3 | TTC | TAT | TAT, TAC | 112-114 | F | Y | 38 |
| 4 | AGT | GAT | GAT, GAC | 169-171 | S | D | 57 |
| 5 | TAC | CAG | CAA, CAG | 181-183 | Y | Q | 61 |
| 6 | TAC | TCG | TCT, TCC, TCA, TCG, AGT, AGC | 181-183 | Y | S | 61 |
| 7 | GCG | ACG | ACT, ACC, ACA, ACG | 184-186 | A | T | 62 |
| 8 | TTT | CAT | CAT, CAC | 187-189 | F | H | 63 |
| 9 | TTT | ACG | ACT, ACC, ACA, ACG | 187-189 | F | T | 63 |
| 10 | ATG | GAG | GAA, GAG | 205-207 | M | E | 69 |
| 11 | ATG | CAT | CAT, CAC | 205-207 | M | H | 69 |
| 12 | ATG | CAG | CAA, CAG | 205-207 | M | Q | 69 |
| 13 | ATG | AGT | TCT, TCC, TCA, TCG, AGT, AGC | 205-207 | M | S | 69 |
| 14 | ATG | TCT | TCT, TCC, TCA, TCG, AGT, AGC | 205-207 | M | S | 69 |
| 15 | ATG | TAT | TAT, TAC | 205-207 | M | Y | 69 |
| 16 | GAT | CCT | CCA, CCC, CCG, CCT | 208-210 | D | P | 70 |
| 17 | CGC | GCG | GCT, GCC, GCA, GCG | 211-213 | R | A | 71 |
| 18 | CGC | GCT | GCT, GCC, GCA, GCG | 211-213 | R | A | 71 |
| 19 | CGC | GAG | GAA, GAG | 211-213 | R | E | 71 |
| 20 | CGC | CCG | CCA, CCC, CCG, CCT | 211-213 | R | P | 71 |
| 21 | CGC | CCT | CCA, CCC, CCG, CCT | 211-213 | R | P | 71 |
| 22 | CGC | CAG | CAA, CAG | 211-213 | R | Q | 71 |
| 23 | CGC | TCT | TCT, TCC, TCA, TCG, AGT, AGC | 211-213 | R | S | 71 |
| 24 | CGC | ACG | ACT, ACC, ACA, ACG | 211-213 | R | T | 71 |
| 25 | AAA | GAG | GAA, GAG | 220-222 | K | E | 74 |
| 26 | AAA | CTG | TTA, TTG, CTT, CTC, CTA, CTG | 220-222 | K | L | 74 |
| 27 | AAA | ATG | ATG | 220-222 | K | M | 74 |
| 28 | ATT | CAG | CAA, CAG | 280-282 | I | Q | 94 |
| 29 | ATG | TAT | TAT, TAC | 301-303 | M | Y | 101 |
| 30 | GAT | TGT | TGT, TGC | 307-309 | D | C | 103 |
| 31 | GAT | CAG | CAA, CAG | 307-309 | D | Q | 103 |
| 32 | GAA | GGG | GGT, GGC, GGA, GGG | 316-318 | E | G | 106 |
| 33 | GAA | GGT | GGT, GGC, GGA, GGG | 316-318 | E | G | 106 |
| 34 | GAA | CTG | TTA, TTG, CTT, CTC, CTA, CTG | 325-327 | E | L | 109 |
| 35 | AAA | GCG | GCT, GCC, GCA, GCG | 346-348 | K | A | 116 |
| 36 | AAA | AGG | CGT, CGC, CGA, CGG, AGA, AGG | 346-348 | K | R | 116 |
| 37 | AAA | CGG | CGT, CGC, CGA, CGG, AGA, AGG | 346-348 | K | R | 116 |
| 38 | TTT | TAT | TAT, TAC | 388-390 | F | Y | 130 |
| 39 | TTT | CTG | TTA, TTG, CTT, CTC, CTA, CTG | 391-393 | F | L | 131 |
| 40 | GAA | CAT | CAT, CAC | 442-444 | E | H | 148 |
| 41 | AAA | CAG | CAA, CAG | 484-486 | K | Q | 162 |
| 42 | ATA | GCG | GCT, GCC, GCA, GCG | 496-498 | I | A | 166 |
| 43 | ATA | GTG | GTT, GTC, GTA, GTG | 496-498 | I | V | 166 |
| 44 | ATA | GTT | GTT, GTC, GTA, GTG | 496-498 | I | V | 166 |
| 45 | TCT | AGG | CGT, CGC, CGA, CGG, AGA, AGG | 547-549 | S | R | 183 |
| 46 | TCT | GTG | GTT, GTC, GTA, GTG | 547-549 | S | V | 183 |
| 47 | AAA | GCG | GCT, GCC, GCA, GCG | 556-558 | K | A | 186 |
| 48 | AAA | GCT | GCT, GCC, GCA, GCG | 556-558 | K | A | 186 |
| 49 | AAA | GAT | GAT, GAC | 556-558 | K | D | 186 |
| 50 | AAA | CCT | CCA, CCC, CCG, CCT | 556-558 | K | P | 186 |
| 51 | AAA | TCT | TCT, TCC, TCA, TCG, AGT, AGC | 556-558 | K | S | 186 |
| 52 | TCT | GCG | GCT, GCC, GCA, GCG | 571-573 | S | A | 191 |
| 53 | TCT | TGT | TGT, TGC | 571-573 | S | C | 191 |
| 54 | TCT | CTT | TTA, TTG, CTT, CTC, CTA, CTG | 571-573 | S | L | 191 |
| 55 | TTC | ATT | ATT, ATC, ATA | 601-603 | F | I | 201 |

TABLE 1-continued

| | Original Codon | Codon Changed To | All Possible Codons For the Mutated Amino Acid | Nucleotide Positions of Changed Codon in SEQ ID NO: 1 | Original Amino Acid | Amino Acid Changed To | Codon Mutation Location |
|---|---|---|---|---|---|---|---|
| 56 | TTC | CCG | CCA, CCC, CCG, CCT | 601-603 | F | P | 201 |
| 57 | TTC | CCT | CCA, CCC, CCG, CCT | 601-603 | F | P | 201 |
| 58 | TTC | GTG | GTT, GTC, GTA, GTG | 601-603 | F | V | 201 |
| 59 | TTC | GTT | GTT, GTC, GTA, GTG | 601-603 | F | V | 201 |
| 60 | GAA | CCG | CCA, CCC, CCG, CCT | 634-636 | E | P | 212 |
| 61 | GAA | CCT | CCA, CCC, CCG, CCT | 634-636 | E | P | 212 |
| 62 | AAA | GCG | GCT, GCC, GCA, GCG | 646-648 | K | A | 216 |
| 63 | CAT | AAG | AAA, AAG | 688-690 | H | K | 230 |
| 64 | CAT | CAG | CAA, CAG | 688-690 | H | Q | 230 |
| 65 | CAT | AGG | CGT, CGC, CGA, CGG, AGA, AGG | 688-690 | H | R | 230 |
| 66 | CAT | CGG | CGT, CGC, CGA, CGG, AGA, AGG | 688-690 | H | R | 230 |
| 67 | CAT | CGT | CGT, CGC, CGA, CGG, AGA, AGG | 688-690 | H | R | 230 |
| 68 | TTG | ATT | ATT, ATC, ATA | 691-693 | L | I | 231 |
| 69 | TTG | ATG | ATG | 691-693 | L | M | 231 |
| 70 | TTG | GTG | GTT, GTC, GTA, GTG | 691-693 | L | V | 231 |
| 71 | TTG | GTT | GTT, GTC, GTA, GTG | 691-693 | L | V | 231 |
| 72 | GAA | GAT | GAT, GAC | 700-702 | E | D | 234 |
| 73 | AAA | CAG | CAA, CAG | 736-738 | K | Q | 246 |
| 74 | AAA | AGT | TCT, TCC, TCA, TCG, AGT, AGC | 736-738 | K | S | 246 |
| 75 | AGA | AGT | TCT, TCC, TCA, TCG, AGT, AGC | 772-774 | R | S | 258 |
| 76 | AGA | TCT | TCT, TCC, TCA, TCG, AGT, AGC | 772-774 | R | S | 258 |
| 77 | AGA | TAT | TAT, TAC | 772-774 | R | Y | 258 |
| 78 | CTT | CAT | CAT, CAC | 784-786 | L | H | 262 |
| 79 | CTT | ATG | ATG | 784-786 | L | M | 262 |
| 80 | CTT | CCT | CCA, CCC, CCG, CCT | 784-786 | L | P | 262 |
| 81 | CTT | CAG | CAA, CAG | 784-786 | L | Q | 262 |
| 82 | TCC | CGG | CGT, CGC, CGA, CGG, AGA, AGG | 808-810 | S | R | 270 |
| 83 | TTT | GCG | GCT, GCC, GCA, GCG | 811-813 | F | A | 271 |
| 84 | ATG | GCG | GCT, GCC, GCA, GCG | 826-828 | M | A | 276 |
| 85 | ATG | GCT | GCT, GCC, GCA, GCG | 826-828 | M | A | 276 |
| 86 | ATG | TGT | TGT, TGC | 826-828 | M | C | 276 |
| 87 | ATG | TCT | TCT, TCC, TCA, TCG, AGT, AGC | 826-828 | M | S | 276 |
| 88 | GAG | TCT | TCT, TCC, TCA, TCG, AGT, AGC | 829-831 | E | S | 277 |
| 89 | AGA | GGG | GGT, GGC, GGA, GGG | 838-840 | R | G | 280 |
| 90 | AGA | GGT | GGT, GGC, GGA, GGG | 838-840 | R | G | 280 |
| 91 | TCC | GCT | GCT, GCC, GCA, GCG | 868-870 | S | A | 290 |
| 92 | ACT | GCG | GCT, GCC, GCA, GCG | 889-891 | T | A | 297 |
| 93 | ACT | CCG | CCA, CCC, CCG, CCT | 889-891 | T | P | 297 |
| 94 | ACT | CCT | CCA, CCC, CCG, CCT | 889-891 | T | P | 297 |
| 95 | CTG | GCG | GCT, GCC, GCA, GCG | 892-894 | L | A | 298 |
| 96 | CTG | AAT | AAT, AAC | 892-894 | L | N | 298 |
| 97 | CTG | CGG | CGT, CGC, CGA, CGG, AGA, AGG | 892-894 | L | R | 298 |
| 98 | CTG | AGT | TCT, TCC, TCA, TCG, AGT, AGC | 892-894 | L | S | 298 |
| 99 | CTG | TCG | TCT, TCC, TCA, TCG, AGT, AGC | 892-894 | L | S | 298 |
| 100 | CTG | GTT | GTT, GTC, GTA, GTG | 892-894 | L | V | 298 |
| 101 | AAA | GGG | GGT, GGC, GGA, GGG | 898-900 | K | G | 300 |
| 102 | ACC | CAG | CAA, CAG | 901-903 | T | Q | 301 |
| 103 | GAT | CCG | CCA, CCC, CCG, CCT | 913-915 | D | P | 305 |
| 104 | GAT | CCT | CCA, CCC, CCG, CCT | 913-915 | D | P | 305 |
| 105 | GGA | ATT | ATT, ATC, ATA | 934-936 | G | I | 312 |
| 106 | AGC | ATT | ATT, ATC, ATA | 943-945 | S | I | 315 |

The invention also provides expression cassettes such as expression vectors, comprising nucleic acids of the invention, which include polynucleotides which encode the polypeptides of the invention. The invention also includes methods for discovering new glucanase sequences using the nucleic acids of the invention. The invention also includes methods for inhibiting the expression of glucanase genes, transcripts and polypeptides using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. The phrases "nucleic acid" or "nucleic acid sequence" as used herein refer to an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. The phrases "nucleic acid" or "nucleic acid sequence" includes oligonucleotide, nucleotide, polynucleotide, or to a fragment of any of these, to DNA or RNA (e.g., mRNA, rRNA, tRNA, iRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., e.g., double stranded iRNAs, e.g., iRNPs, siRNA or miRNA). The term encompasses nucleic acids, i.e., oligonucleotides, containing known analogues of natural nucleotides. The term also encompasses nucleic-acid-like structures with synthetic backbones, see e.g., Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev.* 6:153-156. "Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

A "coding sequence of" or a "nucleotide sequence encoding" a particular polypeptide or protein, is a nucleic acid sequence which is transcribed and translated into a polypeptide or protein when placed under the control of appropriate regulatory sequences. The term "gene" means the segment of DNA involved in producing a polypeptide chain; it includes regions preceding and following the coding region (leader and trailer) as well as, where applicable, intervening sequences (introns) between individual coding segments (exons). "Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

In practicing the methods of the invention, homologous genes can be modified by manipulating a template nucleic acid, as described herein. The invention can be practiced in conjunction with any method or protocol or device known in the art, which are well described in the scientific and patent literature.

The isolated, nucleic acids may comprise DNA, including cDNA, genomic DNA and synthetic DNA. The DNA may be double-stranded or single-stranded and if single stranded may be the coding strand or non-coding (anti-sense) strand. Alternatively, the isolated nucleic acids may comprise RNA. The isolated nucleic acids of the invention may be used to prepare one of the polypeptides of the invention, or fragments thereof. The coding sequences of these nucleic acids may be identical to one of the coding sequences of one of the nucleic acids of the invention or may be different as a result of the redundancy or degeneracy of the genetic code. The genetic code is well known to those of skill in the art and can be obtained, for example, on page 214 of B. Lewin, *Genes VI*, Oxford University Press, 1997.

The isolated nucleic acid which encodes one of the polypeptides of the invention, but is not limited to: only the coding sequence of a nucleic acid of the invention and additional coding sequences, such as leader sequences or proprotein sequences and non-coding sequences, such as introns or non-coding sequences 5' and/or 3' of the coding sequence. Thus, as used herein, the term "polynucleotide encoding a polypeptide" encompasses a polynucleotide which includes only the coding sequence for the polypeptide as well as a polynucleotide which includes additional coding and/or non-coding sequence.

Alternatively, the nucleic acid sequences of the invention can be mutagenized using conventional techniques, such as site directed mutagenesis, or other techniques familiar to those skilled in the art, to introduce silent changes into the polynucleotides of the invention. As used herein, "silent changes" include, for example, changes which do not alter the amino acid sequence encoded by the polynucleotide. Such changes may be desirable in order to increase the level of the polypeptide produced by host cells containing a vector encoding the polypeptide by introducing codons or codon pairs which occur frequently in the host organism.

The invention also relates to polynucleotides which have nucleotide changes which result in amino acid substitutions, additions, deletions, fusions and truncations in the polypeptides of the invention. Such nucleotide changes may be introduced using techniques such as site directed mutagenesis, random chemical mutagenesis, exonuclease III deletion and other recombinant DNA techniques. Alternatively, such nucleotide changes may be naturally occurring allelic variants which are isolated by identifying nucleic acids which specifically hybridize to probes of the invention, e.g., sequences comprising at least 10, 15, 20, 25, 30, 35, 40, 50, 75, 100, 150, 200, 300, 400, or 500 consecutive bases of one of the sequences of the invention (including the sequences complementary thereto) under conditions of high, moderate, or low stringency as provided herein.

General Techniques

The nucleic acids used to practice this invention, whether RNA, iRNA (e.g., siRNA, miRNA), antisense nucleic acid, cDNA, genomic DNA, vectors, viruses or hybrids thereof, may be isolated from a variety of sources, genetically engineered, amplified, and/or expressed/generated recombinantly. Recombinant polypeptides (e.g., glucanases (or cellulases), e.g., endoglucanases, mannanases, xylanases, amylases, xanthanases and/or glycosidases, e.g., cellobiohydrolases, mannanases and/or beta-glucosidases) generated from these nucleic acids can be individually isolated or cloned and tested for a desired activity. Any recombinant expression system can be used, including bacterial, mammalian, yeast, fungal, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

As used herein, the term "recombinant" means that the nucleic acid is adjacent to a "backbone" nucleic acid to which it is not adjacent in its natural environment. In some aspects, to be "enriched" the nucleic acids represent about 1%, 2%, 3%, 4%, 5%, 6%, 10%, 11%, 12%, 13%, 14%, 15%, 20%, 30%, 45%, 50%, 60%, 70%, 80%, 90% or more of the number of nucleic acid inserts in a population of nucleic acid backbone molecules, e.g., recombinant backbone molecules. Backbone molecules include nucleic acids such as expression vectors, self-replicating nucleic acids, viruses, integrating nucleic acids and other vectors or nucleic acids used to maintain or manipulate a nucleic acid insert of interest.

In one aspect, a nucleic acid encoding a polypeptide of the invention is assembled in appropriate phase with a leader sequence capable of directing secretion of the translated polypeptide or fragment thereof. The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Pur.* 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) *DNA Cell. Biol.* 12:441-53.

The term "Saturation Mutagenesis" or "Gene Site Saturation Mutagenesis" or "GSSM" includes a method that uses degenerate oligonucleotide primers to introduce point mutations into a polynucleotide, as described in detail, below. The term "optimized directed evolution system" or "optimized directed evolution" includes a method for reassembling fragments of related nucleic acid sequences, e.g., related genes, and explained in detail, below. The term "synthetic ligation reassembly" or "SLR" includes a method of ligating oligonucleotide fragments in a non-stochastic fashion, and explained in detail, below.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lacI, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

As used herein, the term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light. "Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

Promoters suitable for expressing a polypeptide in bacteria include the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used. Promoters suitable for expressing the polypeptide or fragment thereof in bacteria include the *E. coli* lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK) and the acid phosphatase promoter. Fungal promoters include the ∀ factor promoter. Eukaryotic promoters include the CMV immediate early promoter, the HSV thymidine kinase promoter, heat shock promoters, the early and late SV40 promoter, LTRs from retroviruses and the mouse metallothionein-I promoter. Any promoter known to control expression of genes in prokaryotic or eukaryotic cells or their viruses may also be used.

Plant Expression Cassettes

The invention provides expression cassettes that may be expressed in any manner in a plant. The invention also provides plants or seeds that express an enzyme of the invention in any manner The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

Codon Usage

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

GC/AT Content

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

Sequences Adjacent to the Initiating Methionine

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Removal of Illegitimate Splice Sites

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Plant Promoters

The compositions of the invention may contain nucleic acid sequences for transformation and expression in a plant of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest, which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing polynucleotides. The expression cassette will include in the 5'-3' direction of transcription, a transcriptional and translational initiation region (i.e., a promoter) and a polynucleotide of interest. The expression cassette may optionally comprise a transcriptional and translational termination region (i.e., termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) *Plant J.* 34:383-92 and Chen et al. (2003) *Plant J.* 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g., a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g., DNA) sequence is a nucleic acid (e.g., DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano et al. (1989) *Plant Cell* 1:855-866; Bustos et al. (1989) *Plant Cell* 1:839-854; Green et al. (1988) *EMBO J.* 7, 4035-4044; Meier et al. (1991) *Plant Cell* 3, 309-316; and Zhang et al. (1996) *Plant Physiology* 110:1069-1079.

Several tissue preferred regulated genes and/or promoters have been reported in plants. Some reported tissue preferred genes include the genes encoding the seed storage proteins (such as napin, cruciferin, beta-conglycinin, and phaseolin, prolamines, glutelins, globulins, and zeins) zeins or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al. (1991) *Seed Science Research* 1:209). Examples of tissue-specific promoters, which have been described, include the lectin (Vodkin (1983) *Prog. Clin. Biol. Res.* 138:87; Lindstrom et al. (1990) *Der. Genet.* 11:160), corn alcohol dehydrogenase 1 (Dennis et al., *Nucleic Acids Res.* 12:3983 (1984)), corn light harvesting complex (see, e.g., Simpson (1986) *Science* 233:

34; Bansal (1992) *Proc. Natl. Acad. Sci. USA* 89:3654), corn heat shock protein (see, e.g., Odell et al. (1985) *Nature* 313:810; pea small subunit RuBP carboxylase (see, e.g., Poulsen et al. (1986) *Mol. Gen. Genet.* 205:193-200; Cashmore et al. (1983) *Gen. Eng. of Plants*, Plenum Press, New York, 29-38); Ti plasmid mannopine synthase (see, e.g., Langridge et al. (1989) *Proc. Natl. Acad. Sci. USA* 86:3219-3223), Ti plasmid nopaline synthase (Langridge et al. (1989) *Proc. Natl. Acad. Sci. USA* 86:3219-3223), petunia chalcone isomerase (see, e.g., vanTunen (1988) *EMBO J.* 7:1257); bean glycine rich protein 1 (see, e.g., Keller (1989) *Genes Dev.* 3:1639); truncated CaMV 35S (see, e.g., Odell (1985) *Nature* 313:810); potato patatin (see, e.g., Wenzler (1989) *Plant Mol. Biol.* 13:347; root cell (see, e.g., Yamamoto (1990) *Nucleic Acids Res.* 18:7449); maize zein (see, e.g., Reina (1990) *Nucleic Acids Res.* 18:6425; Lopes et al. (1995) *Mol. Gen. Genet.* 247:603-613; Kriz (1987) *Mol. Gen. Genet.* 207:90; Wandelt (1989) *Nucleic Acids Res.* 17:2354; Langridge (1983) *Cell* 34:1015; Reina (1990) *Nucleic Acids Res.* 18:7449), ADP-gpp promoter (see, e.g., U.S. Pat. No. 7,102,057); globulin-1 (see, e.g., Belanger (1991) *Genetics* 129:863); α-globulin (Sunilkumar et al. (2002) *Transgenic Res.* 11:347-359); α-tubulin; cab (see, e.g., Sullivan (1989) *Mol. Gen. Genet.* 215:431); PEPCase (see e.g., Hudspeth & Grula (1989) *Plant Molec. Biol.* 12:579-589); R gene complex-associated promoters (Chandler et al. (1989) *Plant Cell* 1:1175); pea vicilin promoter (Czako et al. (1992) *Mol. Gen. Genet.* 235:33; U.S. Pat. No. 5,625,136); GTL1 promoter (Takaiwa et al. (1991) *Plant Mol. Biol.* 16(1), 49-58); chalcone synthase promoters (Franken et al. (1991) *EMBO J.* 10:2605); GY1 promoter (Sims & Goldburg (1989) *Nuc. Acid Res.* 17(11) 4368) and the like; all of which are herein incorporated by reference.

A class of fruit-preferred promoters expressed at or during antithesis through fruit development, at least until the beginning of ripening, is discussed in U.S. Pat. No. 4,943,674, the disclosure of which is hereby incorporated by reference. The promoter for polygalacturonase gene is active in fruit ripening. The polygalacturonase gene is described in U.S. Pat. Nos. 4,535,060, 4,769,061, 4,801,590, and 5,107,065, which disclosures are incorporated herein by reference.

Other examples of tissue-preferred promoters include those that direct expression in leaf cells following damage to the leaf (for example, from chewing insects), in tubers (for example, patatin gene promoter), and in fiber cells (an example of a developmentally-regulated fiber cell protein is E6 (John & Crow (1992) *PNAS* 89:5769-5773). The E6 gene is most active in fiber, although low levels of transcripts are found in leaf, ovule and flower.

Promoters active in photosynthetic tissue in order to drive transcription in green tissues such as leaves and stems, are suitable when they drive expression only or predominantly in such tissues. Alternatively, the promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.* 35:773-778), the Cab-1 gene promoter from wheat (Fejes et al. (1990) *Plant Mol. Biol.* 15:921-932), the CAB-1 promoter from spinach (Lubberstedt et al. (1994) *Plant Physiol.* 104:997-1006), the cab1R promoter from rice (Luan et al. (1992) *Plant Cell* 4:971-981), the pyruvate orthophosphate dikinase (PPDK) promoter from corn (Matsuoka et al. (1993) *Proc Natl Acad Sci USA* 90:9586-9590), the tobacco Lhcb1*2 promoter (Cerdan et al. (1997) *Plant Mol. Biol.* 33:245-255), the *Arabidopsis thaliana* SUC2 sucrose-H+ symporter promoter (Truernit et al. (1995) *Planta* 196:564-570), and thylakoid membrane protein promoters from spinach (psaD, psaF, psaE, PC, FNR, atpC, atpD, cab,rbcS. Other promoters that drive transcription in stems, leafs and green tissue are described in U.S. Patent Publication No. 2007/0006346, herein incorporated by reference in its entirety.

The tissue specificity of some "tissue preferred" promoters may not be absolute and may be tested reporter genes such as Gus or green fluorescent protein, cyan fluorescent protein, yellow fluorescent protein or red fluorescent protein. One can also achieve tissue preferred expression with "leaky" expression by a combination of different tissue-preferred promoters. Other tissue preferred promoters can be isolated by one skilled in the art (see U.S. Pat. No. 5,589, 379).

In one aspect, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10:955-966); the auxin-inducible parC promoter from tobacco (Sakai (1996) 37:906-913); a plant biotin response element (Streit (1997) *Mol. Plant. Microbe Interact.* 10:933-937); and, the promoter responsive to the stress hormone abscisic acid (Sheen (1996) *Science* 274:1900-1902).

The nucleic acids of the invention can also be operably linked to plant promoters which are inducible upon exposure to chemicals reagents which can be applied to the plant, such as herbicides or antibiotic. For example, gene expression systems that are activated in the presence of a chemical ligand, including ethanol, such as can be found in WO 96/27673; WO 93/01294; WO 94/03619; WO 02/061102, all of which are hereby incorporated by reference. The maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); estrogen, such as, the ecdysone receptor (WO 01/52620) or, a salicylic acid-responsive element (Stange (1997) *Plant J.* 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant.

Examples of some constitutive promoters which have been described include rice actin 1 (Wang et al. (1992) *Mol. Cell. Biol.* 12:3399; U.S. Pat. No. 5,641,876); other actin isoforms (McElroy et al. (1990) *Plant Cell* 2:163-171 and McElroy et al. (1991) *Mol. Gen. Genet.* 231:150-160); CaMV 35S (Odell et al. (1985) *Nature* 313:810); CaMV 19S (Lawton et al. (1987) *Plant Mol. Biol.* 9:315-324; U.S. Pat. No. 5,639,949); nos (Ebert et al. (1987) *PNAS USA* 84:5745-5749); Adh (Walker et al. (1987) *PNAS USA* 84:6624-6628), sucrose synthase (Yang & Russell (1990) *PNAS USA*

87:4144-4148); and the ubiquitin promoters (e.g., sunflower—Binet et al. (1991) *Plant Science* 79:87-94; maize—Christensen et al. (1989) *Plant Molec. Biol.* 12:619-632; and *Arabidopsis*—Callis et al. (1990) *J. Biol. Chem.* 265:12486-12493; and Norris et al. (1993) *Plant Mol. Biol.* 21:895-906.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Numerous sequences have been found to enhance gene expression from within the transcriptional unit and these sequences can be used in conjunction with the genes of this invention to increase their expression in transgenic plants. For example, various intron sequences have been shown to enhance expression, particularly in monocotyledonous cells. For example, the introns of the maize Adhl gene have been found to significantly enhance the expression of the wild-type gene under its cognate promoter when introduced into maize cells. A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g., Gallie et al. (1987) *Nucl. Acids Res.* 15:8693-8711; Skuzeski et al. (1990) *Plant Molec. Biol.* 15:65-79).

Targeting of the Gene Product within the Cell

Any mechanism for targeting gene products known in plants can be used to practice this invention, and the sequences controlling the functioning of these mechanisms have been characterized in some detail. Sequences that have been characterized to cause the targeting of gene products to other cell compartments also can be used to practice this invention. Amino terminal sequences responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g., Unger et al. (1989) *Plant Molec. Biol.* 13:411-418; Rogers et al. (1985) *Proc. Natl. Acad. Sci. USA* 82:6512-651; U.S. Pat. No. 7,102,057; WO 2005/096704, all of which are hereby incorporated by reference), can be used to practice this invention. In one aspect, the signal sequence i s an N-terminal signal sequence from waxy, an N-terminal signal sequence from γ-zein, a starch binding domain, a C-terminal starch binding domain, a chloroplast targeting sequence, which imports the mature protein to the chloroplast (Comai et al. (1988) *J. Biol. Chem.* 263:15104-15109; van den Broeck et al. (1985) *Nature* 313:358-363; U.S. Pat. No. 5,639,949) or a secretion signal sequence from aleurone cells (Koehler & Ho (1990) *Plant Cell* 2:769-783). Additionally, amino terminal sequences in conjunction with carboxy terminal sequences are responsible for vacuolar targeting of gene products (Shinshi et al. (1990) *Plant Molec. Biol.* 14:357-368) can be used to practice this invention.

In one aspect, the signal sequence selected can include the known cleavage site, and the fusion constructed should take into account any amino acids after the cleavage site(s), which are required for cleavage. In some embodiments, this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment. The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Vectors and Cloning Vehicles

The invention provides vectors, including cloning and expression vectors, or any cloning vehicles comprising nucleic acids of the invention, e.g., sequences encoding the glucanases (or cellulases), e.g., endoglucanases, mannanases, xylanases, amylases, xanthanases and/or glycosidases, e.g., cellobiohydrolases, mannanases and/or beta-glucosidases of the invention. Expression vectors and cloning vehicles of the invention can comprise viral particles, recombinant viruses, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *Pseudomonas, Bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSV-LSV40 (Pharmacia). However, any other plasmid or other vector may be used so long as they are replicable and viable in the host. Low copy number or high copy number vectors may be employed with the present invention.

"Plasmids" can be commercially available, publicly available on an unrestricted basis, or can be constructed from available plasmids in accord with published procedures. Equivalent plasmids to those described herein are known in the art and will be apparent to the ordinarily skilled artisan. The starting plasmids herein are either commercially available, publicly available on an unrestricted basis, or can be constructed from available plasmids in accord with published procedures. In addition, equivalent plasmids to those described herein are known in the art and will be apparent to the ordinarily skilled artisan.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the invention provides an "expression cassette" comprising a sequence of the invention, e.g., an "expression cassette" can comprise a nucleotide sequence which is capable of affecting expression of a nucleic acid, e.g., a structural gene (i.e., a protein-coding sequence, such as a glucanase of the invention) in a host compatible with such sequences. Expression cassettes comprise at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli, and the S. cerevisiae TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from Agrobacterium spp., potato virus X (see, e.g., Angell (1997) EMBO J. 16:3675-3684), tobacco mosaic virus (see, e.g., Casper (1996) Gene 173:69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant. Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204: 161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors in one aspect contain one or more selectable marker genes to provide a phenotypic trait for selection of transformed host cells such as dihydrofolate reductase or neomycin resistance for eukaryotic cell culture, or such as tetracycline or ampicillin resistance in E. coli.

Mammalian expression vectors may also comprise an origin of replication, any necessary ribosome binding sites, a polyadenylation site, splice donor and acceptor sites, transcriptional termination sequences and 5' flanking non-transcribed sequences. In some aspects, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin by 100 to 270, the cytomegalovirus early promoter enhancer, the polyoma enhancer on the late side of the replication origin and the adenovirus enhancers.

In addition, the expression vectors typically contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in E. coli and the S. cerevisiae TRP1 gene.

In some aspects, the nucleic acid encoding one of the polypeptides of the invention, or fragments comprising at least about 5, 10, 15, 20, 25, 30, 35, 40, 50, 75, 100, or 150 consecutive amino acids thereof is assembled in appropriate phase with a leader sequence capable of directing secretion of the translated polypeptide or fragment thereof. Optionally, the nucleic acid can encode a fusion polypeptide in which one of the polypeptides of the invention, or fragments comprising at least 5, 10, 15, 20, 25, 30, 35, 40, 50, 75, 100, or 150 consecutive amino acids thereof is fused to heterologous peptides or polypeptides, such as N-terminal identification peptides which impart desired characteristics, such as increased stability or simplified purification.

The appropriate DNA sequence may be inserted into the vector by a variety of procedures. In general, the DNA sequence is ligated to the desired position in the vector following digestion of the insert and the vector with appropriate restriction endonucleases. Alternatively, blunt ends in both the insert and the vector may be ligated. A variety of cloning techniques are disclosed in Ausubel et al., *Current Protocols in Molecular Biology*, John Wiley 503 Sons, Inc. (1997) and Sambrook et al., *Molecular Cloning: A Laboratory Manual* 2nd ed., Cold Spring Harbor Laboratory Press (1989). Such procedures and others are deemed to be within the scope of those skilled in the art.

The vector may be, for example, in the form of a plasmid, a viral particle, or a phage. Other vectors include chromosomal, nonchromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus and pseudorabies. A variety of cloning and expression vectors for use with prokaryotic and eukaryotic hosts are described by Sambrook et al., *Molecular Cloning: A Laboratory Manual*, 2nd ed., Cold Spring Harbor, N.Y. (1989).

Host Cells and Transformed Cells

The invention also provides a transformed cell comprising a nucleic acid sequence of the invention, e.g., a sequence encoding a glucanase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include any species within the genera *Escherichia*, *Bacillus*, *Streptomyces*, *Salmonella*, *Pseudomonas* and *Staphylococcus*, including, e.g., *Escherichia coli*, *Lactococcus lactis*, *Bacillus subtilis*, *Bacillus cereus*, *Salmonella typhimurium*, *Pseudomonas fluorescens*. Exemplary fungal cells include any species of *Aspergillus*. Exemplary yeast cells include any species of *Pichia*, *Saccharomyces*, *Schizosaccharomyces*, or *Schwanniomyces*, including *Pichia pastoris*, *Saccharomyces cerevisiae*, or *Schizosaccharomyces pombe*. Exemplary insect cells include any species of *Spodoptera* or *Drosophila*, including *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) *Ann. Rev. Genet.* 22:421-477; U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I. (1986) *Basic Methods in Molecular Biology*).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e., through the use of traditional plasmids, utilizing standard regulatory sequences, selection markers, etc.). As many pharmaceutically important screens require human or model mammalian cell targets, retroviral vectors capable of transfecting such targets can be used.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

Host cells containing the polynucleotides of interest, e.g., nucleic acids of the invention, can be cultured in conventional nutrient media modified as appropriate for activating promoters, selecting transformants or amplifying genes. The culture conditions, such as temperature, pH and the like, are those previously used with the host cell selected for expression and will be apparent to the ordinarily skilled artisan. The clones which are identified as having the specified enzyme activity may then be sequenced to identify the polynucleotide sequence encoding an enzyme having the enhanced activity.

The invention provides a method for overexpressing a recombinant glucanase in a cell comprising expressing a vector comprising a nucleic acid of the invention, e.g., an exemplary nucleic acid of the invention, including, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, AND SEQ ID NO:22 and the specific modifications to SEQ ID NO:1 as described herein. The overexpression can be effected by any means, e.g., use of a high activity promoter, a dicistronic vector or by gene amplification of the vector.

The nucleic acids of the invention can be expressed, or overexpressed, in any in vitro or in vivo expression system. Any cell culture systems can be employed to express, or over-express, recombinant protein, including bacterial, insect, yeast, fungal or mammalian cultures. Over-expression can be effected by appropriate choice of promoters, enhancers, vectors (e.g., use of replicon vectors, dicistronic vectors (see, e.g., Gurtu (1996) *Biochem. Biophys. Res. Commun.* 229:295-8), media, culture systems and the like. In one aspect, gene amplification using selection markers, e.g., glutamine synthetase (see, e.g., Sanders (1987) *Dev. Biol. Stand.* 66:55-63), in cell systems are used to overexpress the polypeptides of the invention. Additional details regarding this approach are in the public literature and/or are known to the skilled artisan, e.g., EP 0659215 (WO 9403612 A1) (Nevalainen et al.); Lapidot (1996) *J. Biotechnol.* November 51:259-64; Lüthi (1990) *Appl. Environ. Microbiol.* September 56:2677-83 (1990); Sung (1993) *Protein Expr. Purif.* June 4:200-6 (1993).

The host cell may be any of the host cells familiar to those skilled in the art, including prokaryotic cells, eukaryotic cells, mammalian cells, insect cells, fungal cells, yeast cells and/or plant cells. As representative examples of appropriate hosts, there may be mentioned: bacterial cells, such as *E. coli, Streptomyces, Bacillus subtilis, Bacillus cereus, Salmonella typhimurium* and various species within the genera *Pseudomonas, Streptomyces* and *Staphylococcus,* fungal cells, such as *Aspergillus,* yeast such as any species of *Pichia, Saccharomyces, Schizosaccharomyces, Schwanniomyces,* including *Pichia pastoris, Saccharomyces cerevisiae,* or *Schizosaccharomyces pombe,* insect cells such as *Drosophila* S2 and *Spodoptera* Sf9, animal cells such as CHO, COS or Bowes melanoma and adenoviruses. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (e.g., see Davis, L., Dibner, M., Battey, I. (1986) *Basic Methods in Molecular Biology*).

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described, e.g., by Gluzman (1981) *Cell* 23:175; and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in the recombinant production procedure, the polypeptides produced by host cells containing the vector may be glycosylated or may be non-glycosylated. Polypeptides of the invention may or may not also include an initial methionine amino acid residue.

Alternatively, the polypeptides and peptides of the invention can be synthetically produced by conventional peptide synthesizers. In other aspects, fragments or portions of the polypeptides may be employed for producing the corresponding full-length polypeptide by peptide synthesis; therefore, the fragments may be employed as intermediates for producing the full-length polypeptides.

Cell-free translation systems can also be employed to produce one of the polypeptides of the invention using mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA can be incubated with an appropriate cell-free translation extract, such as a rabbit reticulocyte extract, to produce the desired polypeptide or peptide.

Amplification of Nucleic Acids

In practicing the invention, nucleic acids of the invention and nucleic acids encoding the glucanases (or cellulases), e.g., endoglucanases, mannanases, xylanases, amylases, xanthanases and/or glycosidases, e.g., cellobiohydrolases, mannanases and/or beta-glucosidases of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences. In one aspect, the invention provides a nucleic acid amplified by a primer pair of the invention, e.g., a primer pair as set forth by about the first (the 5') or about 10, 11, 12, 13, 14, 15, 16, 17, 18, 19, 20, 21, 22, 23, 24, 25, 26, 27, 28, 29, 30, 31, 32, 33, 34 or 35 or more residues of a nucleic acid of the invention, and about the first (the 5') or about 10, 11, 12, 13, 14, 15, 16, 17, 18, 19, 20, 21, 22, 23, 24, 25, 26, 27, 28, 29, 30, 31, 32, 33, 34 or 35 or more residues of the complementary strand.

The invention provides an amplification primer sequence pair for amplifying a nucleic acid encoding a polypeptide having a glucanase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence, or about 12, 13, 14, 15, 16, 17, 18, 19, 20, 21, 22, 23, 24, or 25 consecutive bases of the sequence. The invention provides amplification primer pairs, wherein the primer pair comprises a first member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34 or 35 residues of a nucleic acid of the invention, and a second member having a sequence as set forth by about the first (the 5') 10, 11, 12, 13, 14, 15, 16, 17, 18, 19, 20, 21, 22, 23, 24, 25, 26, 27, 28, 29, 30, 31, 32, 33, 34 or 35 residues of the complementary strand of the first member. The invention provides glucanases (or cellulases), e.g., endoglucanases, mannanases, xylanases, amylases, xanthanases and/or glycosidases, e.g., cellobiohydrolases, mannanases and/or beta-glucosidases generated by amplification, e.g., polymerase chain reaction (PCR), using an amplification primer pair of the invention. The invention provides methods of making glucanases (or cellulases), e.g., endoglucanases, mannanases, xylanases, amylases, xanthanases and/or glycosidases, e.g., cellobiohydrolases, mannanases and/or beta-glucosidases by amplification, e.g., polymerase chain reaction (PCR), using an amplification primer pair of the invention. In one aspect, the amplification primer pair amplifies a nucleic acid from a library, e.g., a gene library, such as an environmental library.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) *Proc. Natl. Acad. Sci. USA* 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; Sooknanan (1995) *Biotechnology* 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention, including SEQ ID NO:1, SEQ ID NO:3, SEQ ID NO:6, SEQ ID NO:8, SEQ ID NO:10, SEQ ID NO:12, SEQ ID NO:18, SEQ ID NO:20, AND SEQ ID NO:22, and the sequence modifications to SEQ ID NO:1 described herein, over a region of at least about 10, 20, 30, 40, 50, 60, 70, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

Nucleic acid sequences of the invention can comprise at least 10, 15, 20, 25, 30, 35, 40, 50, 75, 100, 150, 200, 300, 400, or 500 or more consecutive nucleotides of an exemplary sequence of the invention and sequences substantially identical thereto. Homologous sequences and fragments of nucleic acid sequences of the invention can refer to a sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity (homology) to an exemplary nucleic acid of the invention, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, and variations thereof as described herein, as well as SEQ ID NO:6, SEQ ID NO:8, SEQ ID NO:10, SEQ ID NO:12, SEQ ID NO:18, SEQ ID NO:20, and SEQ ID NO:22, to these sequences.

The phrase "substantially identical" in the context of two nucleic acids or polypeptides, refers to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and fed for maximum correspondence, as measured using one of the known sequence comparison algorithms or by visual inspection. The substantial identity can exist over a region of at least about 10, 15, 20, 25, 30, 35, 40, 50, 75, 100, 150, 200, 300, 400, or 500 or more residues. In some aspects, the sequences are substantially identical over the entire length of the coding regions. In one aspect, a "substantially identical" amino acid sequence is a sequence that differs from a reference sequence by one or more conservative or non-conservative amino acid substitutions, deletions, or insertions, particularly when such a substitution occurs at a site that is not the active site (catalytic domains (CDs)) of the molecule and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a glucanase polypeptide, resulting in modification of the structure of the polypeptide, without significantly altering its biological activity. For example, amino- or carboxyl-terminal amino acids that are not required for glucanase biological activity can be removed. Modified polypeptide sequences of the invention can be assayed for glucanase biological activity by any number of methods, including contacting the modified polypeptide sequence with a glucanase substrate and determining whether the modified polypeptide decreases the amount of specific substrate in the assay or increases the bioproducts of the enzymatic reaction of a functional glucanase polypeptide with the substrate.

Sequence identity (homology) may be determined using any of the computer programs and parameters described herein, including FASTA version 3.0t78 with the default parameters. Homologous sequences also include RNA sequences in which uridines replace the thymines in the nucleic acid sequences of the invention. The homologous sequences may be obtained using any of the procedures described herein or may result from the correction of a sequencing error. It will be appreciated that the nucleic acid sequences of the invention can be represented in the traditional single character format (See the inside back cover of Stryer, Lubert. Biochemistry, 3rd Ed., W. H Freeman & Co., New York.) or in any other format which records the identity of the nucleotides in a sequence.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

Various sequence comparison programs identified elsewhere in this patent specification are particularly contemplated for use in this aspect of the invention. Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA and CLUSTALW (Pearson and Lipman (1988) *Proc. Natl. Acad. Sci. USA* 85(8):2444-2448; Altschul et al. (1990) *J. Mol. Biol.* 215(3):403-410; Thompson et al. (1994) *Nucleic Acids Res.* 22(2):4673-4680; Higgins et al. (1996) *Methods Enzymol.* 266:383-402; Altschul et al. (1990) *J. Mol. Biol.* 215(3):403-410; Altschul et al. (1993) *Nature Genetics* 3:266-272).

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, one sequence can acts as a reference sequence, to which test sequences are compared. When using a sequence comparison algorithm, test and reference sequences are entered into a computer, subsequence coordinates are designated, if necessary and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman (1981) Adv. Appl. Math. 2:482, by the homology alignment algorithm of Needleman & Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, M. genitalium (Fraser et al., 1995), M. jannaschii (Bult et al., 1996), H. influenzae (Fleischmann et al., 1995), E. coli (Blattner et al., 1997) and yeast (S. cerevisiae) (Mewes et al., 1997) and D. melanogaster (Adams et al., 2000). Significant progress has also been made in sequencing the genomes of model organism, such as mouse, C. elegans and Arabadopsis sp. Several databases containing genomic information annotated with some functional information are maintained by different organization and are accessible via the internet.

One example of a useful algorithm is BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3 and expectations (E) of 10 and the BLOSUM62 scoring matrix (see Henikoff & Henikoff (1989) Proc. Natl. Acad. Sci. USA 89:10915) alignments (B) of 50, expectation (E) of 10, M=5, N=−4 and a comparison of both strands.

The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more in one aspect less than about 0.01 and most in one aspect less than about 0.001.

In one aspect, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is in one aspect obtained from a protein or nucleic acid sequence database. High-scoring segment pairs are in one aspect identified (i.e., aligned) by means of a scoring matrix, many of which are known in the art. In one aspect, the scoring matrix used is the BLOSUM62 matrix (Gonnet et al (1992) *Science* 256:1443-1445; Henikoff and Henikoff (1993) *Proteins* 17:49-61). Less in one aspect, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some aspects, the parameters may be the default parameters used by the algorithms in the absence of instructions from the user.

Computer Systems and Computer Program Products

To determine and identify sequence identities, structural homologies, motifs and the like in silico, a nucleic acid or polypeptide sequence of the invention can be stored, recorded, and manipulated on any medium which can be read and accessed by a computer.

Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

The polypeptides of the invention comprise amino acid sequences of the invention, e.g., the exemplary sequences of the invention, and sequences substantially identical thereto, and fragments thereof, including enzymatically active tragments. Substantially identical, or homologous, polypeptide sequences refer to a polypeptide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary sequence of the invention.

Homology (sequence identity) may be determined using any of the computer programs and parameters described herein, including FASTA version 3.0t78 with the default parameters or with any modified parameters. The homologous sequences may be obtained using any of the procedures described herein or may result from the correction of a sequencing error. The polypeptide fragments comprise at least about 10, 15, 20, 25, 30, 35, 40, 45, 50, 75, 100, 150, 200, 250, 300, 350, 400, 450, 500 or more consecutive amino acids of the polypeptides of the invention. It will be appreciated that the polypeptide codes as set forth in amino acid sequences of the invention, can be represented in the traditional single character format or three letter format (See the inside back cover of Stryer, Lubert. *Biochemistry*, 3rd Ed., W. H Freeman & Co., New York.) or in any other format which relates the identity of the polypeptides in a sequence.

A nucleic acid or polypeptide sequence of the invention can be stored, recorded and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid sequences of the invention, one or more of the polypeptide sequences of the invention. Another aspect of the invention is a computer readable medium having recorded thereon at least 2, 5, 10, 15, or 20 or more nucleic acid sequences of the invention.

Another aspect of the invention is a computer readable medium having recorded thereon one or more of the nucleic acid sequences of the invention. Another aspect of the invention is a computer readable medium having recorded thereon one or more of the polypeptide sequences of the invention. Another aspect of the invention is a computer readable medium having recorded thereon at least 2, 5, 10, 15, or 20 or more of the sequences as set forth above.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems which store and manipulate the sequence information described herein. One example of a computer system 100 is illustrated in block diagram form in FIG. 1. As used herein, "a computer system" refers to the hardware components, software components and data storage components used to analyze a nucleotide sequence of a nucleic acid sequence of the invention, or a polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

The computer system 100 can be a general purpose system that comprises the processor 105 and one or more internal data storage components 110 for storing data and one or more data retrieving devices for retrieving the data stored on the data storage components. A skilled artisan can readily appreciate that any one of the currently available computer systems are suitable.

In one particular aspect, the computer system 100 includes a processor 105 connected to a bus which is connected to a main memory 115 (in one aspect implemented as RAM) and one or more internal data storage devices 110, such as a hard drive and/or other computer readable media having data recorded thereon. In some aspects, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some aspects, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the nucleotide sequences of a nucleic acid sequence of the invention, or a polypeptide sequence of the invention, (such as search tools, compare tools and modeling tools etc.) may reside in main memory 115 during execution.

In some aspects, the computer system 100 may further comprise a sequence comparison algorithm for comparing a nucleic acid sequence of the invention, or a polypeptide sequence of the invention, stored on a computer readable medium to a reference nucleotide or polypeptide sequence(s) stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of a nucleic acid sequence of the invention, or a polypeptide sequence of the invention, stored on a computer readable medium to reference sequences stored on a computer readable medium to identify homologies or structural motifs.

Figure 2:
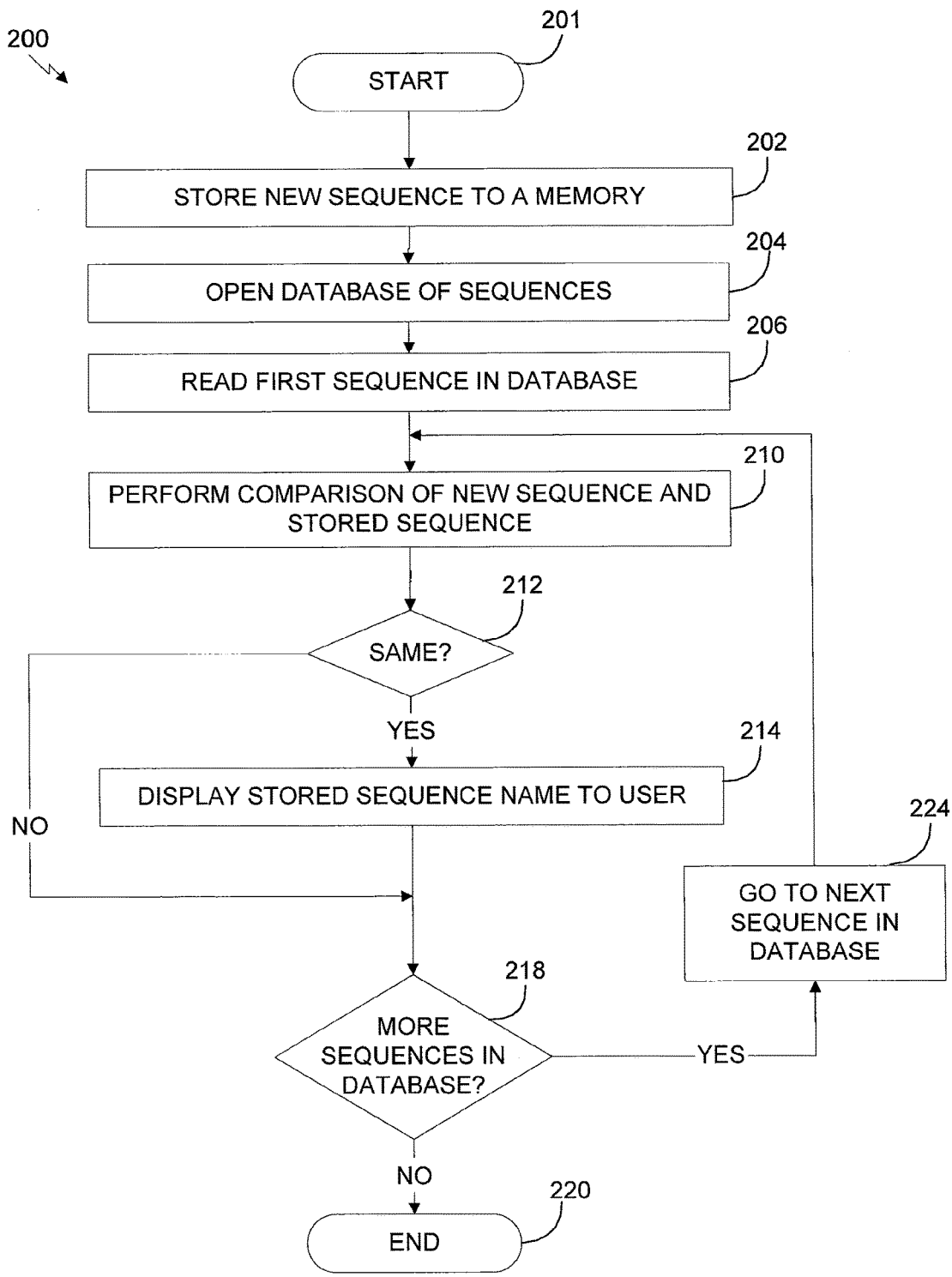
FIG. 2 is a flow diagram illustrating one aspect of a process for comparing a new nucleotide or protein sequence with a database of sequences in order to determine the homology levels between the new sequence and the sequences in the database.

FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GENBANK that is available through the Internet.

The process 200 begins at a start state 201 and then moves to a state 202 wherein the new sequence to be compared is stored to a memory in a computer system 100. As discussed above, the memory could be any type of memory, including RAM or an internal storage device.

The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system.

Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200.

If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database.

It should be noted that if a determination had been made at the decision state 212 that the sequences were not homologous, then the process 200 would move immediately to the decision state 218 in order to determine if any other sequences were available in the database for comparison.

Accordingly, one aspect of the invention is a computer system comprising a processor, a data storage device having stored thereon a nucleic acid sequence of the invention, or a polypeptide sequence of the invention, a data storage device having retrievably stored thereon reference nucleotide sequences or polypeptide sequences to be compared to a nucleic acid sequence of the invention, or a polypeptide sequence of the invention and a sequence comparer for conducting the comparison. The sequence comparer may indicate a homology level between the sequences compared or identify structural motifs in the above described nucleic acid code a nucleic acid sequence of the invention, or a polypeptide sequence of the invention, or it may identify structural motifs in sequences which are compared to these nucleic acid codes and polypeptide codes. In some aspects, the data storage device may have stored thereon the sequences of at least 2, 5, 10, 15, 20, 25, 30 or 40 or more of the nucleic acid sequences of the invention, or the polypeptide sequences of the invention.

Another aspect of the invention is a method for determining the level of homology between a nucleic acid sequence of the invention, or a polypeptide sequence of the invention and a reference nucleotide sequence. The method including reading the nucleic acid code or the polypeptide code and the reference nucleotide or polypeptide sequence through the use of a computer program which determines homology levels and determining homology between the nucleic acid code or polypeptide code and the reference nucleotide or polypeptide sequence with the computer program. The computer program may be any of a number of computer programs for determining homology levels, including those specifically enumerated herein, (e.g., BLAST2N with the default parameters or with any modified parameters). The method may be implemented using the computer systems described above. The method may also be performed by reading at least 2, 5, 10, 15, 20, 25, or 40 or more of the above described nucleic acid sequences of the invention, or the polypeptide sequences of the invention through use of the computer program and determining homology between the nucleic acid codes or polypeptide codes and reference nucleotide sequences or polypeptide sequences.

Figure 3:
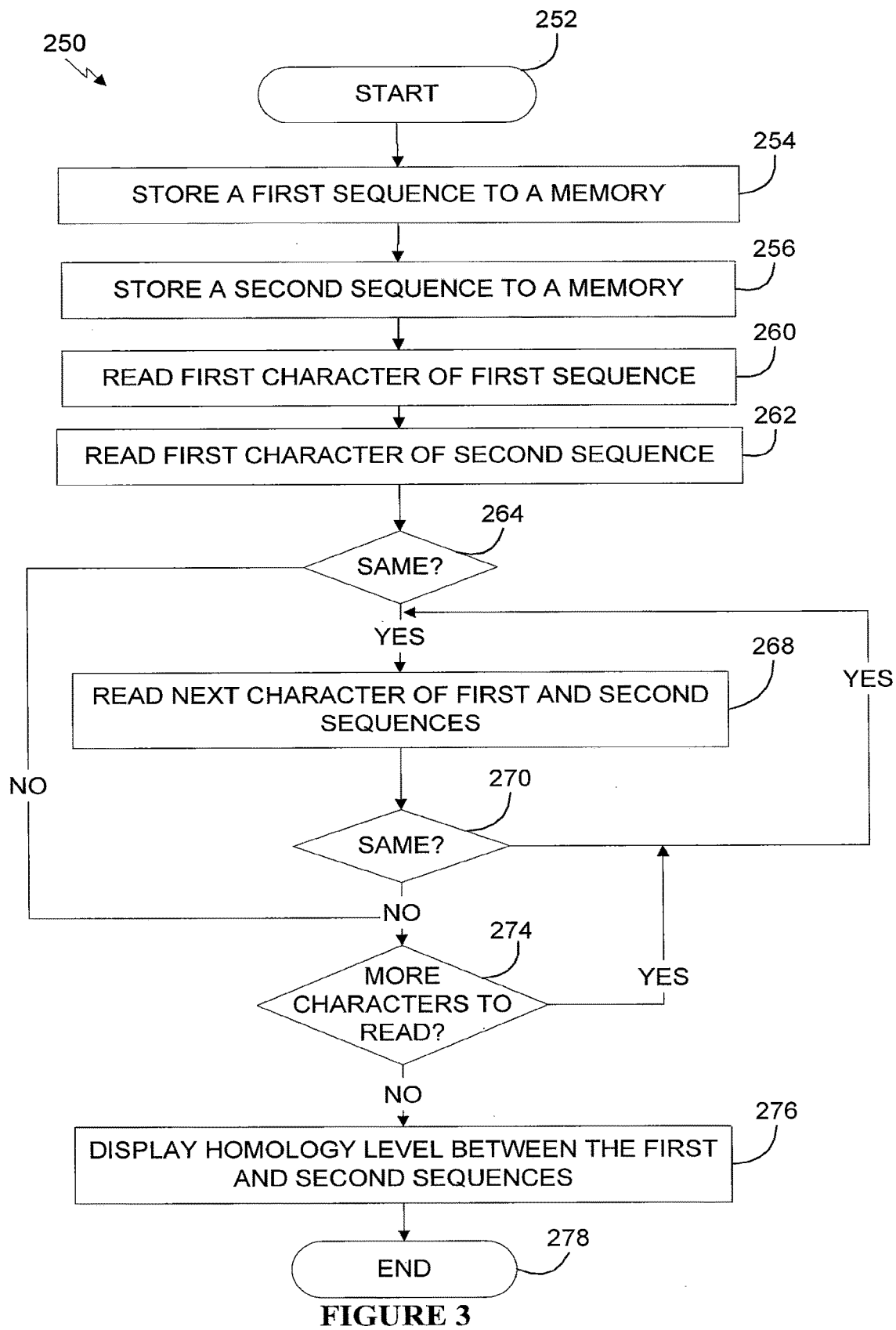
FIG. 3 is a flow diagram illustrating one aspect of a process in a computer for determining whether two sequences are homologous.

FIG. 3 is a flow diagram illustrating one aspect of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it is in one aspect in the single letter amino acid code so that the first and sequence sequences can be easily compared.

A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read.

If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with a every character in a second sequence, the homology level would be 100%.

Alternatively, the computer program may be a computer program which compares the nucleotide sequences of a nucleic acid sequence as set forth in the invention, to one or more reference nucleotide sequences in order to determine whether the nucleic acid code of the invention, differs from a reference nucleic acid sequence at one or more positions. Optionally such a program records the length and identity of inserted, deleted or substituted nucleotides with respect to the sequence of either the reference polynucleotide or a nucleic acid sequence of the invention. In one aspect, the computer program may be a program which determines whether a nucleic acid sequence of the invention, contains a single nucleotide polymorphism (SNP) with respect to a reference nucleotide sequence.

Accordingly, another aspect of the invention is a method for determining whether a nucleic acid sequence of the invention, differs at one or more nucleotides from a reference nucleotide sequence comprising the steps of reading the nucleic acid code and the reference nucleotide sequence through use of a computer program which identifies differences between nucleic acid sequences and identifying differences between the nucleic acid code and the reference nucleotide sequence with the computer program. In some aspects, the computer program is a program which identifies single nucleotide polymorphisms. The method may be implemented by the computer systems described above and the method illustrated in FIG. 3. The method may also be performed by reading at least 2, 5, 10, 15, 20, 25, 30, or 40 or more of the nucleic acid sequences of the invention and the reference nucleotide sequences through the use of the computer program and identifying differences between the nucleic acid codes and the reference nucleotide sequences with the computer program.

In other aspects the computer based system may further comprise an identifier for identifying features within a nucleic acid sequence of the invention or a polypeptide sequence of the invention.

An "identifier" refers to one or more programs which identifies certain features within a nucleic acid sequence of the invention, or a polypeptide sequence of the invention. In one aspect, the identifier may comprise a program which identifies an open reading frame in a nucleic acid sequence of the invention.

Figure 4:
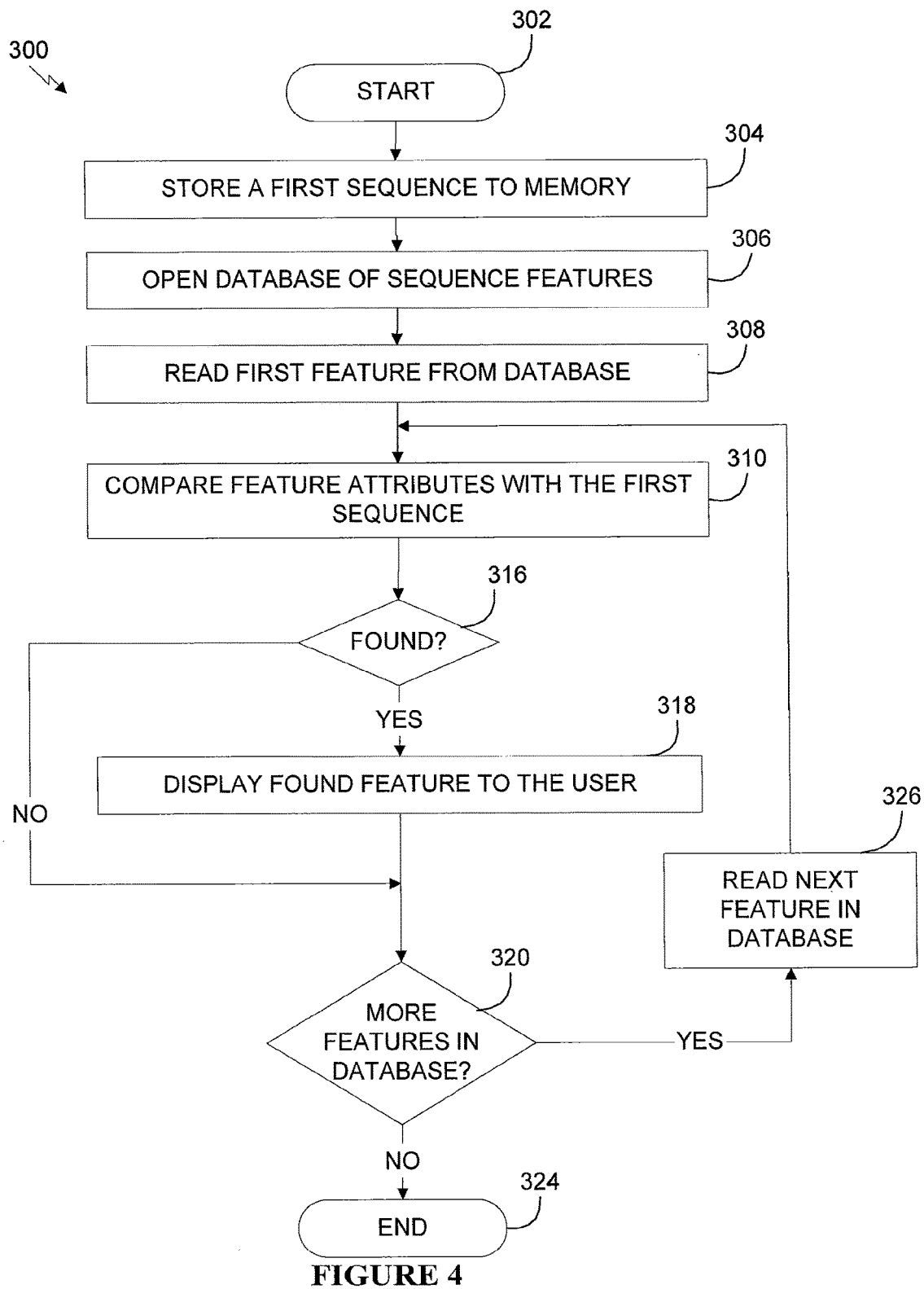
FIG. 4 is a flow diagram illustrating one aspect of an identifier process 300 for detecting the presence of a feature in a sequence.

FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic catalytic domains (CDs), or, active sites, helix-turn-helix motifs or other motifs known to those skilled in the art.

Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user.

The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. It should be noted, that if the feature attribute is not found in the first sequence at the decision state 316, the process 300 moves directly to the decision state 320 in order to determine if any more features exist in the database.

Accordingly, another aspect of the invention is a method of identifying a feature within a nucleic acid sequence of the invention, or a polypeptide sequence of the invention, comprising reading the nucleic acid code(s) or polypeptide code(s) through the use of a computer program which identifies features therein and identifying features within the nucleic acid code(s) with the computer program. In one aspect, computer program comprises a computer program which identifies open reading frames. The method may be performed by reading a single sequence or at least 2, 5, 10, 15, 20, 25, 30, or 40 of the nucleic acid sequences of the invention, or the polypeptide sequences of the invention, through the use of the computer program and identifying features within the nucleic acid codes or polypeptide codes with the computer program.

A nucleic acid sequence of the invention, or a polypeptide sequence of the invention, may be stored and manipulated in a variety of data processor programs in a variety of formats. For example, a nucleic acid sequence of the invention, or a polypeptide sequence of the invention, may be stored as text in a word processing file, such as Microsoft WORD™ or WORDPERFECT™ or as an ASCII file in a variety of database programs familiar to those of skill in the art, such as DB2™, SYBASE™, or ORACLE™. In addition, many computer programs and databases may be used as sequence comparison algorithms, identifiers, or sources of reference nucleotide sequences or polypeptide sequences to be compared to a nucleic acid sequence of the invention, or a polypeptide sequence of the invention. The following list is intended not to limit the invention but to provide guidance to programs and databases which are useful with the nucleic acid sequences of the invention, or the polypeptide sequences of the invention.

The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al., *J. Mol. Biol.* 215:403, 1990), FASTA (Pearson and Lipman, *Proc. Natl. Acad. Sci. USA* 85:2444, 1988), FASTDB (Brutlag et al., *Comp. App. Biosci.* 6:237-245, 1990), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwents's World Drug Index database, the BioByteMasterFile database, the Genbank database and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices and beta sheets, signal sequences encoding signal peptides which direct the secretion of the encoded proteins, sequences implicated in transcription regulation such as homeoboxes, acidic stretches, enzymatic active sites (catalytic domains (CDs)), substrate binding sites and enzymatic cleavage sites.

Hybridization of Nucleic Acids

The invention provides isolated, synthetic or recombinant nucleic acids that hybridize under stringent conditions to an exemplary sequence of the invention, e.g., SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, or a modification of SEQ ID NO:1 as described herein, as well as SEQ ID NO:6, SEQ ID NO:8, SEQ ID NO:10, SEQ ID NO:12, SEQ ID NO:18, SEQ ID NO:20, and SEQ ID NO:22. The stringent conditions can be highly stringent conditions, medium stringent conditions and/or low stringent conditions, including the high and reduced stringency conditions described herein. In one aspect, it is the stringency of the wash conditions that set forth the conditions which determine whether a nucleic acid is within the scope of the invention, as discussed below.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature and are well known in the art. In particular, stringency can be increased by reducing the concentration of salt, increasing the concentration of formamide, or raising the hybridization temperature. In alternative aspects, nucleic acids of the invention are defined by their ability to hybridize under various stringency conditions (e.g., high, medium, and low), as set forth herein.

For example, in one aspect hybridization under high stringency conditions occurs in conditions comprising about 50% formamide at about 37° C. to 42° C. Hybridization also can occur under reduced stringency in conditions comprising about 35% to 25% formamide at about 30° C. to 35° C. In one aspect, hybridization occurs under high stringency in conditions comprising about 42° C. in 50% formamide, 5×SSPE, 0.3% SDS and 200 μg/ml sheared and denatured salmon sperm DNA. In one aspect, hybridization occurs under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA (single or double stranded, siRNA or miRNA), antisense or sequences encoding antibody binding peptides (epitopes), motifs, active sites (catalytic domains (CDs)) and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 μg/ml sheared and denatured salmon sperm DNA). In one aspect, nucleic acids of the invention are defined by their ability to hybridize under reduced stringency conditions comprising 35% formamide at a reduced temperature of 35° C.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content) and nucleic acid type (e.g., RNA v. DNA) of the hybridizing regions of the nucleic acids can be considered in selecting hybridization conditions. An additional consideration is whether one of the nucleic acids is immobilized, for example, on a filter.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's and 0.5 mg/ml polyriboadenylic acid. Approximately $2\times10^7$ cpm (specific activity $4-9\times10^8$ cpm/ug) of $^{32}P$ end-labeled oligonucleotide probe are then added to the solution. After 12-16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at $T_m-10°$ C. for the oligonucleotide probe. The membrane is then exposed to auto-radiographic film for detection of hybridization signals.

All of the foregoing hybridizations are conditions of high stringency.

Following hybridization, a filter can be washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content) and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes. Some other examples are given below. Nucleic acids which have hybridized to the probe can be identified by autoradiography or other conventional techniques.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68oC for 15 minutes; or, equivalent conditions. See Sambrook, Tijssen and Ausubel for a description of SSC buffer and equivalent conditions.

These methods may be used to isolate nucleic acids of the invention. For example, the preceding methods may be used to isolate nucleic acids having a sequence with at least about 97%, at least 95%, at least 90%, at least 85%, at least 80%, at least 75%, at least 70%, at least 65%, at least 60%, at least 55%, or at least 50% homology to a nucleic acid sequence selected from the group consisting of one of the sequences of the invention, or fragments comprising at least about 10, 15, 20, 25, 30, 35, 40, 50, 75, 100, 150, 200, 300, 400, or 500 consecutive bases thereof and the sequences complementary thereto. Homology may be measured using the alignment algorithm. For example, the homologous polynucleotides may have a coding sequence which is a naturally occurring allelic variant of one of the coding sequences described herein. Such allelic variants may have a substitution, deletion or addition of one or more nucleotides when compared to the nucleic acids of the invention.

Additionally, the above procedures may be used to isolate nucleic acids which encode polypeptides having at least about 99%, 95%, at least 90%, at least 85%, at least 80%, at least 75%, at least 70%, at least 65%, at least 60%, at least 55%, or at least 50% homology to a polypeptide of the invention, or fragments comprising at least 5, 10, 15, 20, 25, 30, 35, 40, 50, 75, 100, or 150 consecutive amino acids thereof as determined using a sequence alignment algorithm (e.g., such as the FASTA version 3.0t78 algorithm with the default parameters).

Oligonucleotides Probes and Methods for Using them

The invention also provides nucleic acid probes that can be used, e.g., for identifying nucleic acids encoding a polypeptide with a glucanase activity or fragments thereof or for identifying glucanase genes. In one aspect, the probe comprises at least 10 consecutive bases of a nucleic acid of the invention. Alternatively, a probe of the invention can be at least about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The isolated nucleic acids of the invention, the sequences complementary thereto, or a fragment comprising at least 10, 15, 20, 25, 30, 35, 40, 50, 75, 100, 150, 200, 300, 400, or 500 consecutive bases of one of the sequences of the invention, or the sequences complementary thereto may also be used as probes to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences from which are present therein.

Where necessary, conditions which permit the probe to specifically hybridize to complementary sequences may be determined by placing the probe in contact with complementary sequences from samples known to contain the complementary sequence as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids.

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product.

Many methods for using the labeled probes to detect the presence of complementary nucleic acids in a sample are familiar to those skilled in the art. These include Southern Blots, Northern Blots, colony hybridization procedures and dot blots. Protocols for each of these procedures are provided in Ausubel et al., *Current Protocols in Molecular Biology*, John Wiley 503 Sons, Inc. (1997) and Sambrook et al., *Molecular Cloning: A Laboratory Manual 2nd Ed.*, Cold Spring Harbor Laboratory Press (1989).

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). The probes can comprise oligonucleotides. In one aspect, the amplification reaction may comprise a PCR reaction. PCR protocols are described in Ausubel and Sambrook, supra. Alternatively, the amplification may comprise a ligase chain reaction, 3SR, or strand displacement reaction. (See Barany, F., "The Ligase Chain Reaction in a PCR World", *PCR Methods and Applications* 1:5-16, 1991; E. Fahy et al., "Self-sustained Sequence Replication (3SR): An Isothermal Transcription-based Amplification System Alternative to PCR", *PCR Methods and Applications* 1:25-33, 1991; and Walker G. T. et al., "Strand Displacement Amplification—an Isothermal in vitro DNA Amplification Technique", *Nucleic Acid Research* 20:1691-1696, 1992). In such procedures, the nucleic acids in the sample are contacted with the probes, the amplification reaction is performed and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the ends of the sequences of the invention, may also be used in chromosome walking procedures to identify clones containing genomic sequences located adjacent to the sequences of the invention. Such methods allow the isolation of genes which encode additional proteins from the host organism.

The isolated nucleic acids of the invention, the sequences complementary thereto, or a fragment comprising at least 10, 15, 20, 25, 30, 35, 40, 50, 75, 100, 150, 200, 300, 400, or 500 consecutive bases of one of the sequences of the invention, or the sequences complementary thereto may be used as probes to identify and isolate related nucleic acids. In some aspects, the related nucleic acids may be cDNAs or genomic DNAs from organisms other than the one from which the nucleic acid was isolated. For example, the other organisms may be related organisms. In such procedures, a nucleic acid sample is contacted with the probe under conditions which permit the probe to specifically hybridize to related sequences. Hybridization of the probe to nucleic acids from the related organism is then detected using any of the methods described above.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, $T_m$, is the temperature (under defined ionic strength and pH) at which 50% of the target sequence hybridizes to a perfectly complementary probe. Very stringent conditions are selected to be equal to or about 5° C. lower than the $T_m$ for a particular probe. The melting temperature of the probe may be calculated using the following formulas:

For probes between 14 and 70 nucleotides in length the melting temperature ($T_m$) is calculated using the formula: $T_m = 81.5 + 16.6(\log [Na+]) + 0.41(\text{fraction } G+C) - (600/N)$ where N is the length of the probe.

If the hybridization is carried out in a solution containing formamide, the melting temperature may be calculated using the equation: $T_m = 81.5 + 16.6(\log [Na+]) + 0.41(\text{fraction } G+C) - (0.63\% \text{ formamide}) - (600/N)$ where N is the length of the probe.

Prehybridization may be carried out in 6×SSC, 5×Denhardt's reagent, 0.5% SDS, 100 µg/ml denatured fragmented salmon sperm DNA or 6×SSC, 5×Denhardt's reagent, 0.5% SDS, 100 µg/ml denatured fragmented salmon sperm DNA, 50% formamide. The formulas for SSC and Denhardt's solutions are listed in Sambrook et al., supra.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at about 15 to 25° C. below the $T_m$. For shorter probes, such as oligonucleotide probes, the hybridization may be conducted at about 5° C. to 10° C. below the $T_m$. For hybridizations in 6×SSC, the hybridization can be conducted at approximately 68° C. In one aspect, for hybridizations in 50% formamide-comprising solutions, the hybridization is conducted at approximately 42° C.

Inhibiting Expression of Enzymes (Glucanases)

The invention provides nucleic acids complementary to (e.g., antisense sequences to) the nucleic acids of the invention, e.g., endoglucanase-, mannanase-, or xylanase-encoding nucleic acids. Antisense sequences are capable of inhibiting the transport, splicing or transcription of glucanase-encoding, endoglucanase-, mannanase-, or xylanase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind glucanase (or cellulase), e.g., endoglucanase, mannanase, xylanase, amylase, xanthanase and/or glycosidase, e.g., cellobiohydrolase, mannanase and/or beta-glucosidase gene or message, in either case preventing or inhibiting the production or function of glucanase (or cellulase), e.g., endoglucanase, mannanase, xylanase, amylase, xanthanase and/or glycosidase, e.g., cellobiohydrolase, mannanase and/or beta-glucosidase. The association can be through sequence specific hybridization. Another useful class of inhibitors includes oligonucleotides which cause inactivation or cleavage of glucanase (or cellulase), e.g., endoglucanase, mannanase, xylanase, amylase, xanthanase and/or glycosidase, e.g., cellobiohydrolase, mannanase and/or beta-glucosidase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity. Thus, the invention provides various compositions for the inhibition of glucanase (or cellulase), e.g., endoglucanase, mannanase, xylanase, amylase, xanthanase and/or glycosidase, e.g., cellobiohydrolase, mannanase and/or beta-glucosidase expression on a nucleic acid and/or protein level, e.g., antisense, iRNA (e.g., siRNA, miRNA) and ribozymes comprising glucanase (or cellulase), e.g., endoglucanase, mannanase, xylanase, amylase, xanthanase and/or glycosidase, e.g., cellobiohydrolase, mannanase and/or beta-glucosidase sequences of the invention and the anti-glucanase (or cellulase), e.g., endoglucanase, mannanase, xylanase, amylase, xanthanase and/or glycosidase, e.g., cellobiohydrolase, mannanase and/or beta-glucosidase antibodies of the invention.

Inhibition of glucanase (or cellulase), e.g., endoglucanase, mannanase, xylanase, amylase, xanthanase and/or glycosidase, e.g., cellobiohydrolase, mannanase and/or beta-glucosidase expression can have a variety of industrial applications. For example, inhibition of glucanase (or cellulase), e.g., endoglucanase, mannanase, xylanase, amylase, xanthanase and/or glycosidase, e.g., cellobiohydrolase, mannanase and/or beta-glucosidase expression can slow or prevent food or feed spoilage. Spoilage can occur when polysaccharides, e.g., structural polysaccharides, are enzymatically degraded. This can lead to the deterioration, or rot, of fruits and vegetables. In one aspect, use of compositions of the invention that inhibit the expression and/or activity of glucanases (or cellulase), e.g., endoglucanase, mannanase, xylanase, amylase, xanthanase and/or glycosidase, e.g., cellobiohydrolase, mannanase and/or beta-glucosidase, e.g., antibodies, antisense oligonucleotides, ribozymes and RNAi, are used to slow or prevent spoilage. Thus, in one aspect, the invention provides methods and compositions comprising application onto a plant or plant product (e.g., a cereal, a grain, a fruit, seed, root, leaf, etc.) antibodies, antisense oligonucleotides, ribozymes and RNAi of the invention to slow or prevent spoilage. These compositions also can be expressed by the plant (e.g., a transgenic plant) or another organism (e.g., a bacterium or other microorganism transformed with a glucanase (or cellulase), e.g., endoglucanase, mannanase, xylanase, amylase, xanthanase and/or glycosidase, e.g., cellobiohydrolase, mannanase and/or beta-glucosidase gene of the invention).

The compositions of the invention for the inhibition of glucanase (or cellulase), e.g., endoglucanase, mannanase, xylanase, amylase, xanthanase and/or glycosidase, e.g., cellobiohydrolase, mannanase and/or beta-glucosidase expression (e.g., antisense, iRNA (e.g., siRNA, miRNA), ribozymes, antibodies) can be used as pharmaceutical compositions, e.g., as anti-pathogen agents or in other therapies, e.g., as anti-microbials for, e.g., *Salmonella*.

Antisense Oligonucleotides

The invention provides antisense oligonucleotides capable of binding glucanase (or cellulase), e.g., endoglucanase, mannanase, xylanase, amylase, xanthanase and/or glycosidase, e.g., cellobiohydrolase, mannanase and/or beta-glucosidase message or gene which can inhibit a target gene or message to, e.g., inhibit a glucan, a mannan, an arabinoxylan or a xylan, hydrolase activity (e.g., catalyzing hydrolysis of internal β-1,4-xylosidic linkages) by targeting mRNA. Strategies for designing antisense oligonucleotides are well described in the scientific and patent literature, and the skilled artisan can design such glucanase (or cellulase), e.g., endoglucanase, mannanase, xylanase, amylase, xanthanase and/or glycosidase, e.g., cellobiohydrolase, mannanase and/or beta-glucosidase oligonucleotides using the novel reagents of the invention. For example, gene walking/RNA mapping protocols to screen for effective antisense oligonucleotides are well known in the art, see, e.g., Ho (2000) *Methods Enzymol.* 314:168-183, describing an RNA mapping assay, which is based on standard molecular techniques to provide an easy and reliable method for potent antisense sequence selection. See also Smith (2000) *Eur. J. Pharm. Sci.* 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl)glycine units can be used. Antisense oligonucleotides having phosphorothioate linkages can also be used, as described in WO 97/03211; WO 96/39154; Mata (1997)

*Toxicol Appl Pharmacol* 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense glucanase (or cellulase), e.g., endoglucanase, mannanase, xylanase, amylase, xanthanase and/or glycosidase, e.g., cellobiohydrolase, mannanase and/or beta-glucosidase sequences of the invention (see, e.g., Gold (1995) *J. of Biol. Chem.* 270:13581-13584).

Inhibitory Ribozymes

The invention provides ribozymes capable of binding glucanase (or cellulase), e.g., endoglucanase, mannanase, xylanase, amylase, xanthanase and/or glycosidase, e.g., cellobiohydrolase, mannanase and/or beta-glucosidase message or genes. These ribozymes can inhibit glucanase (or cellulase), e.g., endoglucanase, mannanase, xylanase, amylase, xanthanase and/or glycosidase, e.g., cellobiohydrolase, mannanase and/or beta-glucosidase activity by, e.g., targeting mRNA. Strategies for designing ribozymes and selecting the glucanase-, mannanase-, or xylanase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme can be a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) *Aids Research and Human Retroviruses* 8:183; hairpin motifs by Hampel (1989) *Biochemistry* 28:4929, and Hampel (1990) *Nuc. Acids Res.* 18:299; the hepatitis delta virus motif by Perrotta (1992) *Biochemistry* 31:16; the RNaseP motif by Guerrier-Takada (1983) *Cell* 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising a glucanase (or cellulase), e.g., endoglucanase, mannanase, xylanase, amylase, xanthanase and/or glycosidase, e.g., cellobiohydrolase, mannanase and/or beta-glucosidase sequence of the invention. The RNAi molecule comprises a double-stranded RNA (dsRNA) molecule. The RNAi can inhibit expression of a glucanase (or cellulase), e.g., endoglucanase, mannanase, xylanase, amylase, xanthanase and/or glycosidase, e.g., cellobiohydrolase, mannanase and/or beta-glucosidase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) *Drug Discov. Today* 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding a glucanase (or cellulase), e.g., endoglucanase, mannanase, xylanase, amylase, xanthanase and/or glycosidase, e.g., cellobiohydrolase, mannanase and/or beta-glucosidase. These methods can be repeated or used in various combinations to generate glucanases (or cellulases), e.g., endoglucanases, mannanases, xylanases, amylases, xanthanases and/or glycosidases, e.g., cellobiohydrolases, mannanases and/or beta-glucosidases having an altered or different activity or an altered or different stability from that of a glucanase (or cellulase), e.g., endoglucanase, mannanase, xylanase, amylase, xanthanase and/or glycosidase, e.g., cellobiohydrolase, mannanase and/or beta-glucosidase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

In one aspect, the term "variant" refers to polynucleotides or polypeptides of the invention modified at one or more base pairs, codons, introns, exons, or amino acid residues (respectively) yet still retain the biological activity of a glucanase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), and any combination thereof.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) *Proc. Natl. Acad. Sci. USA* 89:5467-5471; or, combinatorial multiple cassette mutagenesis, see, e.g., Crameri (1995) *Biotechniques* 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" *Tumor Targeting* 4:1-4; Ness (1999) *Nature Biotechnology* 17:893-896; Chang (1999) "Evolution of a cytokine using DNA family shuffling" *Nature Biotechnology* 17:793-797; Minshull (1999) "Protein evolution by molecular breeding" *Current Opinion in Chemical Biology* 3:284-290; Christians (1999) "Directed evolution of thymidine kinase for AZT phosphorylation using DNA family shuffling" *Nature Biotechnology* 17:259-264; Crameri (1998) "DNA shuffling of a family of genes from diverse species accelerates directed evolution" *Nature* 391:288-291; Crameri (1997) "Molecular evolution of an arsenate detoxification pathway by DNA shuffling," *Nature Biotechnology* 15:436-438; Zhang (1997) "Directed evolution of an effective fucosidase from a galactosidase by DNA shuffling and screening" *Proc. Natl. Acad. Sci. USA* 94:4504-4509; Patten et al. (1997) "Applications of DNA Shuffling to Pharmaceuticals and Vaccines" *Current Opinion in Biotechnology* 8:724-733; Crameri et al. (1996) "Construction and evolution of antibody-phage libraries by DNA shuffling" *Nature Medicine* 2:100-103; Gates et al. (1996) "Affinity selective isolation of ligands from peptide libraries through display on a lac repressor 'headpiece dimer'" *Journal of Molecular Biology* 255:373-386; Stemmer (1996) "Sexual PCR and Assembly PCR" In: *The Encyclopedia of Molecular Biology*. VCH Publishers, New York. pp. 447-457; Crameri and Stemmer (1995) "Combinatorial multiple cassette mutagenesis creates all the permutations of mutant and wildtype cassettes" *Bio Techniques* 18:194-195; Stemmer et al. (1995) "Single-step assembly of a gene and entire plasmid form large numbers of oligodeoxyribonucleotides" *Gene,* 164:49-53; Stemmer (1995) "The Evolution of Molecular Computation" *Science* 270:1510; Stemmer (1995) "Searching Sequence Space" *Bio/Technology* 13:549-553; Stemmer (1994) "Rapid evolution of a protein in vitro by DNA shuffling" *Nature* 370:389-391; and Stemmer (1994) "DNA shuffling by random fragmentation and reassembly: In vitro recombination for molecular evolution." *Proc. Natl. Acad. Sci. USA* 91:10747-10751.

Mutational methods of generating diversity include, for example, site-directed mutagenesis (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortie (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100 468-500 (1983); *Methods in Enzymol.* 154:329-350 (1987); Zoller (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100: 468-500; and Zoller (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor (1985) "The use of phosphorothioate-modified DNA in restriction enzyme reactions to prepare nicked DNA" *Nucl. Acids Res.* 13:8749-8764; Taylor (1985) "The rapid generation of oligonucleotide-directed mutations at high frequency using phosphorothioate-modified DNA" *Nucl. Acids Res.* 13:8765-8787 (1985); Nakamaye (1986) "Inhibition of restriction endonuclease Nci I cleavage by phosphorothioate groups and its application to oligonucleotide-directed mutagenesis" *Nucl. Acids Res.* 14:9679-9698; Sayers (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide" *Nucl. Acids Res.* 16:803-814); mutagenesis using gapped duplex DNA (Kramer et al. (1984) "The gapped duplex DNA approach to oligonucleotide-directed mutation construction" *Nucl. Acids Res.* 12:9441-9456; Kramer & Fritz (1987) "Oligonucleotide-directed construction of mutations via gapped duplex DNA" *Methods in Enzymol.* 154:350-367; Kramer (1988) "Improved enzymatic in vitro reactions in the gapped duplex DNA approach to oligonucleotide-directed construction of mutations" *Nucl. Acids Res.* 16:7207; and Fritz (1988) "Oligonucleotide-directed construction of mutations: a gapped duplex DNA procedure without enzymatic reactions in vitro" *Nucl. Acids Res.* 16:6987-6999).

Additional protocols that can be used to practice the methods of the invention, or to make compositions of the invention, include point mismatch repair (see, e.g., Kramer (1984) *Cell* 38:879-887), mutagenesis using repair-deficient host strains (see, e.g., Carter (1985) *Nucl. Acids Res.* 13:4431-4443; Carter (1987) *Methods in Enzymol.* 154:382-403), deletion mutagenesis (see, e.g., Eghtedarzadeh (1986) *Nucl. Acids Res.* 14:5115), restriction-selection and restriction-selection and restriction-purification (see, e.g., Wells (1986) *Phil. Trans. R. Soc. Lond. A* 317:415-423), mutagenesis by total gene synthesis (see, e.g., Nambiar (1984) *Science* 223:1299-1301; Sakamar (1988) *Nucl. Acids Res.* 14:6361-6372; Wells et al. (1985) *Gene* 34:315-323; Grundstrom (1985) *Nucl. Acids Res.* 13:3305-3316), double-strand break repair (see, e.g., Arnold (1993) *Current Opinion in Biotechnology* 4:450-455). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination"; U.S. Pat. No. 5,811,238 to Stemmer et al. (Sep. 22, 1998), "Methods for Generating Polynucleotides having Desired Characteristics by Iterative Selection and Recombination"; U.S. Pat. No. 5,830,721 to Stemmer et al. (Nov. 3, 1998), "DNA Mutagenesis by Random Fragmentation and Reassembly"; U.S. Pat. No. 5,834,252 to Stemmer et al. (Nov. 10, 1998), "End-Complementary Polymerase Reaction"; U.S. Pat. No. 5,837,458 to Minshull et al. (Nov. 17, 1998), "Methods and Compositions for Cellular and Metabolic Engineering"; WO 95/22625, Stemmer and Crameri, "Mutagenesis by Random Fragmentation and Reassembly"; WO 96/33207 by Stemmer and Lipschutz, "End Complementary Polymerase Chain Reaction"; WO 97/20078 by Stemmer and Crameri, "Methods for Generating Polynucleotides having Desired Characteristics by Iterative Selection and Recombination"; WO 97/35966 by Minshull and Stemmer, "Methods and Compositions for Cellular and Metabolic Engineering"; WO 99/41402 by Punnonen et al., "Targeting of Genetic Vaccine Vectors"; WO 99/41383 by Punnonen et al., "Antigen Library Immunization"; WO 99/41369 by Punnonen et al., "Genetic Vaccine Vector Engineering"; WO 99/41368 by Punnonen et al., "Optimization of Immunomodulatory Properties of Genetic Vaccines"; EP 752008 by Stemmer and Crameri, "DNA Mutagenesis by Random Fragmentation and Reassembly"; EP 0932670 by Stemmer, "Evolving Cellular DNA Uptake by Recursive Sequence Recombination"; WO 99/23107 by Stemmer et al., "Modification of Virus Tropism and Host Range by Viral Genome Shuffling"; WO 99/21979 by Apt et al., "Human Papillomavirus Vectors"; WO 98/31837 by del Cardayre et al., "Evolution of Whole Cells and Organisms by Recursive Sequence Recombination"; WO 98/27230 by Patten and Stemmer, "Methods and Compositions for Polypeptide Engineering"; WO 98/27230 by Stemmer et al., "Methods for Optimization of Gene Therapy by Recursive Sequence Shuffling and Selection"; WO 00/00632, "Methods for Generating Highly Diverse Libraries"; WO 00/09679, "Methods for Obtaining in Vitro Recombined Polynucleotide Sequence Banks and Resulting Sequences"; WO 98/42832 by Arnold et al., "Recombination of Polynucleotide Sequences Using Random or Defined Primers"; WO 99/29902 by Arnold et al., "Method for Creating Polynucleotide and Polypeptide Sequences"; WO 98/41653 by Vind, "An in Vitro Method for Construction of a DNA Library"; WO 98/41622 by Borchert et al., "Method for Constructing a Library Using DNA Shuffling"; and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g., "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., Gene Site Saturation Mutagenesis (GSSM), synthetic ligation reassembly (SLR), or a combination thereof are used to modify the nucleic acids of the invention to generate glucanases (or cellulases), e.g., endoglucanases, mannanases, xylanases, amylases, xanthanases and/or glycosidases, e.g., cellobiohydrolases, mannanases and/or beta-glucosidases with new or altered properties (e.g., activity under highly acidic or alkaline conditions, high or low temperatures, and the like). Polypeptides encoded by the modified nucleic acids can be screened for an activity before testing for glucan or other polysaccharide hydrolysis or other activity. Any testing modality or protocol can be used, e.g., using a capillary array platform. See, e.g., U.S. Pat. Nos. 6,361,974; 6,280,926; 5,939,250.

Saturation Mutagenesis or GSSM

The invention also provides methods for making new enzymes, or modifying sequences of the invention, using Gene Site Saturation mutagenesis or GSSM, as described herein, and also in U.S. Pat. Nos. 6,171,820 and 6,579,258.

In one aspect, codon primers containing a degenerate N,N,G/T sequence are used to introduce point mutations into a polynucleotide, e.g., a glucanase (or cellulase), e.g., endoglucanase, mannanase, xylanase, amylase, xanthanase and/or glycosidase, e.g., cellobiohydrolase, mannanase and/or beta-glucosidase or an antibody of the invention, so as to generate a set of progeny polypeptides in which a full range of single amino acid substitutions is represented at each amino acid position, e.g., an amino acid residue in an enzyme active site (catalytic domains (CDs)) or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e., a degenerate (N,N,G/T)n sequence. In another aspect, degenerate cassettes having less degeneracy than the N,N,G/T sequence are used. For example, it may be desirable in some instances to use (e.g., in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e., 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., glucanases (or cellulases), e.g., endoglucanases, mannanases, xylanases, amylases, xanthanases and/or glycosidases, e.g., cellobiohydrolases, mannanases and/or beta-glucosidases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g., cloned into a suitable host, e.g., E. coli host, using, e.g., an expression vector) and subjected to expression screening. When an individual progeny polypeptide is identified by screening to display a favorable change in property (when compared to the parental polypeptide, such as increased glucan hydrolysis activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined—6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

The invention also provides for the use of proprietary codon primers (containing a degenerate N,N,N sequence) to introduce point mutations into a polynucleotide, so as to generate a set of progeny polypeptides in which a full range of single amino acid substitutions is represented at each amino acid position (Gene Site Saturation Mutagenesis (GSSM)). The oligos used are comprised contiguously of a first homologous sequence, a degenerate N,N,N sequence and in one aspect but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,N cassette) is used for subjecting each original codon in a parental polynucleotide template to a full range of codon substitutions. In another aspect, at least two degenerate N,N,N cassettes are used—either in the same oligo or not, for subjecting at least two original codons in a parental polynucleotide template to a full range of codon substitutions. Thus, more than one N,N,N sequence can be contained in one oligo to introduce amino acid mutations at more than one site. This plurality of N,N,N sequences can be directly contiguous, or separated by one or more additional nucleotide sequence(s). In another aspect, oligos serviceable for introducing additions and deletions can be used either alone or in combination with the codons containing an N,N,N sequence, to introduce any combination or permutation of amino acid additions, deletions and/or substitutions.

In a particular exemplification, it is possible to simultaneously mutagenize two or more contiguous amino acid positions using an oligo that contains contiguous N,N,N triplets, i.e., a degenerate $(N,N,N)_n$ sequence.

In another aspect, the present invention provides for the use of degenerate cassettes having less degeneracy than the N,N,N sequence. For example, it may be desirable in some instances to use (e.g., in an oligo) a degenerate triplet sequence comprised of only one N, where the N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, N,N,G/T, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes and point mutations that cause the generation of stop codons and the corresponding expression of polypeptide fragments.

Thus, in one aspect of this invention, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid and each of two favorable changes) and 3 positions. Thus, there are 3×3×3 or 27 total possibilities, including 7 that were previously examined—6 single point mutations (i.e., 2 at each of three positions) and no change at any position.

Thus, in a non-limiting exemplification, this invention provides for the use of saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, the instant invention provides that mutagenesis can be use to replace each of any number of bases in a polynucleotide sequence, wherein the number of bases to be mutagenized is in one aspect every integer from 15 to 100,000. Thus, instead of mutagenizing every position along a molecule, one can subject every or a discrete number of bases (in one aspect a subset totaling from 15 to 100,000) to mutagenesis. In one aspect, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Exemplary cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In one aspect, saturation mutagenesis comprises mutagenizing a complete set of mutagenic cassettes (wherein each cassette is in one aspect about 1-500 bases in length) in defined polynucleotide sequence to be mutagenized (wherein the sequence to be mutagenized is in one aspect from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons and groupings of particular nucleotide cassettes.

Defined sequences to be mutagenized include a whole gene, pathway, cDNA, an entire open reading frame (ORF) and entire promoter, enhancer, repressor/transactivator, origin of replication, intron, operator, or any polynucleotide functional group. Generally, a "defined sequences" for this purpose may be any polynucleotide that a 15 base-polynucleotide sequence and polynucleotide sequences of lengths between 15 bases and 15,000 bases (this invention specifically names every integer in between). Considerations in choosing groupings of codons include types of amino acids encoded by a degenerate mutagenic cassette.

In one exemplification a grouping of mutations that can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19 and 20 amino acids at each position and a library of polypeptides encoded thereby.

Synthetic Ligation Reassembly (SLR)

The invention provides a non-stochastic gene modification system termed "synthetic ligation reassembly," or simply "SLR," a "directed evolution process," to generate polypeptides, e.g., glucanases (or cellulases), e.g., endoglucanases, mannanases, xylanases, amylases, xanthanases and/or glycosidases, e.g., cellobiohydrolases, mannanases and/or beta-glucosidases or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. Pat. Nos. 6,773,900; 6,740,506; 6,713,282; 6,635,449; 6,605,449; 6,537,776.

In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over $10^{100}$ different chimeras. SLR can be used to generate libraries comprised of over $10^{1000}$ different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g., T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are in one aspect shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more in one aspect a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e., the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g., one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated in one aspect comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e., the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In one aspect, the present invention provides a non-stochastic method termed synthetic gene reassembly, that is somewhat related to stochastic shuffling, save that the nucleic acid building blocks are not shuffled or concatenated or chimerized randomly, but rather are assembled non-stochastically.

The synthetic gene reassembly method does not depend on the presence of a high level of homology between polynucleotides to be shuffled. The invention can be used to non-stochastically generate libraries (or sets) of progeny molecules comprised of over $10^{100}$ different chimeras. Conceivably, synthetic gene reassembly can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one aspect of the invention, the annealed building pieces are treated with an enzyme, such as a ligase (e.g., T4 DNA ligase) to achieve covalent bonding of the building pieces.

In a another aspect, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e., chimerized or shuffled.

In one exemplification, the invention provides for the chimerization of a family of related genes and their encoded family of related products. In a particular exemplification, the encoded products are enzymes. The glucanases (or cellulases), e.g., endoglucanases, mannanases, xylanases, amylases, xanthanases and/or glycosidases, e.g., cellobiohydrolases, mannanases and/or beta-glucosidases of the present invention can be mutagenized in accordance with the methods described herein.

Thus according to one aspect of the invention, the sequences of a plurality of progenitor nucleic acid templates (e.g., polynucleotides of the invention) are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

A serviceable demarcation point can be an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates and in one aspect at almost all of the progenitor templates. Even more in one aspect still a serviceable demarcation point is an area of homology that is shared by all of the progenitor templates.

In a one aspect, the gene reassembly process is performed exhaustively in order to generate an exhaustive library. In other words, all possible ordered combinations of the nucleic acid building blocks are represented in the set of finalized chimeric nucleic acid molecules. At the same time, the assembly order (i.e., the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another aspect, the method provides that the gene reassembly process is performed systematically, for example to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant gene reassembly invention, the progeny molecules generated in one aspect comprise a library of finalized chimeric nucleic acid molecules having an overall assembly order that is chosen by design. In a particularly aspect, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one aspect, this polynucleotide is a gene, which may be a man-made gene. According to another aspect, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplification, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutagenesis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another aspect, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In one aspect, the recombination is facilitated by, or occurs at, areas of homology between the man-made, intron-containing gene and a nucleic acid, which serves as a recombination partner. In one aspect, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic gene reassembly method of the invention utilizes a plurality of nucleic acid building blocks, each of which in one aspect has two ligatable ends. The two ligatable ends on each nucleic acid building block may be two blunt ends (i.e., each having an overhang of zero nucleotides), or in one aspect one blunt end and one overhang, or more in one aspect still two overhangs.

A useful overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

In one aspect, a nucleic acid building block is generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Exemplary sizes for building block range from 1 base pair (not including any overhangs) to 100,000 base pairs (not including any overhangs). Other exemplary size ranges are also provided, which have lower limits of from 1 bp to 10,000 bp (including every integer value in between) and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one aspect, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another aspect, the two strands of a double-stranded nucleic acid building block are complementary at fewer than every nucleotide apart from any that form an overhang. Thus, according to this aspect, a double-stranded nucleic acid building block can be used to introduce codon degeneracy. In one aspect the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect the invention described herein is directed to the use of repeated cycles of reductive reassortment, recombination and selection which allow for the directed molecular evolution of highly complex linear sequences, such as DNA, RNA or proteins thorough recombination.

Optimized Directed Evolution System

The invention provides a non-stochastic gene modification system termed "optimized directed evolution system" to generate polypeptides, e.g., glucanases (or cellulases), e.g., endoglucanases, mannanases, xylanases, amylases, xanthanases and/or glycosidases, e.g., cellobiohydrolases, mannanases and/or beta-glucosidases or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. Alternatively protocols for practicing these methods of the invention can be found in U.S. Pat. Nos. 6,773,900; 6,740,506; 6,713,282; 6,635,449; 6,605,449; 6,537,776; 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a 1/3 chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide in one aspect includes a unique region of overlap so that mixing the oligonucleotides together results in a new variant that has each oligonucleotide fragment assembled in the correct order. See also U.S. Pat. Nos. 6,537,776; 6,605,449.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is in one aspect performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new glucanase (or cellulase), e.g., endoglucanase, mannanase, xylanase, amylase, xanthanase and/or glycosidase, e.g., cellobiohydrolase, mannanase and/or beta-glucosidase phenotype is identified, re-isolated, again modified, re-tested for activity. This process can be iteratively repeated until a desired phenotype is engineered. For example, an entire biochemical anabolic or catabolic pathway can be engineered into a cell, including, e.g., glucanase, mannanase, or xylanase activity.

Similarly, if it is determined that a particular oligonucleotide has no affect at all on the desired trait (e.g., a new glucanase (or cellulase), e.g., endoglucanase, mannanase, xylanase, amylase, xanthanase and/or glycosidase, e.g., cellobiohydrolase, mannanase and/or beta-glucosidase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, glucanases (or cellulases), e.g., endoglucanases, mannanases, xylanases, amylases, xanthanases and/or glycosidases, e.g., cellobiohydrolases, mannanases and/or beta-glucosidases and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another aspect, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology (e.g., SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257 and combinations thereof) into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, novel polynucleotides can be generated by the process of reductive reassortment. The method involves the generation of constructs containing consecutive sequences (original encoding sequences), their insertion into an appropriate vector and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences and results in the production of novel molecular species. Various treatments may be applied to enhance the rate of reassortment. These could include treatment with ultra-violet light, or DNA damaging chemicals and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
  a) Primers that include a poly-A head and poly-T tail which when made single-stranded would provide orientation can be utilized. This is accomplished by having the first few bases of the primers made from RNA and hence easily removed RNaseH.
  b) Primers that include unique restriction cleavage sites can be utilized. Multiple sites, a battery of unique sequences and repeated synthesis and ligation steps would be required.
  c) The inner few bases of the primer could be thiolated and an exonuclease used to produce properly tailed molecules.

The recovery of the re-assorted sequences relies on the identification of cloning vectors with a reduced repetitive index (RI). The re-assorted encoding sequences can then be recovered by amplification. The products are re-cloned and expressed. The recovery of cloning vectors with reduced RI can be affected by:
  1) The use of vectors only stably maintained when the construct is reduced in complexity.
  2) The physical recovery of shortened vectors by physical procedures. In this case, the cloning vector would be recovered using standard plasmid isolation procedures and size fractionated on either an agarose gel, or column with a low molecular weight cut off utilizing standard procedures.
  3) The recovery of vectors containing interrupted genes which can be selected when insert size decreases.
  4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are described. Each sequence encodes a protein with a distinct set of properties. Each of the sequences differs by a single or a few base pairs at a unique position in the sequence. The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalytic domain of an enzyme) with a predetermined macromolecule, such as for example a proteinaceous receptor, an oligosaccharide, virion, or other predetermined compound or structure.

The polypeptides that are identified from such libraries can be used for therapeutic, diagnostic, research and related purposes (e.g., catalysts, solutes for increasing osmolarity of an aqueous solution and the like) and/or can be subjected to one or more additional cycles of shuffling and/or selection.

In another aspect, it is envisioned that prior to or during recombination or reassortment, polynucleotides generated by the method of the invention can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N3-Adenine (See Sun and Hurley, (1992); an N-acetylated or deacetylated 4'-fluoro-4-aminobiphenyl adduct capable of inhibiting DNA synthesis (See, for example, van de Poll et al. (1992)); or a N-acetylated or deacetylated 4-aminobiphenyl adduct capable of inhibiting DNA synthesis (See also, van de Poll et al. (1992), pp. 751-758); trivalent chromium, a trivalent chromium salt, a polycyclic aromatic hydrocarbon (PAH) DNA adduct capable of inhibiting DNA replication, such as 7-bromomethyl-benz[a]anthracene ("BMA"), tris(2,3-dibromopropyl) phosphate ("Tris-BP"), 1,2-dibromo-3-chloropropane ("DBCP"), 2-bromoacrolein (2BA), benzo[a]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ") and N-hydroxy-2-amino-1-methyl-6-phenylimidazo[4,5-f]-pyridine ("N-hydroxy-PhIP"). Exemplary means for slowing or halting PCR amplification consist of UV light (+)-CC-1065 and (+)-CC-1065-(N3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

Producing Sequence Variants

The invention also provides additional methods for making sequence variants of the nucleic acid (e.g., glucanase (or cellulase), e.g., endoglucanase, mannanase, xylanase, amylase, xanthanase and/or glycosidase, e.g., cellobiohydrolase, mannanase and/or beta-glucosidase) sequences of the invention, including the exemplary sequences of the invention. The invention also provides additional methods for isolating glucanases (or cellulases), e.g., endoglucanases, mannanases, xylanases, amylases, xanthanases and/or glycosidases, e.g., cellobiohydrolases, mannanases and/or beta-glucosidases using the nucleic acids and polypeptides of the invention. In (or cellulases), e.g., endoglucanases, mannanases, xylanases, amylases, xanthanases and/or glycosidases, e.g., cellobiohydrolases, mannanases and/or beta-glucosidases (or cellulase), e.g., endoglucanase, mannanase, xylanase, amylase, xanthanase and/or glycosidase, e.g., cellobiohydrolase, mannanase and/or beta-glucosidase coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial, agricultural, research and medical applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al. (1989) *Technique* 1:11-15, and Caldwell, R. C. & Joyce G. F. (1992) *PCR Methods Applic.* 2:28-33. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids are evaluated.

Variants may also be created using oligonucleotide directed mutagenesis to generate site-specific mutations in any cloned DNA of interest. Oligonucleotide mutagenesis is described, e.g., in Reidhaar-Olson (1988) *Science* 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) *Proc. Natl. Acad. Sci. USA* 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/μl in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described in PCT Publication No. WO 91/16427, published Oct. 31, 1991, entitled "Methods for Phenotype Creation from Multiple Gene Populations".

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in Arkin, A. P. and Youvan, D. C. (1992) *PNAS, USA* 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in Delegrave, S, and Youvan, D. C. (1993) *Biotechnology Research* 11:1548-1552. Random and site-directed mutagenesis are described in Arnold, F. H. (1993) *Current Opinion in Biotechnology* 4:450-455.

In some aspects, the variants are created using shuffling procedures wherein portions of a plurality of nucleic acids which encode distinct polypeptides are fused together to create chimeric nucleic acid sequences which encode chimeric polypeptides as described in U.S. Pat. No. 5,965,408, filed Jul. 9, 1996, entitled, "Method of DNA Reassembly by Interrupting Synthesis" and U.S. Pat. No. 5,939,250, filed May 22, 1996, entitled, "Production of Enzymes Having Desired Activities by Mutagenesis."

The variants of the polypeptides of the invention may be variants in which one or more of the amino acid residues of the polypeptides of the sequences of the invention are substituted with a conserved or non-conserved amino acid residue (in one aspect a conserved amino acid residue) and such substituted amino acid residue may or may not be one encoded by the genetic code.

The invention provides alternative embodiments of the polypeptides of the invention (and the nucleic acids that encode them) comprising at least one conservative amino acid substitution, as discussed herein (e.g., conservative amino acid substitutions are those that substitute a given amino acid in a polypeptide by another amino acid of like characteristics). The invention provides polypeptides (and the nucleic acids that encode them) wherein any, some or all amino acids residues are substituted by another amino acid of like characteristics, e.g., a conservative amino acid substitution.

Conservative substitutions are those that substitute a given amino acid in a polypeptide by another amino acid of like characteristics. Conservative substitutions of the invention can comprise any one of the following replacements: an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. In alternative aspects, these conservative substitutions can also be synthetic equivalents of these amino acids.

In alternative aspects, variants are those in which one or more of the amino acid residues of a polypeptide of the invention comprises a substituent group. In alternative aspects, variants comprise polypeptides associated with another compound, such as a compound to increase the half-life of the polypeptide (for example, polyethylene glycol). Additional variants are those in which additional amino acids are fused to the polypeptide, such as a leader sequence, a secretory sequence, a proprotein sequence or a sequence which facilitates purification, enrichment, or stabilization of the polypeptide.

In some aspects, the fragments, derivatives and analogs retain the same biological function or activity as the polypeptides of the invention. In other aspects, the fragment, derivative, or analog includes a proprotein, such that the fragment, derivative, or analog can be activated by cleavage of the proprotein portion to produce an active polypeptide.

Optimizing Codons to Achieve High Levels of Protein Expression in Host Cells

The invention provides methods for modifying glucanase-, mannanase-, or xylanase-encoding nucleic acids to modify codon usage. In one aspect, the invention provides methods for modifying codons in a nucleic acid encoding a glucanase to increase or decrease its expression in a host cell. The invention also provides nucleic acids encoding a glucanase (or cellulase), e.g., endoglucanase, mannanase, xylanase, amylase, xanthanase and/or glycosidase, e.g., cellobiohydrolase, mannanase and/or beta-glucosidase modified to increase its expression in a host cell, glucanase (or cellulase), e.g., endoglucanase, mannanase, xylanase, amylase, xanthanase and/or glycosidase, e.g., cellobiohydrolase, mannanase and/or beta-glucosidase so modified, and methods of making the modified glucanase (or cellulase), e.g., endoglucanase, mannanase, xylanase, amylase, xanthanase and/or glycosidase, e.g., cellobiohydrolase, mannanase and/or beta-glucosidase. The method comprises identifying a "non-preferred" or a "less preferred" codon in glucanase-(or cellulase), e.g., endoglucanase, mannanase, xylanase, amylase, xanthanase and/or glycosidase, e.g., cellobiohydrolase, mannanase and/or beta-glucosidase encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli*; gram positive bacteria, such as *Streptomyces, Lactobacillus gasseri, Lactococcus lactis, Lactococcus cremoris, Bacillus* sp., *Bacillus subtilis, Bacillus cereus*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorphs, Aspergillus niger*, and mammalian cells and cell lines and insect cells and cell lines. Thus, the invention also includes nucleic acids and polypeptides optimized for expression in these organisms and species, e.g., the nucleic acids of the invention are codon-optimized for expression in a host cell, e.g., a *Pichia* sp., e.g., *P. pastoris*, a *Saccharomyces* sp., or a *Bacillus* sp., a *Streptomyces* sp., and the like.

For example, the codons of a nucleic acid encoding a polypeptide of the invention, e.g., a glucanase (or cellulase), e.g., endoglucanase, mannanase, xylanase, amylase, xanthanase and/or glycosidase, e.g., cellobiohydrolase, mannanase and/or beta-glucosidase, or a similar enzyme isolated from a bacterial cell, are modified such that the nucleic acid (encoding the enzyme) is optimally expressed in a bacterial cell different from the bacteria from which the enzyme (e.g., glucanase (or cellulase), e.g., endoglucanase, mannanase, xylanase, amylase, xanthanase and/or glycosidase, e.g., cellobiohydrolase, mannanase and/or beta-glucosidase) was derived, a yeast, a fungi, a plant cell, an insect cell or a mammalian cell. Methods for optimizing codons are well known in the art, see, e.g., U.S. Pat. No. 5,795,737; Baca (2000) *Int. J. Parasitol.* 30:113-118; Hale (1998) *Protein Expr. Pur* 12:185-188; Narum (2001) *Infect. Immun.* 69:7250-7253. See also Narum (2001) *Infect. Immun.* 69:7250-7253, describing optimizing codons in mouse systems; Outchkourov (2002) *Protein Expr. Pur* 24:18-24, describing optimizing codons in yeast; Feng (2000) *Biochemistry* 39:15399-15409, describing optimizing codons in *E. coli*; Humphreys (2000) *Protein Expr. Pur* 20:252-264, describing optimizing codon usage that affects secretion in *E. coli*; Gao (2004) *Biotechnol Prog.* 20:443-448, describing "UpGene", an application of a web-based DNA codon optimization algorithm.

Transgenic Non-Human Animals

The invention provides transgenic non-human animals comprising a nucleic acid, a polypeptide (e.g., a glucanase (or cellulase), e.g., endoglucanase, mannanase, xylanase, amylase, xanthanase and/or glycosidase, e.g., cellobiohydrolase, mannanase and/or beta-glucosidase), an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study glucanase (or cellulase), e.g., endoglucanase, mannanase, xylanase, amylase, xanthanase and/or glycosidase, e.g., cellobiohydrolase, mannanase and/or beta-glucosidase activity, or, as models to screen for agents that change the glucanase (or cellulase), e.g., endoglucanase, mannanase, xylanase, amylase, xanthanase and/or glycosidase, e.g., cellobiohydrolase, mannanase and/or beta-glucosidase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) *J. Immunol. Methods* 231:147-157, describing the production of recombinant proteins in the milk of transgenic dairy animals; Baguisi (1999) *Nat. Biotechnol.* 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing a glucanase (or cellulase), e.g., endoglucanase, mannanase, xylanase, amylase, xanthanase and/or glycosidase, e.g., cellobiohydrolase, mannanase and/or beta-glucosidase of the invention, or, a fusion protein comprising a glucanase (or cellulase), e.g., endoglucanase, mannanase, xylanase, amylase, xanthanase and/or glycosidase, e.g., cellobiohydrolase, mannanase and/or beta-glucosidase of the invention.

Transgenic Plants and Seeds

The invention provides transgenic plants and seeds comprising a nucleic acid, a polypeptide (e.g., a glucanase (or cellulase), e.g., endoglucanase, mannanase, xylanase, amylase, xanthanase and/or glycosidase, e.g., cellobiohydrolase, mannanase and/or beta-glucosidase), an expression cassette or vector or a transfected or transformed cell of the invention. The invention also provides plant products, e.g., oils, seeds, leaves, extracts and the like, comprising a nucleic acid and/or a polypeptide (e.g., a glucanase (or cellulase), e.g., endoglucanase, mannanase, xylanase, amylase, xanthanase and/or glycosidase, e.g., cellobiohydrolase, mannanase and/or beta-glucosidase) of the invention. The transgenic plant can be dicotyledonous (a dicot) or monocotyledonous (a monocot). The invention provides transgenic plants with a modified taste, solids content and/or texture, wherein that modification is generated by expressing at least one enzyme of the invention either constitutively or selectively in the transgenic plant (or seed, or fruit, etc.), as described, e.g., in U.S. Pat. Application No. 20060195940.

The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations. Introduction into the genome of a desired plant can be such that the enzyme is regulated by endogenous transcriptional or translational control elements. Transformation techniques for both monocotyledons and dicotyledons are well known in the art.

The nucleic acids of the invention can be used to confer desired traits on essentially any plant. Nucleic acids of the invention can be used to manipulate metabolic pathways of a plant in order to optimize or alter host's expression of glucanase (or cellulase), e.g., endoglucanase, mannanase, xylanase, amylase, xanthanase and/or glycosidase, e.g., cellobiohydrolase, mannanase and/or beta-glucosidase. They can change glucanase (or cellulase), e.g., endoglucanase, mannanase, xylanase, amylase, xanthanase and/or glycosidase, e.g., cellobiohydrolase, mannanase and/or beta-glucosidase activity in a plant. Alternatively, a glucanase (or cellulase), e.g., endoglucanase, mannanase, xylanase, amylase, xanthanase and/or glycosidase, e.g., cellobiohydrolase, mannanase and/or beta-glucosidase of the invention can be used in production of a transgenic plant to produce a compound not naturally produced by that plant. This can lower production costs or create a novel product. In one embodiment, the enzyme of the invention may be expressed in such a way that the enzyme will not come in contact with it's substrate until desired. For example, an enzyme of the invention may be targeted and retained in the endoplasmic reticulum of a plant cell. Retention of the enzyme, in the endoplasmic reticulum of the cell, will prevent the enzyme from coming in contact with its substrate. The enzyme and substrate may then be brought into contact through any means able to disrupt the subcellular architecture, such as, grinding, milling, heating, and the like. See, WO 98/11235, WO 2003/18766, and WO 2005/096704, all of which are hereby incorporated by reference.

Selectable marker genes can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. Selection markers used routinely in transformation, and that can be used to practice this invention, include the nptII gene, which confers resistance to kanamycin and related antibiotics (Messing & Vierra (1982) Gene 19: 259-268; Bevan et al. (1983) Nature 304:184-187), the bar gene, which confers resistance to the herbicide phosphinothricin (White et al. (1990) Nucl. Acids Res 18:1062; Spencer et al. (1990) Theor. Appl. Genet. 79:625-631), the hph gene, which confers resistance to the antibiotic hygromycin (Blochinger & Diggelmann, Mol Cell Biol 4:2929-2931), the dhfr gene, which confers resistance to methatrexate (Bourouis et al. (1983) EMBO J. 2(7):1099-1104), the EPSPS gene, which confers resistance to glyphosate (U.S. Pat. Nos. 4,940,935 and 5,188,642).

Alternatively, transgenic plant material can be identified through a positive selection system, such as, the system utilizing the mannose-6-phosphate isomerase gene, which provides the ability to metabolize mannose (U.S. Pat. Nos. 5,767,378 and 5,994,629).

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. One or more of the sequences of the invention may be combined with sequences that confer resistance to insect, disease, drought, increase yield, improve nutritional quality of the grain, improve ethanol yield and the like.

For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) *Plant Mol. Biol.* 33:989-999), see Porta (1996) "Use of viral replicons for the expression of genes in plants" *Mol. Biotechnol.* 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) *Science* 233:496-498; Fraley (1983) *Proc. Natl. Acad. Sci. USA* 80:4803 (1983); *Gene Transfer to Plants*, Potrykus, ed. (Springerlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) *Plant Mol. Biol.* 35:205-218. See also, e.g., Horsch (1984) *Science* 233:496; Fraley (1983) *Proc. Natl. Acad. Sci. USA* 80:4803; Thykjaer (1997) supra; Park (1996) *Plant Mol. Biol.* 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) *Ann. Rev. of Plant Phys.* 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., a glucanase (or cellulase), e.g., endoglucanase, mannanase, xylanase, amylase, xanthanase and/or glycosidase, e.g., cellobiohydrolase, mannanase and/or beta-glucosidase) of the invention. The desired effects can be passed to future plant generations by standard propagation means.

Any plant may be used for introduction of the nucleotide of interest, including, but not limited to, corn or maize (*Zea mays*), *Brassica* sp. (e.g., *B. napus, B. rapa, B. juncea*), particularly those *Brassica* species useful as sources of seed oil, such as canola, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables may include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals may include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), canna (*Cannaceae* spp.) and chrysanthemum. Conifers that may be employed, including, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants may include, but are not limited to, beans and peas. Beans may include guar, locust bean, fenugreek, soybean, garden beans, cowpea, mungbean, lima bean, fava bean, lentils, chickpea, etc. Legumes may include, but are not limited to, *Arachis*, e.g., peanuts, *Vicia*, e.g., crown vetch, hairy vetch, adzuki bean, mung bean, and chickpea, Lupinus, e.g., lupine, trifolium, Phaseolus, e.g., common bean and lima bean, Pisum, e.g., field bean, Melilotus, e.g., clover, Medicago, e.g., alfalfa, Lotus, e.g., trefoil, lens, e.g., lentil, and false indigo. Forage and turf grasses may include alfalfa, switchgrass (*Panicum virgatum*), *Miscanthus*, orchard grass, tall fescue, perennial ryegrass, creeping bent grass, and redtop.

Plants of particular interest may include crop plants and plants used to produce energy or fuel, for example, maize, alfalfa, sunflower, *Brassica*, soybean, cotton, safflower, peanut, sorghum, wheat, oat, rye, millet, barley, rice, conifers, grasses, e.g., switch grass and *Miscanthus*, legume crops, e.g., pea, bean and soybean, starchy tuber/roots, e.g., potato, sweet potato, cassava, taro, canna and sugar beet and the like.

In alternative embodiments, the nucleic acids of the invention are expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides transgenic plants to be used for producing large amounts of the polypeptides (e.g., a glucanase (or cellulase), e.g., endoglucanase, mannanase, xylanase, amylase, xanthanase and/or glycosidase, e.g., cellobiohydrolase, mannanase and/or beta-glucosidase or antibody) of the invention. For example, see Palmgren (1997) *Trends Genet*. 13:348; Chong (1997) *Transgenic Res*. 6:289-296 (producing human milk protein beta-casein in transgenic potato plants using an auxin-inducible, bidirectional mannopine synthase (mas1',2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated, synthetic or recombinant polypeptides and peptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., proteins having the sequence of SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, and the specific modifications to SEQ ID NO:2 as described herein. Exemplary polypeptide or peptide sequences of the invention include SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, subsequences thereof and variants thereof, wherein in one aspect exemplary polypeptide sequences of the invention comprise, or alternatively—consist of, one, two, three, four, five, six, seven, eight, nine, ten, eleven (11), twelve (12), 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 or more or all of the following amino acid residue changes to SEQ ID NO:2:

the glycine at amino acid position 2 is asparagine,
the glycine at amino acid position 13 is asparagine,
the phenylalanine at amino acid position 38 is tyrosine,
the serine at amino acid position 57 is aspartic acid,
the tyrosine at amino acid position 61 is glutamine,
the tyrosine at amino acid position 61 is serine,
the alanine at amino acid position 62 is threonine,
the phenylalanine at amino acid position 63 is histidine,
the phenylalanine at amino acid position 63 is threonine,
the methionine at amino acid position 69 is glutamic acid,
the methionine at amino acid position 69 is glutamine,
the methionine at amino acid position 69 is histidine,
the methionine at amino acid position 69 is serine,
the methionine at amino acid position 69 is tyrosine,
the aspartic acid at amino acid position 70 is proline,
the arginine at amino acid position 71 is alanine,
the arginine at amino acid position 71 is glutamic acid,
the arginine at amino acid position 71 is glutamine,
the arginine at amino acid position 71 is proline,
the arginine at amino acid position 71 is serine,
the arginine at amino acid position 71 is threonine,
the lysine at amino acid position 74 is glutamic acid,
the lysine at amino acid position 74 is leucine,
the lysine at amino acid position 74 is methionine,
the isoleucine at amino acid position 94 is glutamine,
the methionine at amino acid position 101 is tyrosine,
the aspartic acid at amino acid position 103 is cysteine,
the aspartic acid at amino acid position 103 is glutamine,
the glutamic acid at amino acid position 106 is glycine,
the glutamic acid at amino acid position 109 is leucine,
the lysine at amino acid position 116 is alanine,
the lysine at amino acid position 116 is arginine,
the phenylalanine at amino acid position 130 is tyrosine,
the phenylalanine at amino acid position 131 is leucine,
the glutamic acid at amino acid position 148 is histidine,
the lysine at amino acid position 162 is glutamine,
the isoleucine at amino acid position 166 is alanine,
the isoleucine at amino acid position 166 is valine,
the serine at amino acid position 183 is arginine,
the serine at amino acid position 183 is valine, the lysine at amino acid position 186 is alanine,
the lysine at amino acid position 186 is aspartic acid,
the lysine at amino acid position 186 is proline,
the lysine at amino acid position 186 is serine,
the serine at amino acid position 191 is alanine,
the serine at amino acid position 191 is cysteine,
the serine at amino acid position 191 is leucine,
the phenylalanine at amino acid position 201 is isoleucine,
the phenylalanine at amino acid position 201 is proline,
the phenylalanine at amino acid position 201 is valine,
the glutamic acid at amino acid position 212 is proline,
the lysine at amino acid position 216 is alanine,
the histidine at amino acid position 230 is arginine,
the histidine at amino acid position 230 is glutamine,
the histidine at amino acid position 230 is lysine,
the leucine at amino acid position 231 is isoleucine,
the leucine at amino acid position 231 is methionine,
the leucine at amino acid position 231 is valine,
the glutamic acid at amino acid position 234 is aspartic acid,
the lysine at amino acid position 246 is glutamine,
the lysine at amino acid position 246 is serine,
the arginine at amino acid position 258 is serine,
the arginine at amino acid position 258 is tyrosine,
the leucine at amino acid position 262 is glutamine,
the leucine at amino acid position 262 is histidine,
the leucine at amino acid position 262 is methionine,
the leucine at amino acid position 262 is proline,
the serine at amino acid position 270 is arginine,
the phenylalanine at amino acid position 271 is alanine,
the methionine at amino acid position 276 is alanine,
the methionine at amino acid position 276 is cysteine,
the methionine at amino acid position 276 is serine,
the glutamic acid at amino acid position 277 is serine,
the arginine at amino acid position 280 is glycine,
the serine at amino acid position 290 is alanine,
the threonine at amino acid position 297 is alanine,
the threonine at amino acid position 297 is proline,
the leucine at amino acid position 298 is alanine,
the leucine at amino acid position 298 is arginine,
the leucine at amino acid position 298 is asparagine,
the leucine at amino acid position 298 is serine,
the leucine at amino acid position 298 is valine,
the lysine at amino acid position 300 is glycine,
the threonine at amino acid position 301 is glutamine,
the aspartic acid at amino acid position 305 is proline,
the glycine at amino acid position 312 is isoleucine, and/or
the serine at amino acid position 315 is isoleucine.

All of these sequences are exemplary amino acid sequences of the invention having specific residue changes to the "parent" SEQ ID NO:2, summarized (in part) in Table 1, above, and Table 2, in Example 5, below.

In one aspect, the polypeptide has a glucanase (or cellulase), e.g., endoglucanase, mannanase, xylanase, amylase, xanthanase and/or glycosidase, e.g., cellobiohydrolase, mannanase and/or beta-glucosidase activity, e.g., can hydrolyze a glycosidic bond in a polysaccharide, e.g., a glucan. In one aspect, the polypeptide has a glucanase activity comprising catalyzing hydrolysis of 1,4-beta-D-glycosidic linkages or β-1,3-glucosidic linkages. In one aspect, the endoglucanase activity comprises an endo-1,4-beta-endoglucanase activity. In one aspect, the endoglucanase activity comprises hydrolyzing a glucan, a mannan, an arabinoxylan or a xylan, to produce a smaller molecular weight glucan or glucan-oligomer. In one aspect, the glucan comprises a beta-glucan, such as a water soluble beta-glucan.

Enzymes encoded by the polynucleotides of the invention include, but are not limited to hydrolases such as glucanases, e.g., endoglucanases (or cellulases), e.g., endoglucanases, mannanases, xylanases, amylases, xanthanases and/or glycosidases, e.g., cellobiohydrolases, mannanases and/or beta-glucosidases. In one aspect, an enzyme of the invention can also have a mannanase activity, e.g., it can degrade (or hydrolyze) mannans. Mannan containing polysaccharides are a major component of the hemicellulose fraction in both hardwoods and softwoods as well as in the endosperm in many leguminous seeds and in some mature seeds of non-leguminous plants. In one aspect, a mannanase of the invention hydrolyses beta-1,4 linkages in mannans, glucomannans, galactomannans and galactoglucomannans (mannans are polysaccharides having a backbone composed of beta-1,4 linked mannose, glucomannans are polysaccharides having a backbone of more or less regularly alternating beta.-1,4 linked mannose and glucose). Assays to determine mannanase activity are well known in the art, see, e.g., U.S. Patent Application Nos. 20030215812; 20030119093; U.S. Pat. Nos. 5,661,021; 5,795,764; 6,376,445; 6,420,331. Assays to determine xylanase activity are well known in the art, see, e.g., U.S. Pat. Nos. 5,693,518; 5,885,819; 6,200,797; 6,586,209; 6,682,923.

"Amino acid" or "amino acid sequence" as used herein refer to an oligopeptide, peptide, polypeptide, or protein sequence, or to a fragment, portion, or subunit of any of these and to naturally occurring or synthetic molecules. "Amino acid" or "amino acid sequence" include an oligopeptide, peptide, polypeptide, or protein sequence, or to a fragment, portion, or subunit of any of these, and to naturally occurring or synthetic molecules. The term "polypeptide" as used herein, refers to amino acids joined to each other by peptide bonds or modified peptide bonds, i.e., peptide isosteres and may contain modified amino acids other than the 20 gene-encoded amino acids. The polypeptides may be modified by either natural processes, such as post-translational processing, or by chemical modification techniques which are well known in the art. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, glucan hydrolase processing, phosphorylation, prenylation, racemization, selenoylation, sulfation and transfer-RNA mediated addition of amino acids to protein such as arginylation. (See Creighton, T. E., *Proteins—Structure and Molecular Properties* 2nd Ed., W.H. Freeman and Company, New York (1993); *Posttranslational Covalent Modification of Proteins*, B. C. Johnson, Ed., Academic Press, New York, pp. 1-12 (1983)). The peptides and polypeptides of the invention also include all "mimetic" and "peptidomimetic" forms, as described in further detail, below.

"Fragments" as used herein are a portion of a naturally occurring protein which can exist in at least two different conformations. Fragments can have the same or substantially the same amino acid sequence as the naturally occurring protein. "Substantially the same" means that an amino acid sequence is largely, but not entirely, the same, but retains at least one functional activity of the sequence to which it is related, e.g., only has conservative amino acids substitutions, as described herein. Fragments which have different three dimensional structures as the naturally occurring protein are also included. An example of this is a "pro-form" molecule, such as a low activity proprotein, that can be modified by cleavage to produce a mature enzyme with significantly higher activity.

As used herein, the term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment. As used herein, the term "purified" does not require absolute purity; rather, it is intended as a relative definition. Individual nucleic acids obtained from a library have been conventionally purified to electrophoretic homogeneity. The sequences obtained from these clones could not be obtained directly either from the library or from total human DNA. The purified nucleic acids of the invention have been purified from the remainder of the genomic DNA in the organism by at least $10^4$-$10^6$ fold. However, the term "purified" also includes nucleic acids which have been purified from the remainder of the genomic DNA or from other sequences in a library or other environment by at least one order of magnitude, typically two or three orders and more typically four or five orders of magnitude.

"Recombinant" polypeptides or proteins refer to polypeptides or proteins produced by recombinant DNA techniques; i.e., produced from cells transformed by an exogenous DNA construct encoding the desired polypeptide or protein. "Synthetic" polypeptides or protein are those prepared by chemical synthesis. Solid-phase chemical peptide synthesis methods can also be used to synthesize the polypeptide or fragments of the invention. Such method have been known in the art since the early 1960's (Merrifield, R. B. (1963) *J. Am. Chem. Soc.* 85:2149-2154) (See also Stewart, J. M. and Young, J. D., *Solid Phase Peptide Synthesis, 2nd Ed.*, Pierce Chemical Co., Rockford, Ill., pp. 11-12)) and have recently been employed in commercially available laboratory peptide design and synthesis kits (Cambridge Research Biochemicals). Commercially available laboratory kits have generally utilized the teachings of H. M. Geysen et al. (1984) *Proc. Natl. Acad. Sci., USA,* 81:3998 and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A automated peptide synthesizer. Such equipment provides ready access to the peptides of the invention, either by direct synthesis or by synthesis of a series of fragments that can be coupled using other known techniques.

The invention provides glucanases having a common novelty in that they were first derived from similar "glycosidase hydrolase" families. Glycosidase hydrolases were first classified into families in 1991, see, e.g., Henrissat (1991) *Biochem. J.* 280:309-316. Since then, the classifications have been continually updated, see, e.g., Henrissat (1993) *Biochem. J.* 293:781-788; Henrissat (1996) *Biochem. J.* 316:695-696; Henrissat (2000) *Plant Physiology* 124: 1515-1519. There are approximately 87 identified families of glycosidase hydrolases. Glucanases of the invention can be categorized as families, see, e.g., Strohmeier (2004) *Protein Sci.* 13:3200-3213.

The polypeptides of the invention include glucanases (or cellulases), e.g., endoglucanases, mannanases, xylanases, amylases, xanthanases and/or glycosidases, e.g., cellobiohydrolases, mannanases and/or beta-glucosidases in an active or inactive form. For example, the polypeptides of the invention include proproteins before "maturation" or processing of prepro sequences, e.g., by a proprotein-processing enzyme, such as a proprotein convertase to generate an "active" mature protein. The polypeptides of the invention include glucanases (or cellulases), e.g., endoglucanases, mannanases, xylanases, amylases, xanthanases and/or glycosidases, e.g., cellobiohydrolases, mannanases and/or beta-glucosidases inactive for other reasons, e.g., before "activation" by a post-translational processing event, e.g., an endo- or exo-peptidase or proteinase action, a phosphorylation event, an amidation, a glycosylation or a sulfation, a dimerization event, and the like. The polypeptides of the invention include all active forms, including active subsequences, e.g., catalytic domains or active sites, of the glucanase (or cellulase), e.g., endoglucanase, mannanase, xylanase, amylase, xanthanase and/or glycosidase, e.g., cellobiohydrolase, mannanase and/or beta-glucosidases. Methods for identifying "prepro" domain sequences and signal sequences are well known in the art, see, e.g., Van de Ven (1993) *Crit. Rev. Oncog.* 4(2):115-136. For example, to identify a prepro sequence, the protein is purified from the extracellular space and the N-terminal protein sequence is determined and compared to the unprocessed form.

As noted above, the invention provides isolated, synthetic or recombinant polypeptides and peptides having a sequence identity to an exemplary sequence of the invention, e.g., proteins having the sequence of SEQ ID NO:2, SEQ ID NO:7, SEQ ID NO:9, SEQ ID NO:11, SEQ ID NO:13, SEQ ID NO:19, SEQ ID NO:21, AND SEQ ID NO:23, and the specific modifications to SEQ ID NO:2 as described herein, where in various aspects the percent sequence identity can be over the full length of the polypeptide, or, the identity can be over a region of at least about 10, 20, 30, 40, 50, 60, 70, 80, 90, 100, 150, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 residues and the full length of a polypeptide, e.g., an enzyme, such as a glucanase (or cellulase), e.g., endoglucanase, mannanase, xylanase, amylase, xanthanase and/or glycosidase, e.g., cellobiohydrolase, mannanase and/or beta-glucosidase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary glucanase (or cellulase), e.g., endoglucanase, mannanase, xylanase, amylase, xanthanase and/or glycosidase, e.g., cellobiohydrolase, mannanase and/or beta-glucosidase of the invention.

Peptides of the invention (e.g., a subsequence of an exemplary polypeptide of the invention) can be useful as, e.g., labeling probes, antigens, epitopes, toleragens, motifs, glucanase (or cellulase), e.g., endoglucanase, mannanase, xylanase, amylase, xanthanase and/or glycosidase, e.g., cellobiohydrolase, mannanase and/or beta-glucosidase active sites (e.g., "catalytic domains"), signal sequences and/or prepro domains. Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) *Nucleic Acids Res. Symp. Ser.* 215-223; Horn (1980) *Nucleic Acids Res. Symp. Ser.* 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a glucanase (or cellulase), e.g., endoglucanase, mannanase, xylanase, amylase, xanthanase and/or glycosidase, e.g., cellobiohydrolase, mannanase and/or beta-glucosidase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N=C=N—R') such as, e.g., 1-cyclohexyl-3 (2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, in one aspect under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc.), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960s (Merrifield, R. B. (1963) J. Am. Chem. Soc. 85:2149-2154) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al. (1984) Proc. Natl. Acad. Sci., USA 81:3998 and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention includes glucanases (or cellulases), e.g., endoglucanases, mannanases, xylanases, amylases, xanthanases and/or glycosidases, e.g., cellobiohydrolases, mannanases and/or beta-glucosidases of the invention with and without signal. The polypeptide comprising a signal sequence of the invention can be a glucanase of the invention or another glucanase or another enzyme or other polypeptide.

The invention includes immobilized glucanases (or cellulases), e.g., endoglucanases, mannanases, xylanases, amylases, xanthanases and/or glycosidases, e.g., cellobiohydrolases, mannanases and/or beta-glucosidases, anti-glucanase, -mannanase, or -xylanase antibodies and fragments thereof. The invention provides methods for inhibiting glucanase (or cellulase), e.g., endoglucanase, mannanase, xylanase, amylase, xanthanase and/or glycosidase, e.g., cellobiohydrolase, mannanase and/or beta-glucosidase activity, e.g., using dominant negative mutants or anti-glucanase, -mannanase, or -xylanase antibodies of the invention. The invention includes heterocomplexes, e.g., fusion proteins, heterodimers, etc., comprising the glucanases of the invention.

Polypeptides of the invention can have a glucanase (or cellulases), e.g., endoglucanases, mannanases, xylanases, amylases, xanthanases and/or glycosidases, e.g., cellobiohydrolases, mannanases and/or beta-glucosidases activity under various conditions, e.g., extremes in pH and/or temperature, oxidizing agents, and the like. The invention provides methods leading to alternative glucanase (or cellulase), e.g., endoglucanase, mannanase, xylanase, amylase, xanthanase and/or glycosidase, e.g., cellobiohydrolase, mannanase and/or beta-glucosidase preparations with different catalytic efficiencies and stabilities, e.g., towards temperature, oxidizing agents and changing wash conditions. In one aspect, glucanase (or cellulase), e.g., endoglucanase, mannanase, xylanase, amylase, xanthanase and/or glycosidase, e.g., cellobiohydrolase, mannanase and/or beta-glucosidase variants can be produced using techniques of site-directed mutagenesis and/or random mutagenesis. In one aspect, directed evolution can be used to produce a great variety of glucanase (or cellulase), e.g., endoglucanase, mannanase, xylanase, amylase, xanthanase and/or glycosidase, e.g., cellobiohydrolase, mannanase and/or beta-glucosidase variants with alternative specificities and stability.

The proteins of the invention are also useful as research reagents to identify glucanase (or cellulase), e.g., endoglucanase, mannanase, xylanase, amylase, xanthanase and/or glycosidase, e.g., cellobiohydrolase, mannanase and/or beta-glucosidase modulators, e.g., activators or inhibitors of glucanase (or cellulase), e.g., endoglucanase, mannanase, xylanase, amylase, xanthanase and/or glycosidase, e.g., cellobiohydrolase, mannanase and/or beta-glucosidase activity. Briefly, test samples (compounds, broths, extracts, and the like) are added to glucanase (or cellulase), e.g., endoglucanase, mannanase, xylanase, amylase, xanthanase and/or glycosidase, e.g., cellobiohydrolase, mannanase and/or beta-glucosidase assays to determine their ability to inhibit substrate cleavage Inhibitors identified in this way can be used in industry and research to reduce or prevent undesired proteolysis. Glucanase (or cellulase), e.g., endoglucanase, mannanase, xylanase, amylase, xanthanase and/or glycosidase, e.g., cellobiohydrolase, mannanase and/or beta-glucosidase inhibitors can be combined to increase the spectrum of activity.

The enzymes of the invention are also useful as research reagents to digest proteins or in protein sequencing. For example, a glucanase (or cellulase), e.g., endoglucanase, mannanase, xylanase, amylase, xanthanase and/or glycosidase, e.g., cellobiohydrolase, mannanase and/or beta-glucosidase may be used to break polypeptides into smaller fragments for sequencing using, e.g., an automated sequencer.

The invention also provides methods of discovering a new glucanase (or cellulase), e.g., endoglucanase, mannanase, xylanase, amylase, xanthanase and/or glycosidase, e.g., cellobiohydrolase, mannanase and/or beta-glucosidase using the nucleic acids, polypeptides and antibodies of the invention. In one aspect, phagemid libraries are screened for expression-based discovery of a glucanase (or cellulase), e.g., endoglucanase, mannanase, xylanase, amylase, xanthanase and/or glycosidase, e.g., cellobiohydrolase, mannanase and/or beta-glucosidase. In another aspect, lambda phage libraries are screened for expression-based discovery of a glucanase (or cellulase), e.g., endoglucanase, mannanase, xylanase, amylase, xanthanase and/or glycosidase, e.g., cellobiohydrolase, mannanase and/or beta-glucosidase. Screening of the phage or phagemid libraries can allow the detection of toxic clones; improved access to substrate; reduced need for engineering a host, by-passing the potential for any bias resulting from mass excision of the library; and, faster growth at low clone densities. Screening of phage or phagemid libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

Another aspect of the invention is an isolated or purified polypeptide comprising the sequence of one of the invention, or fragments comprising at least about 5, 10, 15, 20, 25, 30, 35, 40, 50, 75, 100, or 150 consecutive amino acids thereof. As discussed above, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for amplifying expression.

Another aspect of the invention is polypeptides or fragments thereof which have at least about 50%, at least about 55%, at least about 60%, at least about 65%, at least about 70%, at least about 75%, at least about 80%, at least about 85%, at least about 90%, at least about 95%, or more than about 95% sequence identity (homology) to one of the polypeptides of the invention, or a fragment comprising at least 5, 10, 15, 20, 25, 30, 35, 40, 50, 75, 100, or 150 or more consecutive amino acids thereof. Sequence identity (homology) may be determined using any of the programs described above which aligns the polypeptides or fragments being compared and determines the extent of amino acid identity or similarity between them. It will be appreciated that amino acid equivalence, or sequence identity, or "homology," includes conservative amino acid substitutions such as those described above.

The polypeptides or fragments having homology to one of the polypeptides of the invention, or a fragment comprising at least about 5, 10, 15, 20, 25, 30, 35, 40, 50, 75, 100, or 150 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by glucan hydrolase digestion, gel electrophoresis and/or microsequencing. The sequence of the prospective homologous polypeptide or fragment can be compared to one of the polypeptides of the invention, or a fragment comprising at least about 5, 10, 15, 20, 25, 30, 35, 40, 50, 75, 100, or 150 consecutive amino acids thereof using any of the programs described above.

Another aspect of the invention is an assay for identifying fragments or variants of the invention, which retain the enzymatic function of the polypeptides of the invention. For example the fragments or variants of said polypeptides, may be used to catalyze biochemical reactions, which indicate that the fragment or variant retains the enzymatic activity of a polypeptide of the invention.

The assay for determining if fragments of variants retain the enzymatic activity of the polypeptides of the invention includes the steps of: contacting the polypeptide fragment or variant with a substrate molecule under conditions which allow the polypeptide fragment or variant to function and detecting either a decrease in the level of substrate or an increase in the level of the specific reaction product of the reaction between the polypeptide and substrate.

The polypeptides of the invention or fragments comprising at least 5, 10, 15, 20, 25, 30, 35, 40, 50, 75, 100, or 150 consecutive amino acids thereof may be used in a variety of applications. For example, the polypeptides or fragments thereof may be used to catalyze biochemical reactions. In accordance with one aspect of the invention, there is provided a process for utilizing the polypeptides of the invention or polynucleotides encoding such polypeptides for hydrolyzing glycosidic linkages. In such procedures, a substance containing a glycosidic linkage (e.g., a starch) is contacted with one of the polypeptides of the invention, or sequences substantially identical thereto under conditions which facilitate the hydrolysis of the glycosidic linkage.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds, such as small molecules. Each biocatalyst is specific for one functional group, or several related functional groups and can react with many starting compounds containing this functional group.

The biocatalytic reactions produce a population of derivatives from a single starting compound. These derivatives can be subjected to another round of biocatalytic reactions to produce a second population of derivative compounds. Thousands of variations of the original small molecule or compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods.

In a particular aspect, the invention provides a method for modifying small molecules, comprising contacting a polypeptide encoded by a polynucleotide described herein or enzymatically active fragments thereof with a small molecule to produce a modified small molecule. A library of modified small molecules is tested to determine if a modified small molecule is present within the library which exhibits a desired activity. A specific biocatalytic reaction which produces the modified small molecule of desired activity is identified by systematically eliminating each of the biocatalytic reactions used to produce a portion of the library and then testing the small molecules produced in the portion of the library for the presence or absence of the modified small molecule with the desired activity. The specific biocatalytic reactions which produce the modified small molecule of desired activity is optionally repeated. The biocatalytic reactions are conducted with a group of biocatalysts that react with distinct structural moieties found within the structure of a small molecule, each biocatalyst is specific for one structural moiety or a group of related structural moieties; and each biocatalyst reacts with many different small molecules which contain the distinct structural moiety.

Signal Sequences, Prepro and Catalytic Domains

The invention provides glucanase (or cellulase), e.g., endoglucanase, mannanase, xylanase, amylase, xanthanase and/or glycosidase, e.g., cellobiohydrolase, mannanase and/or beta-glucosidase signal sequences (e.g., signal peptides (SPs)), prepro domains and catalytic domains (CDs) (e.g., active sites). A "signal sequence" can be a secretion signal or other domain that facilitates secretion of a polypeptide of the invention from the host cell. The SPs, prepro domains and/or CDs of the invention can be isolated or recombinant peptides or can be part of a fusion protein, e.g., as a heterologous domain in a chimeric protein. The invention provides nucleic acids encoding these catalytic domains (CDs), prepro domains and signal (leader) sequences (SPs, e.g., a peptide having a sequence comprising/consisting of amino terminal residues of a polypeptide of the invention). In one aspect, the invention provides a signal (leader) sequence comprising a peptide comprising/consisting of a sequence as set forth in residues 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 28, 1 to 30, 1 to 31, 1 to 32, 1 to 33, 1 to 34, 1 to 35, 1 to 36, 1 to 37, 1 to 38, 1 to 39, 1 to 40, 1 to 41, 1 to 42, 1 to 43, 1 to 44 of a polypeptide of the invention.

The invention also provides chimeric polypeptides (and the nucleic acids encoding them) comprising at least two enzymes of the invention or subsequences thereof, e.g., active sites, or catalytic domains (CDs). A chimeric protein of the invention (e.g., a fusion protein, or, other heterodimer, e.g., two domains joined by other means, e.g., a linker, or, electrostatically) can comprise one polypeptide (e.g., active site or catalytic domain peptide) of the invention and another polypeptide (e.g., active site or catalytic domain peptide) of the invention or other polypeptide. For example, a chimeric protein of the invention can have mannanase and xylanase activity, mannanase and glycanase activity, etc. In one aspect the chimeric protein of the invention comprises a fusion of domains, e.g., a single domain can exhibit glucanase/xylanase/mannanase or any combination of activities (e.g., as a recombinant chimeric protein).

The invention includes polypeptides with or without a signal sequence and/or a prepro sequence. The invention includes polypeptides with heterologous signal sequences and/or prepro sequences. The prepro sequence (including a sequence of the invention used as a heterologous prepro domain) can be located on the amino terminal or the carboxy terminal end of the protein. The invention also includes isolated or recombinant signal sequences, prepro sequences and catalytic domains (e.g., "active sites") comprising sequences of the invention.

The glucanase (or cellulase), e.g., endoglucanase, mannanase, xylanase, amylase, xanthanase and/or glycosidase, e.g., cellobiohydrolase, mannanase and/or beta-glucosidase signal sequences (SPs) and/or prepro sequences of the invention can be isolated peptides, or, sequences joined to another glucanase (or cellulase), e.g., endoglucanase, mannanase, xylanase, amylase, xanthanase and/or glycosidase, e.g., cellobiohydrolase, mannanase and/or beta-glucosidase or a non-glucanase (or cellulase), e.g., endoglucanase, mannanase, xylanase, amylase, xanthanase and/or glycosidase, e.g., cellobiohydrolase, mannanase and/or beta-glucosidase polypeptide, e.g., as a fusion (chimeric) protein. In one aspect, the invention provides polypeptides comprising glucanase (or cellulase), e.g., endoglucanase, mannanase, xylanase, amylase, xanthanase and/or glycosidase, e.g., cellobiohydrolase, mannanase and/or beta-glucosidase signal sequences of the invention. In one aspect, polypeptides comprising glucanase (or cellulase), e.g., endoglucanase, mannanase, xylanase, amylase, xanthanase and/or glycosidase, e.g., cellobiohydrolase, mannanase and/or beta-glucosidase signal sequences SPs and/or prepro of the invention comprise sequences heterologous to a glucanase (or cellulase), e.g., endoglucanase, mannanase, xylanase, amylase, xanthanase and/or glycosidase, e.g., cellobiohydrolase, mannanase and/or beta-glucosidase of the invention (e.g., a fusion protein comprising an SP and/or prepro of the invention and sequences from another glucanase or a non-glucanase protein). In one aspect, the invention provides a glucanase (or cellulase), e.g., endoglucanase, mannanase, xylanase, amylase, xanthanase and/or glycosidase, e.g., cellobiohydrolase, mannanase and/or beta-glucosidase of the invention with heterologous SPs and/or prepro sequences, e.g., sequences with a yeast signal sequence. A glucanase (or cellulase), e.g., endoglucanase, mannanase, xylanase, amylase, xanthanase and/or glycosidase, e.g., cellobiohydrolase, mannanase and/or beta-glucosidase of the invention can comprise a heterologous SP and/or prepro in a vector, e.g., a pPIC series vector (Invitrogen, Carlsbad, Calif.).

In one aspect, SPs and/or prepro sequences of the invention are identified following identification of novel glucanase (or cellulase), e.g., endoglucanase, mannanase, xylanase, amylase, xanthanase and/or glycosidase, e.g., cellobiohydrolase, mannanase and/or beta-glucosidase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from 13 to 36 amino acid residues. Various methods of recognition of signal sequences are known to those of skill in the art. For example, in one aspect, novel glucanase (or cellulase), e.g., endoglucanase, mannanase, xylanase, amylase, xanthanase and/or glycosidase, e.g., cellobiohydrolase, mannanase and/or beta-glucosidase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects a glucanase (or cellulase), e.g., endoglucanase, mannanase, xylanase, amylase, xanthanase and/or glycosidase, e.g., cellobiohydrolase, mannanase and/or beta-glucosidase of the invention may not have SPs and/or prepro sequences, or "domains." In one aspect, the invention provides a glucanase (or cellulase), e.g., endoglucanase, mannanase, xylanase, amylase, xanthanase and/or glycosidase, e.g., cellobiohydrolase, mannanase and/or beta-glucosidase of the invention lacking all or part of an SP and/or a prepro domain. In one aspect, the invention provides a nucleic acid sequence encoding a signal sequence (SP) and/or prepro from one glucanase (or cellulase), e.g., endoglucanase, mannanase, xylanase, amylase, xanthanase and/or glycosidase, e.g., cellobiohydrolase, mannanase and/or beta-glucosidase operably linked to a nucleic acid sequence of a different glucanase or, optionally, a signal sequence (SPs) and/or prepro domain from a non-glucanase (or cellulase), e.g., endoglucanase, mannanase, xylanase, amylase, xanthanase and/or glycosidase, e.g., cellobiohydrolase, mannanase and/or beta-glucosidase protein may be desired.

The invention also provides isolated or recombinant polypeptides comprising signal sequences (SPs), prepro domain and/or catalytic domains (CDs) of the invention and heterologous sequences. The heterologous sequences are sequences not naturally associated (e.g., to a glucanase (or cellulase), e.g., endoglucanase, mannanase, xylanase, amylase, xanthanase and/or glycosidase, e.g., cellobiohydrolase, mannanase and/or beta-glucosidase) with an SP, prepro domain and/or CD. The sequence to which the SP, prepro domain and/or CD are not naturally associated can be on the SP's, prepro domain and/or CD's amino terminal end, carboxy terminal end, and/or on both ends of the SP and/or CD. In one aspect, the invention provides an isolated or recombinant polypeptide comprising (or consisting of) a polypeptide comprising a signal sequence (SP), prepro domain and/or catalytic domain (CD) of the invention with the proviso that it is not associated with any sequence to which it is naturally associated (e.g., a glucanase (or cellulase), e.g., endoglucanase, mannanase, xylanase, amylase, xanthanase and/or glycosidase, e.g., cellobiohydrolase, mannanase and/or beta-glucosidase sequence). Similarly in one aspect, the invention provides isolated or recombinant nucleic acids encoding these polypeptides. Thus, in one aspect, the isolated or recombinant nucleic acid of the invention comprises coding sequence for a signal sequence (SP), prepro domain and/or catalytic domain (CD) of the invention and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Hybrid (Chimeric) Glucanase, Mannanase, or Xylanase and Peptide Libraries

In one aspect, the invention provides hybrid glucanases (or cellulases), e.g., endoglucanases, mannanases, xylanases, amylases, xanthanases and/or glycosidases, e.g., cellobiohydrolases, mannanases and/or beta-glucosidases and fusion proteins, including peptide libraries, comprising sequences of the invention. The peptide libraries of the invention can be used to isolate peptide modulators (e.g., activators or inhibitors) of targets, such as glucanase (or cellulase), e.g., endoglucanase, mannanase, xylanase, amylase, xanthanase and/or glycosidase, e.g., cellobiohydrolase, mannanase and/or beta-glucosidase substrates, receptors, enzymes. The peptide libraries of the invention can be used to identify formal binding partners of targets, such as ligands, e.g., cytokines, hormones and the like. In one aspect, the invention provides chimeric proteins comprising a signal sequence (SP), prepro domain and/or catalytic domain (CD) of the invention or a combination thereof and a heterologous sequence (see above).

In one aspect, the fusion proteins of the invention (e.g., the peptide moiety) are conformationally stabilized (relative to linear peptides) to allow a higher binding affinity for targets. The invention provides fusions of a glucanase (or cellulase), e.g., endoglucanase, mannanase, xylanase, amylase, xanthanase and/or glycosidase, e.g., cellobiohydrolase, mannanase and/or beta-glucosidase of the invention and other peptides, including known and random peptides. They can be fused in such a manner that the structure of a glucanase (or cellulase), e.g., endoglucanase, mannanase, xylanase, amylase, xanthanase and/or glycosidase, e.g., cellobiohydrolase, mannanase and/or beta-glucosidase is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g., an allelic or interspecies variation of a glucanase (or cellulase), e.g., endoglucanase, mannanase, xylanase, amylase, xanthanase and/or glycosidase, e.g., cellobiohydrolase, mannanase and/or beta-glucosidase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed glucanase (or cellulase), e.g., endoglucanase, mannanase, xylanase, amylase, xanthanase and/or glycosidase, e.g., cellobiohydrolase, mannanase and/or beta-glucosidase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using, e.g., assays of glucan hydrolysis. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides a glucanase (or cellulase), e.g., endoglucanase, mannanase, xylanase, amylase, xanthanase and/or glycosidase, e.g., cellobiohydrolase, mannanase and/or beta-glucosidase where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. The variants can exhibit the same qualitative biological activity (i.e., endoglucanase (or cellulase), e.g., endoglucanase, mannanase, xylanase, amylase, xanthanase and/or glycosidase, e.g., cellobiohydrolase, mannanase and/or beta-glucosidase activity) although variants can be selected to modify the characteristics of the glucanase (or cellulase), e.g., endoglucanase, mannanase, xylanase, amylase, xanthanase and/or glycosidase, e.g., cellobiohydrolase, mannanase and/or beta-glucosidase as needed.

In one aspect, glucanase (or cellulase), e.g., endoglucanase, mannanase, xylanase, amylase, xanthanase and/or glycosidase, e.g., cellobiohydrolase, mannanase and/or beta-glucosidase of the invention comprise epitopes or purification tags, signal sequences or other fusion sequences, etc. In one aspect, the glucanase (or cellulase), e.g., endoglucanase, mannanase, xylanase, amylase, xanthanase and/or glycosidase, e.g., cellobiohydrolase, mannanase and/or beta-glucosidase of the invention can be fused to a random peptide to form a fusion polypeptide. By "fused" or "operably linked" herein is meant that the random peptide and the glucanase (or cellulase), e.g., endoglucanase, mannanase, xylanase, amylase, xanthanase and/or glycosidase, e.g., cellobiohydrolase, mannanase and/or beta-glucosidase are linked together, in such a manner as to minimize the disruption to the stability of the glucanase structure, e.g., it retains glucanase (or cellulase), e.g., endoglucanase, mannanase, xylanase, amylase, xanthanase and/or glycosidase, e.g., cellobiohydrolase, mannanase and/or beta-glucosidase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g., in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Endoglucanases are multidomain enzymes that consist optionally of a signal peptide, a carbohydrate binding module, a glucanase catalytic domain, a linker and/or another catalytic domain.

The invention provides a means for generating chimeric polypeptides which may encode biologically active hybrid polypeptides (e.g., hybrid glucanases (or cellulases), e.g., endoglucanases, mannanases, xylanases, amylases, xanthanases and/or glycosidases, e.g., cellobiohydrolases, mannanases and/or beta-glucosidases). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, the hydrolase may be screened to ascertain those chemical functionalities which distinguish the hybrid hydrolase from the original hydrolases, such as: (a) amide (peptide bonds), i.e., endoglucanases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

Additionally, subcloning may be performed to further isolate sequences of interest. In subcloning, a portion of DNA is amplified, digested, generally by restriction enzymes, to cut out the desired sequence, the desired sequence is ligated into a recipient vector and is amplified. At each step in subcloning, the portion is examined for the activity of interest, in order to ensure that DNA that encodes the structural protein has not been excluded. The insert may be purified at any step of the subcloning, for example, by gel electrophoresis prior to ligation into a vector or where cells containing the recipient vector and cells not containing the recipient vector are placed on selective media containing, for example, an antibiotic, which will kill the cells not containing the recipient vector. Specific methods of subcloning cDNA inserts into vectors are well-known in the art (Sambrook et al., *Molecular Cloning: A Laboratory Manual, 2nd Ed.*, Cold Spring Harbor Laboratory Press (1989)). In another aspect, the enzymes of the invention are subclones. Such subclones may differ from the parent clone by, for example, length, a mutation, a tag or a label.

In one aspect, the signal sequences of the invention are identified following identification of novel glucanase (or cellulase), e.g., endoglucanase, mannanase, xylanase, amylase, xanthanase and/or glycosidase, e.g., cellobiohydrolase, mannanase and/or beta-glucosidase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The sequences vary in length from 13 to 36 amino acid residues. Various methods of recognition of signal sequences are known to those of skill in the art. In one aspect, the peptides are identified by a method referred to as SignalP. SignalP uses a combined neural network which recognizes both signal peptides and their cleavage sites. See, e.g., Nielsen (1997) "Identification of prokaryotic and eukaryotic signal peptides and prediction of their cleavage sites." Protein Engineering, vol. 10, no. 1, p. 1-6. It should be understood that some of the glucanases (or cellulases), e.g., endoglucanases, mannanases, xylanases, amylases, xanthanases and/or glycosidases, e.g., cellobiohydrolases, mannanases and/or beta-glucosidases of the invention may or may not contain signal sequences. It may be desirable to include a nucleic acid sequence encoding a signal sequence from one glucanase (or cellulase), e.g., endoglucanase, mannanase, xylanase, amylase, xanthanase and/or glycosidase, e.g., cellobiohydrolase, mannanase and/or beta-glucosidase operably linked to a nucleic acid sequence of a different glucanase (or cellulase), e.g., endoglucanase, mannanase, xylanase, amylase, xanthanase and/or glycosidase, e.g., cellobiohydrolase, mannanase and/or beta-glucosidase or, optionally, a signal sequence from a non-glucanase (or cellulase), e.g., endoglucanase, mannanase, xylanase, amylase, xanthanase and/or glycosidase, e.g., cellobiohydrolase, mannanase and/or beta-glucosidase protein may be desired.

The microorganisms from which the polynucleotide may be prepared include prokaryotic microorganisms, such as Eubacteria and Archaebacteria and lower eukaryotic microorganisms such as fungi, some algae and protozoa. Polynucleotides may be discovered, isolated or prepared from samples, such as environmental samples, in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms can be used. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides are in one aspect already in a vector which includes appropriate control sequences. The host cell can be a higher eukaryotic cell, such as a mammalian cell, or a lower eukaryotic cell, such as a yeast cell, or in one aspect, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* S19; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981) and other cell lines capable of expressing a compatible vector, for example, the C127, 3T3, CHO, HeLa and BHK cell lines. Mammalian expression vectors will comprise an origin of replication, a suitable promoter and enhancer and also any necessary ribosome binding sites, polyadenylation site, splice donor and acceptor sites, transcriptional termination sequences and 5' flanking nontranscribed sequences. DNA sequences derived from the SV40 splice and polyadenylation sites may be used to provide the required nontranscribed genetic elements.

In another aspect, it is envisioned the method of the present invention can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters are polyketides.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affects high-frequency transfer of itself during conjugation and is ideal to achieve and stably propagate large DNA fragments, such as gene clusters from mixed microbial samples. One aspect is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library." Another type of vector for use in the present invention is a cosmid vector. Cosmid vectors were originally designed to clone and propagate large segments of genomic DNA. Cloning into cosmid vectors is described in detail in Sambrook et al., *Molecular Cloning: A Laboratory Manual, 2nd Ed.*, Cold Spring Harbor Laboratory Press (1989). Once ligated into an appropriate vector, two or more vectors containing different polyketide synthase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one aspect, the invention relates to a method for producing a biologically active hybrid polypeptide and screening such a polypeptide for enhanced activity by:

1) introducing at least a first polynucleotide in operable linkage and a second polynucleotide in operable linkage, the at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;

4) screening the hybrid polypeptide under conditions which promote identification of enhanced biological activity; and
5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

Screening Methodologies and "On-line" Monitoring Devices

In practicing the methods of the invention, a variety of apparatus and methodologies can be used to in conjunction with the polypeptides and nucleic acids of the invention, e.g., to screen polypeptides for glucanase (or cellulase), e.g., endoglucanase, mannanase, xylanase, amylase, xanthanase and/or glycosidase, e.g., cellobiohydrolase, mannanase and/or beta-glucosidase activity (e.g., assays such as hydrolysis of casein in zymograms, the release of fluorescence from gelatin, or the release of p-nitroanalide from various small peptide substrates), to screen compounds as potential modulators, e.g., activators or inhibitors, of a glucanase (or cellulase), e.g., endoglucanase, mannanase, xylanase, amylase, xanthanase and/or glycosidase, e.g., cellobiohydrolase, mannanase and/or beta-glucosidase activity, for antibodies that bind to a polypeptide of the invention, for nucleic acids that hybridize to a nucleic acid of the invention, to screen for cells expressing a polypeptide of the invention and the like. In addition to the array formats described in detail below for screening samples, alternative formats can also be used to practice the methods of the invention. Such formats include, for example, mass spectrometers, chromatographs, e.g., high-throughput HPLC and other forms of liquid chromatography, and smaller formats, such as 1536-well plates, 384-well plates and so on. High throughput screening apparatus can be adapted and used to practice the methods of the invention, see, e.g., U.S. Patent Application No. 20020001809.

Capillary Arrays

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays, such as the GIGAMATRIX®, Diversa Corporation, San Diego, Calif.; and arrays described in, e.g., U.S. Patent Application No. 20020080350 A1; WO 0231203 A; WO 0244336 A, provide an alternative apparatus for holding and screening samples. In one aspect, the capillary array includes a plurality of capillaries formed into an array of adjacent capillaries, wherein each capillary comprises at least one wall defining a lumen for retaining a sample. The lumen may be cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. Additionally, the capillary array can include interstitial material disposed between adjacent capillaries in the array, thereby forming a solid planar device containing a plurality of through-holes.

A capillary array can be formed of any number of individual capillaries, for example, a range from 100 to 4,000,000 capillaries. Further, a capillary array having about 100,000 or more individual capillaries can be formed into the standard size and shape of a MICROTITER® plate for fitment into standard laboratory equipment. The lumens are filled manually or automatically using either capillary action or microinjection using a thin needle. Samples of interest may subsequently be removed from individual capillaries for further analysis or characterization. For example, a thin, needle-like probe is positioned in fluid communication with a selected capillary to either add or withdraw material from the lumen.

In a single-pot screening assay, the assay components are mixed yielding a solution of interest, prior to insertion into the capillary array. The lumen is filled by capillary action when at least a portion of the array is immersed into a solution of interest. Chemical or biological reactions and/or activity in each capillary are monitored for detectable events. A detectable event is often referred to as a "hit", which can usually be distinguished from "non-hit" producing capillaries by optical detection. Thus, capillary arrays allow for massively parallel detection of "hits".

In a multi-pot screening assay, a polypeptide or nucleic acid, e.g., a ligand, can be introduced into a first component, which is introduced into at least a portion of a capillary of a capillary array. An air bubble can then be introduced into the capillary behind the first component. A second component can then be introduced into the capillary, wherein the second component is separated from the first component by the air bubble. The first and second components can then be mixed by applying hydrostatic pressure to both sides of the capillary array to collapse the bubble. The capillary array is then monitored for a detectable event resulting from reaction or non-reaction of the two components.

In a binding screening assay, a sample of interest can be introduced as a first liquid labeled with a detectable particle into a capillary of a capillary array, wherein the lumen of the capillary is coated with a binding material for binding the detectable particle to the lumen. The first liquid may then be removed from the capillary tube, wherein the bound detectable particle is maintained within the capillary, and a second liquid may be introduced into the capillary tube. The capillary is then monitored for a detectable event resulting from reaction or non-reaction of the particle with the second liquid.

Arrays or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a glucanase (or cellulase), e.g., endoglucanase, mannanase, xylanase, amylase, xanthanase and/or glycosidase, e.g., cellobiohydrolase, mannanase and/or beta-glucosidase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array (including "microarray" or "biochip" or "chip") and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated, synthetic or recombinant antibodies that specifically bind to a glucanase (or cellulase), e.g., endoglucanase, mannanase, xylanase, amylase, xanthanase and/or glycosidase, e.g., cellobiohydrolase, mannanase and/or beta-glucosidase of the invention. These antibodies can be used to isolate, identify or quantify a glucanase (or cellulase), e.g., endoglucanase, mannanase, xylanase, amylase, xanthanase and/or glycosidase, e.g., cellobiohydrolase, mannanase and/or beta-glucosidase of the invention or related polypeptides. These antibodies can be used to isolate other polypeptides within the scope the invention or other related glucanases (or cellulases), e.g., endoglucanases, mannanases, xylanases, amylases, xanthanases and/or glycosidases, e.g., cellobiohydrolases, mannanases and/or beta-glucosidases. The antibodies can be designed to bind to an active site of a glucanase (or cellulase), e.g., endoglucanase, mannanase, xylanase, amylase, xanthanase and/or glycosidase, e.g., cellobiohydrolase, mannanase and/or beta-glucosidase. Thus, the invention provides methods of inhibiting glucanases (or cellulases), e.g., endoglucanases, mannanases, xylanases, amylases, xanthanases and/or glycosidases, e.g., cellobiohydrolases, mannanases and/or beta-glucosidases using the antibodies of the invention (see discussion above regarding applications for anti-glucanase (or cellulase), e.g., endoglucanase, mannanase, xylanase, amylase, xanthanase and/or glycosidase, e.g., cellobiohydrolase, mannanase and/or beta-glucosidase compositions of the invention).

The term "antibody" includes a peptide or polypeptide derived from, modeled after or substantially encoded by an immunoglobulin gene or immunoglobulin genes, or fragments thereof, capable of specifically binding an antigen or epitope, see, e.g., Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites" (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH domain; and (vi) an isolated complementarity determining region (CDR). Single chain antibodies are also included by reference in the term "antibody."

The invention provides fragments of the enzymes of the invention, including immunogenic fragments of a polypeptide of the invention. The invention provides compositions comprising a polypeptide or peptide of the invention and adjuvants or carriers and the like.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

The polypeptides of the invention or fragments comprising at least 5, 10, 15, 20, 25, 30, 35, 40, 50, 75, 100, or 150 consecutive amino acids thereof, may also be used to generate antibodies which bind specifically to the polypeptides or fragments. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention, or fragments comprising at least 5, 10, 15, 20, 25, 30, 35, 40, 50, 75, 100, or 150 consecutive amino acids thereof.

In immunoaffinity procedures, the antibody is attached to a solid support, such as a bead or other column matrix. The protein preparation is placed in contact with the antibody under conditions in which the antibody specifically binds to one of the polypeptides of the invention, or fragment thereof. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays and Western Blots.

Polyclonal antibodies generated against the polypeptides of the invention, or fragments comprising at least 5, 10, 15, 20, 25, 30, 35, 40, 50, 75, 100, or 150 consecutive amino acids thereof can be obtained by direct injection of the polypeptides into an animal or by administering the polypeptides to an animal, for example, a nonhuman. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique (Kohler and Milstein, Nature, 256:495-497, 1975), the trioma technique, the human B-cell hybridoma technique (Kozbor et al. (1983) *Immunology Today* 4:72) and the EBV-hybridoma technique (Cole, et al. (1985) Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to the polypeptides of the invention, or fragments comprising at least 5, 10, 15, 20, 25, 30, 35, 40, 50, 75, 100, or 150 consecutive amino acids thereof. Alternatively, transgenic mice may be used to express humanized antibodies to these polypeptides or fragments thereof.

Antibodies generated against the polypeptides of the invention, or fragments comprising at least 5, 10, 15, 20, 25, 30, 35, 40, 50, 75, 100, or 150 consecutive amino acids thereof may be used in screening for similar polypeptides from other organisms and samples. In such techniques, polypeptides from the organism are contacted with the antibody and those polypeptides which specifically bind the antibody are detected. Any of the procedures described above may be used to detect antibody binding. One such screening assay is described in "Methods for Measuring Cellulase Activities", *Methods in Enzymology*, Vol 160, pp. 87-116.

Kits

The invention provides kits comprising the compositions, e.g., nucleic acids, expression cassettes, vectors, cells, transgenic seeds or plants or plant parts, polypeptides (e.g., endoglucanases (or cellulase), e.g., endoglucanase, mannanase, xylanase, amylase, xanthanase and/or glycosidase, e.g., cellobiohydrolase, mannanase and/or beta-glucosidase) and/or antibodies of the invention. The kits also can contain instructional material teaching the methodologies and industrial, agricultural, research and medical uses of the invention, as described herein.

Whole Cell Engineering and Measuring Metabolic Parameters

The methods of the invention provide whole cell evolution, or whole cell engineering, of a cell to develop a new cell strain having a new phenotype, e.g., a new or modified glucanase (or cellulase), e.g., endoglucanase, mannanase, xylanase, amylase, xanthanase and/or glycosidase, e.g., cellobiohydrolase, mannanase and/or beta-glucosidase activity, by modifying the genetic composition of the cell. The genetic composition can be modified by addition to the cell of a nucleic acid of the invention, e.g., a coding sequence for an enzyme of the invention. See, e.g., WO0229032; WO0196551.

To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using a glucanase (or cellulase), e.g., endoglucanase, mannanase, xylanase, amylase, xanthanase and/or glycosidase, e.g., cellobiohydrolase, mannanase and/or beta-glucosidase of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g., allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., a glucanase (or cellulase), e.g., endoglucanase, mannanase, xylanase, amylase, xanthanase and/or glycosidase, e.g., cellobiohydrolase, mannanase and/or beta-glucosidase message) or generating new (e.g., glucanase (or cellulase), e.g., endoglucanase, mannanase, xylanase, amylase, xanthanase and/or glycosidase, e.g., cellobiohydrolase, mannanase and/or beta-glucosidase) transcripts in a cell. This increased or decreased expression can be traced by testing for the presence of a glucanase (or cellulase), e.g., endoglucanase, mannanase, xylanase, amylase, xanthanase and/or glycosidase, e.g., cellobiohydrolase, mannanase and/or beta-glucosidase of the invention or by glucanase (or cellulase), e.g., endoglucanase, mannanase, xylanase, amylase, xanthanase and/or glycosidase, e.g., cellobiohydrolase, mannanase and/or beta-glucosidase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., a glucanase (or cellulase), e.g., endoglucanase, mannanase, xylanase, amylase, xanthanase and/or glycosidase, e.g., cellobiohydrolase, mannanase and/or beta-glucosidase) or generating new polypeptides in a cell. This increased or decreased expression can be traced by determining the amount of glucanase (or cellulase), e.g., endoglucanase, mannanase, xylanase, amylase, xanthanase and/or glycosidase, e.g., cellobiohydrolase, mannanase and/or beta-glucosidase present or by glucanase (or cellulase), e.g., endoglucanase, mannanase, xylanase, amylase, xanthanase and/or glycosidase, e.g., cellobiohydrolase, mannanase and/or beta-glucosidase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g., immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, one or more, or, all the polypeptides of a cell can be measured using a protein array.

Industrial, Drilling, Energy, Agricultural, Research and Medical Applications

The invention provides many industrial, drilling, energy, agricultural, research and medical applications for the polypeptides, including enzymes, peptides, antibodies, and "enzyme cocktails" of the invention, including for example the polypeptides of the invention having glucanase, mannanase or xylanase activity. Polypeptides of the invention can be used in food processing (e.g., bread and dough processing), brewing, bath additives, alcohol production, peptide synthesis, enantioselectivity, hide preparation in the leather industry, waste management and animal degradation, medical treatment, biofilm degradation, biomass conversion to ethanol, biodefense, antimicrobial agents and disinfectants, personal care and cosmetics, biotech reagents, hydrolyzing, breaking up or disrupting a glucan-comprising composition, as pharmaceuticals or digestive aids, e.g., as anti-inflammatory (anti-phlogistic) agents, and/or in the energy, oil or gas industry. The method and compositions (e.g., the "enzyme cocktails") of the invention can be used in any oil and gas discovery and/or drilling process, or any oil and gas well washing and/or fracturing process.

In one embodiment, combinations of enzymes may be used. A mixture of enzymes or an "enzyme cocktail" can include, but is not limited to, any combination of enzymes such as xylanases, esterases, cellulases, pectinases, pectate lyases, amylases, decarboxylases, laccases, glucanases, proteases, peptidases, proteinases, amyloglucosidases, glucose isomerases, glucoamylases, beta-glucanases, endo-beta-1,3 (4)-glucanases, hemicellulases, endoglycosidases, endobeta.-1,4-glucanases, glycosyltransferases, phospholipases, lipooxygenases, reductases, oxidases, phenoloxidases, ligninases, pullulanases, arabinanases, other mannanases, xyloglucanases, pectin acetyl esterases, rhamnogalacturonan acetyl esterases, polygalacturonases, rhamnogalacturonases, galactanases, transglutaminases, pectin methylesterases, cellobiohydrolases and/or transglutaminases. The glucanase, mannanase or xylanase enzymes of the invention can be combined with each other or with additional enzymes.

The glucanase (or cellulase), e.g., endoglucanase, mannanase, xylanase, amylase, xanthanase and/or glycosidase, e.g., cellobiohydrolase, mannanase and/or beta-glucosidase enzymes of the invention can be highly selective catalysts. They can catalyze reactions with exquisite stereo-, regio- and chemo-selectivities that are unparalleled in conventional synthetic chemistry. Moreover, enzymes are remarkably versatile. The enzymes of the invention can be tailored to function in organic solvents, operate at extreme pHs (for example, high pHs and low pHs) extreme temperatures (for example, high temperatures and low temperatures), extreme salinity levels (for example, high salinity and low salinity) and catalyze reactions with compounds that are structurally unrelated to their natural, physiological substrates.

Detergent Compositions

The invention provides detergent compositions comprising one or more polypeptides (e.g., endoglucanases (or cellulase), e.g., endoglucanase, mannanase, xylanase, amylase, xanthanase and/or glycosidase, e.g., cellobiohydrolase, mannanase and/or beta-glucosidase) of the invention, and methods of making and using these compositions. The invention incorporates all methods of making and using detergent compositions, see, e.g., U.S. Pat. Nos. 6,413,928; 6,399,561; 6,365,561; 6,380,147.

The detergent compositions can be a one and two part aqueous composition, a non-aqueous liquid composition, a cast solid, a granular form, a particulate form, a compressed tablet, a gel and/or a paste and a slurry form. The glucanases (or cellulases), mannanases, xylanases, amylases, xanthanases and/or glycosidases, e.g., cellobiohydrolases, mannanases and/or beta-glucosidases of the invention can also be used as a detergent additive product in a solid or a liquid form. Such additive products are intended to supplement or boost the performance of conventional detergent compositions and can be added at any stage of the cleaning process.

The actual active enzyme content depends upon the method of manufacture of a detergent composition and is not critical, assuming the detergent solution has the desired enzymatic activity. In one aspect, the amount of glucanase (or cellulase), e.g., endoglucanase, mannanase, xylanase, amylase, xanthanase and/or glycosidase, e.g., cellobiohydrolase, mannanase and/or beta-glucosidase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the glucanases (or cellulases), mannanases, xylanases, amylases, xanthanases and/or glycosidases, e.g., cellobiohydrolases, mannanases and/or beta-glucosidases of the present invention are active in the pH ranges of from about 4 to about 12 and in the temperature range of from about 20° C. to about 95° C. The detergents of the invention can comprise cationic, semipolar nonionic or zwitterionic surfactants; or, mixtures thereof.

Glucanases (or cellulases), mannanases, xylanases, amylases, xanthanases and/or glycosidases, e.g., cellobiohydrolases, mannanases and/or beta-glucosidases of the invention can be formulated into powdered and liquid detergents having pH between 4.0 and 12.0 at levels of about 0.01 to about 5% (in one aspect 0.1% to 0.5%) by weight. These detergent compositions can also include other enzymes such as other glucanases, mannanases, or xylanases, or cellulases, endoglycosidases, endo-beta.-1,4-glucanases, beta-glucanases, endo-beta-1,3(4)-glucanases, catalases, cutinases, peroxidases, laccases, lipases, amylases, glucoamylases, pectinases, reductases, oxidases, phenoloxidases, ligninases, pullulanases, arabinanases, hemicellulases, mannanases, xyloglucanases, pectin acetyl esterases, rhamnogalacturonan acetyl esterases, polygalacturonases, rhamnogalacturonases, galactanases, proteases, pectate lyases, pectin methylesterases, cellobiohydrolases and/or transglutaminases. These detergent compositions can also include builders and stabilizers. These detergent compositions can also include builders and stabilizers.

The addition of a glucanase (or cellulase), e.g., endoglucanase, mannanase, xylanase, amylase, xanthanase and/or glycosidase, e.g., cellobiohydrolase, mannanase and/or beta-glucosidase of the invention to conventional cleaning compositions does not create any special use limitation. In other words, any temperature and pH suitable for the detergent is also suitable for the compositions of the invention as long as the enzyme is active at or tolerant of the pH and/or temperature of the intended use. In addition, a glucanase (or cellulase), e.g., endoglucanase, mannanase, xylanase, amylase, xanthanase and/or glycosidase, e.g., cellobiohydrolase, mannanase and/or beta-glucosidase of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A glucanase (or cellulase), e.g., endoglucanase, mannanase, xylanase, amylase, xanthanase and/or glycosidase, e.g., cellobiohydrolase, mannanase and/or beta-glucosidase of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a glucanase (or cellulase), e.g., endoglucanase, mannanase, xylanase, amylase, xanthanase and/or glycosidase, e.g., cellobiohydrolase, mannanase and/or beta-glucosidase of the invention.

Alternatively, a glucanase (or cellulase), e.g., endoglucanase, mannanase, xylanase, amylase, xanthanase and/or glycosidase, e.g., cellobiohydrolase, mannanase and/or beta-glucosidase of the invention can be formulated as a detergent composition for use in general household hard surface cleaning operations. In alternative aspects, detergent additives and detergent compositions of the invention may comprise one or more other enzymes such as another glucanase (or cellulase), e.g., endoglucanase, mannanase, xylanase, amylase, xanthanase and/or glycosidase, e.g., cellobiohydrolase, mannanase and/or beta-glucosidase, or, a xylanase, a lipase, a cutinase, a carbohydrase, a cellulase, a pectinase, an arabinase, a galactanase, an oxidase, e.g., a lactase, and/or a peroxidase (see also, above). The properties of the enzyme(s) of the invention are chosen to be compatible with the selected detergent (i.e., pH-optimum, compatibility with other enzymatic and non-enzymatic ingredients, etc.) and the enzyme(s) is present in effective amounts. In one aspect, enzymes of the invention are used to remove malodorous materials from fabrics. Various detergent compositions and methods for making them that can be used in practicing the invention are described in, e.g., U.S. Pat. Nos. 6,387,690; 6,333,301; 6,329,333; 6,326,341; 6,297,038; 6,309,871; 6,204,232; 6,197,070; 5,856,164.

Enzymes of the invention can be used in a detergent or cleaning agent comprising a dispersion of solid particles in a dispersion agent, e.g., a nonionic polymer such as polyethylene glycol or polypropylene glycol, as described, e.g., in U.S. Patent Application No. 20060122089. Enzymes of the invention can be used in a water-soluble and/or waterdispersible particle, e.g., comprising a polyvinyl alcohol, as described for example in U.S. Patent Application No. 20050075261.

Enzymes of the invention can be used in a detergent, e.g., a hand dishwashing detergent, effective in the removal of cooked-, baked-, or burnt-on food residue soils as described, e.g., in U.S. Patent Application No. 20060281653.

When formulated as compositions suitable for use in a laundry machine washing method, the enzymes of the invention can comprise both a surfactant and a builder compound. They can additionally comprise one or more detergent components, e.g., organic polymeric compounds, bleaching agents, additional enzymes, suds suppressors, dispersants, lime-soap dispersants, soil suspension and anti-redeposition agents and corrosion inhibitors. Laundry compositions of the invention can also contain softening agents, as additional detergent components. Such compositions containing carbohydrase can provide fabric cleaning, stain removal, whiteness maintenance, softening, color appearance, dye transfer inhibition and sanitization when formulated as laundry detergent compositions.

The density of the laundry detergent compositions of the invention can range from about 200 to 1500 g/liter, or, about 400 to 1200 g/liter, or, about 500 to 950 g/liter, or, 600 to 800 g/liter, of composition; this can be measured at about 20° C.

The "compact" form of laundry detergent compositions of the invention is best reflected by density and, in terms of composition, by the amount of inorganic filler salt. Inorganic filler salts are conventional ingredients of detergent compositions in powder form. In conventional detergent compositions, the filler salts are present in substantial amounts, typically 17% to 35% by weight of the total composition. In one aspect of the compact compositions, the filler salt is present in amounts not exceeding 15% of the total composition, or, not exceeding 10%, or, not exceeding 5% by weight of the composition. The inorganic filler salts can be selected from the alkali and alkaline-earth-metal salts of sulphates and chlorides, e.g., sodium sulphate.

Liquid detergent compositions of the invention can also be in a "concentrated form." In one aspect, the liquid detergent compositions can contain a lower amount of water, compared to conventional liquid detergents. In alternative aspects, the water content of the concentrated liquid detergent is less than 40%, or, less than 30%, or, less than 20% by weight of the detergent composition. Detergent compounds of the invention can comprise formulations as described in WO 97/01629.

Enzymes of the invention can be useful in formulating various cleaning compositions. A number of known compounds are suitable surfactants including nonionic, anionic, cationic, or zwitterionic detergents, can be used, e.g., as disclosed in U.S. Pat. Nos. 4,404,128; 4,261,868; 5,204,015. In addition, glucanases (or cellulases), mannanases, xylanases, amylases, xanthanases and/or glycosidases, e.g., cellobiohydrolases, mannanases and/or beta-glucosidases of the invention can be used, for example, in bar or liquid soap applications, dish care formulations, contact lens cleaning solutions or products, peptide hydrolysis, waste treatment, textile applications, as fusion-cleavage enzymes in protein production, and the like. Glucanases, (or cellulases), mannanases, xylanases, amylases, xanthanases and/or glycosidases, e.g., cellobiohydrolases, mannanases and/or beta-glucosidases of the invention may provide enhanced performance in a detergent composition as compared to another detergent glucanase, that is, the enzyme group may increase cleaning of certain enzyme sensitive stains such as grass or blood, as determined by usual evaluation after a standard wash cycle. Glucanases, (or cellulases), mannanases, xylanases, amylases, xanthanases and/or glycosidases, e.g., cellobiohydrolases, mannanases and/or beta-glucosidases of the invention can be formulated into known powdered and liquid detergents having pH between 6.5 and 12.0 at levels of about 0.01 to about 5% (for example, about 0.1% to 0.5%) by weight. These detergent cleaning compositions can also include other enzymes such as known glucanases, mannanases, xylanases, amylases, cellulases, lipases or endoglycosidases, as well as builders and stabilizers.

Detergent compositions of the invention, e.g., those comprising glucanases (or cellulases), mannanases, xylanases, amylases, xanthanases and/or glycosidases, e.g., cellobiohydrolases, mannanases and/or beta-glucosidases of the invention, also can be used for cleaning fruit, vegetables and/or mud and clay compounds; see, for example, U.S. Pat. No. 5,786,316.

In one aspect, the invention provides detergent compositions having glucanase (or cellulase), e.g., endoglucanase, mannanase, xylanase, amylase, xanthanase and/or glycosidase, e.g., cellobiohydrolase, mannanase and/or beta-glucosidase activity (a glucanase (or cellulase), e.g., endoglucanase, mannanase, xylanase, amylase, xanthanase and/or glycosidase, e.g., cellobiohydrolase, mannanase and/or beta-glucosidase of the invention) for use with fruit, vegetables and/or mud and clay compounds (see, for example, U.S. Pat. No. 5,786,316).

Treating Fibers and Textiles

The invention provides methods of treating fibers, textiles, clothes, threads, fabrics and the like, using one or more glucanases (or cellulases), mannanases, xylanases, amylases, xanthanases and/or glycosidases, e.g., cellobiohydrolases, mannanases and/or beta-glucosidases of the invention. The enzymes of the invention can be used in any textile-, thread-, cloth-, fiber- or fabric-treating method, which are well known in the art, see, e.g., U.S. Pat. Nos. 6,387,690; 6,261,828; 6,077,316; 6,024,766; 6,021,536; 6,017,751; 5,980,581; US Patent Publication No. 20020142438 A1.

For example, enzymes of the invention can be used in fiber and/or fabric desizing. In one aspect, the feel and appearance of a fabric is improved by a method comprising contacting the fabric with an enzyme of the invention in a solution. In one aspect, the fabric is treated with the solution under pressure. For example, enzymes of the invention can be used in the removal of stains. Thus, in another aspect, the invention provides fibers, textiles, clothes, threads, fabrics and the like comprising a polypeptide of the invention.

In one aspect, enzymes of the invention are applied during or after the weaving of textiles, or during the desizing stage, or during one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. After the textiles have been woven, a fabric can proceed to a desizing stage. This can be followed by one or more additional fabric processing steps. Desizing is the act of removing "size" from textiles. After weaving, the size coating must be removed before further processing the fabric in order to ensure a homogeneous and wash-proof result.

The enzymes of the invention can be used to treat any cellulosic material, including fibers (e.g., fibers from cotton, hemp, flax or linen), sewn and unsewn fabrics, e.g., knits, wovens, denims, yarns, and toweling, made from cotton, cotton blends or natural or manmade cellulosics (e.g., originating from glucan-comprising cellulose fibers such as from wood pulp) or blends thereof. Examples of blends are blends of cotton or rayon/viscose with one or more companion material such as wool, synthetic fibers (e.g., polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g., rayon/viscose, ramie, hemp, flax/linen, jute, cellulose acetate fibers, lyocell).

The enzymes of the invention can be used to treat fabrics or any glucan, mannanan, xylan or cellulose-comprising material, including cotton-containing fabrics, as detergent additives, e.g., in aqueous compositions. For the manufacture of clothes, the fabric can be cut and sewn into clothes or garments. These can be finished before or after the treatment. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of treating textiles, e.g., finishing denim garments, enzymatic desizing and providing softness to fabrics by using any combination of enzymes, such the, mannanases, xylanases, or glucanases (e.g., endoglucanases) of the invention. In one aspect, enzymes of the invention can be used in treatments to prevent the graying of a textile.

In one aspect, an alkaline and/or thermostable mannanases, xylanases, and glucanases (e.g., endoglucanases) of the invention are combined in a single bath desizing and bioscouring. Among advantages of combining desizing and scouring in one step are cost reduction and lower environmental impact due to savings in energy and water usage and lower waste production. Application conditions for desizing and bioscouring can be between about pH 8.5 to pH 10.0 and temperatures at about 40° C. and up. Low enzyme dosages (e.g., about 5 g per a ton of cotton) and short reaction times (e.g., about 15 minutes) can be used to obtain efficient desizing and scouring with out added calcium.

The enzymes of the invention can be used in the treatment of cellulose-containing fabrics for harshness reduction, for color clarification, or to provide a localized variation in the color of such fabrics. See, e.g., U.S. Pat. No. 6,423,524. For example, enzymes of the invention can be used to reduce the harshness of cotton-containing fabrics, e.g., as a harshness reducing detergent additive. The enzymes of the invention can be used in the treatment of fabrics to give a "stone-washed" look in a colored fabric while reducing the amount of redeposition of colorant onto the fabric.

The textile treating processes of the invention (using enzymes of the invention) can be used in conjunction with other textile treatments, e.g., scouring and bleaching. Scouring is the removal of non-cellulosic material from the cotton fiber, e.g., the cuticle (mainly consisting of waxes) and primary cell wall (mainly consisting of pectin, protein and xyloglucan). A proper wax removal is necessary for obtaining a high wettability. This is needed for dyeing. Removal of the primary cell walls by the processes of the invention improves wax removal and ensures a more even dyeing. Treating textiles with the processes of the invention can improve whiteness in the bleaching process. The main chemical used in scouring is sodium, hydroxide in high concentrations and at high temperatures. Bleaching comprises oxidizing the textile. Bleaching typically involves use of hydrogen peroxide as the oxidizing agent in order to obtain either a fully bleached (white) fabric or to ensure a clean shade of the dye.

The invention also provides alkaline glucanases (e.g., endoglucanases active under alkaline conditions), mannanases, or xylanases. These have wide-ranging applications in textile processing, degumming of plant fibers (e.g., plant bast fibers), treatment of waste, e.g., pectic wastewaters, paper-making, and coffee and tea fermentations. See, e.g., Hoondal (2002) *Applied Microbiology and Biotechnology* 59:409-418.

The textile treating processes of the invention can also include the use of any combination of other enzymes (including carbohydrate degrading enzymes) such as catalases, other glucanases, cellulases, lipases, endoglycosidases, endo-beta.-1,4-glucanases, beta-glucanases, endo-beta-1,3 (4)-glucanases, cutinases, peroxidases, laccases, amylases, glucoamylases, pectinases, reductases, oxidases, phenoloxidases, ligninases, pullulanases, arabinanases, hemicellulases, other mannanases, xyloglucanases, other xylanases, pectin acetyl esterases, rhamnogalacturonan acetyl esterases, proteases, polygalacturonases, rhamnogalacturonases, galactanases, pectate lyases, pectin methylesterases, cellobiohydrolases and/or transglutaminases. The enzymes of the invention can be used in combination with other carbohydrate degrading enzymes, e.g., cellulase, arabinanase, xyloglucanase, pectinase, xylanase, and the like, for the preparation of fibers or for cleaning of fibers. Proteases can also be used in a combination of enzymes of the invention. These can be used in combination with detergents.

Treating Foods and Food Processing

The glucanases (or cellulases), mannanases, xylanases, amylases, xanthanases and/or glycosidases, e.g., cellobiohydrolases, mannanases and/or beta-glucosidases of the invention have numerous applications in food processing industry. For example, in one aspect, the enzymes of the invention are used to improve the extraction of oil from oil-rich plant material, e.g., oil-rich seeds, for example, soybean oil from soybeans, olive oil from olives, rapeseed oil from rapeseed and/or sunflower oil from sunflower seeds.

The enzymes of the invention can be used for separation of components of plant cell materials. For example, enzymes of the invention can be used in the separation of glucan-rich material (e.g., plant cells) into components. In one aspect, enzymes of the invention can be used to separate glucan-rich or oil-rich crops into valuable protein and oil and hull fractions. The separation process may be performed by use of methods known in the art.

The enzymes of the invention can be used in the preparation of fruit or vegetable juices, syrups, extracts and the like to increase yield. The enzymes of the invention can be used in the enzymatic treatment (e.g., hydrolysis of glucan-comprising plant materials) of various plant cell wall-derived materials or waste materials, e.g., from cereals, grains, wine or juice production, or agricultural residues such as vegetable hulls, bean hulls, sugar beet pulp, olive pulp, potato pulp, and the like. The enzymes of the invention can be used to modify the consistency and appearance of processed fruit or vegetables. The enzymes of the invention can be used to treat plant material to facilitate processing of plant material, including foods, facilitate purification or extraction of plant components. The enzymes of the invention can be used to improve feed value, decrease the water binding capacity, improve the degradability in waste water plants and/or improve the conversion of plant material to ensilage, and the like.

The enzymes of the invention can also be used in the fruit and brewing industry for equipment cleaning and maintenance.

The enzymes of the invention can be used in any food or feed (including additives and nutritional supplements), or in a process for making or preserving any food or feed; for example, enzymes of the invention can be used in processes for increasing viscosity or gel strength of food products, such as jam, marmalade, jelly, juice, paste, soup, salsa, etc., as described, e.g., in U.S. Pat. No. 6,036,981. Flavors in foods can be enhanced using an enzyme of this invention as described, e.g., in U.S. Pat. application No. 20070020744. The enzymes of the invention can be used for mold control and extended shelf life processes, e.g., for preparing any food or feed, such as an edible dough-based product as described, e.g., in U.S. Pat. application No. 20060286213.

In one aspect, enzymes, e.g., glucanases (or cellulases), mannanases, xylanases, amylases, xanthanases and/or glycosidases, e.g., cellobiohydrolases, mannanases and/or beta-glucosidases of the invention, are used in baking applications, e.g., breads, cookies, crackers and the like, to hydrolyze glucans, mannans, arabinoxylans or xylans, or other polysaccharides and reduce viscosity. The glucanases (or cellulases), mannanases, xylanases, amylases, xanthanases and/or glycosidases, e.g., cellobiohydrolases, mannanases and/or beta-glucosidases of the invention can also be used to create non-sticky doughs that are not difficult to machine and to reduce biscuit size. Use enzymes of the invention to hydrolyze glucans, mannans, arabinoxylans or xylans, or other polysaccharides, is used to prevent rapid rehydration of the baked product resulting in loss of crispiness and reduced shelf-life. In one aspect, enzymes of the invention are used as additives in dough processing. In one aspect, enzymes of the invention of the invention are used in dough conditioning, wherein in one aspect the enzymes possess high activity over a temperature range of about 25-35° C. and at near neutral pH (7.0-7.5). In one aspect, dough conditioning enzymes can be inactivated at the extreme temperatures of baking (>500° F.). The glucanases (or cellulases), mannanases, xylanases, amylases, xanthanases and/or glycosidases, e.g., cellobiohydrolases, mannanases and/or beta-glucosidases of the invention also can be used as flour, dough and bread improvers, see, for example, U.S. Pat. Nos. 5,108,765 and 5,306,633; thus, the invention provides flours, doughs and breads comprising an enzyme of the invention. Enzymes of the invention of the invention can be used in making breads, e.g., high fiber breads, as described e.g., in U.S. Pat. Application No. 20070054024; in one aspect, the invention provides high-fibre breads comprising an enzyme of this invention, or a bread processed using an enzyme of this invention, and also, e.g., comprising carboxymethylcellulose and at least one other type of fibre material to improve softness of the crumb and provide prolonged softness in time.

The food treatment processes of the invention can also include the use of any combination of other enzymes such as catalases, glucanases, cellulases, endoglycosidases, endo-beta.-1,4-glucanases, amyloglucosidases, glucose isomerases, glycosyltransferases, lipases, phospholipases, lipooxygenases, beta-glucanases, endo-beta-1,3(4)-glucanases, cutinases, peroxidases, laccases, amylases, glucoamylases, pectinases, reductases, oxidases, decarboxylases, phenoloxidases, ligninases, pullulanases, arabinanases, hemicellulases, mannanases, xyloglucanases, xylanases, pectin acetyl esterases, rhamnogalacturonan acetyl esterases, proteases, peptidases, proteinases, polygalacturonases, rhamnogalacturonases, galactanases, pectate lyases, transglutaminases, pectin methylesterases, cellobiohydrolases and/or transglutaminases. In some embodiments, by including an enzyme of the invention, these enzyme mixtures comprise "enzyme cocktails" of the invention.

Paper or Pulp Treatment

The glucanases (or cellulases), mannanases, xylanases, amylases, xanthanases and/or glycosidases, e.g., cellobiohydrolases, mannanases and/or beta-glucosidases of the invention can be in paper or pulp treatment or paper deinking. For example, in one aspect, the invention provides a paper treatment process using a glucanase (or cellulase), e.g., endoglucanase, mannanase, xylanase, amylase, xanthanase and/or glycosidase, e.g., cellobiohydrolase, mannanase and/or beta-glucosidase of the invention. Thus, the invention also provides a paper, pulp, wood, wood pulp, Kraft pulp, paper or wood waste and the like comprising an enzyme of the invention, or, a non-wood paper product or by-product, such as a rice paper. Glucanases, (or cellulases), mannanases, xylanases, amylases, xanthanases and/or glycosidases, e.g., cellobiohydrolases, mannanases and/or beta-glucosidases of the invention can be used in manufacturing and/or processing any cellulose-comprising solution; see, for example, U.S. Pat. No. 5,760,211.

Glucanases, (or cellulases), mannanases, xylanases, amylases, xanthanases and/or glycosidases, e.g., cellobiohydrolases, mannanases and/or beta-glucosidases may also be used in hydrolysis of hemicellulose for which it is selective, particularly in the presence of cellulose; for example in processes described in U.S. Pat. No. 4,725,544. Enzymes of the invention can be used to process cellulase rich retentate, using enzymes suitable for the hydrolysis of cellulose (see U.S. Pat. No. 4,725,544).

In one aspect, an enzyme of the invention, e.g., the exemplary SEQ ID NO:2, SEQ ID NO:7, SEQ ID NO:9, SEQ ID NO:11, SEQ ID NO:13, SEQ ID NO:19, SEQ ID NO:21, and/or SEQ ID NO:23, encoded, e.g., by SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, or the exemplary variants to these "parental" sequences, as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), is applicable both in reduction of the need for a chemical bleaching agent, such as chlorine dioxide, and in high alkaline and high temperature environments. In one aspect, an enzyme of the invention is a thermostable alkaline glucanase which can effect a greater than 25% reduction in the chlorine dioxide requirement of kraft pulp with a less than 0.5% pulp yield loss. In one aspect, boundary parameters are pH 10, 65-85° C. and treatment time of less than 60 minutes at an enzyme loading of less than 0.001 wt %. A pool of endoglucanases may be tested for the ability to hydrolyze dye-labeled glucan at, for example, pH 10 and 60° C. The enzymes that test positive under these conditions may then be evaluated at, for example pH 10 and 70° C. Alternatively, enzymes may be tested at pH 8 and pH 10 at 70° C. In discovery of endoglucanases desirable in the pulp and paper industry libraries from high temperature or highly alkaline environments were targeted. Specifically, these libraries were screened for enzymes functioning at alkaline pH and a temperature of approximately 45° C. In another aspect, the glucanases of the invention are useful in the pulp and paper industry in degradation of a lignin hemicellulose linkage, in order to release the lignin.

Glucanases, (or cellulases), mannanases, xylanases, amylases, xanthanases and/or glycosidases, e.g., cellobiohydrolases, mannanases and/or beta-glucosidases of the invention can be used in the paper and pulp industry as described in e.g., U.S. Pat. Nos. 5,661,021; 6,387,690; 6,083,733; 6,140,095 and 6,346,407. For example, as in U.S. Pat. No. 6,140,095, an enzyme of the invention can be an alkali-tolerant glucanase. An enzyme of the invention, e.g., the exemplary SEQ ID NO:2, encoded, e.g., by SEQ ID NO:1, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), can be used in the paper and pulp industry where the enzyme is active in the temperature range of 65° C. to 75° C. and at a pH of approximately 10. Additionally, an enzyme of the invention useful in the paper and pulp industry would decrease the need for bleaching chemicals, such as chlorine dioxide.

Enzymes of the invention, for example, the variants or evolved enzymes of the invention, e.g., the specific variations to SEQ ID NO:2, as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), can have activity (e.g., binding and/or enzymatic activity) that is thermotolerant or thermoactive in acidic or basic conditions. For example, an enzyme of the invention, e.g., the exemplary enzymes of the invention including SEQ ID NO:2, SEQ ID NO:7, SEQ ID NO:9, SEQ ID NO:11, SEQ ID NO:13, SEQ ID NO:19, SEQ ID NO:21, and/or SEQ ID NO:23, encoded, e.g., by SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, and the specific variations to SEQ ID NO:2, as set forth in Table 1, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), above, can have activity in slightly acidic pH, e.g., between about pH 5.5 to pH 6.0, e.g., in a temperature range of between about 40° C. to 70° C. In one aspect, an enzyme of the invention, e.g., the exemplary SEQ ID NO:2, SEQ ID NO:7, SEQ ID NO:9, SEQ ID NO:11, SEQ ID NO:13, SEQ ID NO:19, SEQ ID NO:21, and/or SEQ ID NO:23, encoded, e.g., by SEQ ID NO:1, SEQ ID NO:3, SEQ ID NO:6, SEQ ID NO:8, SEQ ID NO:10, SEQ ID NO:12, SEQ ID NO:18, SEQ ID NO:20, and/or SEQ ID NO:22, has an optimal activity between about 40° C. to 75° C., and between about pH 5.5 to 6.0; is stable at 70° C. for at least 50 minutes, and is inactivated at between about 96° C. to 100° C. In another aspect, enzymes of the invention, e.g., variants of SEQ ID NO:2, e.g., as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), are thermotolerant and/or thermostable; for example, an enzyme of the invention, e.g., variants of SEQ ID NO:2, e.g., as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), can retain at least 75% residual activity (e.g., glucanase activity) after 2 minutes at 95° C.; and in another aspect, retains 100% activity after heating for 30 minutes at 95° C. In yet another aspect, an enzyme of the invention, e.g., variants of SEQ ID NO:2, e.g., as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), retains 100% activity after heating for 30 minutes at 96° C., 97° C., 98° C. or 99° C. In yet another aspect, an enzyme of the invention, e.g., variants of SEQ ID NO:2, e.g., as set forth in Tables 1 and 2, as well as SEQ ID NO:7 (encoded by SEQ ID NO:6), SEQ ID NO:9 (encoded by SEQ ID NO:8), SEQ ID NO:11 (encoded by SEQ ID NO:10), SEQ ID NO:13 (encoded by SEQ ID NO:12), SEQ ID NO:19 (encoded by SEQ ID NO:18), SEQ ID NO:21 (encoded by SEQ ID NO:20), and SEQ ID NO:23 (encoded by SEQ ID NO:22), retains at least 90% activity after heating for 30 minutes at 100° C.

Additionally, glucanases (or cellulases), mannanases, xylanases, amylases, xanthanases and/or glycosidases, e.g., cellobiohydrolases, mannanases and/or beta-glucosidases of the invention can be useful in biobleaching and treatment of chemical pulps, as described, e.g., in U.S. Pat. No. 5,202,249, biobleaching and treatment of wood or paper pulps, as described, e.g., in U.S. Pat. Nos. 5,179,021, 5,116,746, 5,407,827, 5,405,769, 5,395,765, 5,369,024, 5,457,045, 5,434,071, 5,498,534, 5,591,304, 5,645,686, 5,725,732, 5,759,840, 5,834,301, 5,871,730 and 6,057,438, in reducing lignin in wood and modifying wood, as described, e.g., in U.S. Pat. Nos. 5,486,468 and 5,770,012.

In one aspect, a glucanases (or cellulases), mannanases, amylases, xanthanases and/or glycosidases, e.g., cellobiohydrolases, mannanases and/or beta-glucosidases or other enzymes of the invention is used in the paper and pulp industry either alone or together with a xylanase (e.g., a xylanase of the invention). In one aspect, the enzyme of the invention is used in a bleaching process to enhance the brightness of bleached pulps, e.g., fully or partially from softwood. Using an enzyme of the invention, the amount of chlorine used in the bleaching stages may be reduced. In one aspect, a mannanase of the invention is used to increase the freeness of pulps in recycled paper process. In one aspect, a glucanases (or cellulases), mannanases, amylases, xanthanases and/or glycosidases, e.g., cellobiohydrolases, mannanases and/or beta-glucosidases of the invention is used alone or in combination with a xylanase (e.g., a xylanase of the invention) in the treatment of lignocellulosic pulp (e.g., fully or partially from softwood) to improve the bleachability thereof. See, e.g., U.S. Pat. No. 5,795,764.

The pulp and paper processes of the invention can also include the use of any combination of other enzymes such as catalases, glucanases, cellulases, endoglycosidases, endo-beta-1,4-glucanases, amyloglucosidases, glucose isomerases, glycosyltransferases, lipases, phospholipases, lipooxygenases, beta-glucanases, endo-beta-1,3(4)-glucanases, cutinases, peroxidases, laccases, amylases, glucoamylases, pectinases, reductases, oxidases, decarboxylases, phenoloxidases, ligninases, pullulanases, arabinanases, hemicellulases, mannanases, xyloglucanases, xylanases, pectin acetyl esterases, rhamnogalacturonan acetyl esterases, proteases, peptidases, proteinases, polygalacturonases, rhamnogalacturonases, galactanases, pectate lyases, transglutaminases, pectin methylesterases, cellobiohydrolases and/or transglutaminases. In some embodiments, by including an enzyme of the invention, these enzyme mixtures comprise "enzyme cocktails" of the invention.

Feeds, Foods, Food Additives, Feed Additives, Nutritional Supplements and/or Dietary Supplements The invention provides methods for treating feeds, foods, food additives, feed additives, nutritional supplements and/or dietary supplements using glucanases of the invention, for humans and/or animals (including, e.g., mammals, birds, reptiles, fish and the like; including ruminants). The invention provides feeds, foods, food additives, feed additives, nutritional supplements and/or dietary supplements, comprising polypeptides of the invention, e.g., glucanases (or cellulases), mannanases, xylanases, amylases, xanthanases and/or glycosidases, e.g., cellobiohydrolases, mannanases and/or beta-glucosidases of the invention, including the enzyme cocktails of the invention. The invention provides feeds, foods, food additives, feed additives, nutritional supplements and/or dietary supplements comprising enzymes and "cocktails" of the invention as described, e.g., in U.S. Pat. Application No. 20060193897.

In one aspect, treating feeds, foods, food additives, feed additives, nutritional supplements and/or dietary supplements using glucanases (or cellulases), mannanases, xylanases, amylases, xanthanases and/or glycosidases, e.g., cellobiohydrolases, mannanases and/or beta-glucosidases of the invention can help in the availability of nutrients, e.g., starch, protein, and the like, in the feed, food, food additive, feed additive, nutritional supplement and/or dietary supplement. By breaking down difficult to digest proteins or indirectly or directly unmasking starch (or other nutrients), the enzyme of the invention makes nutrients more accessible to other endogenous or exogenous enzymes. The enzyme of the invention can also simply cause the release of readily digestible and easily absorbed nutrients and sugars. In another aspect, the enzymes of the invention are used in feeds, foods, food additives, feed additives, nutritional supplements and/or dietary supplements to decrease the viscosity of glucans, mannans, arabinoxylans or xylans, or other polysaccharides, in a food, feed, foodstuff or other edible material, e.g., in a high-barley or a high-wheat diet, such as a poultry diet. In one aspect, this can minimize wet droppings.

Glucanases, (or cellulases), mannanases, xylanases, amylases, xanthanases and/or glycosidases, e.g., cellobiohydrolases, mannanases and/or beta-glucosidases of the invention can be used as or in feeds, foods, food additives, feed additives, nutritional supplements and/or dietary supplements, including use in any feed, food, food additive, feed additive, nutritional supplement and/or dietary supplement known in the art, for example as set forth in U.S. Pat. Nos. 5,432,074, 5,429,828, 5,612,055, 5,720,971, 5,981,233, 5,948,667, 6,099,844, 6,132,727 and 6,132,716.

When added to feeds, foods, food additives, feed additives, nutritional supplements and/or dietary supplements, glucanases, xylanases and/or a mannanases of the invention improve the in vivo break-down of plant cell wall material partly due to a reduction of the intestinal viscosity (see, e.g., Bedford et al., Proceedings of the 1st Symposium on Enzymes in Animal Nutrition, 1993, pp. 73-77), whereby a better utilization of the plant nutrients by the animal is achieved. Thus, by using enzymes (e.g., glucanases (or cellulases), mannanases, xylanases, amylases, xanthanases and/or glycosidases, e.g., cellobiohydrolases, mannanases and/or beta-glucosidases) of the invention in feeds, foods, food additives, feed additives, nutritional supplements and/or dietary supplements the growth rate and/or feed conversion ratio (i.e., the weight of ingested feed relative to weight gain) of the animal is improved.

The feed additive, food additive, nutritional supplement and/or dietary supplement of the invention may be a granulated enzyme product which may readily be-mixed with food or feed components. Alternatively, feeds, foods, food additives, feed additives, nutritional supplements and/or dietary supplements of the invention can form a component of a pre-mix. The granulated enzyme product of the invention may be coated or uncoated. The particle size of the enzyme granulates can be compatible with that of feed and pre-mix components. This provides a safe and convenient mean of incorporating enzymes into feeds, foods, food additives, feed additives, nutritional supplements and/or dietary supplements. Alternatively, the feeds, foods, food additives, feed additives, nutritional supplements and/or dietary supplements of the invention may be a stabilized liquid composition. This may be an aqueous or oil-based slurry. See, e.g., U.S. Pat. No. 6,245,546.

Glucanases, (or cellulases), mannanases, xylanases, amylases, xanthanases and/or glycosidases, e.g., cellobiohydrolases, mannanases and/or beta-glucosidases of the present invention, in the modification of feeds, foods, food additives, feed additives, nutritional supplements and/or dietary supplements, can process the feeds, foods, food additives, feed additives, nutritional supplements and/or dietary supplements either in vitro (by modifying components of the feeds, foods, food additives, feed additives, nutritional supplements and/or dietary supplements) or in vivo. Glucanases, (or cellulases), mannanases, xylanases, amylases, xanthanases and/or glycosidases, e.g., cellobiohydrolases, mannanases and/or beta-glucosidases of the invention can be added to feed, food, food additive, feed additive, nutritional supplement and/or dietary supplement compositions containing high amounts of glucans, e.g., feed, food, food additive, feed additive, nutritional supplement and/or dietary supplement containing plant material from cereals, grains and the like. When added to the feed, food, food additive, feed additive, nutritional supplement and/or dietary supplement, the glucanase significantly improves the in vivo breakdown of glucan-containing material, e.g., plant cell walls, whereby a better utilization of the plant nutrients by the human or animal is achieved. In one aspect, the growth rate and/or food/feed conversion ratio (i.e., the weight of ingested food/feed relative to weight gain) of the human or animal is improved. For example a partially or indigestible glucan-comprising protein is fully or partially degraded by glucanases (or cellulases), mannanases, xylanases, amylases, xanthanases and/or glycosidases, e.g., cellobiohydrolases, mannanases and/or beta-glucosidases of the invention, e.g., in combination with another enzyme, e.g., beta-galactosidase, to peptides and galactose and/or galactooligomers. These enzyme digestion products are more digestible by the human or animal. Thus, glucanases (or cellulases), mannanases, xylanases, amylases, xanthanases and/or glycosidases, e.g., cellobiohydrolases, mannanases and/or beta-glucosidases of the invention can contribute to the available energy of the feed or food. Also, by contributing to the degradation of glucan-comprising proteins, a glucanase of the invention can improve the digestibility and uptake of carbohydrate and non-carbohydrate feed or food constituents such as protein, fat and minerals.

In another aspect, glucanases (or cellulases), mannanases, xylanases, amylases, xanthanases and/or glycosidases, e.g., cellobiohydrolases, mannanases and/or beta-glucosidases of the invention can be supplied by expressing the enzymes directly in transgenic food and/or feed crops (as, e.g., transgenic plants, seeds and the like), such as grains, cereals, corn, soy bean, rape seed, lupin and the like. As discussed above, the invention provides transgenic plants, plant parts and plant cells comprising a nucleic acid sequence encoding a polypeptide of the invention. In one aspect, the nucleic acid is expressed such that the enzyme (e.g., glucanase) of the invention is produced in recoverable quantities. The glucanases (or cellulases), mannanases, xylanases, amylases, xanthanases and/or glycosidases, e.g., cellobiohydrolases, mannanases and/or beta-glucosidases of the invention can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

In one aspect, the invention provides methods for removing oligosaccharides from a food or feed prior to consumption by an animal subject using glucanases (or cellulases), mannanases, xylanases, amylases, xanthanases and/or glycosidases, e.g., cellobiohydrolases, mannanases and/or beta-glucosidases of the invention. In this process a food or feed is formed having an increased metabolizable energy value. In addition to glucanases (or cellulases), mannanases, xylanases, amylases, xanthanases and/or glycosidases, e.g., cellobiohydrolases, mannanases and/or beta-glucosidases s of the invention, galactosidases, cellulases and combinations thereof can be used. In one aspect, the enzyme may be added in an amount equal to between about 0.001% and 1% by weight of the food or feed material. In one aspect, the food or feed is a cereal, a wheat, a grain, a soybean (e.g., a ground soybean) material. See, e.g., U.S. Pat. No. 6,399,123.

In another aspect, the invention provides methods for utilizing glucanases (or cellulases), mannanases, xylanases, amylases, xanthanases and/or glycosidases, e.g., cellobiohydrolases, mannanases and/or beta-glucosidases of the invention as a nutritional supplement or dietary supplement in the diets of humans or animals by preparing a nutritional or dietary supplement containing a recombinant enzyme of the invention, and administering the nutritional or dietary supplement to a human or animal to increase the utilization of glucan contained in the food or feed ingested by the human or animal.

In one aspect, the enzymes of the invention can be used to treat/process "DDGS", or Distillers dried grain with solubles, which is dry-grind ethanol plant by-product, e.g., for food or feed applications, e.g., for poultry, bovine, swine and other domestic animals.

In yet another aspect, the invention provides an edible pelletized enzyme delivery matrix and method of use for delivery of glucanases (or cellulases), mannanases, xylanases, amylases, xanthanases and/or glycosidases, e.g., cellobiohydrolases, mannanases and/or beta-glucosidases of the invention to a human or animal, for example as a nutritional or dietary supplement. The enzyme delivery matrix readily releases an enzyme of the invention (e.g., a glucanase), such as one having an amino acid sequence of the invention, or an enzymatically active fragment thereof (e.g., a subsequence of at least 30, 40, 50, 60, 70, 80, 90 or 100 or more contiguous amino acids thereof), in aqueous media, such as, for example, the digestive fluid of a human or animal.

The invention's enzyme delivery matrix can be prepared from a granulate edible carrier selected from such components as grain germ that is spent of oil, hay, alfalfa, timothy, soy hull, sunflower seed meal, wheat midd, and the like, that readily disperse the recombinant enzyme contained therein into aqueous media. In use, the edible pelletized enzyme delivery matrix is administered to an animal to delivery of glucanase to the human or animal. Suitable grain-based or grass-based substrates may comprise or be derived from any suitable edible grain or grass, such as wheat, buckwheat, millet, rye, corn, soy, rice, sorghum, alfalfa, barley, an annual grass and the like. An exemplary grain-based substrate is a corn-based substrate. The substrate may be derived from any suitable part of the grain, but is in one aspect a grain germ approved for animal feed use, such as corn germ that is obtained in a wet or dry milling process. The grain germ in one aspect comprises spent germ, which is grain germ from which oil has been expelled, such as by pressing or hexane or other solvent extraction. Alternatively, the grain germ is expeller extracted, that is, the oil has been removed by pressing.

The enzyme delivery matrix of the invention can be in the form of discrete plural particles, pellets or granules. By "granules" is meant particles that are compressed or compacted, such as by a pelletizing, extrusion, or similar compacting to remove water from the matrix. Such compression or compacting of the particles also promotes intraparticle cohesion of the particles. For example, the granules can be prepared by pelletizing the grain-based substrate in a pellet mill. The pellets prepared thereby are ground or crumbled to a granule size suitable for use as an adjuvant in food or feed. The matrix itself may be used as a diluent for delivery of enzymes in food or feed.

In one aspect, the enzyme delivery matrix is in the form of granules having a granule size ranging from about 4 to about 400 mesh (USS); more in one aspect, about 8 to about 80 mesh; and most in one aspect about 14 to about 20 mesh. If the grain germ is spent via solvent extraction, use of a lubricity agent such as corn oil may be necessary in the pelletizer, but such a lubricity agent ordinarily is not necessary if the germ is expeller extracted. In other aspects of the invention, the matrix is prepared by other compacting or compressing processes such as, for example, by extrusion of the grain-based substrate through a die and grinding of the extrudate to a suitable granule size.

The enzyme delivery matrix may further include a polysaccharide component as a cohesiveness agent to enhance the cohesiveness of the matrix granules. The cohesiveness agent is believed to provide additional hydroxyl groups, which enhance the bonding between grain proteins within the matrix granule. It is further believed that the additional hydroxyl groups so function by enhancing the hydrogen bonding of proteins to starch and to other proteins. The cohesiveness agent may be present in any amount suitable to enhance the cohesiveness of the granules of the enzyme delivery matrix. Suitable cohesiveness agents include one or more of dextrins, maltodextrins, starches, such as corn starch, flours, cellulosics, hemicellulosics, and the like. For example, the percentage of grain germ and cohesiveness agent in the matrix (not including the enzyme) is 78% corn germ meal and 20% by weight of corn starch.

In one embodiment, because the enzyme-releasing matrix of the invention is made from biodegradable materials, the matrix may be subject to spoilage, such as by molding. To prevent or inhibit such molding, the matrix may include a mold inhibitor, such as a propionate salt, which may be present in any amount sufficient to inhibit the molding of the enzyme-releasing matrix, thus providing a delivery matrix in a stable formulation that does not require refrigeration.

In one embodiment, the invention provides an enzyme of the invention in an enzyme delivery matrix of the invention, and methods of using them; and in one aspect, the enzyme is a thermostable glucanase, mannanase or xylanase as described herein, so as to resist inactivation of the glucanase during manufacture where elevated temperatures and/or steam may be employed to prepare the pelletized enzyme delivery matrix. During digestion of the feed, food, food additive, feed additive, nutritional supplement and/or dietary supplement containing the invention enzyme delivery matrix, aqueous digestive fluids will cause release of the active enzyme. Other types of thermostable enzymes and nutritional supplements that are thermostable can also be incorporated in the delivery matrix for release under any type of aqueous conditions.

A coating can be applied to the invention enzyme matrix particles for many different purposes, such as to add a flavor or nutritional supplement to the feed, food, food additive, feed additive, nutritional supplement and/or dietary supplement, to delay release of supplements and/or enzymes in gastric conditions, and the like. Or, the coating may be applied to achieve a functional goal, for example, whenever it is desirable to slow release of the enzyme from the matrix particles or to control the conditions under which the enzyme will be released. The composition of the coating material can be such that it is selectively broken down by an agent to which it is susceptible (such as heat, acid or base, enzymes or other chemicals). Alternatively, two or more coatings susceptible to different such breakdown agents may be consecutively applied to the matrix particles.

The invention is also directed towards a process for preparing an enzyme-releasing matrix. In accordance with the invention, the process comprises providing discrete plural particles of a grain-based substrate in a particle size suitable for use as an enzyme-releasing matrix, wherein the particles comprise a glucanase, xylanase and/or a mannanase encoded by an amino acid sequence of the invention. In one aspect, the process includes compacting or compressing the particles of enzyme-releasing matrix into granules, which most in one aspect is accomplished by pelletizing. The mold inhibitor and cohesiveness agent, when used, can be added at any suitable time, and in one aspect are mixed with the grain-based substrate in the desired proportions prior to pelletizing of the grain-based substrate. Moisture content in the pellet mill feed in one aspect is in the ranges set forth above with respect to the moisture content in the finished product, and in one aspect is about 14-15%. In one aspect, moisture is added to the feedstock in the form of an aqueous preparation of the enzyme to bring the feedstock to this moisture content. The temperature in the pellet mill in one aspect is brought to about 82° C. with steam. The pellet mill may be operated under any conditions that impart sufficient work to the feedstock to provide pellets. The pelleting process itself is a cost-effective process for removing water from the enzyme-containing composition.

In one aspect, the pellet mill is operated with a ⅛ in. by 2 in. die at 100 lb./min. pressure at 82° C. to provide pellets, which then are crumbled in a pellet mill crumbler to provide discrete plural particles having a particle size capable of passing through an 8 mesh screen but being retained on a 20 mesh screen.

The thermostable glucanases (or cellulases), mannanases, xylanases, amylases, xanthanases and/or glycosidases, e.g., cellobiohydrolases, mannanases and/or beta-glucosidases of the invention can be used in the pellets of the invention. They can have high optimum temperatures and high heat resistance such that an enzyme reaction at a temperature not hitherto carried out can be achieved. The gene encoding the glucanase according to the present invention (e.g., as set forth in any of the sequences of the invention) can be used in preparation of glucanases (or cellulases), mannanases, xylanases, amylases, xanthanases and/or glycosidases, e.g., cellobiohydrolases, mannanases and/or beta-glucosidases (e.g., using GSSM technology, as described herein) having characteristics different from those of the glucanases (or cellulases), mannanases, xylanases, amylases, xanthanases and/or glycosidases, e.g., cellobiohydrolases, mannanases and/or beta-glucosidases of the invention (in terms of optimum pH, optimum temperature, heat resistance, stability to solvents, specific activity, affinity to substrate, secretion ability, translation rate, transcription control and the like). Furthermore, a polynucleotide of the invention may be employed for screening of variant glucanases (or cellulases), mannanases, xylanases, amylases, xanthanases and/or glycosidases, e.g., cellobiohydrolases, mannanases and/or beta-glucosidases prepared by the methods described herein to determine those having a desired activity, such as improved or modified thermostability or thermotolerance. For example, U.S. Pat. No. 5,830,732, describes a screening assay for determining thermotolerance of a glucanase.

In one aspect, glucanases (or cellulases), mannanases, xylanases, amylases, xanthanases and/or glycosidases, e.g., cellobiohydrolases, mannanases and/or beta-glucosidases of the invention in feeds, foods, food additives, feed additives, nutritional supplements and/or dietary supplements are active in the human's or animal's stomach. Thus, in one aspect, an enzyme of the invention, e.g., in a feed, food, food additive, feed additive, nutritional supplement and/or dietary supplement, has an activity at about 37° C. and at low pH for monogastrics (pH 2-4) and near neutral pH for ruminants (pH 6.5-7). The enzyme of the invention has resistance to gut enzymes, e.g., proteases, and stability at the higher temperatures involved in food and feed pelleting. In one aspect, glucanases (or cellulases), mannanases, xylanases, amylases, xanthanases and/or glycosidases, e.g., cellobiohydrolases, mannanases and/or beta-glucosidases of the invention are used in feeds, foods, food additives, feed additives, nutritional supplements and/or dietary supplements, and can have a high specific activity, e.g., activity at 35-40° C. and pH 2-4, half life greater than 30 minutes in SGF and a half-life>5 minutes at 85° C. in formulated state. For ruminant feed, glucanases (or cellulases), mannanases, xylanases, amylases, xanthanases and/or glycosidases, e.g., cellobiohydrolases, mannanases and/or beta-glucosidases of the invention in feeds, foods, food additives, feed additives, nutritional supplements and/or dietary supplements have a high specific activity, e.g., activity at 35-40° C. and pH 6.5-7.0, half life greater than 30 minutes in SRF and stability as a concentrated dry powder.

The feed, food, food additive, feed additive, nutritional supplement and/or dietary supplement production processes of the invention can include any combination of other enzymes such as catalases, other glucanases, cellulases, endoglycosidases, endo-beta.-1,4-glucanases, amyloglucosidases, glucose isomerases, glycosyltransferases, lipases, phospholipases, lipooxygenases, beta-glucanases, endo-beta-1,3(4)-glucanases, cutinases, peroxidases, laccases, amylases, glucoamylases, pectinases, reductases, oxidases, decarboxylases, phenoloxidases, ligninases, pullulanases, phytases, arabinanases, hemicellulases, other mannanases, xyloglucanases, xylanases, pectin acetyl esterases, rhamnogalacturonan acetyl esterases, polygalacturonases, rhamnogalacturonases, galactanases, pectate lyases, transglutaminases, pectin methylesterases, cellobiohydrolases and/or transglutaminases. In some embodiments, by including an enzyme of the invention, these enzyme mixtures comprise "enzyme cocktails" of the invention.

Waste Treatment

The glucanases (or cellulases), mannanases, xylanases, amylases, xanthanases and/or glycosidases, e.g., cellobiohydrolases, mannanases and/or beta-glucosidases of the invention can be used in a variety of other industrial applications, e.g., in waste treatment (in addition to, e.g., biomass conversion to fuels). For example, in one aspect, the invention provides a solid waste digestion process using glucanases (or cellulases), mannanases, xylanases, amylases, xanthanases and/or glycosidases, e.g., cellobiohydrolases, mannanases and/or beta-glucosidases of the invention. The methods can comprise reducing the mass and volume of substantially untreated solid waste. Solid waste can be treated with an enzymatic digestive process in the presence of an enzymatic solution (including glucanases (or cellulases), mannanases, xylanases, amylases, xanthanases and/or glycosidases, e.g., cellobiohydrolases, mannanases and/or beta-glucosidases of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796. Thus, the invention provides waste products, such as liquefied waste or any residual solid waste comprising a polypeptide of the invention, e.g., an enzyme of the invention.

The invention provides processes for treating waste material derived from human, animal and/or industrial areas using an enzyme or enzyme cocktail of this invention; and these processes can also be used to recover important nutritional elements and toxic heavy metals, as described e.g., in U.S. Pat. Application No. 20060194299. In one aspect, the invention provides a process for releasing plant nutritional elements and utilizing toxic metals and carbon energy resources present in such waste, comprising treating the waste with one or more enzymes of this invention.

The waste treatment processes of the invention can include the use of any combination of other enzymes such as catalases, other glucanases, cellulases, endoglycosidases, endo-beta.-1,4-glucanases, amyloglucosidases, glucose isomerases, glycosyltransferases, lipases, phospholipases, lipooxygenases, beta-glucanases, endo-beta-1,3(4)-glucanases, cutinases, peroxidases, laccases, amylases, glucoamylases, pectinases, reductases, oxidases, decarboxylases, phenoloxidases, ligninases, pullulanases, phytases, arabinanases, hemicellulases, other mannanases, xyloglucanases, xylanases, pectin acetyl esterases, rhamnogalacturonan acetyl esterases, proteases, peptidases, proteinases, polygalacturonases, rhamnogalacturonases, galactanases, pectate lyases, transglutaminases, pectin methylesterases, cellobiohydrolases and/or transglutaminases. In some embodiments, by including an enzyme of the invention, these enzyme mixtures comprise "enzyme cocktails" of the invention.

Oral Care Products

The invention provides oral care product comprising glucanases (or cellulases), mannanases, xylanases, amylases, xanthanases and/or glycosidases, e.g., cellobiohydrolases, mannanases and/or beta-glucosidases of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

The oral products of the invention can include any combination of other enzymes such as proteases, peptidases, proteinases, glucose oxidases, peroxidases, glucanases, cellulases, endoglycosidases, endo-beta-1,4-glucanases, amyloglucosidases, endo-beta-1,3(4)-glucanases, amyloglucosidases and glucosidases.

Brewing and Fermenting

The invention provides methods of brewing (e.g., fermenting) beer comprising glucanases (or cellulases), mannanases, xylanases, amylases, xanthanases and/or glycosidases, e.g., cellobiohydrolases, mannanases and/or beta-glucosidases of the invention. In one exemplary process, starch-containing raw materials are disintegrated and processed to form a malt. An enzyme of the invention is used at any point in the fermentation process. Glucanases, (or cellulases), mannanases, xylanases, amylases, xanthanases and/or glycosidases, e.g., cellobiohydrolases, mannanases and/or beta-glucosidases of the invention can be used in the brewing industry for the degradation of beta-glucans. In one aspect, glucanases (or cellulases), mannanases, xylanases, amylases, xanthanases and/or glycosidases, e.g., cellobiohydrolases, mannanases and/or beta-glucosidases of the invention are used in the brewing industry for the clarification of the beverage. Enzymes of the invention can be used in the beverage industry in improving filterability of wort or beer, as described, e.g., in U.S. Pat. No. 4,746,517.

In one aspect, glucanases (or cellulases), mannanases, xylanases, amylases, xanthanases and/or glycosidases, e.g., cellobiohydrolases, mannanases and/or beta-glucosidases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15 to 25° C. for 3 to 6 days when enzyme synthesis is stimulated under the control of gibberellins. In one aspect, enzymes of the invention are added at this (or any other) stage of the process.

In one aspect, enzymes of the invention are used in mashing and conversion processes. In the brewing and fermentation industries, mashing and conversion processes are performed at temperatures that are too low to promote adequate degradation of water-soluble glucans, mannans, arabinoxylans or xylans, or other polysaccharides. These polymers form gummy substrates that can cause increased viscosity in the mashing wort, resulting in longer mash run-off, residual haze and precipitates in the final beer product due to inefficient filtration and low extraction yield. For these reasons, enzymes are added during the brewing processes to breakdown β-1,4- and β-1,3-linked glucan, or other polysaccharides.

In one aspect, enzymes of the invention are used in malthouse operations, e.g., glucanase is added to the process water, to shorten germination times and/or to encourage conversion of poor quality barley to acceptable malts. In one aspect, enzymes of the invention are used for mashing, e.g., they are added to increase wort filterability and/or improve lautering (separating the wort from the mash). In one aspect, enzymes of the invention are used in the fermenter and/or settling tank to, e.g., assist in haze clearing and/or to improve filtration. In one aspect, enzymes of the invention are used in adjunct brewing, e.g., a glucanase of the invention is added to breakdown glucans, mannans, arabinoxylans or xylans, or other polysaccharides from barley, wheat, and/or other cereals, including glycans in malt. In one aspect, enzymes of the invention are used in malt brewing, e.g., a glucanase of the invention is added to modify poor malts with high glucan content.

Glucanases, (or cellulases), mannanases, xylanases, amylases, xanthanases and/or glycosidases, e.g., cellobiohydrolases, mannanases and/or beta-glucosidases of the invention can be used in any beer or alcoholic beverage producing process, as described, e.g., in U.S. Pat. Nos. 5,762,991; 5,536,650; 5,405,624; 5,021,246; 4,788,066.

The brewing processes of the invention can include the use of any combination of other enzymes such as other xylanases, esterases, cellulases, pectinases, pectate lyases, amylases, decarboxylases, laccases, glucanases, proteases, peptidases, proteinases, amyloglucosidases, glucose isomerases, glucoamylases, beta-glucanases, endo-beta-1,3(4)-glucanases, hemicellulases, endoglycosidases, endo-beta.-1,4-glucanases, glycosyltransferases, phospholipases, lipooxygenases, reductases, oxidases, phenoloxidases, ligninases, pullulanases, arabinanases, other mannanases, xyloglucanases, pectin acetyl esterases, rhamnogalacturonan acetyl esterases, polygalacturonases, rhamnogalacturonases, galactanases, transglutaminases, pectin methylesterases, cellobiohydrolases and/or transglutaminases. In some embodiments, by including an enzyme of the invention, these enzyme mixtures comprise "enzyme cocktails" of the invention.

Medical and Research Applications

Glucanases, (or cellulases), mannanases, xylanases, amylases, xanthanases and/or glycosidases, e.g., cellobiohydrolases, mannanases and/or beta-glucosidases of the invention can be used as antimicrobial agents, e.g., pharmaceutical compositions, due to their bacteriolytic properties and antifungal properties. Enzymes of the invention can be used to ameliorate, eliminate or protect animals from fungal, yeast or bacteria infections, e.g., bacterial toxins or bacterial spores, such as salmonellae or *Bacillus*, e.g., as described in PCT Application Nos. WO0049890 and WO9903497. Glucanases, (or cellulases), mannanases, xylanases, amylases, xanthanases and/or glycosidases, e.g., cellobiohydrolases, mannanases and/or beta-glucosidases of the invention can be used in a method of use and composition of a carbohydrase and/or a glucanase for the manufacture of an agent for the treatments and/or prophylaxis of coccidiosis. The manufactured agent can be in the form of a cereal-based animal feed, see, for example, U.S. Pat. No. 5,624,678.

Enzymes of the invention can be used in, and in the manufacture of, an agent for the treatment and/or prophylaxis of bacterial infection in an animal, e.g., an infection caused by *Salmonella, Campylobacter* or *Clostridium perfringens*, as described for example, U.S. Pat. Application No. 20060083731; and in one embodiment, the enzymes are added in a feed, feed additive or nutritional supplement.

Biomass Conversion and Production of Clean Biofuels

The invention provides polypeptide, including enzymes (glucanases (or cellulases), mannanases, xylanases, amylases, xanthanases and/or glycosidases, e.g., cellobiohydrolases, mannanases and/or beta-glucosidases of the invention) and antibodies, and methods for the conversion of a biomass or any lignocellulosic material (e.g., any composition comprising cellulose, hemicellulose and lignin), to a fuel (e.g., bioethanol, biopropanol, biobutanol, biopropanol, biomethanol, biodiesel), in addition to feeds, foods and chemicals. For example, in one aspect, an enzyme of the invention has β-glucosidase activity to liberate D-glucose from cellobiose dimers. In one aspect, the enzymes have exo- or endo-beta-glucanase activity.

Thus, the compositions and methods of the invention provide effective and sustainable alternatives or adjuncts to use of petroleum-based products, e.g., as a mixture of a biofuel such as biomethanol, bioethanol, biopropanol, biobutanol, and the like, to diesel fuel, gasoline, kerosene and the like. The invention provides organisms expressing enzymes of the invention for participation in chemical cycles involving natural biomass conversion. In one aspect, enzymes and methods for the conversion are used in enzyme ensembles for the efficient depolymerization of polysaccharides, cellulosic and/or hemicellulosic polymers to metabolizeable (e.g., fermentable) carbon moieties. The invention provides methods for discovering and implementing the most effective of enzymes to enable these important new "biomass conversion" and alternative energy industrial processes.

The compositions and methods of the invention can be used to provide effective and sustainable alternatives or adjuncts to use of petroleum-based products, e.g., as a mixture of bioethanol, biopropanol, biobutanol, biopropanol, biomethanol and/or biodiesel and gasoline. The invention provides organisms expressing enzymes of the invention for participation in chemical cycles involving natural biomass conversion. The invention provides methods for discovering and implementing the most effective of enzymes to enable these important new "biomass conversion" and alternative energy industrial processes.

The invention provides methods, enzymes and mixtures of enzymes or "cocktails" of the invention, for processing a material, e.g., a biomass material, comprising a cellooligsaccharide, an arabinoxylan oligomer, a lignin, a lignocellulose, a xylan, a glucan, a cellulose and/or a fermentable sugar comprising contacting the composition with a polypeptide of the invention, or a polypeptide encoded by a nucleic acid of the invention, wherein optionally the material is derived from an agricultural crop (e.g., wheat, barley, potatoes, switchgrass, poplar wood), is a byproduct of a food or a feed production, is a lignocellulosic waste product, or is a plant residue or a waste paper or waste paper product, and optionally the plant residue comprise stems, leaves, hulls, husks, corn or corn cobs, corn stover, corn fiber, hay, straw (e.g., rice straw or wheat straw), sugarcane bagasse, sugar beet pulp, *citrus* pulp, and *citrus* peels, wood, wood thinnings, wood chips, wood pulp, pulp waste, wood waste, wood shavings and sawdust, construction and/or demolition wastes and debris (e.g., wood, wood shavings and sawdust), and optionally the paper waste comprises discarded or used photocopy paper, computer printer paper, notebook paper, notepad paper, typewriter paper, newspapers, magazines, cardboard and paper-based packaging materials, and recycled paper materials. In addition, urban wastes, e.g., the paper fraction of municipal solid waste, municipal wood waste, and municipal green waste, along with other materials containing sugar, starch, and/or cellulose can be used. Optionally the processing of the material, e.g., the biomass material, generates a bioalcohol, e.g., a bioethanol, biomethanol, biobutanol or biopropanol.

Alternatively, the polypeptide of the invention may be expressed in the biomass plant material or feedstock itself.

The methods of the invention also include taking the converted lignocellulosic material (processed by enzymes of the invention) and making it into a fuel (e.g., a bioalcohol, e.g., a bioethanol, biomethanol, biobutanol or biopropanol, or biodiesel) by fermentation and/or by chemical synthesis.

In one aspect, the produced sugars are fermented and/or the non-fermentable products are gasified.

The methods of the invention also include converting algae, virgin vegetable oils, waste vegetable oils, animal fats and greases (e.g., tallow, lard, and yellow grease), or sewage, using enzymes of the invention, and making it into a fuel (e.g., a bioalcohol, e.g., a bioethanol, biomethanol, biobutanol or biopropanol, or biodiesel) by fermentation and/or by chemical synthesis or conversion.

The enzymes of the invention (including, for example, organisms, such as microorganisms, e.g., fungi, yeast or bacteria, making and in some aspects secreting recombinant enzymes of the invention) can be used in or included/integrated at any stage of any biomass conversion process, e.g., at any one step, several steps, or included in all of the steps, or all of the following methods of biomass conversion processes, or all of these biofuel alternatives:

Direct Combustion: the burning of material by direct heat and is the simplest biomass technology; can be very economical if a biomass source is nearby.

Pyrolysis: is the thermal degradation of biomass by heat in the absence of oxygen. In one aspect, biomass is heated to a temperature between about 800 and 1400 degrees Fahrenheit, but no oxygen is introduced to support combustion resulting in the creation of gas, fuel oil and charcoal.

Gasification: biomass can be used to produce methane through heating or anaerobic digestion. Syngas, a mixture of carbon monoxide and hydrogen, can be derived from biomass.

Landfill Gas: is generated by the decay (anaerobic digestion) of buried garbage in landfills. When the organic waste decomposes, it generates gas consisting of approximately 50% methane, the major component of natural gas.

Anaerobic Digestion: converts organic matter to a mixture of methane, the major component of natural gas, and carbon dioxide. In one aspect, biomass such as waterwaste (sewage), manure, or food processing waste, is mixed with water and fed into a digester tank without air.

Fermentation
  Alcohol Fermentation: fuel alcohol is produced by converting cellulosic mass and/or starch to sugar, fermenting the sugar to alcohol, then separating the alcohol water mixture by distillation. Feedstocks such as dedicated crops (e.g., wheat, barley, potatoes, switchgrass, poplar wood), agricultural residues and wastes (e.g., rice straw, corn stover, wheat straw, sugarcane bagasse, rice hulls, corn fiber, sugar beet pulp, *citrus* pulp, and *citrus* peels), forestry wastes (e.g., hardwood and softwood thinnings, hardwood and softwood residues from timber operations, wood shavings, and sawdust), urban wastes (e.g., paper fraction of municipal solid waste, municipal wood waste, municipal green waste), wood wastes (e.g., saw mill waste, pulp mill waste, construction waste, demolition waste, wood shavings, and sawdust), and waste paper or other materials containing sugar, starch, and/or cellulose can be converted to sugars and then to alcohol by fermentation with yeast. Alternatively, materials containing sugars can be converted directly to alcohol by fermentation.
  Transesterification: An exemplary reaction for converting oil to biodiesel is called transesterification. The transesterification process reacts an alcohol (like methanol) with the triglyceride oils contained in vegetable oils, animal fats, or recycled greases, forming fatty acid alkyl esters (biodiesel) and glycerin. The reaction requires heat and a strong base catalyst, such as sodium hydroxide or potassium hydroxide.
  Biodiesel: Biodiesel is a mixture of fatty acid alkyl esters made from vegetable oils, animal fats or recycled greases. Biodiesel can be used as a fuel for vehicles in its pure form, but it is usually used as a petroleum diesel additive to reduce levels of particulates, carbon monoxide, hydrocarbons and air toxics from diesel-powered vehicles.
  Hydrolysis: includes hydrolysis of a compound, e.g., a biomass, such as a lignocellulosic material, catalyzed using an enzyme of the instant invention.
  Congeneration: is the simultaneous production of more than one form of energy using a single fuel and facility. In one aspect, biomass cogeneration has more potential growth than biomass generation alone because cogeneration produces both heat and electricity.

In one aspect, the polypeptides of the invention have hydrolase/cellulolytic activity, e.g., glucanase, endoglucanase, mannase and/or other enzymatic activity for generating a fuel (e.g., a bioalcohol, e.g., a bioethanol, biomethanol, biobutanol or biopropanol, or biodiesel) from an organic material, e.g., a biomass, such as compositions derived from plants and animals, including any agricultural crop or other renewable feedstock, an agricultural residue or an animal waste, the organic components of municipal and industrial wastes, or construction or demolition wastes or debris, or microorganisms such as algae or yeast.

In one aspect, polypeptides of the invention are used in processes for converting lignocellulosic biomass to a fuel (e.g., a bioalcohol, e.g., a bioethanol, biomethanol, biobutanol or biopropanol, or biodiesel), or otherwise are used in processes for hydrolyzing or digesting biomaterials such that they can be used as a fuel (e.g., a bioalcohol, e.g., a bioethanol, biomethanol, biobutanol or biopropanol, or biodiesel), or for making it easier for the biomass to be processed into a fuel.

In an alternative aspect, polypeptides of the invention, including the mixture of enzymes or "cocktails" of the invention, are used in processes for a transesterification process reacting an alcohol (like ethanol, propanol, butanol, propanol, methanol) with a triglyceride oil contained in a vegetable oil, animal fat or recycled greases, forming fatty acid alkyl esters (biodiesel) and glycerin. In one aspect, biodiesel is made from soybean oil or recycled cooking oils. Animal's fats, other vegetable oils, and other recycled oils can also be used to produce biodiesel, depending on their costs and availability. In another aspect, blends of all kinds of fats and oils are used to produce a biodiesel fuel of the invention.

Enzymes of the invention, including the mixture of enzymes or "cocktails" of the invention, can also be used in glycerin refining. The glycerin by-product contains unreacted catalyst and soaps that are neutralized with an acid. Water and alcohol are removed to produce 50% to 80% crude glycerin. The remaining contaminants include unreacted fats and oils, which can be processes using the polypeptides of the invention. In a large biodiesel plants of the invention, the glycerin can be further purified, e.g., to 99% or higher purity, for the pharmaceutical and cosmetic industries.

Fuels (including bioalcohols such as bioethanols, biomethanols, biobutanols or biopropanols, or biodiesels)

made using the polypeptides of the invention, including the mixture of enzymes or "cocktails" of the invention, can be used with fuel oxygenates to improve combustion characteristics. Adding oxygen results in more complete combustion, which reduces carbon monoxide emissions. This is another environmental benefit of replacing petroleum fuels with biofuels (e.g., a fuel of the invention). A biofuel made using the compositions and/or methods of this invention can be blended with gasoline to form an E10 blend (about 5% to 10% ethanol and about 90% to 95% gasoline), but it can be used in higher concentrations such as E85 or in its pure form. A biofuel made using the compositions and/or methods of this invention can be blended with petroleum diesel to form a B20 blend (20% biodiesel and 80% petroleum diesel), although other blend levels can be used up to B100 (pure biodiesel).

The invention also provides processes for making biofuels (including bioalcohols such as bioethanols, biomethanols, biobutanols or biopropanols, or biodiesels) from compositions comprising lignocellulosic biomass. The lignocellulose biomass material can be obtained from agricultural crops, as a byproduct of food or feed production, or as lignocellulosic waste products, such as plant residues, waste paper or construction and/or demolition wastes or debris. Examples of suitable plant sources or plant residues for treatment with polypeptides of the invention include kelp, algae, grains, seeds, stems, leaves, hulls, husks, corn cobs, corn stover, straw, grasses (e.g., Indian grass, such as *Sorghastrum nutans*; or, switch grass, e.g., *Panicum* species, such as *Panicum virgatum*), and the like, as well as wood, wood chips, wood pulp, and sawdust. Examples of paper waste suitable for treatment with polypeptides of the invention include discard photocopy paper, computer printer paper, notebook paper, notepad paper, typewriter paper, and the like, as well as newspapers, magazines, cardboard, and paper-based packaging materials. Examples of construction and demolition wastes and debris include wood, wood scraps, wood shavings and sawdust.

In one embodiment, the enzymes, including the mixture of enzymes or "cocktails" of the invention, and methods of the invention can be used in conjunction with more "traditional" means of making ethanol, methanol, propanol, butanol, propanol and/or diesel from biomass, e.g., as methods comprising hydrolyzing lignocellulosic materials by subjecting dried lignocellulosic material in a reactor to a catalyst comprised of a dilute solution of a strong acid and a metal salt; this can lower the activation energy, or the temperature, of cellulose hydrolysis to obtain higher sugar yields; see, e.g., U.S. Pat. Nos. 6,660,506 and 6,423,145.

Another exemplary method that incorporated use of enzymes of the invention, including the mixture of enzymes or "cocktails" of the invention, comprises hydrolyzing lignocellulosic material containing hemicellulose, cellulose and lignin, or any other polysaccharide that can be hydrolyzed by an enzyme of this invention, by subjecting the material to a first stage hydrolysis step in an aqueous medium at a temperature and a pressure chosen to effect primarily depolymerization of hemicellulose without major depolymerization of cellulose to glucose. This step results in a slurry in which the liquid aqueous phase contains dissolved monosaccharides resulting from depolymerization of hemicellulose and a solid phase containing cellulose and lignin. A second stage hydrolysis step can comprise conditions such that at least a major portion of the cellulose is depolymerized, such step resulting in a liquid aqueous phase containing dissolved/soluble depolymerization products of cellulose. See, e.g., U.S. Pat. No. 5,536,325. Enzymes of the invention (including the invention's mixtures, or "cocktails" of enzymes) can be added at any stage of this exemplary process.

Another exemplary method that incorporated use of enzymes of the invention, including the mixture of enzymes or "cocktails" of the invention, comprises processing a lignocellulose-containing biomass material by one or more stages of dilute acid hydrolysis with about 0.4% to 2% strong acid; and treating an unreacted solid lignocellulosic component of the acid hydrolyzed biomass material by alkaline delignification to produce precursors for biodegradable thermoplastics and derivatives. See, e.g., U.S. Pat. No. 6,409,841. Enzymes of the invention can be added at any stage of this exemplary process.

Another exemplary method that incorporated use of enzymes of the invention, including the mixture of enzymes or "cocktails" of the invention, comprises prehydrolyzing lignocellulosic material in a prehydrolysis reactor; adding an acidic liquid to the solid lignocellulosic material to make a mixture; heating the mixture to reaction temperature; maintaining reaction temperature for time sufficient to fractionate the lignocellulosic material into a solubilized portion containing at least about 20% of the lignin from the lignocellulosic material and a solid fraction containing cellulose; removing a solubilized portion from the solid fraction while at or near reaction temperature wherein the cellulose in the solid fraction is rendered more amenable to enzymatic digestion; and recovering a solubilized portion. See, e.g., U.S. Pat. No. 5,705,369. Enzymes of the invention can be added at any stage of this exemplary process.

The invention provides methods for making motor fuel compositions (e.g., for spark ignition motors) based on liquid hydrocarbons blended with a fuel grade alcohol made by using an enzyme or a method of the invention. In one aspect, the fuels made by use of an enzyme of the invention comprise, e.g., coal gas liquid- or natural gas liquid-ethanol blends. In one aspect, a co-solvent is biomass-derived 2-methyltetrahydrofuran (MTHF). See, e.g., U.S. Pat. No. 6,712,866.

In one aspect, methods of the invention for the enzymatic degradation of lignocellulose, e.g., for production of biofuels (including bioalcohols such as bioethanols, biomethanols, biobutanols or biopropanols, or biodiesels) from lignocellulosic material, can also comprise use of ultrasonic treatment of the biomass material; see, e.g., U.S. Pat. No. 6,333,181.

In another aspect, methods of the invention for producing biofuels (including bioalcohols such as bioethanols, biomethanols, biobutanols or biopropanols, or biodiesels) from a cellulosic substrate comprise providing a reaction mixture in the form of a slurry comprising cellulosic substrate, an enzyme of this invention and a fermentation agent (e.g., within a reaction vessel, such as a semi-continuously solids-fed bioreactor), and the reaction mixture is reacted under conditions sufficient to initiate and maintain a fermentation reaction (as described, e.g., in U.S. Pat. App. No. 20060014260). In one aspect, experiment or theoretical calculations can determine an optimum feeding frequency. In one aspect, additional quantities of the cellulosic substrate and the enzyme are provided into the reaction vessel at an interval(s) according to the optimized feeding frequency.

One exemplary process for making biofuels (including bioalcohols such as bioethanols, biomethanols, biobutanols or biopropanols, or biodiesels) of the invention is described in U.S. Pat. App. Pub. Nos. 20050069998; 20020164730; and in one aspect comprises stages of grinding the lignocellulosic biomass (e.g., to a size of 15-30 mm), subjecting the product obtained to steam explosion pre-treatment (e.g., at a temperature of 190-230° C.) for between 1 and 10 minutes in a reactor; collecting the pre-treated material in a cyclone or related product of manufacture; and separating the liquid and solid fractions by filtration in a filter press; introducing the solid fraction in a fermentation deposit and adding one or more enzymes of the invention, e.g., a cellulase and/or beta-glucosidase enzyme (e.g., dissolved in citrate buffer pH 4.8).

Another exemplary process for making biofuels (including bioalcohols such as bioethanols, biomethanols, biobutanols or biopropanols, or biodiesels) of the invention comprising bioethanols, biomethanols, biobutanols or biopropanols using enzymes of the invention comprises pretreating a starting material comprising a lignocellulosic feedstock comprising at least hemicellulose and cellulose. In one aspect, the starting material comprises potatoes, soybean (rapeseed), barley, rye, corn, oats, wheat, beets or sugar cane or a component or waste or food or feed production byproduct. The starting material ("feedstock") is reacted at conditions which disrupt the plant's fiber structure to effect at least a partial hydrolysis of the hemicellulose and cellulose. Disruptive conditions can comprise, e.g., subjecting the starting material to an average temperature of 180° C. to 270° C. at pH 0.5 to 2.5 for a period of about 5 seconds to 60 minutes; or, temperature of 220° C. to 270° C., at pH 0.5 to 2.5 for a period of 5 seconds to 120 seconds, or equivalent. This generates a feedstock with increased accessibility to being digested by an enzyme, e.g., a cellulase enzyme of the invention. U.S. Pat. No. 6,090,595.

Exemplary conditions for using enzymes of the invention in the hydrolysis of lignocellulosic material include reactions at temperatures between about 30° C. and 48° C., and/or a pH between about 4.0 and 6.0. Other exemplary conditions include a temperature between about 30° C. and 60° C. and a pH between about 4.0 and 8.0.

Glucanases, (or cellulases), mannanases, xylanases, amylases, xanthanases and/or glycosidases, e.g., cellobiohydrolases, mannanases and/or beta-glucosidases of the invention can be used in the conversion of biomass to fuels, and in the production of ethanol, e.g., as described in PCT Application Nos. WO0043496 and WO8100857. Glucanases (or cellulases), mannanases, xylanases, amylases, xanthanases and/or glycosidases, e.g., cellobiohydrolases, mannanases and/or beta-glucosidases of the invention can be used to produce fermentable sugars and glucan-containing biomass that can be converted into fuel ethanol.

Industrial, Drilling and Energy Applications

The method and compositions (including the "enzyme cocktails"—see below) of the invention can be used in any oil and gas discovery and/or drilling process, or any oil and gas well washing and/or fracturing process; for example:

Glucanases, (or cellulases), mannanases, xylanases, amylases, xanthanases and/or glycosidases, e.g., cellobiohydrolases, mannanases and/or beta-glucosidases of the invention can be used in modifying the viscosity of any plant derived material, e.g., where it applies to the oil and gas industry. For example, in one aspect, enzymes of the invention are used in the oil and gas industry where guar gum and modified guar are used in, e.g., fracturing fluids and drilling muds. The enzymes of the invention can be used to clean oil wells, e.g., to break the high viscosity or gel structure in fractural fluid after the fracturation. In one aspect, the enzymes of the invention used in these applications have a high thermostability. In one aspect, the enzymes of the invention used in these applications are resistant to the elevated temperatures in the ground or generated by drilling processes. Glucanases, (or cellulases), mannanases, xylanases, amylases, xanthanases and/or glycosidases, e.g., cellobiohydrolases, mannanases and/or beta-glucosidases of the invention can be used to treat drill mud (e.g., used mud).

Enzymes of the invention can be used in compositions for preventing flow capacity damage to wellbore screens and slotted liners, including their use with or in coatings applied to wellbore screens or slotted liners prior to insertion of the screens or slotted liners into a wellbore, e.g., as described in U.S. Pat. Application No. 20050065037.

Increasing the Flow of Production Fluids from a Subterranean Formation

The invention provides methods using one or more enzymes or enzyme cocktail(s) as described herein, wherein the method increases the flow of production fluids from a subterranean formation by removing viscous, starch-containing, damaging fluids formed during production operations; these fluids can be found within the subterranean formation which surrounds a completed well bore. Thus, this method of the invention results in production fluids being able to flow from the well bore. This method of the invention also addresses the problem of damaging fluids reducing the flow of production fluids from a formation below expected flow rates. In one aspect, the invention provides for formulating an enzyme treatment (using an enzyme of the invention) by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the polysaccharide-containing fluid.

The subterranean formation enzyme treatment processes of the invention can also include (in addition to the enzymes of this invention) the use of any combination of other enzymes such as amylases, xanthanases, glycosidases, cellulases, tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1, 3(4)-laccases, cutinases, peroxidases, other amylases, xanthanases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

Use in Drilling Well and Mining Operations

The invention also includes methods using enzymes of this invention (e.g., amylase, xanthanase, glycosidase and/or cellulase, a lignin degrading enzyme, alpha amylase, beta amylase, glucoamylase, dextrinase, cellulase, cellobiohydrolase, avicelase, carboxymethylcellulase, beta-glucanase, glucosidase, xylanase, mannanase, arabinofuranosidase, laccase, lignin peroxidase, pectinase, pectate lyase, xanthanase, xanthan lyase, xanthan depolymerase, pullulanase, lichenase, pachymanase, lipase, protease, proteinase, phytase, peptidase and/or catalase enzymes) in well and drilling operations, e.g., gas, oil or other drilling or mining operations, including any oil and gas well washing and/or fracturing processes. For example, in one aspect, enzymes of the invention are used to increase the flow of production fluids from a subterranean formation, e.g., a well or a mine. In one aspect, the enzymes or enzyme cocktails used to practice invention are used to remove viscous, polysaccharide-containing (e.g., starch-containing) fluids that can be damaging, e.g., fluids formed during production operations. These polysaccharide-containing (e.g., starch-containing) fluids can be found within a subterranean formation which surrounds a completed well bore. In one aspect, enzymes or enzyme cocktails of the invention is used in an oil well drilling fluid to aid in the carrying away of drilling mud.

In one aspect, the method comprises allowing production fluids (comprising enzymes or enzyme cocktails of the invention) to flow from the well bore or a mine. The methods can comprise reducing the flow of production fluids from the formation below expected flow rates and formulating an enzyme treatment by blending together an aqueous fluid and a polypeptide of the invention. The methods can comprise pumping the enzyme treatment to a desired location within the well bore or other drilled shaft and allowing the enzyme treatment to degrade the viscous, polysaccharide-containing, damaging fluid. The methods can comprise removing the fluid from the subterranean formation to the well or shaft surface. In one aspect, the enzyme treatment is effective to attack the alpha glucosidic linkages in the polysaccharide-containing fluid. In one aspect, enzymes or enzyme cocktails of the invention are used in mine drilling, well drilling (e.g., gas or oil well drilling), and the like to carry away drilling mud, e.g., while drilling the hole (well bore or shaft).

The enzymes or enzyme cocktails of the invention can be used in any well, shaft or mine drilling operation, many of which are well known in the art. For example, the invention provides methods of introducing enzymes or enzyme cocktails of the invention, which in one aspect can also comprise an oil or gas field production chemical, into a rock formation comprising oil and/or gas, which comprises passing a microemulsion comprising the enzyme (and, in one aspect, the chemical) down a production well and then into the formation. In one aspect, a production well is subjected to a "shut-in" treatment whereby an aqueous composition comprising an enzyme of the invention is injected into the production well under pressure and "squeezed" into the formation and held there. See, e.g., U.S. Pat. No. 6,581,687.

In one aspect, enzymes or enzyme cocktails of the invention that are used in these gas, oil or other drilling or mining operations, or including any oil and gas well washing and/or fracturing processes, are active at high or low pH and/or high or low temperatures, e.g., polymer-degrading or polysaccharide-degrading ("polymer breaker") enzymes of this invention, which include using "cocktails" of these and other enzymes such as amylase, xanthanase, glycosidase and/or cellulase enzymes, or a lignin degrading enzyme, alpha amylase, beta amylase, glucoamylase, dextrinase, cellulase, cellobiohydrolase, avicelase, carboxymethylcellulase, beta-glucanase, glucosidase, xylanase, mannanase, arabinofuranosidase, laccase, lignin peroxidase, pectinase, pectate lyase, xanthanase, xanthan lyase, xanthan depolymerase, pullulanase, lichenase, pachymanase, lipase, protease, proteinase, phytase, peptidase and catalase, which include using "cocktails" of these and other enzymes, are used in these processes are active under conditions comprising about pH 6.5, pH 6, pH 5.5, pH 5, pH 4.5, pH 4.0, pH 3.5, pH 3.0 or less (more acidic), or, under conditions comprising about pH 7, pH 7.5 pH 8.0, pH 8.5, pH 9, pH 9.5, pH 10, pH 10.5, pH 11.0, pH 11.5, pH 12, pH 12.5 or more (more basic). In one aspect, enzymes or enzyme cocktails of the invention used in these processes are active under conditions comprising a temperature range of anywhere between about −100° C. to about −80° C., about −80° C. to about −40° C., about −40° C. to about −20° C., about −20° C. to about 0° C., about 0° C. to about 37° C., about 0° C. to about 5° C., about 5° C. to about 15° C., about 15° C. to about 25° C., about 25° C. to about 37° C., about 37° C. to about 45° C., about 45° C. to about 55° C., about 55° C. to about 70° C., about 70° C. to about 75° C., about 75° C. to about 85° C., about 85° C. to about 90° C., about 90° C. to about 95° C., about 95° C. to about 100° C., about 100° C. to about 105° C., about 105° C. to about 110° C., about 110° C. to about 120° C., or 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 120° C. or more.

Use of Free and Immobilized Enzymes in Hydraulic Fracturing and Drilling Operations The invention provides compositions and methods comprising the inclusion of polymer-breaking (polymer-degrading), e.g., polysaccharide-degrading, enzymes in a free form or in an immobilized form, e.g., in an immobilized form as on a coating, e.g., of a particle, e.g., of a sand grain or a ceramic material such as a sintered bauxite.

In one aspect, the compositions and methods comprising the inclusion of polymer-breaking (polymer-degrading), e.g., polysaccharide-degrading, enzymes in or on a resin or similar material that coats particles, e.g., sand grains or a ceramic material such as a sintered bauxite; these particles (e.g., sand grains) can be used as the proppant in a hydraulic fracturing fluid. In one aspect, a proppant used to practice this invention is a sized particles mixed with a fracturing fluid to hold fractures open after a hydraulic fracturing treatment. In addition to naturally occurring sand grains, man-made or specially engineered proppants, such as resin-coated sand or high-strength ceramic materials like sintered bauxite, can also be used. Proppant materials can be sorted for size and sphericity to provide an efficient conduit for production of fluid from the reservoir to the wellbore. After the settling of the sand in the well fissures and fractures, the resin-bound enzymes can diffuse out and work on the concentrated and unbroken polymer that is often deposited on the formation surface at the completion of fracturing operations. Thus, this aspect of the invention can effectively remove a polysaccharide, a xanthan or a guar, e.g., a guar filter cake, from fractured oil and gas wells, and/or can enhance the permeability of the fractured zone.

In one embodiment, during the hydraulic fracturing operations, large volumes of water, sand, auxiliary chemicals (including enzymes and the mixtures of enzymes of this invention) and a polysaccharide-based polymer (e.g., a guar and/or its derivatives) are mixed and injected under pressure into the oil and/or gas wells to 'fracture' the surrounding formation and enhance the flow of gas or oil into the wellbore. Enzymes and enzyme mixtures as described herein can be used to hydrolyze these polysaccharide polymers and reduce the viscosity of the fluid (used in the hydraulic fracturing operations) for better penetration into the formation and more effective flow back at the end of the operation.

In one embodiment, the compositions and methods of this invention are used in enzymatic hydrolysis of base polymers (e.g., polysaccharide-based polymers, such as guar, xanthan and/or their derivatives); practicing this invention can solve the problem where enzymatic hydrolysis of these base polymers may be incomplete to leave some "unbroken" polymer in the fluid used in the hydraulic fracturing operations. As the fluid water content is lost to the formation the fluid becomes more concentrated and the unbroken polymers form a thick filter cake; this filter cake plugs the formation pores and reduces the flow of oil or gas into the wellbore—in one embodiment, the compositions and methods of this invention are used to break up these filter cake plugs.

Fracturing fluids contain large amounts of sand, commonly referred to as the proppant. As the fluid is pumped into the well, the proppant settles into the fissures and fractures and prevents them from closing. This helps enhance the porosity and permeability of the formation for better gas/oil flow. The sand grains are often coated with different industrial resins to increase their mechanical strength and prevent them from crushing under formation pressure. Thus, in one embodiment, the invention provides compositions and methods using free or immobilized polymer-degrading ("polymer-breaking") enzymes around, in or on the coating material of the sand. In one aspect, this is done by entrapment of the enzyme in the resin or by immobilization on the coating surface. Thus, in this aspect, enzyme(s) used to practice this invention can remain in contact with the filter cake thereby providing continual hydrolysis of the concentrated polymer, removing the cake from the fractures, and enhancing the permeability of the fractured formation.

In on aspect, the invention provides methods using these described enzyme in drilling operations, e.g., a typical drilling operation, where a well is created by drilling a hole 5 to 30 inches (13-76 cm) diameter into the earth with an oil rig, which rotates a drill bit. After the hole is drilled, a steel pipe (casing) slightly smaller than the hole is placed in the hole, and secured with cement. The casing provides structural integrity to the newly drilled wellbore in addition to isolating potentially dangerous high pressure zones from each other and from the surface.

With these zones safely isolated and the formation protected by the casing, the well can be drilled deeper (into potentially more-unstable and violent formations) with a smaller bit, and also cased with a smaller size casing. A wells can have 2 to 5 sets of subsequently smaller hole sizes drilled inside one another, each cemented with casing.

To drill the well, the drill bit, aided by rotary torque and the compressive weight of drill collars above it, breaks up the earth. Drilling fluid, or "mud", comprising the inclusion of polymer-breaking (polymer-degrading), e.g., polysaccharide-degrading, enzymes and enzyme mixtures of this invention, in a free form or in an immobilized form, is pumped down the inside of the drill pipe. The fluid exits at the drill bit and aids to break up the rock, keeping pressure on top of the bit, as well as cleaning, cooling and lubricating the bit.

The generated rock "cuttings" are swept up by the drilling fluid as it circulates back to surface outside the drill pipe. Fluid comprising polymer-breaking (polymer-degrading), e.g., polysaccharide-degrading, enzymes and enzyme mixtures of this invention, in a free form or in an immobilized form, can be added at this stage, too.

The fluids then go over "shakers" which shakes out the cuttings over screens allowing the good fluid to return back into the pits. Fluid comprising polymer-breaking (polymer-degrading), e.g., polysaccharide-degrading, enzymes and enzyme mixtures of this invention, in a free form or in an immobilized form, can be added at this stage, too.

These processes of the invention can be facilitated by addition of polymer-breaking (polymer-degrading), e.g., polysaccharide-degrading, enzymes and enzyme mixtures of this invention, in a free form or in an immobilized form. The drilling rig can contain all necessary equipment to circulate the drilling fluid, hoist and turn the pipe, control downhole pressures, remove cuttings from the drilling fluid, and generate onsite power for these operations.

The enzymes, enzyme mixtures, and methods of the invention can be practiced with any drilling mud or drilling fluid (some prefer to reserve the term "drilling fluid" for more sophisticated and well-defined "muds"), or any fluid used in operations to drill boreholes into the earth. The enzymes, enzyme mixtures, and methods of the invention can be practiced while drilling oil and/or natural gas wells and on exploration drilling rigs, including use with simpler holes.

The enzymes, enzyme mixtures, and methods of the invention can be used in, mixed with and/or practiced together with any well or drilling operation, e.g., where any mud is used, including use of any of the three main classification schemes of mud, where "mud" is used broadly and is separated into 3 categories based on the main component that makes up the mud: (1) "Water Based Mud" (WBM), which can be subdivided into dispersed and non-dispersed muds; (2) "Non Aqueous" or more commonly "Oil Based Mud" (OBM), including synthetic oils (SBM); and/or (3) Gaseous or Pneumatic mud.

The enzymes, enzyme mixtures, and methods of the invention can be used in, mixed with and/or practiced together with any well or drilling operation, e.g., can also be used in or with:
production wells when they are drilled primarily for producing oil or gas, once the producing structure and characteristics are established,
appraisal wells when they are used to assess characteristics (such as flowrate) of a proven hydrocarbon accumulation,
exploration wells when they are drilled purely for exploratory (information gathering) purposes in a new area,
wildcat wells when a well is drilled, based on a large element of hope, in a frontier area where very little is known about the subsurface.

The enzymes, enzyme mixtures, and methods of the invention can be used in, mixed with and/or practiced together with any well or drilling operation, e.g., can also be used in conjunction with methods, equipment and/or drilling operations as described, e.g., in U.S. Patent Application Publication No. 20070089910, Hewson, et al., describing, e.g., methods of forming a supported subterranean well bore, and uses, e.g., a positive displacement mud motor.

The enzymes, enzyme mixtures, and methods of the invention can be used in, mixed with and/or practiced together with methods, equipment and/or drilling operations as described, e.g., in U.S. Patent Application Publication No. 20070084638, Bohnsack, C., et al., describing, e.g., a system for facilitating flow of settled solids with drilling fluid from a container, the system including pressure nozzle apparatus with at least one nozzle from which is flowable fluid under pressure, powered rotation apparatus for selectively rotating the pressure nozzle apparatus so that the at least one nozzle is movable within the container as fluid is pumped through the at least one nozzle into the container; and, in one aspect, translation apparatus for moving the pressure nozzle apparatus with respect to the container as fluid under pressure is pumped to the at least one rotating nozzle. Mud tanks and mud pits are also described, and the enzymes, enzyme mixtures, and methods of the invention can be used in or with any of these fluids, and/or in any mud tanks and mud pits used in these types of operations.

The enzymes, enzyme mixtures, and methods of the invention can be used in, mixed with and/or practiced together with methods, equipment and/or drilling operations as described, e.g., in U.S. Patent Application Publication No. 20070081157, Csutak, S., et al., describing, e.g., apparatus for estimating a property of a fluid downhole comprising an ultraviolet (UV) light source for inducing light into the fluid at a wavelength that produces Raman scattered light at wavelengths that are shorter than wavelengths of substantial fluorescence reflected from the fluid in response to the induced light; a detector that detects a spectrum of the Raman scattered light and provides signals in response to the detected spectrum; and a processor that processes the signals to provide an estimate of the a property of the fluid. The enzymes, enzyme mixtures, and methods of the invention can be used in or with any of these fluids, and/or in operations to estimate filtrate contamination in a formation fluid. For example, these methods include detecting Raman scatters at a plurality of wavelengths of at least one component present in an oil-based mud that is not naturally present in the formation, and enzymes, enzyme mixtures, and methods of the invention can be used to aid in the accuracy of this detection.

The enzymes, enzyme mixtures, and methods of the invention can be used in, mixed with and/or practiced together with methods, equipment and/or drilling operations as described, e.g., in U.S. Patent Application Publication No. 20070075706, Chen, S., et al., describing, e.g., methods of evaluating an earth formation comprising making measurements with a downhole tool in a borehole in the earth formation; measuring a Quality factor of an antenna of the downhole tool at depths where the measurements are made; and using the measured Q and a resistivity of a mud in the borehole and a formation resistivity, and/or a borehole size indicator (BSI), for estimating the other of the formation resistivity and BSI, including measuring the resistivity of the mud in the borehole. The enzymes, enzyme mixtures, and methods of the invention can be used in or with any of these fluids, and/or in operations to evaluate an earth formation.

The enzymes, enzyme mixtures, and methods of the invention can be used in, mixed with and/or practiced together with methods, equipment and/or drilling operations as described, e.g., in U.S. Patent Application Publication No. 20070068675, Barry, M., et al., describing, e.g., methods for drilling and completing a gravel packed well, comprising drilling a wellbore with a drilling fluid, conditioning the drilling fluid, running the gravel packing assembly tools to depth in the wellbore with the conditioned drilling-fluid, and gravel packing a wellbore interval with a completion-fluid. The completion fluid may be the same as the drilling-fluid. This method may be combined with alternate-path sand screen technology to ensure proper distribution of the gravel pack. The proper fluids for drilling, gravel packing and sand screens installation are essential for well completion success. Careful planning, well preparation and completion execution are required to increase completion productivity and longevity. Usually, a minimum of three fluids have been used to drill and complete gravel packed wells. The first fluid is a solids-laden drilling-fluid used to drill the completion interval. The second fluid is a solids-free completion-fluid used to displace the solids-laden drilling-fluid and to run sand-exclusion equipment and gravel packing tools in a generally solids-free environment. The third fluid is a carrier fluid for the gravel during gravel packing of the completion interval. The enzymes, enzyme mixtures, and methods of the invention can be used in or with any of these fluids (including solids-laden drilling-fluids, solids-free completion-fluids and/or carrier fluids), and/or in operations for drilling and completing a gravel packed well.

The enzymes, enzyme mixtures, and methods of the invention can be used in, mixed with and/or practiced together with methods, equipment and/or drilling operations as described, e.g., in U.S. Patent Application Publication No. 20070066491, Bicerano J., et al., use of particles in the construction, drilling, completion and/or fracture stimulation of oil and natural gas wells; for example, as a proppant partial monolayer, a proppant pack, an integral component of a gravel pack completion, a ball bearing, a solid lubricant, a drilling mud constituent, and/or a cement additive, including use of thermoset polymer particles for use in applications requiring lightweight particles possessing high stiffness, strength, temperature resistance, and/or resistance to aggressive environments. The enzymes, enzyme mixtures, and methods of the invention can be used in or with any of these gravel packs, ball bearings, solid lubricants, drilling mud constituents, cement additives and/or the described thermoset polymer particles. The enzymes, enzyme mixtures, and methods of the invention can be used in or with nanofillers and/or nanocomposites, including heterogeneous nanocomposite morphologies.

The enzymes, enzyme mixtures, and methods of the invention can be used in, mixed with and/or practiced together with methods, equipment and/or drilling operations as described, e.g., in U.S. Patent Application Publication No. 20070039735, Robertson, B., et al., describing, e.g., methods of sealing a permeable zone within a subterranean formation, comprising: preparing a plugging composition comprising oil, clay, magnesium chloride, and magnesium oxide powder; and contacting the plugging composition with water in the subterranean formation such that the plugging composition forms a sealing mass, thereby substantially sealing a permeable zone within the subterranean formation.

The enzymes, enzyme mixtures, and methods of the invention can be used in, mixed with and/or practiced together with variable density drilling muds comprising compressible particulate materials, e.g., as described in U.S. Patent Application Publication No. 20070027036, Polizzotti, R., et al. The enzymes, enzyme mixtures, and methods of the invention can be used in or with, e.g., drilling muds comprising a compressible particulate material in the drilling mud, wherein density of the drilling mud changes due to a volume change of the compressible particulate material in response to pressure or temperature changes and wherein the compressible particulate material is configured to maintain the density of the drilling mud between a pore pressure gradient and a fracture gradient based on the volume change of the compressible particulate material in response to pressure changes at certain depths.

The enzymes, enzyme mixtures, and methods of the invention can be used to modify the viscosity of the drilling mud alone or in conjunction with the described (see Polizzotti, R., et al.) compressible materials, e.g., to place the fluid viscosity within pumpability requirements, and/or to adjust the pore pressure gradient and the fracture gradient. The enzymes, enzyme mixtures, and methods of the invention can be used to effect a volume change in the drilling mud, e.g., where the drilling mud rheology is configured to achieve a desired composite drilling mud rheology.

In one aspect, the enzymes, enzyme mixtures, and methods of the invention are used to alter the properties of the drilling mud to provide a desired composite a mud gel point, e.g., a mud gel point that can suspend rock cuttings in an annulus of a wellbore during drilling operations; and/or to alter the viscosity of the drilling mud in conjunction with, or alone (without), compressible hollow objects (see Polizzotti, R., et al.) to alter pumpability requirements.

In one aspect, the enzymes, enzyme mixtures, and methods of the invention are used to alter the properties well fluids comprising drilling muds, well cleanup fluids, workover fluids, spacer fluids, gravel pack fluids, acidizing fluids and/or fracturing fluids. In one aspect, the enzymes, enzyme mixtures, and methods of the invention are used to facilitate drilling, completing and/or stimulating a subterranean formation using a variable density fluid, and to modify the variable density fluid.

In one aspect, the enzymes, enzyme mixtures, and methods of the invention are used in methods of drilling, completing and/or stimulating subterranean formations using a variable density fluid, e.g., by modifying and/or "adjusting" the density of the fluid; for example, a method (see Polizzotti, R., et al.) comprising the steps of: introducing a fluid having a density that varies as a function of pressure into the subterranean formation, where the fluid comprises a base fluid and a portion of elastic particles; and drilling, completing and/or stimulating a subterranean formation using the variable density fluid (which can comprise the enzymes, enzyme mixtures of the invention, or have been modified by the methods of the invention).

In one aspect, the enzymes, enzyme mixtures, and methods of the invention are used with the methods and compositions as described in U.S. Pat. No. 4,099,583, describing, e.g., a dual gradient drilling system, where a lighter fluid is injected into the mud return annulus (typically in the riser) or other pathway to reduce the mud density from the injection point upwards, and the enzymes, enzyme mixtures, and methods of the invention can modify and/or "adjust" the density of this fluid.

In one aspect, the enzymes, enzyme mixtures, and methods of the invention are used with the methods and compositions as described in U.S. Pat. Nos. 6,530,437 and 6,588,501, describing a multi-gradient drilling method and an apparatus for reduction of hydrostatic pressure in sub sea risers; and U.S. Pat. Nos. 6,422,326, 6,156,708, 5,910,467 and 5,881,826, describing the addition of various fluid aphrons to drilling mud formulations.

In one aspect, the enzymes, enzyme mixtures, and methods of the invention are used with the methods and compositions as described in U.S. Pat. No. 6,497,289, describing use of solid expandable liners, e.g., as tubular systems that are run into a well and expanded.

In alternative embodiments, the enzymes, enzyme mixtures, and methods of the invention are used to tailor drilling mud density with depth so that the effective mud weight remains between the pore pressure and the fracture gradient at all depths. The required variation in mud density can be achieved by changing the properties of fluids with the enzymes, enzyme mixtures, and methods of the invention to modify/change volume and density, to effect a change in response to pressure. The enzymes, enzyme mixtures, and methods of the invention can be used with any particulate components, e.g., various shapes, such as spheres, cubes, pyramids, oblate or prolate spheroids, cylinders, pillows and/or other shapes or structures. The enzymes, enzyme mixtures, and methods of the invention can be used with any particulate components, e.g., compressible hollow objects which are filled with pressurized gas, or compressible solid materials or objects as described in Polizzotti, R., et al., supra.

In alternative aspects, the enzymes, enzyme mixtures, and methods of the invention can be used in or with any well or drilling operation, e.g., including directional drilling, sometimes known as slant drilling, to drill non-vertical wells; including used in any of directional drillings three main groups; Oilfield Directional Drilling, Utility Installation Directional Drilling (commonly known as H.D.D./Horizontal Directional Drilling/Directional boring); and/or in-seam directional drilling (Coal-Bed methane).

In one aspect, the enzymes, enzyme mixtures, and methods of the invention can be used in conjunction with well logging, a technique used in the oil and gas industry for recording rock and fluid properties to find hydrocarbon zones in the geological formations within the Earth's crust. Logging can be performed to measure the effect of practicing the methods of this invention, e.g., pumping fluids comprising the enzymes or enzyme mixtures of this invention into a well. A logging procedure may consist of lowering a 'logging tool' on the end of a wireline into an oil well (or hole) to measure the rock and fluid properties of the formation. An interpretation of these measurements is then made to locate and quantify potential depth zones containing oil and gas (hydrocarbons). Logging tools developed over the years measure the electrical, acoustic, radioactive, electromagnetic, and other properties of the rocks and their contained fluids. Logging is usually performed as the logging tools are pulled out of the hole. This data is recorded to a printed record called a 'Well Log' and is normally transmitted digitally to office locations. Well logging is performed at various intervals during the drilling of the well and when the total depth is drilled, which could range in depths from 300 m to 8000 m (1000 ft to 25,000 ft) or more.

In addition to the methods, enzymes or enzymes mixtures described herein, the methods, the enzyme muds or other drilling fluids used to practice this invention can comprise (use of) a water-based drilling mud that can comprise a bentonite clay (gel), and in some aspects, also comprising additives such as barium sulfate (barite), calcium carbonate (chalk) or hematite. Various thickeners also can be used to influence the viscosity of the fluid, e.g., lignosulfonates, xanthan gum, guar gum, glycol, carboxymethylcellulose, polyanionic cellulose (PAC), or starch. The enzymes or enzymes mixtures described herein, used to practice this invention can be used to modify the properties of (e.g., the viscosity of) the fluids, e.g., to modify the properties of lignosulfonates, xanthan gum, guar gum, glycol, carboxymethylcellulose, polyanionic cellulose (PAC), or starch.

The methods, enzymes or enzymes mixtures described herein, used to practice this invention can be used to modify the properties of deflocculants, which are used to reduce viscosity of clay-based muds; anionic polyelectrolytes, e.g., acrylates, polyphosphates, lignosulfonates (Lig) or tannic acid derivates such as Quebracho (red mud was the name for a Quebracho-based mixture, named after the color of the red tannic acid salts; it was commonly used in 1940s to 1950s, then became obsolete when lignosulfates became available).

The methods, enzymes or enzymes mixtures described herein, used to practice this invention can be used in (e.g., added to) water injectors for injecting water into a formation, either to maintain reservoir pressure or simply to dispose of water produced with a hydrocarbon (e.g., because even after treatment, it would be too oily and too saline to be considered clean for dumping, e.g., dumping overboard or into a fresh water source in the case of onshore wells). Thus, the methods and compositions (e.g., mixtures of enzymes, immobilized enzymes) of this invention are used with water injection as an element of reservoir management and produced water disposal.

The methods, enzymes or enzymes mixtures described herein, used to practice this invention can be used in (e.g., added to) aquifer producers, e.g., as in intentionally producing reservoir water for re-injection (e.g., in a well bore) to manage pressure; this is in effect moving reservoir water from where it is not as useful, to where it is more useful. These wells will generally only be used if produced water from the oil or gas producer is insufficient for reservoir management purposes. Thus, in one aspect, the methods and compositions (e.g., mixtures of enzymes, immobilized enzymes) of this invention are used with aquifer produced water and/or sea water.

Modifying the Properties of Lignosulfonates or Sulfonated Lignins

The methods, enzymes or enzymes mixtures described herein, used to practice this invention can be used to modify the properties of lignosulfonates or sulfonated lignin in any process. For example, the methods, enzymes or enzymes mixtures described herein, used to practice this invention can be used to modify the properties of any water-soluble anionic polyelectrolyte polymers, including sulfonated lignins and lignin byproducts of an acid sulfite and/or a sulfite process for production of wood pulp, including "black liquor".

The methods, enzymes or enzymes mixtures described herein, used to practice this invention can be used to modify the properties of lignosulfonates used as deflocculants in drilling mud used in oil drilling (where it replaced Quebracho). In alternative embodiments, the methods, enzymes or enzymes mixtures described herein, used to practice this invention can be used to modify the lignosulphonates used in the cement industry as a rawmix slurry defiocculant; used in concrete as a plasticizer and/or used as emulsion stabilizers.

Thickening, Suspending and Stabilizing Aqueous Systems

The invention provides methods for using polysaccharides in commercial-industrial processes to thicken, suspend or stabilize aqueous systems. For example, in one aspect, the methods of the invention are used to modify or "adjust the properties of" polysaccharide polymers and surfactants in printing paste. In one aspect, the methods of the invention are used to modify or "adjust the properties of" polysaccharide polymers and surfactants to produce gels and to act as flocculates, binders, lubricants, to serve as modifiers of film properties.

In one aspect, the compositions and methods of the invention are used to modify or "adjust the properties of" polysaccharide polymers and surfactants that act as adjusters of rheological parameters in e.g., flocculates, binders, lubricants, films and/or gels.

In one aspect, the compositions and methods of the invention are used to modify or "adjust the properties of" polysaccharide polymers and surfactants that act as flocculates, binders, lubricants and/or surfactants in dispersants, wetting agents, emulsifiers and antifoaming agents. In one aspect, the methods of the invention are used to modify or "adjust the properties of" polysaccharide polymers and surfactants that modify the property of a polysaccharide thickeners such as a guar gum, with different substitution levels and different producers used at different concentrations and temperatures.

Other Industrial, Medical, Agricultural, Research Applications

Glucanases, (or cellulases), mannanases, xylanases, amylases, xanthanases and/or glycosidases, e.g., cellobiohydrolases, mannanases and/or beta-glucosidases of the invention can be used in a wide variety of industrial, research, agricultural and medical applications, including and in addition to those described herein, for detergents, treating textiles or fibers, treating or preparing food, animal feed and beverages, treating waste, oral care products, medical and research applications, biomass conversion applications, drilling applications for, e.g., oil and gas, and the like.

In one aspect, the compositions and methods of the invention are used to modify polysaccharide polymers for use as anti-scalants and dispersants, where the modified polymers are useful in compositions used in aqueous systems, e.g., in detergent formulations, water treatment, dispersants and oilfield applications and as fiberglass binders, as described e.g., in U.S. Patent Application Publication No. 20070015678, Rodrigues, K., et al. In one aspect, the compositions and methods of the invention are used together with builders, surfactants, enzymes, solvents, hydrotropes, fillers, bleach, perfumes and/or colorants in aqueous systems, e.g., in detergent formulations, water treatment, dispersants and oilfield applications and as fiberglass binders. In one aspect, the compositions and methods of the invention are used to modify polysaccharide polymers for use in aqueous systems such as boiler water or steam generating systems, cooling water systems, gas scrubbing systems, pulp and paper mill systems, desalination systems, fabric, dishware and hard surface cleaning systems and downhole systems encountered during the production of gas, oil, and geothermal wells.

Glucanases, (or cellulases), mannanases, xylanases, amylases, xanthanases and/or glycosidases, e.g., cellobiohydrolases, mannanases and/or beta-glucosidases of the invention can be used in a number of other applications. For example, an alternative use comprises using the compositions (e.g., probes and antibodies) and screening methods of the invention, to identify and/or isolate new glucanases (or cellulases), mannanases, xylanases, amylases, xanthanases and/or glycosidases, e.g., cellobiohydrolases, mannanases and/or beta-glucosidases; these are discovered by screening existing libraries (e.g., DNA libraries) and libraries constructed from diverse environmental sources, including from mesophilic and moderately thermophilic locations as well as from targeted sources including digestive flora, microorganisms in ocean, animal waste, soil bacteria and highly alkaline habitats. Biotrap and primary enrichment strategies using glucan-comprising substrates and/or non-soluble polysaccharide fractions of animal feed material are also useful; see, e.g., U.S. Pat. Nos. 7,018,793; 6,790,605; 6,361,974; 5,939,250.

Glucanases, (or cellulases), mannanases, xylanases, amylases, xanthanases and/or glycosidases, e.g., cellobiohydrolases, mannanases and/or beta-glucosidases of the invention can be used in combination with other enzymes involved in cellulose digestion like cellobiohydrolases and beta-glucosidases, see discussion of enzyme "cocktails" of the invention, as described herein.

Enzymes of the invention can be used in improving the quality and quantity of milk protein production in lactating cows (see, for example, Kung, L., et al., *J. Dairy Science,* 2000 January 83:115-122), increasing the amount of soluble saccharides in the stomach and small intestine of pigs (see, for example, van der Meulen, J. et al., *Arch. Tierernahr,* 2001 54:101-115), improving late egg production efficiency and egg yields in hens (see, for example, Jaroni, D., et al., *Poult. Sci.,* 1999 June 78:841-847).

Additional uses for glucanases (or cellulases), mannanases, xylanases, amylases, xanthanases and/or glycosidases, e.g., cellobiohydrolases, mannanases and/or beta-glucosidases of the invention include: use in the production of water soluble dietary fiber (see, for example, U.S. Pat. No.

5,622,738); in improving the filterability, separation and production of starch (see, for example, U.S. Pat. Nos. 4,960,705 and 5,023,176); in an enzyme composition for promoting the secretion of milk of livestock and improving the quality of the milk (see, for example, U.S. Pat. No. 4,144,354); in reducing viscosity of plant material (see, for example, U.S. Pat. No. 5,874,274).

Various uses of glucanases (or cellulases), mannanases, xylanases, amylases, xanthanases and/or glycosidases, e.g., cellobiohydrolases, mannanases and/or beta-glucosidases of the invention include transformation of a microbe that produces ethanol (see, for example, PCT Application No. WO99/46362), in production of oenological tannins and enzymatic composition (see, for example, PCT Application No. WO0164830), in stimulating the natural defenses of plants (see, for example, PCT Application No. WO0130161), in production of sugars from hemicellulose substrates (see, for example, PCT Application No. WO9203541), in the cleaning of fruit, vegetables, mud or clay containing soils (see, for example, PCT Application No. WO9613568), in cleaning beer filtration membranes (see, for example, PCT Application No. WO9623579), in a method of killing or inhibiting microbial cells (see, for example, PCT Application No. WO9732480) and in determining the characteristics of process waters from wood pulp bleaching by using the ratios of two UV absorption measurements and comparing the spectra (see, for example, PCT Application No. WO9840721).

Enzymes of the invention can be used in air and/or water purifying systems, e.g., in air or water filter media and systems, as described, e.g., in U.S. Pat. Application No. 20060117958, describing air purifying systems having a dry tensile strength, a wet tensile strength in association with water resistance and water repellency and exhibiting bactericidal/sterilizing or antimicrobial means properties using an enzyme reaction (such as an enzyme of this invention).

Two screening formats (activity-based and sequence-based) are used in the discovery of novel glucanases (or cellulases), mannanases, xylanases, amylases, xanthanases and/or glycosidases, e.g., cellobiohydrolases, mannanases and/or beta-glucosidases. The activity-based approach is direct screening for glucanase activity in agar plates using a substrate such as AZO-barley beta glucan (Megazyme). Alternatively a sequence-based approach may be used, which relies on bioinformatics and molecular biology to design probes for hybridization and biopanning See, for example, U.S. Pat. Nos. 6,054,267, 6,030,779, 6,368,798, 6,344,328. Hits from the screening are purified, sequenced, characterized (for example, determination of specificity, temperature and pH optima), analyzed using bioinformatics, subcloned and expressed for basic biochemical characterization. These methods may be used in screening for glucanases (or cellulases), mannanases, xylanases, amylases, xanthanases and/or glycosidases, e.g., cellobiohydrolases, mannanases and/or beta-glucosidases useful in a myriad of applications, including dough conditioning and as animal feed additive enzymes.

In characterizing enzymes obtained from screening, the exemplary utility in dough processing and baking applications may be assessed. Characterization may include, for example, measurement of substrate specificity (glucan, CMC, BBG), temperature and pH stability and specific activity. A commercial enzyme may be used as a benchmark. In one aspect, the enzymes of the invention have significant activity at pH≥7 and 25-35° C., are inactive on insoluble glucan, are stable and active in 50-67% sucrose.

In another aspect, utility as feed additives may be assessed from characterization of candidate enzymes. Characterization may include, for example, measurement of substrate specificity (glucan, CMC, BβG), temperature and pH stability, specific activity and gastric stability. In one aspect the feed is designed for a monogastric animal and in another aspect the feed is designed for a ruminant animal. In one aspect, the enzymes of the invention have significant activity at pH 2-4 and 35-40° C., a half-life greater than 30 minutes in gastric fluid, formulation (in buffer or cells) half-life greater than 5 minutes at 85° C. and are used as a monogastric animal feed additive. In another aspect, the enzymes of the invention have one or more of the following characteristics: significant activity at pH 6.5-7.0 and 35-40° C., a half-life greater than 30 minutes in rumen fluid, formulation stability as stable as dry powder and are used as a ruminant animal feed additive.

Enzymes are reactive toward a wide range of natural and unnatural substrates, thus enabling the modification of virtually any organic lead compound. Moreover, unlike traditional chemical catalysts, enzymes are highly enantio- and regio-selective. The high degree of functional group specificity exhibited by enzymes enables one to keep track of each reaction in a synthetic sequence leading to a new active compound. Enzymes are also capable of catalyzing many diverse reactions unrelated to their physiological function in nature. For example, peroxidases catalyze the oxidation of phenols by hydrogen peroxide. Peroxidases can also catalyze hydroxylation reactions that are not related to the native function of the enzyme. Other examples are glucanases which catalyze the breakdown of polypeptides. In organic solution some glucanases can also acylate sugars, a function unrelated to the native function of these enzymes.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see PCT/US94/09174).

Enzyme Cocktails or Mixtures

In alternative embodiments, any composition, method, product or process of the invention can include any combination of one or any other enzyme(s), either a mixture of a variety of enzymes of this invention, or a mixture with other enzymes of the same or different class: the so-called "enzyme cocktails" of this invention. These enzyme mixtures, or cocktails, can comprise e.g., other glucanases, other mannanases, other xylanases, any hydrolase (e.g., proteases, esterases, etc.), catalases, glucanases, cellulases, endoglycosidases, endo-beta.-1,4-glucanases, amyloglucosidases, glucose isomerases, glycosyltransferases, lipases, esterase, phospholipases, lipooxygenases, beta-glucanases, endo-beta-1,3(4)-glucanases, cutinases, peroxidases, laccases, amylases, glucoamylases, pectinases, reductases, oxidases, decarboxylases, phenoloxidases, ligninases, pullulanases, phytases, arabinanases, hemicellulases, mannanases, xyloglucanases, xylanases, pectin acetyl esterases, rhamnogalacturonan acetyl esterases, polygalacturonases, rhamnogalacturonases, galactanases, pectate lyases, transglutaminases, pectin methylesterases, cellobiohydrolases and/or transglutaminases—any combination thereof.

For example, as noted above, "enzyme cocktails" of this invention can be used in oil or gas drilling processes, e.g., subterranean formation enzyme treatment processes, comprising the use of any combination of at least one enzyme of this invention and any other enzyme(s), such as amylases, xanthanases, glycosidases, cellulases, tryptophanases or tyrosine decarboxylases, laccases, catalases, laccases, other cellulases, endoglycosidases, endo-beta-1,4-laccases, amyloglucosidases, other glucosidases, glucose isomerases, glycosyltransferases, lipases, phospholipases, lipooxygenases, beta-laccases, endo-beta-1,3(4)-laccases, cutinases, peroxidases, other amylases, xanthanases, glucoamylases, pectinases, reductases, oxidases, decarboxylases, phenoloxidases, ligninases, pullulanases, arabinanases, hemicellulases, mannanases, xylolaccases, xylanases, pectin acetyl esterases, rhamnogalacturonan acetyl esterases, proteases, peptidases, proteinases, polygalacturonases, rhamnogalacturonases, galactanases, pectin lyases, transglutaminases, pectin methylesterases, other cellobiohydrolases and/or transglutaminases.

The invention will be further described with reference to the following examples; however, it is to be understood that the invention is not limited to such examples.

EXAMPLES

Example 1

Plate Based Endoglycosidase Enzyme Discovery: Expression Screening

The following example demonstrates the isolation of and confirmation of the enzymatic activity of exemplary enzymes and nucleic acids of the invention. These assays can also be used to determine if a polypeptide has the requisite enzyme (e.g., glucanase (or cellulase), e.g., endo-glucanase, mannanase, xylanase, amylase, xanthanase and/or glycosidase, e.g., cellobiohydrolase, mannanase and/or beta-glucosidase) activity to be within the scope of the invention.

Titer Determination of Lambda Library: Add 1.0 µL of Lambda Zap Express amplified library stock to 600 µL $E.$ $coli$ MRF' cells ($OD_{600}$=1.0). Dilute MRF' stock with 10 mM $MgSO_4$. Incubate mixture at 37° C. for 15 minutes, then transfer suspension to 5-6 mL of NZY top agar at 50° C. and gently mix. Immediately pour agar solution onto large (150 mm) NZY media plate and allow top agar to solidify completely (approximately 30 minutes). Invert the plate. Incubate the plate at 39° C. for 8-12 hours. (The number of plaques is approximated. Phage titer determined to give 50,000 pfu/plate. Dilute an aliquot of Library phage with SM buffer if needed.)

Substrate Screening: Add Lambda Zap Express (50,000 pfu) from amplified library to 600 µL of $E. coli$ MRF' cells ($OD_{600}$=1.0) and incubate at 37° C. for 15 minutes. While phage/cell suspension is incubating, add 1.0 mL of desired polysaccharide dye-labeled substrate (usually 1-2% w/v) to 5.0 mL NZY top agar at 50° C. and mix thoroughly. (Solution kept at 50° C. until needed.) Transfer the cell suspension to substrate/top agar solution and gently mix. Immediately pour solution onto large (150 mm) NZY media plate. Allow top agar to solidify completely (approximately 30 minutes), then invert plate. Incubate plate at 39° C. for 8-12 hours. Observe plate for clearing zones (halos) around plaques. Core plaques with halos out of agar and transfer to a sterile micro tube. (A large bore 200 µL pipette tip works well to remove (core) the agar plug containing the desired plaque.) Resuspend phage in 500 µL SM buffer. Add 200 µL chloroform to inhibit any further cell growth.

Isolation of Pure Clones: Add 5 µL of resuspended phage suspension to 500 µL of $E. coli$ MRF' cells ($OD_{600}$=1.0). Incubate at 37° C. for 15 minutes. While phage/cell suspension is incubating, add 600 µL of desired polysaccharide dye-labeled substrate (usually 1-2% w/v) to 3.0 mL NZY top agar at 50° C. and mix thoroughly. (Solution kept at 50° C. until needed.) Transfer cell suspension to substrate/top agar solution and gently mix. Immediately pour solution onto small (90 mm) NZY media plate and allow top agar to solidify completely (approximately 30 minutes), then invert plate. Incubate plate at 39° C. for 8-12 hours. Plate observed for a clearing zone (halo) around a single plaque (pure clone). (If a single plaque cannot be isolated, adjust titer and replate phage suspension.) Phage are resuspended in 500 µL SM buffer and 200 µL Chloroform is added to inhibit any further cell growth.

Excision of Pure Clone: Allow pure phage suspension to incubate at room temperature for 2 to 3 hours or overnight at 4° C. Add 100 µL of pure phage suspension to 200 µL $E.$ $coli$ MRF' cells ($OD_{600}$=1.0). Add 1.0 µL of ExAssist helper phage (>1×10$^6$ pfu/mL; Stratagene). Incubate suspension at 37° C. for 15 minutes. Add 3.0 mL of 2×YT media to cell suspension. Incubate at 37° C. for 2-2.5 hours while shaking Transfer tube to 70° C. for 20 minutes. Transfer 50-100 µL of phagemid suspension to a micro tube containing 200 µL of $E. coli$ Exp 505 cells ($OD_{600}$=1.0). Incubate suspension at 37° C. for 45 minutes. Plate 100 µL of cell suspension on $LB_{kan\ 50}$ media (LB media with Kanamycin 50 µg/mL). Incubate plate at 37° C. for 8-12 hours. Observe plate for colonies. Any colonies that grow contain the pure phagemid. Pick a colony and grow a small (3-10 mL) liquid culture for 8-12 hours. Culture media is liquid $LB_{kan\ 50}$.

Activity Verification: Transfer 1.0 mL of liquid culture to a sterile micro tube. Centrifuge at 13200 rpm (16000 g's) for 1 minute. Discard supernatant and add 200 μL of phosphate buffer pH 6.2. Sonicate for 5 to 10 seconds on ice using a micro tip. Add 200 μL of appropriate substrate, mix gently and incubate at 37° C. for 1.5-2 hours. A negative control should also be run that contains only buffer and substrate. Add 1.0 mL absolute ethanol (200 proof) to suspension and mixed. Centrifuge at 13200 rpm for 10 minutes. Observe supernatant for color. Amount of coloration may vary, but any tubes with more coloration than control is considered positive for activity. A spectrophotometer can be used for this step if so desired or needed. (For Azo-barley beta glucan, Megazyme, read at 590 nm).

RFLP of Pure Clones from Same Libraries: Transfer 1.0 mL of liquid culture to a sterile micro tube. Centrifuge at 13200 rpm (16000 g's) for 1 minute. Follow QIAprep spin mini kit (Qiagen) protocol for plasmid isolation and use 40 μL holy water as the elution buffer. Transfer 10 μL plasmid DNA to a sterile micro tube. Add 1.5 μL Buffer 3 (New England Biolabs), 1.5 μL 100×BSA solution (New England Biolabs) and 2.0 μL holy water. To this add 1.0 μL Not 1 and 1.0 μL Pst 1 restriction endonucleases (New England Biolabs). Incubate for 1.5 hours at 37° C. Add 3.0 μL, 6× Loading buffer (Invitrogen). Run 15 μL of digested sample on a 1.0% agarose gel for 1-1.5 hours at 120 volts. View the gel with a gel imager. Perform sequence analysis on all clones with a different digest pattern.

FIG. 5 is a table containing characterization of the exemplary "parent" enzyme of the invention SEQ ID NO:2, including summarizing the relative activities of several exemplary enzymes of the invention under various conditions, e.g., varying pH and temperature, as discussed above.

Example 2

Activity Assays

The following example demonstrates the enzymatic activity of exemplary enzymes of the invention. These assays can also be used to determine if a polypeptide has the requisite enzyme (e.g., glucanase (or cellulase), e.g., endoglucanase, mannanase, xylanase, amylase, xanthanase and/or glycosidase, e.g., cellobiohydrolase, mannanase and/or beta-glucosidase) activity to be within the scope of the invention.

Polypeptides of the invention were demonstrated to have glucanase activity, as described below. Specific activity was determined on barley β-glucan (BBG) or carboxymethylcellulose (CMC) using the BCA reducing sugar assay. 1 unit (U) of glucanase activity=1 μmol/min$^{-1}$ glucose reducing equivalents released at 37° C., pH 5.3.

| | | | | Specific Activity (U/mg) | | | | |
|---|---|---|---|---|---|---|---|---|
| Glucanase | Mw (kDa) | pI | GH Family | Native, BBG | 6H tagged, BBG | 6H tagged, CMC | $T_{opt}$ (° C.) | $pH_{opt}$ |
| SEQ ID NO: 2 (encoded, e.g., by SEQ ID NO: 1) | 37.5 | 5.9 | 5 | 22 | ND | ND | ≥90 | 5-7 |

Exemplary polypeptides of the invention were demonstrated to have alkaline endoglucanase/cellulase activity, with various pH and temperature optimums. Activity can be determined using a cellulase activity assay (a BCA reducing ends assay), as described in detail in Example 3, below.

Example 3

Cellulase Activity Assay: BCA Reducing Ends Assay

The following example describes an assay, a cellulase activity assay (a BCA reducing ends assay) that can be used to determine if a polypeptide has the requisite enzyme (e.g., glucanase (or cellulase), e.g., endoglucanase, mannanase, xylanase, amylase, xanthanase and/or glycosidase, e.g., cellobiohydrolase, mannanase and/or beta-glucosidase) activity, e.g., an alkaline endoglucanase/cellulase activity (see Example 2, above) to be within the scope of the invention.

This assay was designed to measure the amount of reducing ends produced during the enzymatic degradation of carboxymethylcellulose (CMC) in a high throughput multiple sample 96-well format.

Materials:
Substrate Solutions:
1% CMC
Dissolve 1 gm CMC in 100 ml 50 mM Britton-Robinson buffer at pH ~4, heat CMC solution in boiling water bath, while mixing, for 20-40 minutes until it dissolves (solution will still appear slightly milky, but translucent). Adjust to desired pH with 1M NaOH or HCl.
Solution A:
64 mg/ml sodium carbonate monohydrate
24 mg/ml sodium bicarbonate
1.95 mg/ml BCA (4,4'-dicarboxy-2,2'-biquinoline disodium salt (Sigma Chemical cat #D-8284)
Add above to dH2O,
Might need to dissolve the BCA by heating, don't heat more than ~80 C.
Solution B:
1.24 mg/ml cupric sulfate pentahydrate
1.26 mg/ml L-serine
Add above to dH2O
Working Reagent:
1:1 of solutions A & B, make fresh working reagent mixture every day (usually only make enough for each assay), make fresh Solutions A & B every week.
Glucose Stock Solution:
10 mM Glucose in dH2O. 0.2 um filter, store at 4 C.
Glucose Standards:
Dilute the 10 mM Glucose stock in 1% CMC at desired pH; to a final concentration of 0, 100, 200, 300, 400, 500 uM. Since the curve is determined by adding 10 ul of the standards to the working reagent it works out to 0-0.005 umole glucose/well. The standard curve needs to be generated for each plate of sample time-points, as the heating cycle can affect the amount of signal observed.
Methods:
Set-Up:
Aliquot 1 ml of substrate solution (1% CMC) into deep-well plate (if using ambient Temp) or Acme-tubes in hot-block, equilibrate to desired temperature (~5 min) in heat block or heated water bath.
While solution is equilibrating, make 10 ml of the working reagent and aliquot 100 ul into 96 well PCR-plate. Set plate on ice.
Reaction/Sampling:
After temperature equilibration is complete, add enzyme solution to substrate solution. Mix immediately by pipetting up/down. Immediately aliquot 10-ul into PCR-plate (this is t=0, zero time point). Aliquot 10-ul into PCR-plate at each desired time point (e.g., 0, 2, 5, 10, 15, 20, 30 minutes).

Save the last row on the plate for addition of 10 ul of glucose standards (I.e. wells should only have the 100-ul working reagent in them)

Assay Color Development:

When all time points are collected and standards are added, cover plate and heat to 100 C for 10 min using PCR machine. Cool plate on ice for 5-10 min (or set PCR machine to 1 C for 10 min).

Add 100 ul H2O to wells. Mix. Aliquot 100 ul of mixture into clear flat bottomed 96-well plate and read absorbance at 560 nm.

Generate Standard Curve:

Plot the A560 vs. umole glucose from the wells containing the glucose standards. Use linear regression to calculate the slope ($S_{std}$).

Generate Graph of Reaction Slope:

Plot A560 vs. time-points. Zero each sample's time points against its own T=0 (i.e., subtract sample's T=0 absorbance value from all other time-points of same sample).

Generate the slope ($S_{rxn}$) for each set of sample time-points (A560/time).

Activity Determination:

Divide $S_{rxn}$ by the $S_{std}$, and multiply by 100 (as the umole product detected is the amount of reducing ends in the 10-ul used in the assay, not the total amount generated in the 1 ml enzyme reaction).

Specific Activity Determination:

Divide the Activity (in units of umole/min) by the total mg of protein added in the 1-ml reaction. Determine the protein concentration by Bradford or similar assay.

Divide the protein concentration by any dilutions used.

Multiply by the volume (in ml) used in the reaction.

All points should be done in duplicate with triplicate being better.

Figure 6:
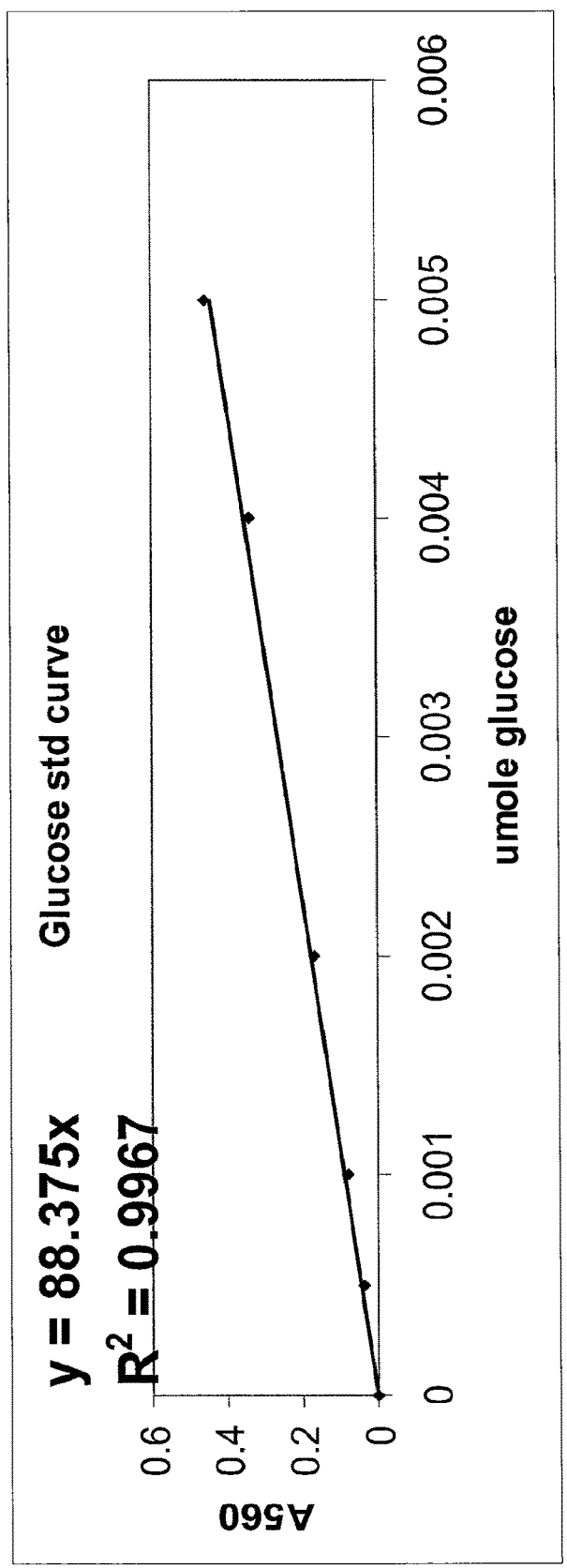
FIG. 6 is an illustration in graph form of an exemplary set of data ("sample data") that is illustrated as a "standard curve", as discussed in Example 3.

The following chart sets forth an exemplary set of data ("sample data") that is illustrated in graph form as a "standard curve" in FIG. 6.

example of a substrate comprises a (1-4)-linked beta-D-mannopyranose backbone with branchpoints from their 6-positions linked to alpha-D-galactose, i.e., 1-6-linked alpha-D-galactopyranose; e.g., as found in guar, tara, Locust Bean or carob gum, or fenugreek (*Trigonella foenum-graecum*)). In another aspect, enzymes are tested to determine if they are within the scope of the invention using a glucanase substrate (many of which are well known in the art), e.g., barley and/or oat glucan, and/or galactomannan-comprising compositions.

Specific Activity of the Glucanase Encoded by SEQ ID NO:2

Specific activity of the exemplary enzyme of the invention having a sequence as set forth in the "parental" SEQ ID NO:2 (encoded by, e.g., SEQ ID NO:1) was demonstrated using the following protocol:

The glucanase encoded by the "parental" SEQ ID NO:2 was purified to homogeneity using ion exchange chromatography. Specific activities were determined on 1% substrate in 50 mM sodium acetate buffer pH 5.3, at 37° C. using the BCA reducing sugar assay. 1 unit (U) of glucanase activity=1 [mmol/min$^{-1}$ glucose reducing equivalents released at 37° C., pH 5.3.

Barley Beta Glucan (BBG): 30 U/mg

Oat Beta Glucan (OBG): 38 U/mg

Carboxymethylcellulose (CMC): 40 U/mg

Carob Galactomannan: 0.3 U/mg

Temperature Profile of the Glucanase Encoded by SEQ ID NO:2

Figure 7:
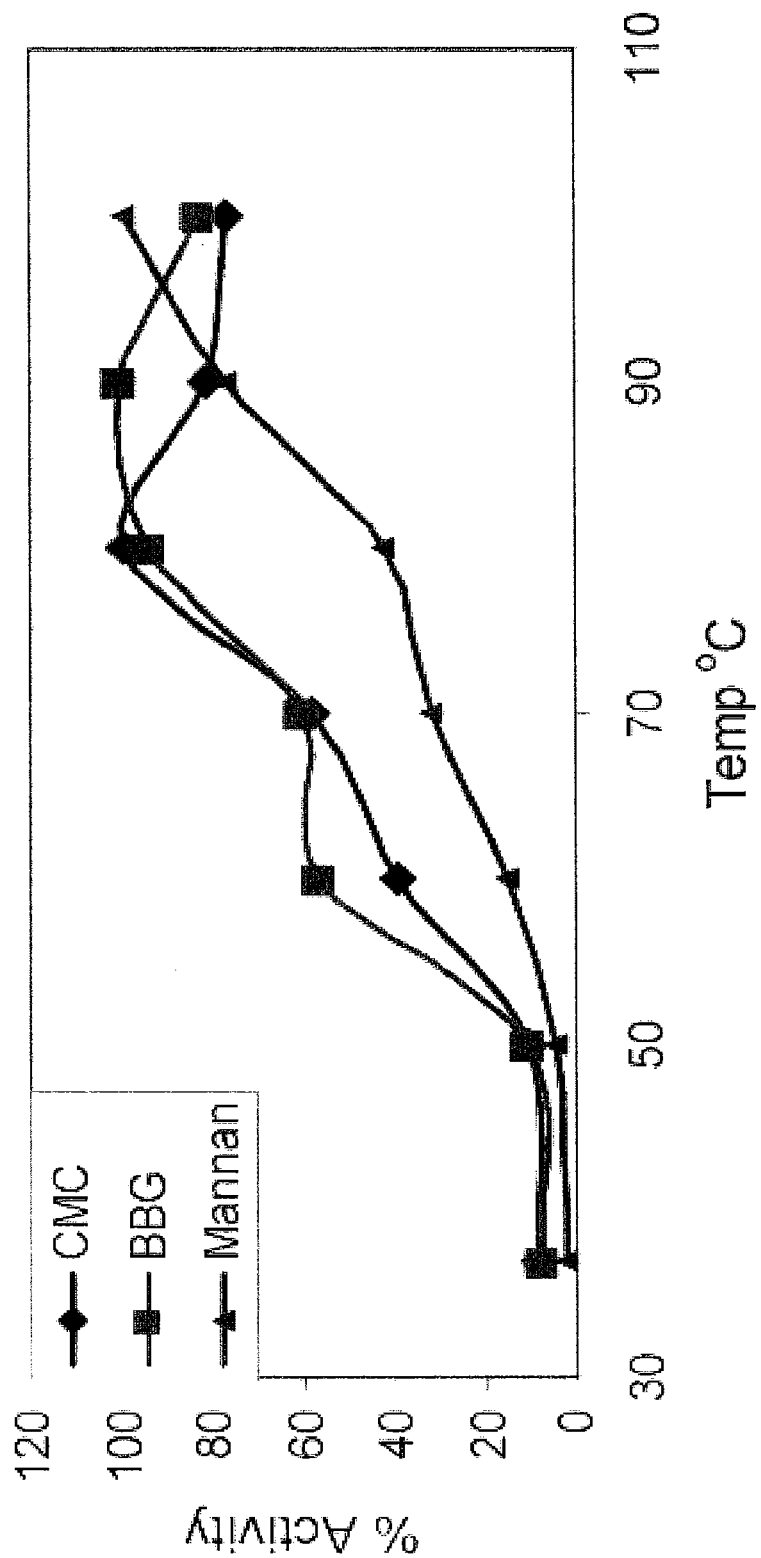
FIG. 7 illustrates the results of glucanase activity assays showing the temperature profile of the exemplary glucanase of the invention encoded by SEQ ID NO:2, as discussed in Example 4, below.

Temperature profile was determined on three separate substrates (BBG, OBG and CMC). The glucanase encoded by the "parental" SEQ ID NO:2 had the highest activity at higher temperatures. Specific activity of the glucanase encoded by SEQ ID NO:2 on BBG and CMC at 80° C. is 10× better than the activity seen at 37° C. In the presence of mannan, the glucanase encoded by SEQ ID NO:2 showed the highest activity at 100° C., as illustrated in FIG. 7.

Temperature profile was determined by incubating SEQ ID NO:2 (encoded by SEQ ID NO:1) in the presence of

| | date | mg/ml | Diln. | ul/rxn | 0 min | 5 min | 8 min | 12 min | 24 min | 36 min | 45 min |
|---|---|---|---|---|---|---|---|---|---|---|---|
| | | | | | SAMPLE DATA | | | | | | |
| Enz x | June 2009 | 20 | 500 | 20 | 0.1252 | 0.1654 | 0.1889 | 0.2315 | 0.3386 | 0.4036 | 0.4695 |

Slope of standard curve: 88.375 A560/umole glucose
Slope of reaction: 0.0076 A560/min
Activity (reaction slope/std slope): 8.70061E−05 umole/min
True activity/1 ml rxn (=Activity × 100): 0.0087 umole/min
Specific Activity: 10.87 umole/min, mg Example 4

Enzyme Activity Assays

The following example describes exemplary enzyme activity assays, and provides data demonstrating/confirming the enzymatic activity of exemplary enzymes of the invention. These assays can also be used to determine if a polypeptide has the requisite enzyme (e.g., glucanase (or cellulase), e.g., endoglucanase, mannanase, xylanase, amylase, xanthanase and/or glycosidase, e.g., cellobiohydrolase, mannanase and/or beta-glucosidase) activity to be within the scope of the invention. For example, enzymes of the invention can catalyze the hydrolysis of barley and/or oat glucan, and/or galactomannan (polysaccharides consisting of a mannose backbone with galactose side groups; a more specific substrate (CMC, BBG or Mannan). Initial velocities were determined using BCA reducing sugar assay and sodium acetate buffer pH 5.3. Initial velocities were normalized and plotted as % activity, as illustrated in FIG. 7.

Half-Life Determination of the Glucanase Encoded by SEQ ID NO:2

The half-life of the glucanase encoded by the "parental" SEQ ID NO:2 was determined at 85° C. and 90° C. The glucanase encoded by SEQ ID NO:2 was heat challenged for various times at 85 and 90 degrees and the residual activity was measured at 37° C. The glucanase encoded by SEQ ID NO:2 retained more than 60% of its activity after 10 minutes of incubation at 85° C. At 90° C., there was no residual activity left after 2 minutes, as illustrated in FIG. 8.

Figure 8:
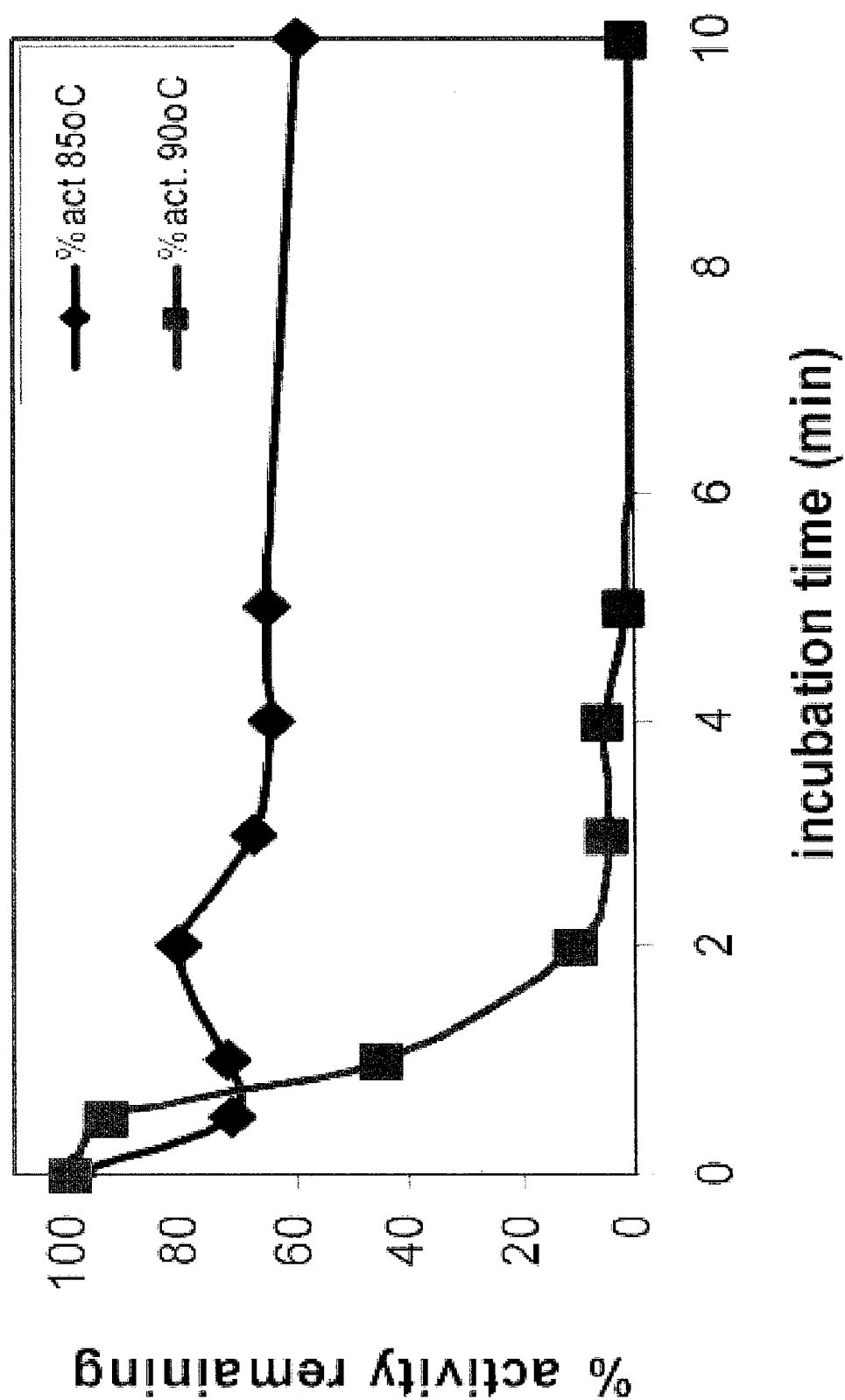
FIG. 8 illustrates the results of glucanase activity assays showing the half-life determination of the exemplary glucanase of the invention encoded by SEQ ID NO:2, as discussed in Example 4, below.

As illustrated in FIG. 8, half-life of SEQ ID NO:2 (encoded by SEQ ID NO:1) was determined by heat challenging the enzyme for 30 sec, 1 min, 2 min, 3 min, 4 min, 5 min, and 10 min at the indicated temperatures (85° C. and 90° C.) and monitoring activity under standard conditions using the BCA reducing sugar.

Example 5

Enzyme Activity Assays

The following example describes exemplary enzymes of the invention, variants of the "parental" or "wild type" SEQ ID NO:2, and data demonstrating their activity. The invention provides sequences having specific residue changes to the "parent" (or "wild type") SEQ ID NO:2 (encoded, e.g., by SEQ ID NO:1), as summarized (in part) in Table 1, above, Table 2, below, and:

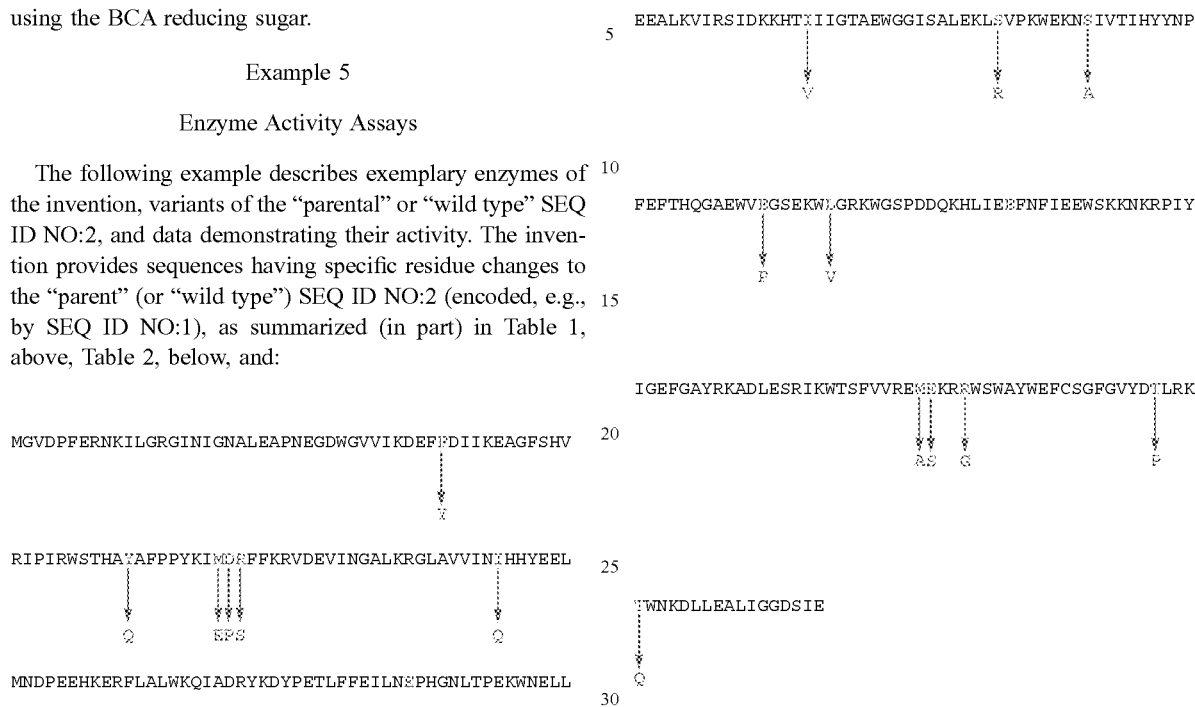

TABLE 2

| Position: | 38 | 61 | 69 | 70 | 71 | 94 | 166 | 183 | 191 | 212 | 231 | 276 | 277 | 280 | 297 | 301 |
|---|---|---|---|---|---|---|---|---|---|---|---|---|---|---|---|---|
| Mutation: | Y | Q | E | P | S | Q | V | R | A | P | V | A | S | G | P | Q |
| 7X | Y | Q | E | | | Q | | R | A | | | A | | | | |
| 10X-1 | Y | Q | E | | | Q | V | R | A | P | | A | | G | | |
| 10X-2 | Y | Q | E | | | Q | V | | A | P | | A | | G | P | |
| 11X-1 | Y | Q | E | | | Q | V | R | A | P | | A | | G | P | |
| 11X-2 | | Q | E | | | Q | V | R | A | P | | A | | G | P | Q |
| 12X-1 | | Q | E | | S | Q | V | R | A | P | | A | | G | P | Q |
| 12X-2 | Y | Q | E | | S | Q | | R | A | P | | A | | G | P | Q |
| 12X-3 | | Q | | P | S | Q | V | R | A | P | | A | | G | P | Q |
| 12X-4 | Y | Q | | | S | Q | V | R | A | P | | A | | G | P | Q |
| 12X-5 | | Q | E | P | | Q | V | R | A | P | | A | | G | P | Q |
| 12X-6 | | Q | E | P | S | | V | R | A | P | | A | | G | P | Q |
| 12X-7 | | Q | E | | | Q | V | R | A | P | V | A | | G | P | Q |
| 13X-1 | Y | Q | E | | S | | V | R | A | P | V | A | | G | P | Q |
| 13X-2 | Y | Q | E | P | S | Q | V | | A | P | | A | | G | P | Q |
| 13X-3 | Y | Q | | P | S | Q | V | R | A | P | | A | | G | P | Q |
| 13X-4 | Y | Q | E | P | | Q | V | R | A | P | V | A | | G | P | |
| 13X-5 | Y | Q | E | P | S | Q | V | R | A | | | A | | G | P | Q |
| 13X-6 | Y | Q | E | P | | Q | V | R | A | P | | A | S | G | P | |
| 13X-7 | Y | Q | E | P | S | Q | | R | A | P | | A | | G | P | Q |
| 14X | Y | Q | E | P | S | Q | V | R | A | P | V | A | | G | P | |

Figure 9:
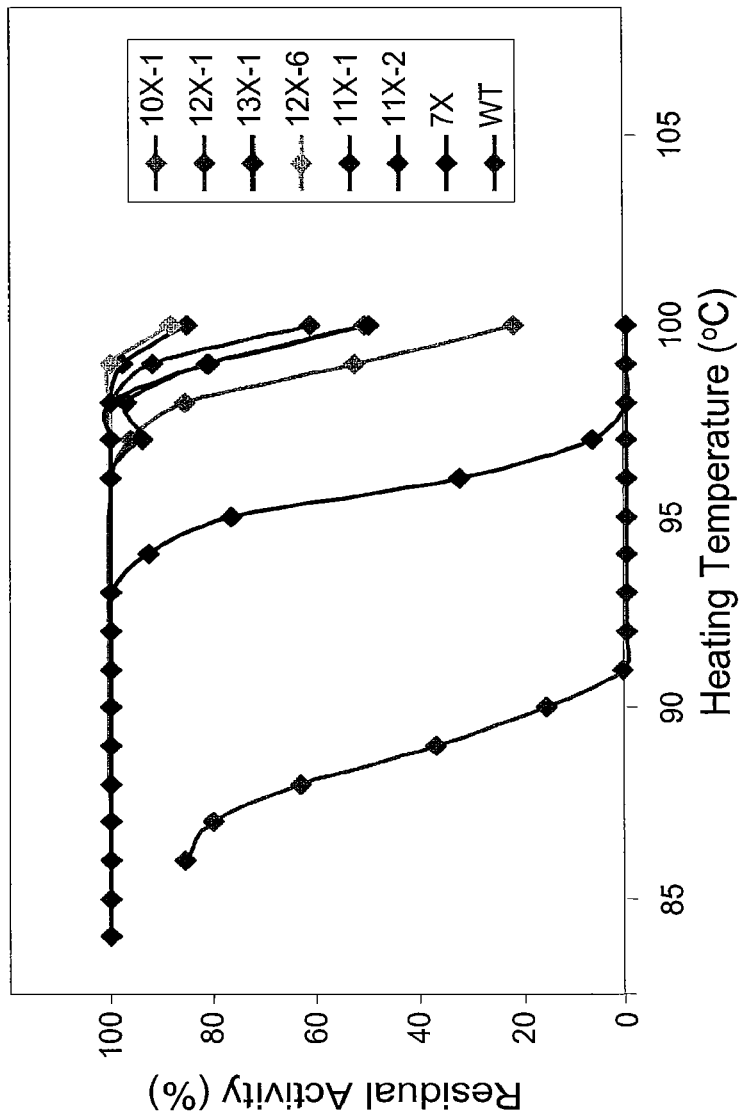
FIG. 9 illustrates data demonstrating the thermal tolerance of exemplary variants of the invention, where activity of purified parental "wild-type" SEQ ID NO:2 and 7X variants was measured and compared, as discussed in Example 5, below.
Figure 10:
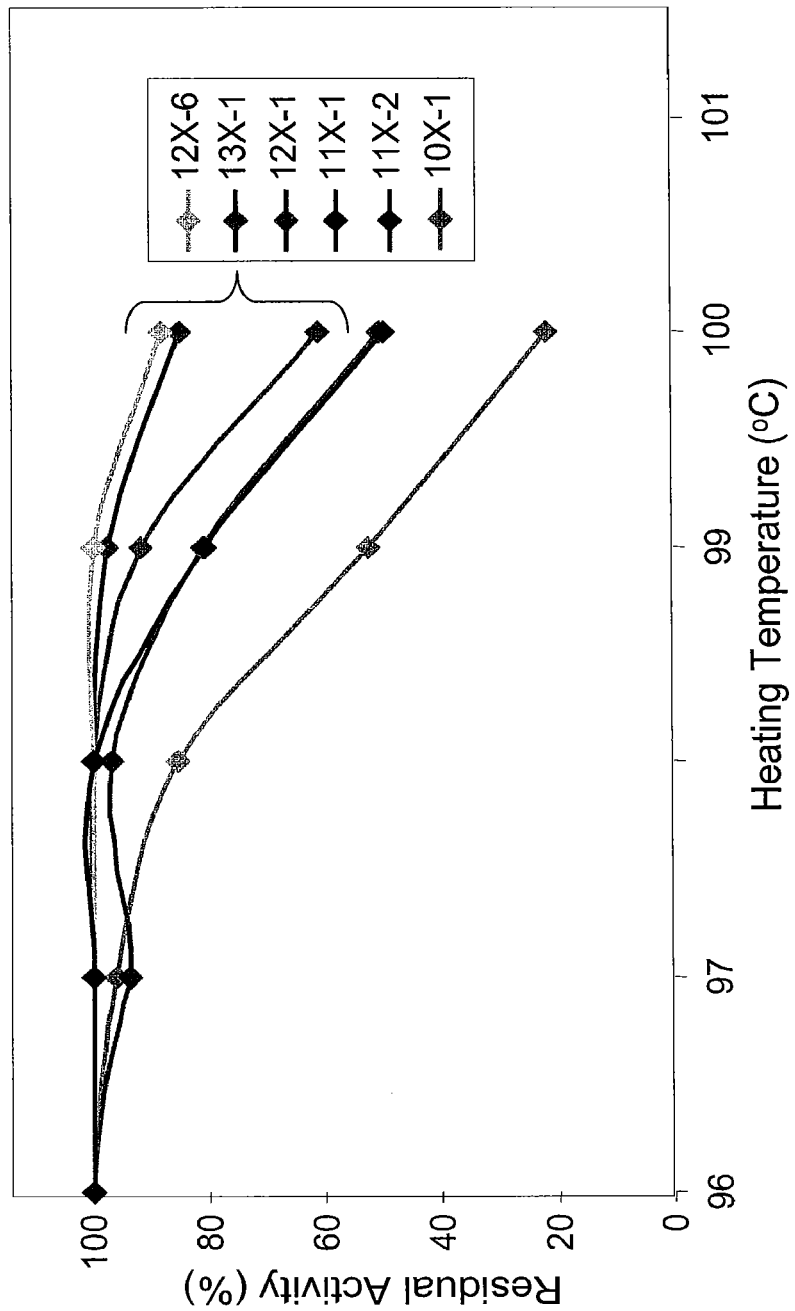
FIG. 10 illustrates data demonstrating the thermal tolerance of exemplary variants of the invention, where activity of purified parental "wild-type" SEQ ID NO:2 and 7X variants was measured and compared, as discussed in Example 5, below.

Thermal tolerance of exemplary variants was measured using purified enzyme compared to the parental "wild-type" SEQ ID NO:2, and a subset of the enzyme variants of Table 2 (the so called "7X variants"), as illustrated in FIG. 9 and FIG. 10; where the data illustrated therein demonstrate the thermal tolerance of the tested exemplary polypeptides (variants of the "parental" or "wild type" SEQ ID NO:2) at 96° C. through 100° C. In these figures, purified enzyme was heated for 30 minutes at the temperature indicated in the figures, and residual (thermotolerant) activity was measured at 37° C. Heating temperatures between 84° C. and 95° C. activates the "thermal tolerant" variants (variants of the "parental" or "wild type" SEQ ID NO:2) slightly, resulting in having a residual (thermotolerant) activity of greater than the initial activity level (i.e., greater than 100%) (possibly due to improved folding upon cooling). As such, residual activity was normalized to 100%. FIG. 9 illustrates a graphic summary of data from these thermal tolerance studies for the enzymes of the invention identified as "10X-1", "12X-1", "13X-1", "12X-6", "11X-1", "11X-2" and "7X", in addition to wild type; and FIG. 10 is a "close-up" of part of FIG. 9.

Thus, in one aspect, enzymes of the invention are thermotolerant and/or thermostable; for example, an enzyme of the invention can retain at least 75% residual activity (e.g., glucanase activity) after 2 minutes at 95° C.; and in another aspect, retains 100% activity after heating for 30 minutes at 95° C. In yet another aspect, an enzyme of the invention retains 100% activity after heating for 30 minutes at 96° C., 97° C., 98° C. or 99° C. In yet another aspect, an enzyme of the invention retains at least 90% activity after heating for 30 minutes at 100° C.

In one aspect, these enzymes of the invention are used in a feed enzyme product, e.g., a monogastric coarse grain feed or food, wherein the monogastric animals include swine (pigs, hogs), sheep, rabbits, birds, horses, pets and humans.

Example 6

Designing Out Alternative Start Sites

The invention also provides glucanase coding sequences that are variants of the exemplary nucleic acid SEQ ID NO:1, encoding the "parent" SEQ ID NO:2, that are specifically modified to remove, or rather alter, a second translational start site within SEQ ID NO:1. This second translational start site causes production of an unwanted truncated version of the protein in non-native hosts (non-native in the context that the host used to express the protein is not the organism from which the enzyme was initially derived). When the exemplary SEQ ID NO:2 enzyme is expressed from its native organism, *Thermotoga maritima* MSB8, this truncated protein is not produced. However, when a nucleic acid having this second (cryptic) SEQ ID NO:1 translational start site is placed in a non-native host, the second translational start site is recognized, causing production of a truncated protein.

To disrupt this unwanted translation (of a truncated protein in a non-native host), SEQ ID NO:1 (encoding SEQ ID NO:2) was altered. In particular, the potential ribosomal binding site (RBS), and the codon of the second ($2^{nd}$) start site at amino acid (aa) residue 32 were altered as shown below. Specifically, nucleotide residue 84 of SEQ ID NO:1 was changed from A to C and nucleotide residue 96 of SEQ ID NO:1 was changed from G to C (the resulting modified sequence is shown in SEQ ID NO:3). The nucleotide changes did not cause any amino acid changes in the polypeptide encoded by altered SEQ ID NO:1.

```
Potential RBS 2nd start site at residue 32
Residues 77-106 of SEQ ID NO: 1 ("WT"):
ATGAGGGAGACTGGGGAGTGGTGATAAAAG Variant, residues 77-106 of SEQ ID NO: 3:
ATGAGGGCGACTGGGGAGTCGTGATAAAAG
```

This illustrated alteration in the ribosome binding site (RBS) and in the second start site were done to ensure that the truncated protein isn't produced in a "non-native" host.

Figure 11:
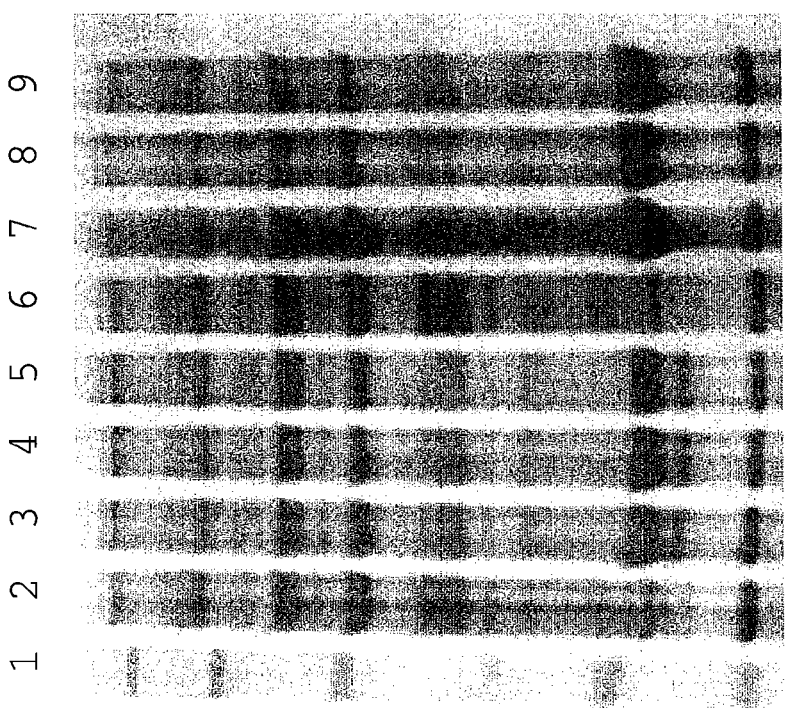
FIG. 11 illustrates a photo of a gel sizing transcripts generated using unmodified "wild type (WT)" and exemplary modified (variant) transcript of the invention to demonstrate the effect of an RBS and second start site alteration on glucanase transcript expression, as discussed in Example 6, below.

FIG. 11 illustrates a photo of a photomicrograph of an SDS-PAGE gel for sizing proteins generated in a non-native *Pseudomonas fluorescens* host using unmodified "wild type (WT) (or, SEQ ID NO:2 protein)" and modified (the variant just illustrated, above) transcripts to demonstrate the effect of this RBS and second start site alteration on glucanase transcript expression. The gel illustrated in FIG. 11 shows protein produced in the uninduced and unaltered "gene", or coding sequence (lane 2), induced and unaltered gene (lanes 3-5, same gene done in triplicate), uninduced and altered gene (lane 6) and induced and altered gene (lanes 7-9). As illustrated by this data, the alterations doubled the amount of activity. In FIG. 11, each lane is loaded with 5 µA of total cell lysate with 10 $OD_{600}$/ml. Glucanase translated from the first starting codon (ATG) is indicated by a black arrow (just to the left of claim 9); the truncated protein translated from second starting codon (GTG) in indicated by the internal, longer arrow (ending internal at row 5).

In FIG. 11: Lane 1: are the protein MW markers; Lane 2 is SEQ ID NO:2 (uninduced)=0.22 U/$OD_{600}$; Lane 3 is SEQ ID NO:2, sample 1=1.82 U/$OD_{600}$; Lane 4 is SEQ ID NO:2, sample 2=2.00 U/$OD_{600}$; Lane 5 is SEQ ID NO:2, sample 3=1.93 U/$OD_{600}$; Lane 6 is SEQ ID NO:3 (uninduced)=0.20 U/$OD_{600}$; Lane 7 is SEQ ID NO:3 sample 1=3.79 U/$OD_{600}$; Lane 8 is SEQ ID NO:3 sample 3=3.60 U/$OD_{600}$; Lane 9 is SEQ ID NO:3 sample 3=4.03 U/$OD_{600}$.

While these data demonstrate that these nucleic acid sequence modifications address the cryptic transcriptional start site problem in the exemplary expression host *Pseudomonas fluorescens*, these modifications or equivalent modifications to eliminate cryptic start site(s) can be used in any host, e.g., in any prokaryotic expression host. In other words, whatever host cell is used to express an enzyme of the invention, cryptic transcriptional start site problems can be readily identified and eliminated with sequence modifications, which techniques are known in the art, and can be analogous to those techniques set forth in this example. In alternative aspects, the host cell is a bacterial cell, a mammalian cell, a fungal cell, a yeast cell, an insect cell or a plant cell, e.g., the bacterial cell can be any species within the genera *Escherichia, Bacillus, Streptomyces, Salmonella, Pseudomonas* or *Staphylococcus*, or *Escherichia coli, Lactococcus lactis, Bacillus subtilis, Bacillus cereus, Salmonella typhimurium* or *Pseudomonas fluorescens*.

Example 7

Enzyme-Comprising Food or Feed Diets

The invention also provides foods or feeds (which include supplements for either) comprising enzymes of the invention, including the enzyme variants of SEQ ID NO:2, e.g., as described in Tables 1 or 2, above. In one aspect, feeding animals diets comprising enzymes of the invention will increase the dietary value of the enzyme-comprising food or feed. In one aspect, feeding animals diets comprising enzymes of the invention will reduce the intestinal fluid viscosity and the feed passage rate in the animal (which can be tested/confirmed as described, e.g., in Sieo (2005) *Poult. Sci.* May 84(5):734-741. Addition of an enzyme of the invention (alone, or together with another enzyme, e.g., a xylanase and/or a known beta-glucanase or phytase) to the diet of an animal can increase intestinal villus size and the villus height-to-crypt depth ratio, increase the concentration of conjugated bile acids in the small intestine contents, improve nutrient digestibility and animal (e.g., poultry, chicken) performance (probably by improving the absorption capacity of the small intestine through increased villus surface and intestinal concentration of conjugated bile acids; see e.g., Mathlouthi (2002) *J. Animal Sci.* November 80(11): 2773-2779). In some aspect, the foods or feeds comprising enzymes of the invention are fed to animals on special diets, for example, poultry fed rye-based diets; rye in feed can impair broiler performance and increase digesta viscosity and incidence of leg disorders—administration of foods or feeds comprising enzymes of the invention can reduce the magnitude of this problem; see, e.g., Lazaro (2004) *Poult. Sci.* February 83(2):152-160.

In one aspect, a feed or food (or drug, dietary supplement, etc.) of the invention can comprise one, two, three or more different polynucleotides of the invention; or in one aspect, a feed or food of the invention can comprise a combination of an enzyme of the invention with another polypeptide (e.g., enzyme, peptide) of the invention or any known enzyme. The food or feed can be in the form of a tablet, a geltab, a pill, an implant, a pellet, a dry premix, a solid, powder or a liquid dietary supplement, and the like.

The value of a particular enzyme of the invention in a diet can be tested using any food or feed system, e.g., by feeding an animal, e.g., a monogastric animal, an energy limiting diet, such as a corn soy diets, with and without supplementation by an enzyme of the invention.

For example, one exemplary study can be designed to determine whether there is any advantage in high temperature (90° C. at die face) processed diets of two variants of the invention (i.e., sequence variants of the "parental" SEQ ID NO:2), compared with the "parental", or "wild type" SEQ ID NO:2, when fed in energy limiting corn soy diets.

One exemplary test system comprises use of poultry, e.g., chickens, such as broiler chickens (e.g., strain Cobb×Cobb, a Commercial Hybrid, origin Cobb-Vantress hatchery, Cleveland, Ga.); and:

| Exemplary Diet Formulations: | |
|---|---|
| Feed availability | Ad libitum |
| Water availability | Ad libitum |
| Start age of trial | 1 day |
| End age of trial | 28 days |
| Lighting program | 24 hours |

| Ingredient | Agri-Stats 0-18 | Agri-Stats 0-18 Neg control | Agri-Stats 18-28 | Agri-Stats 18-28 Neg control |
|---|---|---|---|---|
| Corn | 61.78% | 62.18% | 65.03% | 66.07% |
| Poultry Biproduct meal | 5.00% | 3.17% | 5.00% | 5.00% |
| Soybean meal 48 | 28.96% | 30.84% | 26.02% | 25.62% |
| Wheat Bran | 0.00% | 0.52% | 0.00% | 0.74% |
| Poultry Fat | 1.12% | 0.00% | 1.38% | 0.00% |
| Salt | 0.23% | 0.22% | 0.19% | 0.19% |
| DL Methionine | 0.27% | 0.27% | 0.19% | 0.19% |
| Lysine HCl | 0.15% | 0.15% | 0.00% | 0.00% |
| Limestone | 0.48% | 0.49% | 0.57% | 0.57% |
| Defluor Phos | 1.49% | 1.64% | 1.10% | 1.09% |
| Coccidiostat (Coban-monensin) | 0.02% | 0.02% | 0.02% | 0.02% |
| Vitamin premix | 0.50% | 0.50% | 0.50% | 0.50% |
| Crude protein % | 22.26 | 22.22 | 20.93 | 20.94 |
| Poult ME kcal/kg | 3,060.00 | 2,985.00 | 3,110.00 | 3,035.00 |
| Calcium % | 0.90 | 0.90 | 0.80 | 0.80 |
| Phos % | 0.71 | 0.72 | 0.63 | 0.63 |
| Avail Phos % | 0.44 | 0.44 | 0.37 | 0.37 |
| Fat % | 4.57 | 3.29 | 4.93 | 3.63 |
| Fibre % | 2.54 | 2.63 | 2.52 | 2.59 |
| Met % | 0.63 | 0.63 | 0.54 | 0.53 |
| Cys % | 0.36 | 0.36 | 0.34 | 0.35 |
| Me + Cys % | 0.99 | 0.99 | 0.88 | 0.88 |
| Lys % | 1.30 | 1.30 | 1.10 | 1.10 |
| His % | 0.59 | 0.59 | 0.56 | 0.56 |
| Tryp % | 0.24 | 0.25 | 0.23 | 0.23 |
| Thr % | 0.85 | 0.85 | 0.80 | 0.80 |
| Arg % | 1.47 | 1.47 | 1.38 | 1.38 |
| Iso % | 0.91 | 0.92 | 0.86 | 0.86 |
| Leu % | 1.91 | 1.92 | 1.84 | 1.84 |
| Phe % | 1.06 | 1.07 | 1.00 | 1.00 |
| Tyr % | 0.78 | 0.79 | 0.74 | 0.74 |
| Val % | 1.03 | 1.03 | 0.97 | 0.97 |
| Gly % | 1.09 | 1.02 | 1.05 | 1.05 |
| Ser % | 1.11 | 1.09 | 1.05 | 1.05 |
| Phe + Tyr % | 1.84 | 1.85 | 1.74 | 1.74 |
| Na % | 0.20 | 0.20 | 0.17 | 0.17 |
| Cl % | 0.23 | 0.22 | 0.18 | 0.18 |
| K % | 0.85 | 0.89 | 0.80 | 0.80 |
| Linoleic acid % | 1.62 | 1.32 | 1.73 | 1.43 |
| Na + K − Cl | 240.11 | 252.28 | 225.51 | 225.93 |

-continued

|  | Agri-Stats 0-18 | | Agri-Stats 18-28 | Agri-Stats 18-28 Neg |
|---|---|---|---|---|
| Ingredient | Agri-Stats 0-18 | Neg control | Agri-Stats 18-28 | control |
| DUA | 435.81 | 450.57 | 418.92 | 420.42 |
| Magnesium | 0.19 | 0.19 | 0.19 | 0.19 |
| Choline | 1,471.59 | 1,424.01 | 1,411.46 | 1,417.75 |
| Copper | 0.30 | 0.33 | 0.22 | 0.22 |
| Poult ME MJ/kg | 12.80 | 12.49 | 13.01 | 12.70 |
| Gly + ser | 2.21 | 2.11 | 2.10 | 2.10 |
| Cost £ per MT | 112.67 | 111.05 | 107.14 | 105.36 |

| Trace Mineral Premix | |
|---|---|
| Calcium (Ca) Min. | 3.20% |
| Calicium (Ca) Max. | 4.20% |
| Iron (Fe) Min. | 2.63% |
| Magnesium (Mg) Min. | 2.68% |
| Maganese (Mn) Min. | 13.40% |
| Zinc (Zn) Min | 10.70% |
| Copper (Cu) Min | 4000 ppm |
| Iodine (I) Min. | 1000 ppm |
| Selenium (Se) Min. | 400 ppm |

Premix added at a rate of 1.5 lbs per ton of feed.

| Vitamin Premix | |
|---|---|
| Vitamin A, I..U./LB | 1,000,000 |
| Vitamin D3, I..U./LB | 200,000 |
| Vitamin E, I..U./LB | 2,000 |
| Vitamin B-12, MG./LB | 2.20 |
| Riboflavin, MG./LB | 800 |
| Niacin, MG./LB | 8,000 |
| d-Pantothenic Acid, MG./LB | 2,000 |
| Choline, MG./LB | 34,720 |
| Menadione, MG./LB | 132 |
| Folic Acid, MG./LB | 100 |
| Thiamine, MG./LB | 400 |
| Pyridoxine, MG./LB | 400 |
| Biotin, MG./LB | 20 |
| Ethoxyquin, MG./LB | 23,000 |

Premix added at a rate of 5.0 lbs. per ton of feed

| Diet Related Information | |
|---|---|
| Treatment Batch size/kg | TOTAL About = 2500 kg |
| Diet form | Pelleted |
| Target pellet temperature at die face | Min 88° C., Target 90° C., Max 92° C.—measure at start, mid point and end of each treatment diet manufacture by collection of pellets from die face in a cup and use of a thermometer |
| Samples collected per diet/quantity per sample | open |
| Point of sample collection | Mash from mixer and post —cooler for diet samples for analysis of enzyme and nutrients. For temp measurement, see above |
| Diet/Water availability | Ad libitum/Ad libitum |
| Diet phases | Starter 0-18, Grower 18-28 |
| Analysis of diet requested/reference/place of analysis | Moisture, Crude protein, Crude fiber, Oil, Ash, Calcium, Phosphorus |
| Enzyme Analysis | open |

Exemplary Treatment Schedule

Animals that appear to be in poor condition will be removed prior to the start of the study. If insufficient remaining at the outset to satisfy that the number required for the study, then a fresh batch of animals will be ordered. A suitable employee will examine animals for health status throughout the trial.

Animals will be assigned to their treatment groups using a recognized randomization technique. Animals will be uniquely identified before the start of administration of test article if individual animal data is required, otherwise the pens the animals are kept in will be uniquely labeled.

Exemplary Enzymes

Any enzyme of the invention, including any of the enzyme variants of SEQ ID NO:2 of the invention, e.g., as described in Tables 1 or 2, above can be used alone or in combination in a food or feed of the invention. Thus, exemplary test systems and protocols can use any of the enzymes of the invention alone or in combination with another enzyme of the invention, or a known enzyme. In one aspect, feeding animals diets comprising enzymes of the invention will increase the dietary value of the enzyme-comprising food or feed.

| Treatments | | | | |
|---|---|---|---|---|
| Trt # | Treat | Diet base | Enzyme inclusion rate g/kg diet | Enzyme to be added |
| 1 | Pos control | Pos con | 0 | |
| 2 | Negative control | Neg con | 0 | |
| 3 | SEQ ID NO: 2 40 DNS U/kg | Neg con | | In Mixer |
| 4 | SEQ ID NO: 2 80 DNS U/kg | Neg con | | In Mixer |
| 5 | SEQ ID NO: 2 120 DNS U/kg | Neg con | | In Mixer |
| 6 | "7X" variant 40 DNS U/kg | Neg con | | In Mixer |
| 7 | "7X" variant 80 DNS U/kg | Neg con | | In Mixer |
| 8 | "7X" variant 120 DNS U/kg | Neg con | | In Mixer |
| 9 | "13-1X" variant 40 DNS U/kg | Neg con | | In Mixer |
| 10 | "13-1X" variant 80 DNS U/kg | Neg con | | In Mixer |
| 11 | "13-1X" variant 120 DNS U/kg | Neg con | | In Mixer |

For the "13-1X" and "7X" variants of the glucanase SEQ ID NO:2, see Table 2 and discussion above. The term "DNS U/kg means "DNS units per kilogram of feed". DNS=3,5-dinitrosalicylic acid, a reagent used for the quantification of free reducing ends released by action of glucanase on polysaccharides. DNS indicates that the DNS assay method was used to determine glucanase activity.

All birds will be humanely treated. Only approved methods by the American Veterinary Medical Association will be used for euthanizing birds. All birds will be buried in an on site disposal pit and will not enter the food chain.

All animals will be viewed daily by suitably qualified personnel and any variation in appearance or behavior recorded. If any animal is in poor condition it will be observed more frequently. If deemed unlikely to survive, or to be suffering pain or distress, it will be culled and necropsied. All mortalities shall also be necropsied in an attempt to establish the cause of the death or distress. In all cases, animals should be weighed and date of death recorded. If adverse treatment effects are observed during the study, animals from each affected treatment group are necropsied and tissues evaluated for histopathology.

| Measurements | | |
|---|---|---|
| Parameter | Age | Comments |
| Weight | 1, 18, and 28 d of age | |
| Pen feed intake | 1, 18, and 28 d of age | |
| FCR | 18, and 28 d of age | |
| Mortality | Age and weight of mortality | Record separately from pen weights |
| Pellet die temperature | | Record and report each diet die face temperature. See treatments table |
| Feed Glucanase analysis | | See sample analysis discussion |

All test material and animals fed the test material must be disposed of in such a manner to prevent either from entering other animal feed and/or the human food chain.

| Sample Type | Sample Identification | Analysis | Other |
|---|---|---|---|
| Cereal grain—CORN | CORN | | Three 200 g samples |
| Protein source | SOYBEAN MEAL | | Three 200 g samples |
| Enzyme Premix | SEQ ID NO: 2 dry | Glucanase | 25 g sample |
| Enzyme Premix | "7X" variant | Glucanase | 25 g sample |
| Enzyme Premix | "13-1X" variant | Glucanase | 25 g sample |
| Diet prior to pelleting | Diet 1 pre-pellet | Glucanase | Two 400 g samples* |
| Diet prior to pelleting | Diet 2 pre-pellet | Glucanase | Two 400 g samples |
| Diet prior to pelleting | Diet 3 pre-pellet | Glucanase | Two 400 g samples |
| Diet prior to pelleting | Diet 4 pre-pellet | Glucanase | Two 400 g samples |
| Diet prior to pelleting | Diet 5 pre-pellet | Glucanase | Two 400 g samples |
| Diet prior to pelleting | Diet 6 pre-pellet | Glucanase | Two 400 g samples |
| Diet prior to pelleting | Diet 7 pre-pellet | Glucanase | Two 400 g samples |
| Diet prior to pelleting | Diet 8 pre-pellet | Glucanase | Two 400 g samples |
| Diet prior to pelleting | Diet 9 pre-pellet | Glucanase | Two 400 g samples |
| Diet prior to pelleting | Diet 10 pre-pellet | Glucanase | Two 400 g samples |
| Diet prior to pelleting | Diet 11 pre-pellet | Glucanase | Two 400 g samples |
| Diet prior to pelleting | Diet 12 pre-pellet | Glucanase | Two 400 g samples |
| Diet post pelleting | Diet 1 post-pellet | Glucanase | Two 400 g samples |
| Diet post pelleting | Diet 2 post-pellet | Glucanase | Two 400 g samples |
| Diet post pelleting | Diet 3 post-pellet | Glucanase | Two 400 g samples |
| Diet post pelleting | Diet 4 post-pellet | Glucanase | Two 400 g samples |
| Diet post pelleting | Diet 5 post-pellet | Glucanase | Two 400 g samples |
| Diet post pelleting | Diet 6 post-pellet | Glucanase | Two 400 g samples |
| Diet post pelleting | Diet 7 post-pellet | Glucanase | Two 400 g samples |
| Diet post pelleting | Diet 8 post-pellet | Glucanase | Two 400 g samples |
| Diet post pelleting | Diet 9 post-pellet | Glucanase | Two 400 g samples |
| Diet post pelleting | Diet 10 post-pellet | Glucanase | Two 400 g samples |
| Diet post pelleting | Diet 11 post-pellet | Glucanase | Two 400 g samples |
| Diet post pelleting | Diet 12 post-pellet | Glucanase | Two 400 g samples |

*NOTE,
for the two 400 g pre and post pelleting samples, make each up from 3 separate 200 g grab samples which are mixed and then reduced to 400 g. Collect from different parts of the mixer for the mash samples, and at the start, mid-point and end of manufacture for the pelleted samples and label accordingly. The post pellet samples to be taken post cooler and some description of the cooling process to be provided to contractor, pre-pellet mash samples to be taken from different points of the mixer. Pelleted Samples above are NOT to be confused with temperature testing.

For the "13-1X" and "7X" variants of the glucanase SEQ ID NO:2, see Table 2 and discussion above.

Example 8

Methods for Making Food or Feed Pellets of the Invention

The invention also provides food or feed pellets (which in one aspect can be considered "food or feed supplements) comprising one or more enzymes of the invention, and methods for making and using them. The invention also provides pellets comprising enzymes of the invention, including the enzyme variants of SEQ ID NO:2, e.g., as described in Tables 1 or 2, above, for use as foods or feeds. This example describes one exemplary method for making food or feed pellets of the invention.

This study is designed to generate a robust thermotolerance curve for feed glucanase enzymes of the invention pelleted at 70° C., 83° C., 86° C., 89° C., 92° C., or 95° C. The enzymes were dosed at one level (250 U/kg) at each temperature to develop an activity curve based on the new in-feed assay method of this invention. A second glucanase was pelleted at two temperatures (70° C. and 95° C.) and compared to the leading product. Also, QUANTUM XT™ PHYTASE (or, "QPXT") (Syngenta Biotechnology Inc., Research Triangle Park, N.C.) was supplemented into the blank feed for two runs to be used as an internal marker.

Materials and Methods

Diet Formulation

Diets will be formulated to be a typical commercial broiler diet (corn/soybean meal/meat and bone meal based). There will be only one basal diet used and three experimental diets: (1) a control diet consisting of no glucanase enzyme added (but QUANTUM XT™ PHYTASE (Syngenta Biotechnology Inc., Research Triangle Park, N.C.) added 200 g/mt); (2) the control diet with the glucanase SEQ ID NO:2 at 250 U/kg feed; and, (3) control with 7X Glucanase (see Table 2, Example 5, above) at 250 U/kg feed.

| Diet Presentation/Additives | |
|---|---|
| Diet form | Pelleted |
| Pelleted at temperature determined at | To be recorded at pellet die face |
| Pelleted, die face temperature | 70° C., 83° C., 86° C., 89° C., 92° C., or 95° C. |
| Diet phase feeding program | Starter or Grower |
| Coccidiostat in Starter (type and ppm) | NA |
| Coccidiostat in Grower/Finisher 1 (type and ppm) | None |

| Diet Presentation/Additives | |
|---|---|
| Coccidiostat in Finisher 2 (type and ppm) | None |
| Vitamin premix content and inclusion level | vitamin mix |
| Mineral premix content and inclusion level | mineral mix |

Diet Pelleting and Sampling
Pelleting Procedures—
Initially a 1-mt mixer was cleaned and inspected prior to the start of the test.
Enough feed was mixed based on the amount of feed required for a continuous run to achieve the 6 target temperature increases (at steady state) within each run.
- All dry ingredients were added to the mixer in order of the diet formulation (for glucanase diets it was added in the mixer replacing small amount of corn) and the mixer was operated for 2-3 minutes, then the oil was added, and mixed the final 1-2 minutes. The total run time was 3-4 minutes long.
- Prior to the pellet run two composite sample of mash was removed from the mixer for each test run (each sample approximately 500 g each).
- The feed was pelleted starting at the lowest temperature and once the target temperature is achieved at a steady state feed samples was collected. Approximately 5×500 g samples were collected in the middle of the run post-die and these were cooled before final bagging and identified (labeled).
- After feed samples are collected and hot air blown across samples to decrease moisture levels then cooled to ambient temperature in a cooling chamber.
- Sample bags were labeled for run (replicate), temperature and enzyme level. There were three replicate runs for each individual test diet. There were 5 feed samples for each temperature (6) within a diet with 3 replicates (nm) giving a total of 90 pelleted feed samples per test diet; plus there were 3 composite mash samples for each test diet.
- Label bags as follows:
  Sample labels: run #/enzyme/temperature/sample.
  Where: run number is 1-3, dose is blank, SEQ ID NO:2 or 7X (a variant of SEQ ID NO:2, see table 2 and discussion above), temperature is 70, 83, 86, 89, 92, or 95 and sample within 1-5. E.g., the label 1/SEQ ID NO:2/92/1 describes the sample taken during the first run of SEQ ID NO:2 at 92° C. and was the first sample collected that run.

| Experimental Design: | | | | | | | | | |
|---|---|---|---|---|---|---|---|---|---|
| Test Diets | Replicate (run) | Enzyme | Dose U/kg feed | Post Pellet Die Face Exit Temperature (C. °) | | | | | |
| 1 | 1 | None | 0 | 70 | 83 | 86 | 89 | 92 | 95 |
| 1 | 2 | None; QPXT 200 g/mt | 0 | 70 | 83 | 86 | 89 | 92 | 95 |
| 1 | 3 | None; QPXT 200 g/mt | 0 | 70 | 83 | 86 | 89 | 92 | 95 |
| 2 | 1 | SEQ ID NO: 2 Glucanase | 250 U | 70 | 83 | 86 | 89 | 92 | 95 |
| 2 | 2 | SEQ ID NO: 2 Glucanase | 250 U | 70 | 83 | 86 | 89 | 92 | 95 |
| 2 | 3 | SEQ ID NO: 2 Glucanase | 250 U | 70 | 83 | 86 | 89 | 92 | 95 |
| 3 | 1 | 7X Glucanase | 250 U | 70 | — | — | — | — | 95 |
| 3 | 2 | 7X Glucanase | 250 U | 70 | — | — | — | — | 95 |
| 3 Total | 3 | 7X Glucanase | 250 U | 70 | — | — | — | — | 95 |

* With the pelleting temperatures, at least a 3° C. difference needs to be kept between values, with no change in through-put (retention time) over the run.
** A batch of feed was mixed and used for the entire run within a test diet at the 6 temperatures with samples collected and cooled once the temperature has been achieved and stable. A set of 5 samples was collected for each temperature within a run giving a total of 30 feed samples per run. An overall total of pelleted feed samples was 210 samples, not including mash samples.

| Measurements and Schedule of Events | |
|---|---|
| Parameter | Comments |
| During each run/replicate: | |
| Temperature at the die face was measured and recorded. | |
| Sequence of runs: | |
| Day 1 = Run 1: Blank; Temps 1-6; Sample 1-5:::: Three runs per test diet were completed before moving to next test diet. | |
| Day 1 = Run 1: SEQ ID NO: 2 Gluc; Temps 1-6; Sample 1-5:::: Three runs per test diet were completed before moving to next test diet. | |
| Day 1 = Run 1: 7X Gluc; Temps 1-2; Sample 1-5:::: Three runs per test diet were completed at only two temperatures compared to the other test diets. | |

If not able to complete all the pellet runs the first day they were completed the morning of the second day. Critical step is not to alter the retention time in the conditioner (speed it up) when achieving the high pellet temperatures.

All feed was disposed of by landfill burial.

Results

Figure 12:
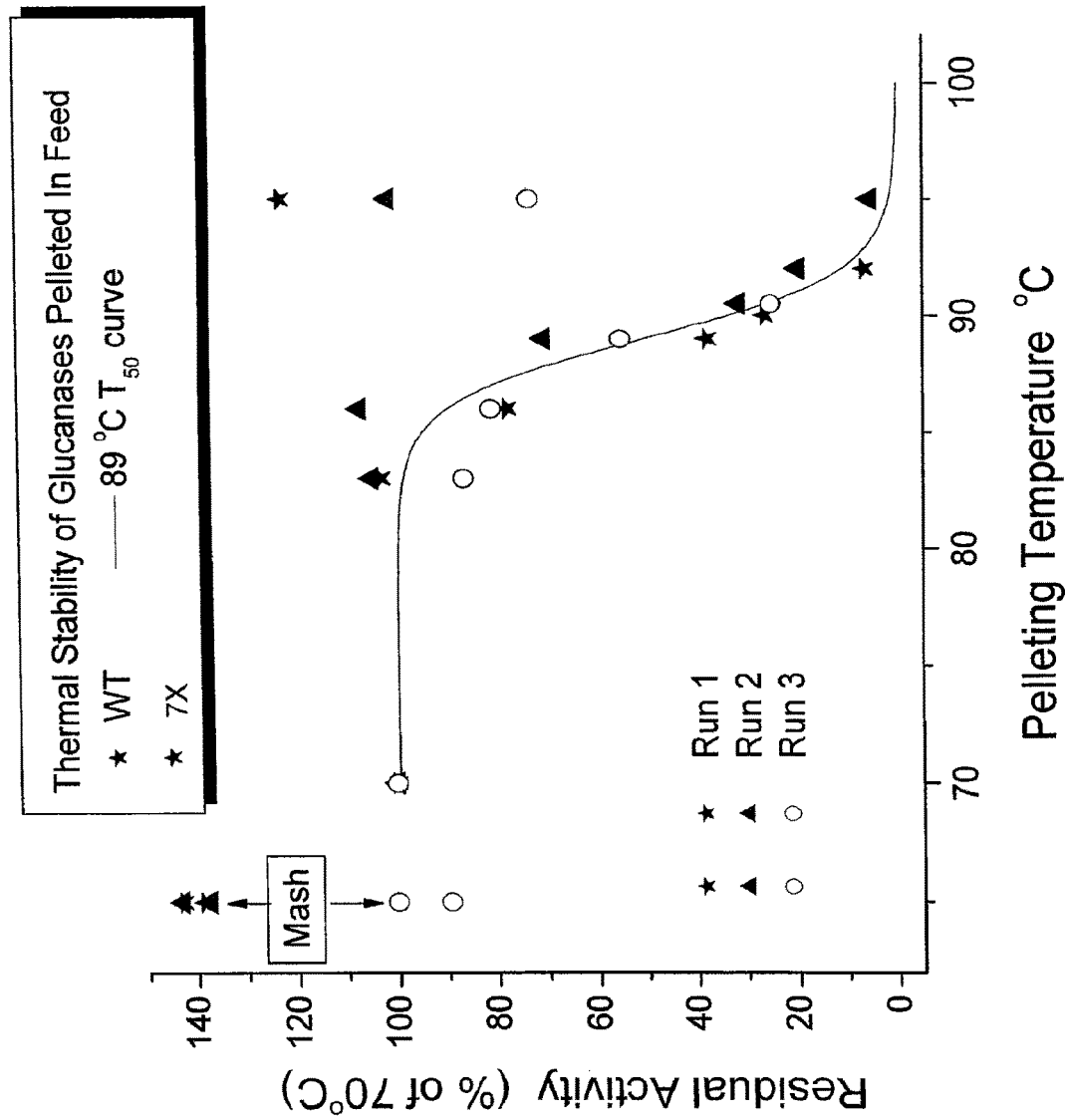
FIG. 12 illustrates the thermostability of these two enzymes of the invention over a range of pelleting temperatures, as discussed in Example 8, below.

Results of studies that confirm the thermostability of enzymes of the invention after pelleting are illustrated in FIG. 12, where "wild type" (or WT), i.e., SEQ ID NO:2, and the variant designated "the 7X variant", which has is a sequence variation of SEQ ID NO:2 consisting of the amino acid residue changes: 38Y, 61Q, 69E, 94Q, 183R, 191A, and 276A (see Table 2, and discussion, above). The data in FIG. 12 illustrate the thermostability of these two enzymes of the invention over a range of pelleting temperatures from about 70° C. to about 100° C. over three runs; the data compares the percent (%) residue activity of the enzyme at the test temperature compared to its activity at 70° C. compared to the "pelleting temperature".

Example 9

Enzymes of the Invention Modified to Avoid "Ragged N-Termini"

The invention also provides enzyme-encoding sequences, and the nucleic acids encoding them, wherein the sequences are modified such that a better recognition sequence for protease cleavage of signal sequence is generated.

Figure 13:
FIG. 13, two codons were inserted between the second (2nd codon) of the SEQ ID NO:2 enzyme (glucanase) coding sequence and an alpha factor signal sequence (leader sequence), as discussed in Example 9, below.

For example, as illustrated in FIG. 13, two codons were inserted between the second (2nd codon) of the enzyme (glucanase) coding sequence (i.e., without the ATG start) (from SEQ ID NO:1) and the alpha factor signal sequence (leader sequence). These two additional codons encode for the amino acid residues glutamic acid (Glu) and alanine (Ala). Addition of these two additional codons generates a better recognition sequence for the protease that cleaves the protein between the signal sequence and the glucanase. Cleavage occurs on the N-terminal side of the Glu-Ala sequence and as such the N-terminus of the mature protein begins with Glu-Ala. Without these additional amino acids there was incomplete processing of nascent protein, resulting in the production of a heterogeneous protein, having a so-called "ragged N-terminus". The addition of the Glu-Ala (or "EA") sequence generates a homogeneous protein with a "clean" (or, not "ragged", or heterogeneous) amino terminus (N-terminus). All of this was verified by N-terminal sequencing. FIG. 13 illustrates Doublet N-terminal Sequencing of SEQ ID NO:2.

Figure 14:
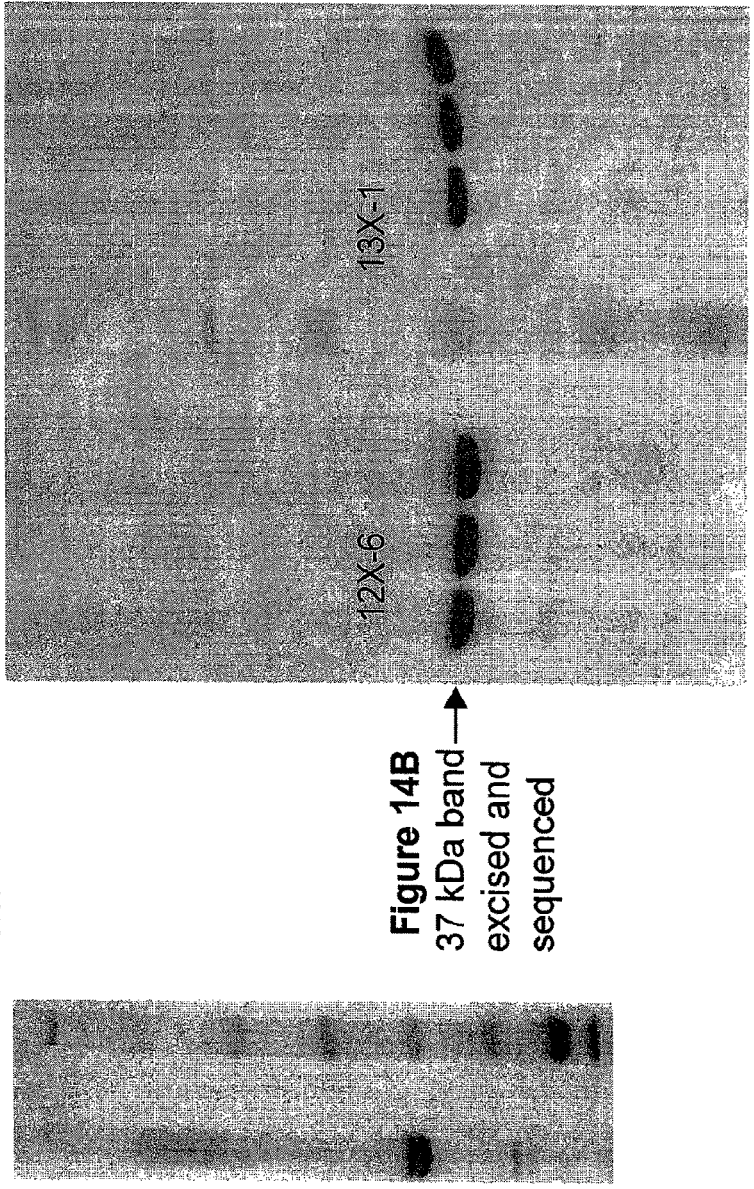
FIG. 14A and FIG. 14B illustrate N-terminal sequencing results for the *Pichia*-expressed glucanase enzymes of the invention designated "12X-6" and "13X-1"

FIG. 14 illustrates N-terminal sequencing results for the Pichia-expressed glucanase enzymes of the invention designated "12X-6" and "13X-1", which are SEQ ID NO:2 variants, see Table 2, and discussion above. FIG. 14A illustrates an radiograph of an SDS-PAGE gel showing a glucanase doublet caused by inconsistent signal processing; FIG. 14B illustrates an radiograph of an SDS-PAGE gel showing a 37 kDa band; which was excised and sequenced, as shown in the figure. These data illustrate that insertion of the Glu-Ala sequence, as described above results in a "clean" amino terminus.

While these data demonstrate that addition of additional amino acid residues between the leader (signal) sequence and the enzyme sequence addresses the problem of "ragged ends" in the recombinant glucanase enzyme expressed in the exemplary Pichia expression host, these modifications or equivalent modifications can be used for expression in any host, e.g., in any prokaryotic or eukaryotic expression host, for example, and bacterial host cell. In alternative aspects, the cell is a bacterial cell, a mammalian cell, a fungal cell, a yeast cell, an insect cell or a plant cell, e.g., the bacterial cell can be any species within the genera Escherichia, Bacillus, Streptomyces, Salmonella, Pseudomonas or Staphylococcus, or Escherichia coli, Lactococcus lactis, Bacillus subtilis, Bacillus cereus, Salmonella typhimurium or Pseudomonas fluorescens.

Example 10

Enzymes of the Invention Expressed in Transgenic Plants and Seeds

One embodiment of the invention provides transgenic plants (or plant cell derived therefrom) and seeds comprising sequences encoding enzymes of this invention. As discussed above, the transgenic plant (or plant cell) or seed can be engineered to constitutively, inducibly, or in a tissue preferred manner express an enzyme of this invention, e.g., by selection of the appropriate promoter or other transcriptional regulator, as discussed above. Optionally, the enzyme may be targeted to a specific subcellular compartment. In one aspect, the transgenic plant or seed of this invention is modified to express a "plant-optimized" thermotolerant enzyme, e.g., as in one exemplary plant of the invention, the transgenic plant expresses an endoglucanase directly in a cell or seed, e.g., directly in a maize seed, for example, for a food or feed, such as a monogastric animal feed or for use in an industrial process requiring the breakdown of cellulose. This example describes direct expression of an enzyme in a (maize) corn seed; in particular, it describes thermotolerant endoglucanase expressed directly in a (maize) corn seed for improved utilization of feed or for use in an industrial process requiring the breakdown of cellulose. Delivery of an enzyme expressed in a plant can be used as a purified or unpurified enzyme source, expressed in the feedstock itself for use in industrial processes requiring the breakdown of cellulose or used as a feed component.

Maize seed-specific expression of plant codon-optimized thermotolerant endoglucanases allows for delivery of this enzyme directly in the crop that is the source of one of the basic components of the animal feed (dietary corn). Expression in corn also provides a low cost, large scale, and flexible production of this—or any other enzyme—of this invention. The enzyme can be stored as dried seed or in a ground form for direct addition to feed alone or in combination with other feed enzymes and feed ingredients.

Alternatively, maize seed preferred expression of plant codon-optimized thermotolerant endoglucanases can allow for delivery of the enzyme into the biomass feedstock for hydrolysis of the cellulose into fermentable sugars. The fermentable sugars have many uses including fermentation of the sugars into alcohol for energy or fuel. The plant expressed enzymes may be added to the feedstock or actually expressed in feedstock used to produce fermentable sugars. A plant expressed enzyme may be targeted to a subcellular location to prevent access to the substrate and thus premature degradation of the substrate. The enzyme and substrate may then be brought together by any method needed to break down the subcellular organization, such as, milling, grinding, heating and the like. The addition of a liquid may improve the degradation of the substrate. Thus, ground or milled corn seed may be added to any feedstock before or during hydrolysis of the feedstock.

A second important feature is the ability of the enzymes to withstand the harsh conditions (high temperature and steam) of the feed pelleting process. Thus, in one embodiment, correct subcellular targeting of the enzyme to the endoplasmic reticulum (ER) to achieve high level expression without negatively impacting the seed development is also critical (Please see WO 2005/096704). To achieve this embodiment, synthetic gene sequences and seed-specific expression vectors can be used, and such sequences are described in this example.

Glycerol stocks were prepared for each clone, 7X (SEQ ID NO:7, encoded by SEQ ID NO:6), 12X-1 (SEQ ID NO:13, encoded by SEQ ID NO:12), 12X-6 (SEQ ID NO:9, encoded by SEQ ID NO:8), and 13X-1 (SEQ ID NO:11, encoded by SEQ ID NO:10). DNA was prepared for each clone and sequenced.

Maize optimized genes were designed for glucanase variants 7X (SEQ ID NO:7, encoded by SEQ ID NO:6), 12X-6 (SEQ ID NO:9, encoded by SEQ ID NO:8), and 13X-1 (SEQ ID NO:11, encoded by SEQ ID NO:10) using the back translation program in Vector NTI 9.0 (Invitrogen, Carlsbad, Calif.). Synthetic genes were synthesized by Entelechon GmbH (Germany). Additional sequence was added to the 5' and 3' end of each variant. These sequences included a BamHI cloning site, Kozak sequence, gamma zein signal sequence at the 5' end, a SEKDEL ER retention sequence (Munro and Pelham (1987) Cell, 48:899-907), and a SacI cloning site at the 3' end. An internal BamHI restriction site was removed from each of the maize optimized genes by mutating the DNA sequence for arginine (R69) from AGG to AGA near the 5' end of the gene.

The final maize optimized variant sequences were translated and aligned to the translated sequence for each of the microbial sequences. The protein deduced sequences encoded by the maize-optimized sequences were found to match 100% with the deduced protein sequence encoded by the microbial sequences. The correlation of the DNA and protein sequence between each of the maize optimized glucanase variants and its wild-type glucanase variant is shown below.

| Wild-type Glucanase Variant | Maize Optimized (MO) Glucanase Variant |
|---|---|
| 7X (SEQ ID NO: 7, encoded by SEQ ID NO: 6) | 7XMO (SEQ ID NO: 19, encoded by SEQ ID NO: 18) |
| 12X-6 (SEQ ID NO: 9, encoded by SEQ ID NO: 8) | 12X-6MO (SEQ ID NO: 21, encoded by SEQ ID NO: 20) |
| 13X-1 (SEQ ID NO: 11, encoded by SEQ ID NO: 10) | 13X-1MO (SEQ ID NO: 23, encoded by SEQ ID NO: 22) |

Construction of Plant Transformation Vectors

Each of the maize optimized glucanase variants was cloned behind the Rice Glutelin promoter (prGTL, Takaiwa et al. (1991) *Plant Mol. Biol.* 16 (1), 49-58) and the Maize gamma zein promoter (prGzein, WO 2005/096704) for expression in the endosperm of the maize seed. The terminator used for all constructs was the 35S terminator (WO 2005/096704). As described above, additional sequences were added for targeting of the protein to the ER of the endosperm. Each gene was excised from the original Entelechon cloning vector, pMBL, as a BamHI-SacI fragment (1039 bp). For construction of the Rice Glutelin promoter constructs, the 1039 bp fragment was cloned into pSM323 at the BamHI-SacI sites. For the Gamma zein promoter constructs, the 1039 bp fragments were cloned into pSH231. Promoter-GOI fragments were cut from each of the cloning vectors as a HindIII-KpnI fragment and subcloned into the agro vector, pNOV2117 (a binary vector, see Negrotto et al. (2000) *Plant Cell Reports* 19:798-803). The DNA sequences of all Agro vectors was confirmed by sequence analysis. The vectors can be described as follows:

| Vector identification # | Gene | Promoter | Targeting Sequence | Terminator |
|---|---|---|---|---|
| 15666 | 13X-1MO (SEQ ID NO: 23, encoded by SEQ ID NO: 22) | prGZein | ER retention | 35S terminator |
| 15674 | 7XMO (SEQ ID NO: 19, encoded by SEQ ID NO: 18) | prGZein | SEKDEL | 35S terminator |
| 15714 | 12X-6MO (SEQ ID NO: 21, encoded by SEQ ID NO: 20) | prGZein | ER Retention | 35S terminator |
| 15660 | 12X-6MO (SEQ ID NO: 21, encoded by SEQ ID NO: 20) | prGTL | SEKDEL | 35S terminator |
| 15662 | 13X-1MO (SEQ ID NO: 23, encoded by SEQ ID NO: 22) | prGTL | SEKDEL | 35S terminator |
| 15671 | 7XMO (SEQ ID NO: 19, encoded by SEQ ID NO: 18) | prGTL | SEKDEL | 35S terminator |

Constructs 15660 and 15671 were transformed into *Agrobacterium* strain LBA4404 according to Negrotto et al. (2000) *Plant Cell Rep* 19:798-803. *Agrobacterium* strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* were suspended in LS-infection media supplemented with 100 µM As. Bacteria were pre-induced in this medium for 30-60 minutes.

Transformation of immature maize embryos was performed as generally described in Negrotto et al. (2000) *Plant Cell Rep* 19:798-803. Briefly, immature embryos from maize inbred JHAX707 were excised from 8-12 day old ears into liquid LS-inf+100 µM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

Immature embryos producing embryogenic callus were transferred to LSD1M0.5S medium. The cultures were selected on this medium for 6 weeks with a subculture step at 3 weeks. Surviving calli were transferred to Reg1 medium supplemented with mannose. Following culturing in the light (16 hour light/8 hour dark regiment), green tissues were then transferred to Reg2 medium without growth regulators and incubated for 1-2 weeks. Plantlets are transferred to Magenta GA-7 boxes (Magenta Corp, Chicago Ill.) containing Reg3 medium and grown in the light. After 2-3 weeks, plants were tested for the presence of the PMI genes and other genes of interest by PCR. Positive plants from the PCR assay were transferred to the greenhouse and grown to produce seed.

In order to test for glucanase activity, the following assay was performed.

Reagents Used in Assay:

Extraction buffer is buffered at pH 5.30 and contains 100 mM sodium acetate, 100 mM NaCl, 1 mg/ml Gelatin, 1 mM EDTA, 0.02% Tween-20 & 0.02% $NaN_3$ DNS Reagent: One liter of DNS reagent contains 5.0 g 3,5-dinitrosalicylic acid, 150. g sodium potassium tartrate tetrahydrate and 0.36 mol sodium hydroxide.

Substrate Solution is at pH 5.3 and contains 0.7% (w/v) oat beta-glucan, 100 mM sodium acetate pH 5.3 and 0.02% (w/v) sodium azide.

Milling and Extraction:

A pool of 16 transgenic seed was ground using the Kleco Model 8200 8 canister ball mill. 100 mg of the ground flour was then extracted in 10 ml of extraction buffer shaking at RT for 30 minutes. The mixture was then centrifuged and the supernatant was removed.

Assay of Extracted Enzyme

The supernatant was diluted 1:50 in the extraction buffer. Ten microliters of the dilute extract was added to 50 microliters of 0.7% oat beta-glucan substrate and incubated at 80° C. for one hour. It is also possible to incubate the mixture at lower temperatures, such as, 70° C. Fifty microliters of DNS reagent was immediately added and heated at 95° C. for ten minutes. Samples for 0 time points were prepared by mixing 50 microliters of DNS reagent with 50 microliters of substrate solution and 10 microliters of extract. Standards were prepared by mixing 10 microliters of known concentrations of glucose (dissolved in extraction buffer) with 50 microliters of substrate solution and 50 microliters of DNS reagent. The standards, 0 and 60 min time point samples are then incubated 10 min at 95° C. then cooled to room temperature. This was followed by reading the sample absorbance at A540. The amount of reducing ends produced (in micromoles) was determined by comparison of the absorbance readings of the samples to that of the standards.

One unit of activity is the amount of enzyme that produces one micromole of reducing end per minute. Enzyme composition of seed is reported as units of enzyme/g of flour.

A total of 306 transgenic seed samples were analyzed. For events containing construct 15660, 164 samples were analyzed for glucanase activity. For events containing construct 15671, 142 samples were analyzed for glucanase activity. The highest expressing event containing construct 15660 had an activity level of 3527 U/g (+/−49 U/g) while the highest expressing event containing construct 15671 had an activity level of 2794 U/g (+/−80 U/g).

Example 11

Glucanase Activity in Feed Assays

Reagents Used in Assay:

Extraction buffer is buffered at pH 5.30 and contains 100 mM sodium acetate, 100 mM NaCl, 1 mg/ml Gelatin, 1 mM EDTA, 0.02% Tween-20 & 0.02% $NaN_3$ DNS Reagent:

One liter of DNS reagent contains 5.0 g 3,5-dinitrosalicylic acid, 150. g sodium potassium tartrate tetrahydrate and 0.36 mol sodium hydroxide.

Substrate Solution is at pH 5.3 and contains 0.7% (w/v) oat beta-glucan, 100 mM sodium acetate pH 5.3 and 0.02% (w/v) sodium azide.

Milling and Extraction Steps:

Feed samples were milled by passage through a laboratory hammer mill (Perten 3100) equipped with a 0.8 mm screen. Enzyme was extracted from feed by shaking it in extraction buffer. Extraction was performed at 60° C. with 10 g buffer/1 g milled feed. Elevated temperature can increase extraction efficiency.

Assay of Extracted Enzyme

The enzyme was assayed at 70° C. with activity being monitored by measuring the increase in reducing ends from 0 to 60 minutes. Samples for 0 time points were prepared by mixing 50 microliters of DNS reagent with 50 microliters of substrate solution and 10 microliters of extract. Samples for 60 min time points were prepared by mixing 50 microliters of substrate solution and 10 microliters of extract, incubating for 60 min at 70° C. then adding 50 microliters of DNS reagent. Standards were prepared by mixing 10 microliters of known concentrations of glucose (dissolved in extraction buffer) with 50 microliters of substrate solution and 50 microliters of DNS reagent. The standards, 0 and 60 min time point samples were then incubated 10 min at 95° C. then cooled to room temperature. This was followed by reading the sample absorbance at A540. The amount of reducing ends produced (in micromoles) is determined by comparison of the absorbance readings of the samples to that of the standards.

One unit of activity is the amount of enzyme that produces one micromole of reducing end per minute. Enzyme composition of feed is reported as units of enzyme/kg feed.

Example 12

Performance Broilers when Fed a Diet Containing Enzymes

Enzyme was added to an energy-limiting corn/soy diet prior to processing at a high temperature (90° C. at die face). The performance of the chickens on enzyme-containing, energy-limiting diets was compared to energy-limiting diets without enzyme (negative control diet) and to diets that are not energy-limiting (positive control diet). The enzymes were expressed and produced in *Pichia*.

Male Cobb×Cobb chicks at one-day of age were fed for 28 days. The chickens were fed a starter diet for days 1-18 and a grower diet for days 18-28. Eight treatments are used with 6 replicates per treatment and 6 birds per replicate. The treatments and diets are outlined in the tables below.

Treatment Identification

| Trt | Diet base | Enzyme | Enzyme inclusion rate (g/kg diet) | Dose (U/kg diet) | Route of application |
|---|---|---|---|---|---|
| 1 | positive control | None | 0 | 0 | NA |
| 2 | negative control | None | 0 | 0 | NA |
| 3 | negative control | SEQ ID NO: 7, encoded by, e.g., SEQ ID NO: 6 (7X) | 0.031 | 60 | In Mixer |
| 4 | negative control | SEQ ID NO: 7, encoded by, e.g., SEQ ID NO: 6 (7X) | 0.063 | 120 | In Mixer |
| 5 | negative control | SEQ ID NO: 9, E encoded by, e.g., SEQ ID NO: 8 (12x-6) | 0.053 | 60 | In Mixer |
| 6 | negative control | SEQ ID NO: 9, E encoded by, e.g., SEQ ID NO: 8 (12x-6) | 0.105 | 120 | In Mixer |
| 7 | negative control | SEQ ID NO: 11, encoded by, e.g. ,SEQ ID NO: 10 (13x-1) | 0.055 | 60 | In Mixer |
| 8 | negative control | SEQ ID NO: 11, encoded by, e.g., SEQ ID NO: 10 (13x-1) | 0.110 | 120 | In Mixer |
| 1 duplicate | negative control | None | 0 | 0 | NA |

Diet Formulation

| Ingredient (%) | 0-18 days | | 18-28 days | |
|---|---|---|---|---|
| | Positive control | Negative control | Positive control | Negative control |
| Corn | 61.14 | 62.18 | 65.79 | 67.08 |
| Poultry Biproduct meal | 5.00 | 3.17 | 5.00 | 2.74 |
| Soybean meal 48 | 29.07 | 30.84 | 24.92 | 27.41 |
| Wheat Bran | 0.00 | 0.52 | 0.00 | 0.00 |
| Poultry Fat | 1.67 | 0.00 | 1.71 | 0.00 |
| Salt | 0.23 | 0.22 | 0.15 | 0.15 |
| DL Methionine | 0.27 | 0.27 | 0.20 | 0.20 |
| Lysine HCl | 0.14 | 0.15 | 0.03 | 0.03 |
| Limestone | 0.48 | 0.49 | 0.57 | 0.57 |
| Defluor Phos | 1.49 | 1.64 | 1.11 | 1.30 |
| Coccidiostat (Coban-monensin) | 0.02 | 0.02 | 0.02 | 0.02 |
| Vitamin premix | 0.25 | 0.25 | 0.25 | 0.25 |
| Trace Mineral Premix | 0.075 | 0.075 | 0.075 | 0.075 |

Trace Mineral Premix

| | |
|---|---|
| Calcium (Ca) Min. | 3.20% |
| Calcium (Ca) Max. | 4.20% |
| Iron (Fe) Min. | 2.63% |
| Magnesium (Mg) Min. | 2.68% |
| Manganese (Mn) Min. | 13.40% |
| Zinc (Zn) Min | 10.70% |
| Copper (Cu) Min | 4000 ppm |
| Iodine (I) Min. | 1000 ppm |
| Selenium (Se) Min. | 400 ppm |

| Vitamin Premix | |
| --- | --- |
| Vitamin A, I..U./LB | 1,000,000 |
| Vitamin D3, I..U./LB | 200,000 |
| Vitamin E, I..U./LB | 2,000 |
| Vitamin B-12, MG./LB | 2.20 |
| Riboflavin, MG./LB | 800 |
| Niacin, MG./LB | 8,000 |
| d-Pantothenic Acid, MG./LB | 2,000 |
| Choline, MG./LB | 34,720 |
| Menadione, MG./LB | 132 |
| Folic Acid, MG./LB | 100 |
| Thiamine, MG./LB | 400 |
| Pyridoxine, MG./LB | 400 |
| Biotin, MG./LB | 20 |
| Ethoxyquin, MG./LB | 23,000 |

The tables below present the performance of the chickens in the various treatments. FCR means feed conversion ratio, e.g., kg feed per kg body weight gain. Feed samples from each treatment were collected and analyzed for enzyme activity. Enzyme activity was detected at or above the expected level except for the 0-18 day diet for treatment 3.

As seen below in the Tables below, birds fed an energy-sufficient diet (positive control) had better gain than those fed the negative control; a difference of 70 g of weight is economically significant. The enzymes generally increased the gain of the birds, at some doses close to the level of the positive control. The corrected feed conversion ratio (FCRc) was not as clear-cut. In this trial SEQ ID NO:7 (encoded by, e.g., SEQ ID NO:6) and SEQ ID NO:9 (encoded by, e.g., SEQ ID NO:8) each had at least one dose that gave an FCR significantly better (lower) than the negative control. SEQ ID NO:11 (encoded by, e.g., SEQ ID NO:10), however was similar to the negative control on FCR.

TABLE

| 0-28 Day Performance | | | |
| --- | --- | --- | --- |
| Treatment | Feed Intake (kg) | Gain (kg) | FCRc* |
| 1 positive control | 1.772 | 1.133 | 1.540 |
| 2 negative control | 1.666 | 1.053 | 1.565 |
| 3 SEQ ID NO: 7, encoded by, e.g., SEQ ID NO: 6 (60 U/kg) | 1.696 | 1.058 | 1.571 |
| 4 SEQ ID NO: 7, encoded by, e.g., SEQ ID NO: 6 (120 U/kg) | 1.758 | 1.113 | 1.548 |
| 5 SEQ ID NO: 9, encoded by, e.g., SEQ ID NO: 8 (60 U/kg) | 1.703 | 1.099 | 1.549 |
| 6 SEQ ID NO: 9, encoded by, e.g., SEQ ID NO: 8 (120 U/kg) | 1.810 | 1.117 | 1.550 |
| 7 SEQ ID NO: 11, encoded by, e.g., SEQ ID NO: 10 (60 U/kg) | 1.723 | 1.067 | 1.571 |
| 8 SEQ ID NO: 11, encoded by, e.g., SEQ ID NO: 10 (120 U/kg) | 1.662 | 1.068 | 1.561 |
| Treatment (p=) | 0.0334 | 0.0043 | 0.1505 |
| Enzyme (p=) | 0.4202 | 0.1729 | 0.2806 |
| Dose (p=) | 0.1138 | 0.1225 | 0.2658 |
| Enzyme*Dose (p=) | 0.2252 | 0.4374 | 0.4427 |

*FCR corrected for mortality

Example 13

Stability of Enzyme in Pelleted Feed

Recovery of SEQ ID NO:7, encoded by, e.g., SEQ ID NO:6 glucanase from pellets was determined by measuring activity extracted from mash feed pelleted at various temperatures. The results are displayed in FIG. 15. Diets were formulated as a typical commercial broiler diet (corn/soybean meal/meat and bone meal based). A basal diet was prepared and as indicated and supplemented with SEQ ID NO:7, encoded by, e.g., SEQ ID NO:6 at 250 U/kg. Three mash samples were prepared for each pelleting run. During pelleting runs the temperature was raised in increments from 70° C. to 95° C. The mill was carefully monitored to ensure the retention of the samples did not increase with temperature. Samples (500 g each) were collected from mash and pellets at each temperature and analyzed for glucanase activity according the protocol of Example 11.

Run 1 and 2 showed no loss in glucanase activity when pelleted at 95° C. However, Run 3 showed about 30% loss of enzyme activity when pelleted at 95° C. The enzyme can lose activity in solution with temperatures over 95° C., dropping from 86% activity at 95° C. to about 8% activity at 97° C. Thus, variability in the pelleting temperature could explain the variability in recovery of SEQ ID NO:7, encoded by, e.g., SEQ ID NO:6 from the third pelleting run.

Example 14

Statistical Analysis of Five Feeding Trials of Glucanase Enzymes

The "wild-type" glucanase and 3 of the variants (SEQ ID NO:11 (encoded by, e.g., SEQ ID NO:10), SEQ ID NO:9 (encoded by, e.g., SEQ ID NO:8) and SEQ ID NO:7 (encoded by, e.g., SEQ ID NO:6)) were tested in for efficacy in improving performance of broiler chickens fed diets which are marginally deficient in energy but sufficient in amino acids. A positive result would be viewed as a variant returning performance that was better than the negative control.

A series of 5 identically designed experiments were set up, whereby birds were fed an Agri-stats standard corn-soy diet as a positive control, and a negative control which was identical in all regards with the exception that the energy level of the ration was reduced by 80-90 kcals/kg (depending upon trial). The trials lasted either from 0-28 d (3 trials) or 0-35 d (2 trials) of age. (See Example xy for details of experimental design of a typical trial).

Holo-Analysis of all Variants Data

A holo-analysis of all the combined data was carried to determine a measure of the effect of the enzymes on bird performance. Analyses were performed on FCR (feed conversion ratio), on weight gain and on enzyme recovery from feed.

N=78 tests in total (where a test=one treatment in a trial where an enzyme is present)

FCR model—no significant effect of enzyme or dose

Gain model—significant effects of enzyme and dose.

Enzyme recovery from feed was better with the variants (SEQ ID NO:7 (encoded by, e.g., SEQ ID NO:6), SEQ ID NO:11 (encoded by, e.g., SEQ ID NO:10) & SEQ ID NO:9 (encoded by, e.g., SEQ ID NO:8)) than the wild-type enzyme.

Effect of enzyme presence on gain was modeled using stepwise regression using the following terms: Intercept, Log Dose of enzyme, Maize %, Light regimen (hours per day), Gain of negative control, Gain of positive control & Log dose of enzyme). The estimated parameters are given below.

| Parameter Estimates | | | | |
|---|---|---|---|---|
| Term | Estimate | Std Error | t Ratio | Prob > \|t\| |
| Intercept | −395.44 | 117.80 | −3.36 | 0.0013 |
| Product[wild-type]: Log dose | 33.84 | 36.59 | 0.92 | 0.3584 |
| Product [SEQ ID NO: 7 (encoded by, e.g., SEQ ID NO: 6)]: Log dose | 89.69 | 32.07 | 2.80 | 0.0068 |
| Product[SEQ ID NO: 11 (encoded by, e.g., SEQ ID NO: 10)]: Log dose | 25.29 | 33.76 | 0.75 | 0.4564 |
| Product[SEQ ID NO: 9 (encoded by, e.g., SEQ ID NO: 8)]: Log dose | 77.23 | 43.75 | 1.77 | 0.0821 |
| Maize % | 4.154 | 1.921 | 2.16 | 0.0342 |
| Light | 2.562 | 0.914 | 2.80 | 0.0067 |

| Parameter Estimates (continued) | | | | |
|---|---|---|---|---|
| Term | Estimate | Std Error | t Ratio | Prob > \|t\| |
| Negative control gain | −0.262 | 0.085 | −3.08 | 0.0030 |
| Positive control gain | 0.240 | 0.089 | 2.70 | 0.0088 |
| Product[wild-type] | 54.70 | 61.05 | 0.90 | 0.3735 |
| Product[SEQ ID NO: 7 (encoded by, e.g., SEQ ID NO: 6)] | −76.58 | 58.87 | −1.30 | 0.1978 |
| Product[SEQ ID NO: 11 (encoded by, e.g., SEQ ID NO: 10)] | 54.14 | 58.02 | 0.93 | 0.3542 |

All four enzymes had a dose effect on gain. The largest effects of dose were associated with SEQ ID NO:7 (encoded by, e.g., SEQ ID NO:6) and SEQ ID NO:9 (encoded by, e.g., SEQ ID NO:8).

The tables below analyze the goodness of fit overall ($P<0.0001$) and for various parameters. Combining the data from the enzymes there was a significant enzyme dose effect ($P<0.05$)

| Summary of Fit | |
|---|---|
| RSquare | 0.743 |
| RSquare Adj | 0.700 |
| Root Mean Square Error | 26.34 |
| Mean of Response | −6.85 |
| Observations (or Sum Wgts) | 78 |

| Analysis of Variance | | | | |
|---|---|---|---|---|
| Source | DF | Sum of Squares | Mean Square | F Ratio |
| Model | 11 | 132117.31 | 12010.7 | 17.3106 |
| Error | 66 | 45792.84 | 693.8 | Prob > F |
| C. Total | 77 | 177910.15 | | <.0001 |

| Effect Tests | | | | | |
|---|---|---|---|---|---|
| Source | Nparm | DF | Sum of Squares | F Ratio | Prob > F |
| Log dose[Product] | 4 | 4 | 8535.7520 | 3.0756 | 0.0220 |
| Maize % | 1 | 1 | 3245.1270 | 4.6771 | 0.0342 |
| Light | 1 | 1 | 5448.9483 | 7.8534 | 0.0067 |
| Negative control gain | 1 | 1 | 6568.3975 | 9.4669 | 0.0030 |
| Positive control gain | 1 | 1 | 5064.0781 | 7.2987 | 0.0088 |
| Product | 3 | 3 | 1937.1962 | 0.9307 | 0.4309 |

While the invention has been described in detail with reference to certain exemplary aspects thereof, it will be understood that modifications and variations are within the spirit and scope of that which is described and claimed.

What is claimed is:

1. A synthetic or recombinant polypeptide with endoglucanase activity comprising:
   (a) the amino acid sequence as set forth in SEQ ID NO: 9;
   (b) the synthetic or recombinant polypeptide encoded by the nucleic acid sequence as set forth in SEQ ID NO: 8; or
   (c) the polypeptide of (a) or the polypeptide encoded by (b) but lacking a signal sequence or a carbohydrate binding module;
   wherein, the polypeptide further comprises a heterologous sequence.

2. The polypeptide of claim 1, wherein the endoglucanase activity is thermostable or thermotolerant.

3. A food or feed composition and/or food additive comprising the polypeptide of claim 1.

4. A method for preparing a food or feed composition and/or food or feed additive, comprising mixing the polypeptide of claim 1 with one or more food or feed and/or food or feed additive ingredients.

5. A detergent composition comprising the polypeptide of claim 1.

6. The detergent composition of claim 5 further comprising one or more additional polypeptides.

7. The detergent composition of claim 5 or 6 additionally comprising a surfactant.

8. A fracturing fluid composition comprising:
   (a) an aqueous fluid,
   (b) a hydratable polymer; and
   (c) the polypeptide of claim 1.

9. The fracturing fluid of claim 8 wherein the composition further comprises a crosslinking agent capable of crosslinking the hydratable polymer.

10. The fracturing fluid of claim 8 or 9, wherein the hydratable polymer is selected from the group consisting of guar, guar derivatives, cellulose derivatives, water soluble biopolymers, or combinations thereof.

11. The fracturing fluid of claim 8, 9, or 10, further comprising one or more additional polypeptides.

12. A method of fracturing a subterranean formation that surrounds a well bore, the method comprising the steps of:
  (a) combining an aqueous fluid, a hydratable polymer, a crosslinking agent, and an enzyme breaker, comprising the polypeptide of claim 1;
  (b) injecting the crosslinked polymer fluid into the well bore and into contact with the formation under sufficient pressure to fracture the surrounding subterranean formation; and
  (c) allowing the enzyme breaker to degrade the crosslinked polymer gel so that it can be removed from the subterranean formation, the enzyme breaker being catalytically active and temperature stable in a temperature range of about 60° F. to about 225° F. and in a pH range of about 7 to about 12.

13. A method of modifying a composition comprising lignocellulose, a cellulose, a hemicellulose, a lignin, a xylan, a glucan, or a mannan comprising contacting the composition with the polypeptide of claim 1.

14. A polypeptide having endoglucanase activity comprising SEQ ID NO: 9.

15. A polypeptide having endoglucanase activity encoded by SEQ ID NO: 8.

16. A cellulose, wood, wood pulp, wood product, paper, paper pulp, paper product, pharmaceutical composition, dietary supplement, fuel, dairy product, textile, fabric , processed waste, disinfectant, biodefense, bio-detoxifying agent comprising the polypeptide of claim 1.

17. A method of hydrolyzing or disrupting a cellulose containing composition comprising contacting the composition with the polypeptide of claim 1, thereby hydrolyzing or disrupting the composition.

18. The polypeptide of claim 15, wherein the endoglucanase activity is thermostable.

19. A composition comprising a mixture of SEQ ID NO:9 or a polypeptide having at least 98% or more sequence identity to SEQ ID NO:9 and at least one or more additional polypeptides.

20. A method of hydrolyzing or disrupting a cellulose containing composition comprising contacting the cellulose containing composition with a composition of claim 19, thereby hydrolyzing or disrupting the cellulose containing composition.

* * * * *

SEQUENCE LISTING

<160> NUMBER OF SEQ ID NOS: 26

<210> SEQ ID NO 1
<211> LENGTH: 954
<212> TYPE: DNA
<213> ORGANISM: Thermotoga maritima

<400> SEQUENCE: 1
atgggtgttg atccttttga aaggaacaaa atattgggaa gaggcattaa tataggaaat      60
gcgcttgaag caccaaatga gggagactgg ggagtggtga taaagatga gttcttcgac      120

```
attataaaag aagccggttt ctctcatgtt cgaattccaa taagatggag tacgcacgct    180
tacgcgtttc ctccttataa aatcatggat cgcttcttca aaagagtgga tgaagtgata    240
aacggagccc tgaaaagagg actggctgtt gttataaata ttcatcacta cgaggagtta    300
atgaatgatc cagaagaaca caaggaaaga tttcttgctc tttggaaaca aattgctgat    360
cgttataaag actatcccga aactctattt tttgaaattc tgaatgaacc tcacggaaat    420
cttactccgg aaaatggaa tgaactgctt gaggaagctc taaaagttat aagatcaatt    480
gacaaaaagc acactataat tataggcaca gctgaatggg ggggtatatc tgcccttgaa    540
aaactgtctg tcccaaaatg ggaaaaaaat tctatagtta caattcacta ctacaatcct    600
ttcgaattta cccatcaagg agctgagtgg gtggaaggat ctgagaaatg gttgggaaga    660
aagtggggat ctccagatga tcagaaacat ttgatagaag aattcaattt tatagaagaa    720
tggtcaaaaa agaacaaaag accaatttac ataggtgagt ttggtgccta cagaaaagct    780
gaccttgaat caagaataaa atggacctcc tttgtcgttc gcgaaatgga gaaaaggaga    840
tggagctggg catactggga attttgttcc ggttttggtg tttatgatac tctgagaaaa    900
acctggaata aagatctttt agaagcttta ataggaggag atagcattga ataa           954
```

<210> SEQ ID NO 2
<211> LENGTH: 317
<212> TYPE: PRT
<213> ORGANISM: Thermotoga maritima
<220> FEATURE:
<221> NAME/KEY: DOMAIN
<222> LOCATION: (19)...(296)
<223> OTHER INFORMATION: Cellulase (glycosyl hydrolase family 5)

<400> SEQUENCE: 2

```
Met Gly Val Asp Pro Phe Glu Arg Asn Lys Ile Leu Gly Arg Gly Ile
1               5                  10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205
```

```
Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
            275                 280                 285

Cys Ser Gly Phe Gly Val Tyr Asp Thr Leu Arg Lys Thr Trp Asn Lys
        290                 295                 300

Asp Leu Leu Glu Ala Leu Ile Gly Gly Asp Ser Ile Glu
305                 310                 315

<210> SEQ ID NO 3
<211> LENGTH: 954
<212> TYPE: DNA
<213> ORGANISM: Artificial sequence
<220> FEATURE:
<223> OTHER INFORMATION: Synthetically generated polynucleotide

<400> SEQUENCE: 3
atgggtgttg atccttttga aaggaacaaa atattgggaa gaggcattaa tataggaaat      60
gcgcttgaag caccaaatga gggcgactgg ggagtcgtga taaagatga gttcttcgac     120 attataaaag aagccggttt ctctcatgtt cgaattccaa taagatggag tacgcacgct     180
tacgcgtttc ctccttataa aatcatggat cgcttcttca aaagagtgga tgaagtgata     240
aacggagccc tgaaaagagg actggctgtt gttataaata ttcatcacta cgaggagtta     300
atgaatgatc agaagaacaa caaggaaaga tttcttgctc tttggaaaca aattgctgat     360
cgttataaag actatcccga aactctattt tttgaaattc tgaatgaacc tcacggaaat     420
cttactccgg aaaaatggaa tgaactgctt gaggaagctc taaaagttat aagatcaatt     480
gacaaaaagc acactataat tataggcaca gctgaatggg ggggtatatc tgcccttgaa     540
aaactgtctg tcccaaaatg ggaaaaaaat tctatagtta caattcacta ctacaatcct     600
ttcgaattta cccatcaagg agctgagtgg gtggaaggat ctgagaaatg gttgggaaga     660
aagtggggat ctccagatga tcagaaacat ttgatagaag aattcaattt tatagaagaa     720
tggtcaaaaa agaacaaaag accaatttac ataggtgagt ttggtgccta cagaaaagct     780
gaccttgaat caagaataaa atggacctcc tttgtcgttc gcgaaatgga gaaaaggaga     840
tggagctggg catactggga attttgttcc ggttttggtg tttatgatac tctgagaaaa     900
acctggaata aagatctttt agaagcttta ataggaggag atagcattga ataa            954

<210> SEQ ID NO 4
<211> LENGTH: 102
<212> TYPE: PRT
<213> ORGANISM: Artificial sequence
<220> FEATURE:
<223> OTHER INFORMATION: Alpha-mating factor plus amino acids 2-18 of
      SEQ ID NO:2

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
```

```
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Gly Val Asp Pro Phe Glu Arg Asn Lys Ile Leu
                85                  90                  95

Gly Arg Gly Ile Asn Ile
            100
```

<210> SEQ ID NO 5
<211> LENGTH: 104
<212> TYPE: PRT
<213> ORGANISM: Artificial sequence
<220> FEATURE:
<223> OTHER INFORMATION: Alpha-mating factor plus amino acids "E" and
      "A" plus amino acids 2-18 of SEQ ID NO:2

<400> SEQUENCE: 5

```
Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Gly Val Asp Pro Phe Glu Arg Asn Lys
                85                  90                  95

Ile Leu Gly Arg Gly Ile Asn Ile
            100
```

<210> SEQ ID NO 6
<211> LENGTH: 974
<212> TYPE: DNA
<213> ORGANISM: Artificial sequence
<220> FEATURE:
<223> OTHER INFORMATION: Synthetically generated polynucleotide

<400> SEQUENCE: 6

```
atgggtgttg atccttttga aggaacaaa atattgggaa gaggcattaa tataggaaat      60
gcgcttgaag caccaaatga gggagactgg ggagtggtga taaagatgaa gtatttcgac    120
attataaaag aagccggttt ctctcatgtt cgaattccaa taagatggag tacgcacgct    180
caggcgtttc ctcctttataa aatcgaggat cgcttcttca aaagagtgga tgaagtgata    240
aacggagccc tgaaaagagg actggctgtt gttataaatc agcatcacta cgaggagtta    300
atgaatgatc cagaagaaca caaggaaga tttcttgctc tttggaaaca aattgctgat    360
cgttataaag actatcccga aactctattt tttgaaattc tgaatgaacc tcacggaaat    420
cttactccgg aaaatggaa tgaactgctt gaggaagctc taaaagttat aagatcaatt    480
gacaaaaagc acactataat tataggcaca gctgatgggg gggtatatc tgcccttgaa    540 aaactgaggg tcccaaaatg ggaaaaaaat gcgatagtta caattcacta ctacaatcct    600
```

| | | | | |
|---|---|---|---|---|
| ttcgaattta | cccatcaagg | agctgagtgg | gtggaaggat | ctgagaaatg | gttgggaaga | 660 |
| aagtggggat | ctccagatga | tcagaaacat | ttgataaag | aattcaattt | tatagaagaa | 720 |
| tggtcaaaaa | agaacaaaag | accaatttac | ataggtgagt | ttggtgccta | cagaaaagct | 780 |
| gaccttgaat | caagaataaa | atggacctcc | tttgtcgttc | gcgaagctga | gaaaggaga | 840 |
| tggagctggg | catactggga | attttgttcc | ggttttggtg | tttatgatac | tctgagaaaa | 900 |
| acctggaata | agatcttt | agaagcttta | ataggaggag | atagcattga | ataacaccat | 960 |
| tccaagatgg | cgtg | | | | | 974 |

<210> SEQ ID NO 7
<211> LENGTH: 323
<212> TYPE: PRT
<213> ORGANISM: Artificial sequence
<220> FEATURE:
<223> OTHER INFORMATION: Synthetically generated polypeptide

<400> SEQUENCE: 7

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Tyr Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

Pro Tyr Lys Ile Glu Asp Arg Phe Phe Lys Arg Val Asp Glu Val Ile
65                  70                  75                  80

Asn Gly Ala Leu Lys Arg Gly Leu Ala Val Val Ile Asn Gln His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Ala Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
```

```
                290                295                300
Asp Leu Leu Glu Ala Leu Ile Gly Gly Asp Ser Ile Glu His His Ser
305                310                315                320

Lys Met Ala
```

<210> SEQ ID NO 8
<211> LENGTH: 954
<212> TYPE: DNA
<213> ORGANISM: Artificial sequence
<220> FEATURE:
<223> OTHER INFORMATION: Synthetically generated polynucleotide

<400> SEQUENCE: 8

```
atgggtgttg atccttttga aggaacaaa atattgggaa gaggcattaa tataggaaat      60
gcgcttgaag caccaaatga gggagactgg ggagtggtga taaagatga gttcttcgac     120
attataaaag aagccggttt ctctcatgtt cgaattccaa taagatggag tacgcacgct    180
caggcgtttc ctccttataa aatcgagcct tctttcttca aaagagtgga tgaagtgata    240
aacggagccc tgaaaagagg actggctgtt gttataaata ttcatcacta cgaggagtta    300
atgaatgatc agaagaaca caaggaaaga tttcttgctc tttggaaaca aattgctgat    360
cgttataaag actatcccga aactctattt tttgaaattc tgaatgaacc tcacggaaat    420
cttactccgg aaaaatggaa tgaactgctt gaggaagctc taaagttat aagatcaatt     480
gacaaaaagc acactgtgat ataggcaca gctgaatggg ggggtatatc tgcccttgaa    540
aaactgaggg tcccaaaatg gaaaaaaat gcgatagtta caattcacta ctacaatcct    600
ttcgaattta cccatcaagg agctgagtgg gtgcctggat ctgagaaatg gttgggaaga    660
aagtggggat ctccagatga tcagaaacat tgatagaag aattcaattt tatagaagaa    720
tggtcaaaaa agaacaaaag accaatttac ataggtgagt ttggtgccta cagaaaagct    780
gaccttgaat caagaataaa atggacctcc tttgtcgttc gcgaagccga gaaaaggggg    840
tggagctggg catactggga attttgttcc ggttttggtg tttatgatcc tctgagaaaa    900
cagtggaata agatctttt agaagcttta ataggaggag atagcattga ataa           954
```

<210> SEQ ID NO 9
<211> LENGTH: 317
<212> TYPE: PRT
<213> ORGANISM: Artificial sequence
<220> FEATURE:
<223> OTHER INFORMATION: Synthetically generated polypeptide

<400> SEQUENCE: 9

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
                20                  25                  30

Val Ile Lys Asp Glu Phe Phe Asp Ile Ile Lys Glu Ala Gly Phe Ser
            35                  40                  45

His Val Arg Ile Pro Ile Arg Trp Ser Thr His Ala Gln Ala Phe Pro
        50                  55                  60

Pro Tyr Lys Ile Glu Pro Ser Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Glu Arg Phe Leu
                100                 105                 110
```

```
Ala Leu Trp Lys Gln Ile Ala Asp Arg Tyr Lys Asp Tyr Pro Glu Thr
            115                 120                 125
Leu Phe Phe Glu Ile Leu Asn Glu Pro His Gly Asn Leu Thr Pro Glu
        130                 135                 140
Lys Trp Asn Glu Leu Leu Glu Glu Ala Leu Lys Val Ile Arg Ser Ile
145                 150                 155                 160
Asp Lys Lys His Thr Val Ile Ile Gly Thr Ala Glu Trp Gly Gly Ile
                165                 170                 175
Ser Ala Leu Glu Lys Leu Arg Val Pro Lys Trp Glu Lys Asn Ala Ile
            180                 185                 190
Val Thr Ile His Tyr Tyr Asn Pro Phe Glu Phe Thr His Gln Gly Ala
        195                 200                 205
Glu Trp Val Pro Gly Ser Glu Lys Trp Leu Gly Arg Lys Trp Gly Ser
    210                 215                 220
Pro Asp Asp Gln Lys His Leu Ile Glu Glu Phe Asn Phe Ile Glu Glu
225                 230                 235                 240
Trp Ser Lys Lys Asn Lys Arg Pro Ile Tyr Ile Gly Glu Phe Gly Ala
                245                 250                 255
Tyr Arg Lys Ala Asp Leu Glu Ser Arg Ile Lys Trp Thr Ser Phe Val
            260                 265                 270
Val Arg Glu Ala Glu Lys Arg Gly Trp Ser Trp Ala Tyr Trp Glu Phe
        275                 280                 285
Cys Ser Gly Phe Gly Val Tyr Asp Pro Leu Arg Lys Gln Trp Asn Lys
    290                 295                 300
Asp Leu Leu Glu Ala Leu Ile Gly Gly Asp Ser Ile Glu
305                 310                 315

<210> SEQ ID NO 10
<211> LENGTH: 954
<212> TYPE: DNA
<213> ORGANISM: Artificial sequence
<220> FEATURE:
<223> OTHER INFORMATION: Synthetically generated polynucleotide

<400> SEQUENCE: 10
atgggtgttg atccttttga aaggaacaaa atattgggaa gaggcattaa tataggaaat      60
gcgcttgaag caccaaatga gggagactgg ggagtggtga taaaagatga gtatttcgac     120
attataaaag aagccggttt ctctcatgtt cgaattccaa taagatggag tacgcacgct     180
caggcgtttc ctccttataa aatcgaggat tctttcttca aaagagtgga tgaagtgata     240
aacggagccc tgaaaagagg actggctgtt gttataaata ttcatcacta cgaggagtta     300
atgaatgatc cagaagaaca caaggaagag ttttcttgctc tttggaaaca aattgctgat     360
cgttataaag actatcccga aactctattt tttgaaattc tgaatgaacc tcacggaaat     420
cttactccgg aaaaatggaa tgaactgctt gaggaagctc taaagttat aagatcaatt     480 gacaaaaagc acactgtgat tataggcaca gctgaatggg ggggtatatc tgcccttgaa     540
aaactgaggg tcccaaaatg gaaaaaaat gcgatagtta caattcacta ctacaatcct     600
ttcgaattta cccatcaagg agctgagtgg gtgcctggat ctgagaaatg gttgggaaga     660
aagtggggat ctccagatga tcagaaacat gtgatagaag aattcaattt tatagaagaa     720
tggtcaaaaa agaacaaaag accaatttac ataggtgagt ttggtgccta cagaaaagct     780
gaccttgaat caagaataaa atggacctcc tttgtcgttc gcgaagccga gaaagggggg     840
tggagctggg catactggga attttgttcc ggttttggtg tttatgatcc tctgagaaaa     900
```
cagtggaata aagatctttt agaagctcta ataggaggag atagcattga ataa       954

<210> SEQ ID NO 11
<211> LENGTH: 317
<212> TYPE: PRT
<213> ORGANISM: Artificial sequence
<220> FEATURE:
<223> OTHER INFORMATION: Synthetically generated polypeptide

<400> SEQUENCE: 11

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Tyr Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

Pro Tyr Lys Ile Glu Asp Ser Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Val Ile Ile Gly Thr Ala Glu Trp Gly Gly Ile
                165                 170                 175

Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
        195                 200                 205

Glu Trp Val Pro Gly Ser Glu Lys Trp Leu Gly Arg Lys Trp Gly Ser
    210                 215                 220

Pro Asp Asp Gln Lys His Val Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Ala Glu Lys Arg Gly Trp Ser Trp Ala Tyr Trp Glu Phe
        275                 280                 285

Cys Ser Gly Phe Gly Val Tyr Asp Pro Leu Arg Lys Gln Trp Asn Lys
    290                 295                 300

Asp Leu Leu Glu Ala Leu Ile Gly Gly Asp Ser Ile Glu
305                 310                 315

<210> SEQ ID NO 12
<211> LENGTH: 954
<212> TYPE: DNA
<213> ORGANISM: Artificial sequence
<220> FEATURE:

-continued

<223> OTHER INFORMATION: Synthetically generated polynucleotide

<400> SEQUENCE: 12

```
atgggtgttg atccttttga aggaacaaa atattgggaa gaggcattaa tataggaaat      60
gcgcttgaag caccaaatga gggagactgg ggagtggtga taaaagatga gttcttcgac   120
attataaaag aagccggttt ctctcatgtt cgaattccaa taagatggag tacgcacgct   180
caggcgtttc ctccttataa aatcgaggat tctttcttca aaagagtgga tgaagtgata   240
aacggagccc tgaaaagagg actggctgtt gttataaatc agcatcacta cgaggagtta   300
atgaatgatc cagaagaaca caaggaaaga tttcttgctc tttggaaaca aattgctgat   360
cgttataaag actatcccga aactctattt tttgaaattc tgaatgaacc tcacggaaat   420
cttactccgg aaaaatggaa tgaactgctt gaggaagctc taaaagttat aagatcaatt   480
gacaaaaagc acactgtgat tataggcaca gctgaatggg ggggtatatc tgcccttgaa   540
aaactgaggg tcccaaaatg gaaaaaaat gcgatagtta caattcacta ctacaatcct   600
ttcgaattta cccatcaagg agctgagtgg gtgcctggat ctgagaaatg gttgggaaga   660
aagtggggat ctccagatga tcagaaacat ttgatagaag aattcaattt tatagaagaa   720
tggtcaaaaa agaacaaaag accaatttac ataggtgagt ttggtgccta cagaaaagct   780
gaccttgaat caagaataaa atggacctcc tttgtcgttc gcgaagccga gaaaaggggg   840
tggagctggg catactggga attttgttcc ggttttggtg tttatgatcc tctgagaaaa   900
cagtggaata agatcttttt agaagcttta ataggaggag atagcattga ataa          954
```

<210> SEQ ID NO 13
<211> LENGTH: 317
<212> TYPE: PRT
<213> ORGANISM: Artificial sequence
<220> FEATURE:
<223> OTHER INFORMATION: Synthetically generated polypeptide

<400> SEQUENCE: 13

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Gln Ala Phe Pro
    50                  55                  60

Pro Tyr Lys Ile Glu Asp Ser Phe Phe Lys Arg Val Asp Glu Val Ile
65                  70                  75                  80

Asn Gly Ala Leu Lys Arg Gly Leu Ala Val Val Ile Asn Gln His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Val Ile Ile Gly Thr Ala Glu Trp Gly Gly Ile
                165                 170                 175
```

```
Ser Ala Leu Glu Lys Leu Arg Val Pro Lys Trp Glu Lys Asn Ala Ile
            180                 185                 190

Val Thr Ile His Tyr Tyr Asn Pro Phe Glu Phe Thr His Gln Gly Ala
            195                 200                 205

Glu Trp Val Pro Gly Ser Glu Lys Trp Leu Gly Arg Lys Trp Gly Ser
        210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Ala Glu Lys Arg Gly Trp Ser Trp Ala Tyr Trp Glu Phe
        275                 280                 285

Cys Ser Gly Phe Gly Val Tyr Asp Pro Leu Arg Lys Gln Trp Asn Lys
    290                 295                 300

Asp Leu Leu Glu Ala Leu Ile Gly Gly Asp Ser Ile Glu
305                 310                 315

<210> SEQ ID NO 14
<211> LENGTH: 1311
<212> TYPE: DNA
<213> ORGANISM: Artificial sequence
<220> FEATURE:
<223> OTHER INFORMATION: Synthetically generated polynucleotide

<400> SEQUENCE: 14
atggccaagt actccgagct ggaaaagggc ggggtcataa tgcaggcgtt ctactgggac      60
gtgccttcag aggaatatg  gtgggacaca atacggcaga agataccgga gtggtacgat     120
gccggaatct ccgcaatatg gattccccg gcgagcaagg gcatgggcgg cgcctattcg      180
atgggctacg accctacga cttctttgac ctcggtgagt acgaccagaa gggaacggta      240
gagacgcgct ttggctccaa gcaggagctc gtgaacatga taaacaccgc ccacgcctat     300
ggcatgaagg taatagccga tatagtcatc aaccaccgcg ccggcggtga cctggagtgg     360
aaccccttcg tgaacgacta ccctggacc  gacttctcaa aggtcgcgtc gggtaaaatac   420 acggccaact acctcgactt ccacccgaac gagctccatg cgggcgattc cggaacattt     480
ggaggctatc ccgacatatg ccacgacaag agctgggacc agtactggct ctgggccagc     540
caggagagct acgcggcata tctcaggagc atcggcatcg atgcctggcg cttcgactac     600
gtcaagggct atgctccctg gtcgtcaag  gactggctga ctggtgggg  aggctgggcg    660 gttggagagt actgggacac caacgtcgac gctgttctca actgggcata ctcgagcggt     720
gccaaggtct ttgacttcgc cctctactac aagatggatg aggcctttga caacaaaaac     780
attccagcgc tcgtctctgc ccttcagaac ggccagactg ttgtctcccg cgacccgttc     840
aaggccgtaa cctttgtagc aaaccacgac accgatataa tctggaacaa gtatccagcc     900
tacgcgttca tcctcaccta cgagggccag ccgacaatat tctaccgcga ctacgaggag     960
tggctcaaca aggataagct caagaacctc atctggatac atgagaacct cgccggagga    1020
agcaccgaca tagtctacta cgataacgat gaactcatct tcgtcaggaa cggctacggg    1080
gacaagccgg ggcttataac ctacatcaac ctaggctcga gcaaggccgg aagtgtgtt    1140 tatgtgccga agttcgcggg cgcgtgcatc acgagtata  ctggtaacct cggaggctgg   1200
gtagacaagt acgtctactc aagcggctgg gtctatctcg aagctccagc ttacgaccct    1260
```
gccaacgggc agtatggcta ctccgtgtgg agctactgcg ggtgggctg a        1311

<210> SEQ ID NO 15
<211> LENGTH: 436
<212> TYPE: PRT
<213> ORGANISM: Artificial sequence
<220> FEATURE:
<223> OTHER INFORMATION: Synthetically generated polypeptide

<400> SEQUENCE: 15

```
Met Ala Lys Tyr Ser Glu Leu Glu Lys Gly Gly Val Ile Met Gln Ala
1               5                   10                  15

Phe Tyr Trp Asp Val Pro Ser Gly Gly Ile Trp Trp Asp Thr Ile Arg
            20                  25                  30

Gln Lys Ile Pro Glu Trp Tyr Asp Ala Gly Ile Ser Ala Ile Trp Ile
        35                  40                  45

Pro Pro Ala Ser Lys Gly Met Gly Gly Ala Tyr Ser Met Gly Tyr Asp
    50                  55                  60

Pro Tyr Asp Phe Phe Asp Leu Gly Glu Tyr Asp Gln Lys Gly Thr Val
65                  70                  75                  80

Glu Thr Arg Phe Gly Ser Lys Gln Glu Leu Val Asn Met Ile Asn Thr
                85                  90                  95

Ala His Ala Tyr Gly Met Lys Val Ile Ala Asp Ile Val Ile Asn His
            100                 105                 110

Arg Ala Gly Gly Asp Leu Glu Trp Asn Pro Phe Val Asn Asp Tyr Thr
        115                 120                 125

Trp Thr Asp Phe Ser Lys Val Ala Ser Gly Lys Tyr Thr Ala Asn Tyr
    130                 135                 140

Leu Asp Phe His Pro Asn Glu Leu His Ala Gly Asp Ser Gly Thr Phe
145                 150                 155                 160

Gly Gly Tyr Pro Asp Ile Cys His Asp Lys Ser Trp Asp Gln Tyr Trp
                165                 170                 175

Leu Trp Ala Ser Gln Glu Ser Tyr Ala Ala Tyr Leu Arg Ser Ile Gly
            180                 185                 190

Ile Asp Ala Trp Arg Phe Asp Tyr Val Lys Gly Tyr Ala Pro Trp Val
        195                 200                 205

Val Lys Asp Trp Leu Asn Trp Trp Gly Gly Trp Ala Val Gly Glu Tyr
    210                 215                 220

Trp Asp Thr Asn Val Asp Ala Val Leu Asn Trp Ala Tyr Ser Ser Gly
225                 230                 235                 240

Ala Lys Val Phe Asp Phe Ala Leu Tyr Tyr Lys Met Asp Glu Ala Phe
                245                 250                 255

Asp Asn Lys Asn Ile Pro Ala Leu Val Ser Ala Leu Gln Asn Gly Gln
            260                 265                 270

Thr Val Val Ser Arg Asp Pro Phe Lys Ala Val Thr Phe Val Ala Asn
        275                 280                 285

His Asp Thr Asp Ile Ile Trp Asn Lys Tyr Pro Ala Tyr Ala Phe Ile
    290                 295                 300

Leu Thr Tyr Glu Gly Gln Pro Thr Ile Phe Tyr Arg Asp Tyr Glu Glu
305                 310                 315                 320

Trp Leu Asn Lys Asp Lys Leu Lys Asn Leu Ile Trp Ile His Glu Asn
                325                 330                 335

Leu Ala Gly Gly Ser Thr Asp Ile Val Tyr Tyr Asp Asn Asp Glu Leu
            340                 345                 350

Ile Phe Val Arg Asn Gly Tyr Gly Asp Lys Pro Gly Leu Ile Thr Tyr
```

```
                355                 360                 365
Ile Asn Leu Gly Ser Ser Lys Ala Gly Arg Trp Val Tyr Val Pro Lys
    370                 375                 380

Phe Ala Gly Ala Cys Ile His Glu Tyr Thr Gly Asn Leu Gly Gly Trp
385                 390                 395                 400

Val Asp Lys Tyr Val Tyr Ser Ser Gly Trp Val Tyr Leu Glu Ala Pro
                405                 410                 415

Ala Tyr Asp Pro Ala Asn Gly Gln Tyr Gly Tyr Ser Val Trp Ser Tyr
            420                 425                 430

Cys Gly Val Gly
        435

<210> SEQ ID NO 16
<211> LENGTH: 972
<212> TYPE: DNA
<213> ORGANISM: Thermotoga sp.

<400> SEQUENCE: 16
atggaacagt cagttgctga agtgatagc  aactcagcat ttgaatacaa caaaatggta       60
ggtaaaggag taaatattgg aaatgcttta gaagctcctt tcgaaggagc ttggggagta      120
agaattgagg atgaatattt tgagataata agaaaaggg  gatttgattc tgttaggatt      180
cccataagat ggtcagcaca tatatccgaa aagccaccat atgatattga caggaatttc      240
ctcgaaagag ttaaccatgt tgtcgatagg gctcttgaga ataatttaac agtaatcatc      300
aatacgcacc atttttgaaga actctatcaa gaaccggata atacggcga  tgttttggtg      360
gaaatttgga gacagattgc aaaattcttt aaagattacc cggaaaatct gttctttgaa      420
atctacaacg agcctgctca gaacttgaca gctgaaaaat ggaacgcact ttatccaaaa      480
gtgctcaaag ttatcaggga gagcaatcca acccggattg tcattatcga tgctccaaac      540
tgggcacact atagcgcagt gagaagtcta aaattagtca acgacaaacg catcattgtt      600
tccttccatt actacgaacc tttcaaattc acacatcagg gtgccgaatg ggttaatccc      660
atcccacctg ttagggttaa gtggaatggc gaggaatggg aaattaacca atcagaagt      720
catttcaaat acgtgagtga ctgggcaaag caaaataacg taccaatctt tcttggtgaa      780
ttcggtgctt attcaaaagc agacatggac tcaagggtta gtggaccga  agtgtgaga       840
aaaatggcgg aagaatttgg attttcatac gcgtattggg aattttgtgc aggatttggc      900
atatacgata atggtctca  aaactggatc gaaccattgg caacagctgt ggttggcaca      960
ggcaaagagt aa                                                         972

<210> SEQ ID NO 17
<211> LENGTH: 323
<212> TYPE: PRT
<213> ORGANISM: Thermotoga sp.

<400> SEQUENCE: 17

Met Glu Gln Ser Val Ala Glu Ser Asp Ser Asn Ser Ala Phe Glu Tyr
1               5                   10                  15

Asn Lys Met Val Gly Lys Gly Val Asn Ile Gly Asn Ala Leu Glu Ala
            20                  25                  30

Pro Phe Glu Gly Ala Trp Gly Val Arg Ile Glu Asp Glu Tyr Phe Glu
        35                  40                  45

Ile Ile Lys Lys Arg Gly Phe Asp Ser Val Arg Ile Pro Ile Arg Trp
    50                  55                  60
```

Ser Ala His Ile Ser Glu Lys Pro Pro Tyr Asp Ile Asp Arg Asn Phe
 65                  70                  75                  80

Leu Glu Arg Val Asn His Val Val Asp Arg Ala Leu Glu Asn Asn Leu
                 85                  90                  95

Thr Val Ile Ile Asn Thr His His Phe Glu Glu Leu Tyr Gln Glu Pro
            100                 105                 110

Asp Lys Tyr Gly Asp Val Leu Val Glu Ile Trp Arg Gln Ile Ala Lys
        115                 120                 125

Phe Phe Lys Asp Tyr Pro Glu Asn Leu Phe Phe Glu Ile Tyr Asn Glu
    130                 135                 140

Pro Ala Gln Asn Leu Thr Ala Glu Lys Trp Asn Ala Leu Tyr Pro Lys
145                 150                 155                 160

Val Leu Lys Val Ile Arg Glu Ser Asn Pro Thr Arg Ile Val Ile Ile
                165                 170                 175

Asp Ala Pro Asn Trp Ala His Tyr Ser Ala Val Arg Ser Leu Lys Leu
            180                 185                 190

Val Asn Asp Lys Arg Ile Ile Val Ser Phe His Tyr Tyr Glu Pro Phe
        195                 200                 205

Lys Phe Thr His Gln Gly Ala Glu Trp Val Asn Pro Ile Pro Pro Val
    210                 215                 220

Arg Val Lys Trp Asn Gly Glu Glu Trp Glu Ile Asn Gln Ile Arg Ser
225                 230                 235                 240

His Phe Lys Tyr Val Ser Asp Trp Ala Lys Gln Asn Asn Val Pro Ile
                245                 250                 255

Phe Leu Gly Glu Phe Gly Ala Tyr Ser Lys Ala Asp Met Asp Ser Arg
            260                 265                 270

Val Lys Trp Thr Glu Ser Val Arg Lys Met Ala Glu Glu Phe Gly Phe
        275                 280                 285

Ser Tyr Ala Tyr Trp Glu Phe Cys Ala Gly Phe Gly Ile Tyr Asp Arg
    290                 295                 300

Trp Ser Gln Asn Trp Ile Glu Pro Leu Ala Thr Ala Val Val Gly Thr
305                 310                 315                 320

Gly Lys Glu

<210> SEQ ID NO 18
<211> LENGTH: 1042
<212> TYPE: DNA
<213> ORGANISM: Artificial sequence
<220> FEATURE:
<223> OTHER INFORMATION: Synthetically generated polynucleotide

<400> SEQUENCE: 18
ggatccacca tgagggtgtt gctcgttgcc ctcgctctcc tggctctcgc tgcgagcgcc      60
accagcggcg tggacccgtt cgagaggaac aagatcctgg caggggcat caacatcggc     120 aacgccctgg aggccccgaa cgagggcgac tggggcgtgg tgatcaagga cgagtacttc     180
gacatcatca aggaggccgg cttcagccac gtgagaatcc cgatcaggtg gagcacccac     240
gcccaggcct tcccgccgta caagatcgag acaggttct tcaagagggt ggacgaggtg     300
atcaacggcg ccctgaagag gggcctggcc gtggtgatca accagcacca ctacgaggag     360
ctgatgaacg acccggagga gcacaaggag aggttcctgg ccctgtggaa gcagatcgcc     420
gacaggtaca aggactaccc ggagaccctg ttcttcgaga tcctgaacga gccgcacggc     480
aacctgaccc cggagaagtg gaacgagctg ctggaggagg ccctgaaggt gatcaggagc     540
atcgacaaga agcacaccat catcatcggc accgccgagt ggggcggcat cagcgccctg     600

```
gagaagctga gggtgccgaa gtgggagaag aacgccatcg tgaccatcca ctactacaac    660
ccgttcgagt tcacccacca gggcgccgag tgggtggagg cagcgagaa gtggctgggc    720 aggaagtggg gcagcccgga cgaccagaag cacctgatcg aggagttcaa cttcatcgag    780
gagtggagca agaagaacaa gaggccgatc tacatcggcg agttcggcgc ctacaggaag    840
gccgacctgg agagcaggat caagtggacc agcttcgtgg tgagggaggc cgagaagagg    900
aggtggagct gggcctactg ggagttctgc agcggcttcg gcgtgtacga caccctgagg    960
aagacctgga acaaggacct gctggaggcc ctgatcggcg gcgacagcat cgagagcgag   1020
aaggacgagc tgtgagagct ca                                            1042
```

<210> SEQ ID NO 19
<211> LENGTH: 341
<212> TYPE: PRT
<213> ORGANISM: Artificial sequence
<220> FEATURE:
<223> OTHER INFORMATION: Synthetically generated polypeptide

<400> SEQUENCE: 19

```
Met Arg Val Leu Leu Val Ala Leu Ala Leu Leu Ala Leu Ala Ala Ser
1               5                   10                  15

Ala Thr Ser Gly Val Asp Pro Phe Glu Arg Asn Lys Ile Leu Gly Arg
            20                  25                  30

Gly Ile Asn Ile Gly Asn Ala Leu Glu Ala Pro Asn Glu Gly Asp Trp
        35                  40                  45

Gly Val Val Ile Lys Asp Glu Tyr Phe Asp Ile Lys Glu Ala Gly
    50                  55                  60

Phe Ser His Val Arg Ile Pro Ile Arg Trp Ser Thr His Ala Gln Ala
65                  70                  75                  80

Phe Pro Pro Tyr Lys Ile Glu Asp Arg Phe Lys Arg Val Asp Glu
            85                  90                  95

Val Ile Asn Gly Ala Leu Lys Arg Gly Leu Ala Val Val Ile Asn Gln
        100                 105                 110

His His Tyr Glu Glu Leu Met Asn Asp Pro Glu Glu His Lys Glu Arg
    115                 120                 125

Phe Leu Ala Leu Trp Lys Gln Ile Ala Asp Arg Tyr Lys Asp Tyr Pro
130                 135                 140

Glu Thr Leu Phe Phe Glu Ile Leu Asn Glu Pro His Gly Asn Leu Thr
145                 150                 155                 160

Pro Glu Lys Trp Asn Glu Leu Leu Glu Glu Ala Leu Lys Val Ile Arg
            165                 170                 175

Ser Ile Asp Lys Lys His Thr Ile Ile Ile Gly Thr Ala Glu Trp Gly
        180                 185                 190

Gly Ile Ser Ala Leu Glu Lys Leu Arg Val Pro Lys Trp Glu Lys Asn
    195                 200                 205

Ala Ile Val Thr Ile His Tyr Tyr Asn Pro Phe Glu Phe Thr His Gln
    210                 215                 220

Gly Ala Glu Trp Val Glu Gly Ser Glu Lys Trp Leu Gly Arg Lys Trp
225                 230                 235                 240

Gly Ser Pro Asp Asp Gln Lys His Leu Ile Glu Glu Phe Asn Phe Ile
            245                 250                 255

Glu Glu Trp Ser Lys Lys Asn Lys Arg Pro Ile Tyr Ile Gly Glu Phe
        260                 265                 270

Gly Ala Tyr Arg Lys Ala Asp Leu Glu Ser Arg Ile Lys Trp Thr Ser
```

```
                275                 280                 285
Phe Val Val Arg Glu Ala Glu Lys Arg Arg Trp Ser Trp Ala Tyr Trp
            290                 295                 300
Glu Phe Cys Ser Gly Phe Gly Val Tyr Asp Thr Leu Arg Lys Thr Trp
305                 310                 315                 320
Asn Lys Asp Leu Leu Glu Ala Leu Ile Gly Gly Asp Ser Ile Glu Ser
                325                 330                 335
Glu Lys Asp Glu Leu
            340
```

<210> SEQ ID NO 20
<211> LENGTH: 1042
<212> TYPE: DNA
<213> ORGANISM: Artificial sequence
<220> FEATURE:
<223> OTHER INFORMATION: Synthetically generated polynucleotide

<400> SEQUENCE: 20

```
ggatccacca tgagggtgtt gctcgttgcc ctcgctctcc tggctctcgc tgcgagcgcc     60
accagcggcg tggacccgtt cgagaggaac aagatcctgg gcaggggcat caacatcggc    120
aacgccctgg aggccccgaa cgagggcgac tggggcgtgg tgatcaagga cgagttcttc    180
gacatcatca ggaggccgg  cttcagccac gtgagaatcc cgatcaggtg gagcacccac    240
gcccaggcct ccccgccgta caagatcgag ccgagcttct tcaagagggt ggacgaggtg    300
atcaacggcg ccctgaagag gggcctggcc gtggtgatca acatccacca ctacgaggag    360
ctgatgaacg accggagga  gcacaaggag aggttcctgg ccctgtggaa gcagatcgcc    420
gacaggtaca aggactaccc ggagaccctg ttcttcgaga tcctgaacga gccgcacggc    480
aacctgaccc cggagaagtg gaacgagctg ctggaggagg ccctgaaggt gatcaggagc    540
atcgacaaga agcacaccgt gatcatcggc accgccgagt ggggcggcat cagcgccctg    600
gagaagctga ggtgccgaa  gtgggagaag aacgccatcg tgaccatcca ctactacaac    660
ccgttcgagt tcacccacca gggcgccgag tgggtgccgg cagcgagaa  gtggctgggc    720
aggaagtggg gcagcccgga cgaccagaag cacctgatcg aggagttcaa cttcatcgag    780
gagtggagca agaagaacaa gaggccgatc tacatcggcg agttcggcgc ctacaggaag    840
gccgacctgg agagcaggat caagtggacc agcttcgtgg tgagggaggc cgagaagagg    900
ggctggagct gggcctactg ggagttctgc agcggcttcg gcgtgtacga cccgctgagg    960
aagcagtgga acaaggacct gctggaggcc ctgatcggcg gcgacagcat cgagagcgag   1020
aaggacgagc tgtgagagct ca                                            1042
```

<210> SEQ ID NO 21
<211> LENGTH: 341
<212> TYPE: PRT
<213> ORGANISM: Artificial sequence
<220> FEATURE:
<223> OTHER INFORMATION: Synthetically generated polypeptide

<400> SEQUENCE: 21

```
Met Arg Val Leu Leu Val Ala Leu Ala Leu Leu Ala Leu Ala Ala Ser
1               5                   10                  15
Ala Thr Ser Gly Val Asp Pro Phe Glu Arg Asn Lys Ile Leu Gly Arg
            20                  25                  30
Gly Ile Asn Ile Gly Asn Ala Leu Glu Ala Pro Asn Glu Gly Asp Trp
        35                  40                  45
```

Gly Val Val Ile Lys Asp Glu Phe Phe Asp Ile Ile Lys Glu Ala Gly
    50                  55                  60

Phe Ser His Val Arg Ile Pro Ile Arg Trp Ser Thr His Ala Gln Ala
65                  70                  75                  80

Phe Pro Pro Tyr Lys Ile Glu Pro Ser Phe Phe Lys Arg Val Asp Glu
                85                  90                  95

Val Ile Asn Gly Ala Leu Lys Arg Gly Leu Ala Val Val Ile Asn Ile
            100                 105                 110

His His Tyr Glu Glu Leu Met Asn Asp Pro Glu His Lys Glu Arg
        115                 120                 125

Phe Leu Ala Leu Trp Lys Gln Ile Ala Asp Arg Tyr Lys Asp Tyr Pro
130                 135                 140

Glu Thr Leu Phe Phe Glu Ile Leu Asn Glu Pro His Gly Asn Leu Thr
145                 150                 155                 160

Pro Glu Lys Trp Asn Glu Leu Leu Glu Ala Leu Lys Val Ile Arg
                165                 170                 175

Ser Ile Asp Lys Lys His Thr Val Ile Ile Gly Thr Ala Glu Trp Gly
            180                 185                 190

Gly Ile Ser Ala Leu Glu Lys Leu Arg Val Pro Lys Trp Glu Lys Asn
        195                 200                 205

Ala Ile Val Thr Ile His Tyr Tyr Asn Pro Phe Glu Phe Thr His Gln
210                 215                 220

Gly Ala Glu Trp Val Pro Gly Ser Glu Lys Trp Leu Gly Arg Lys Trp
225                 230                 235                 240

Gly Ser Pro Asp Asp Gln Lys His Leu Ile Glu Glu Phe Asn Phe Ile
                245                 250                 255

Glu Glu Trp Ser Lys Lys Asn Lys Arg Pro Ile Tyr Ile Gly Glu Phe
            260                 265                 270

Gly Ala Tyr Arg Lys Ala Asp Leu Glu Ser Arg Ile Lys Trp Thr Ser
        275                 280                 285

Phe Val Val Arg Glu Ala Glu Lys Arg Gly Trp Ser Trp Ala Tyr Trp
290                 295                 300

Glu Phe Cys Ser Gly Phe Gly Val Tyr Asp Pro Leu Arg Lys Gln Trp
305                 310                 315                 320

Asn Lys Asp Leu Leu Glu Ala Leu Ile Gly Gly Asp Ser Ile Glu Ser
                325                 330                 335

Glu Lys Asp Glu Leu
            340

<210> SEQ ID NO 22
<211> LENGTH: 1042
<212> TYPE: DNA
<213> ORGANISM: Artificial sequence
<220> FEATURE:
<223> OTHER INFORMATION: Synthetically generated polynucleotide

<400> SEQUENCE: 22
ggatccacca tgagggtgtt gctcgttgcc ctcgctctcc tggctctcgc tgcgagcgcc    60
accagcggcg tggacccgtt cgagaggaac aagatcctgg caggggcat caacatcggc    120 aacgccctgg aggccccgaa cgagggcgac tggggcgtgg tgatcaagga cgagtacttc    180
gacatcatca aggaggccgg cttcagccac gtgagaatcc cgatcaggtg gagcacccac    240
gcccaggcct tccgccgta caagatcgag gacagcttct tcaagagggt ggacgaggtg    300
atcaacggcg ccctgaagag gggcctggcc gtggtgatca acatccacca ctacgaggag    360

```
ctgatgaacg acccggagga gcacaaggag aggttcctgg ccctgtggaa gcagatcgcc    420
gacaggtaca aggactaccc ggagaccctg ttcttcgaga tcctgaacga gccgcacggc    480
aacctgaccc cggagaagtg gaacgagctg ctggaggagg ccctgaaggt gatcaggagc    540
atcgacaaga agcacaccgt gatcatcggc accgccgagt ggggcggcat cagcgccctg    600
gagaagctga gggtgccgaa gtgggagaag aacgccatcg tgaccatcca ctactacaac    660
ccgttcgagt tcacccacca gggcgccgag tgggtgccgg gcagcgagaa gtggctgggc    720
aggaagtggg gcagcccgga cgaccagaag cacgtgatcg aggagttcaa cttcatcgag    780
gagtggagca agaagaacaa gaggccgatc tacatcggcg agttcggcgc ctacaggaag    840
gccgacctgg agagcaggat caagtggacc agcttcgtgg tgagggaggc cgagaagagg    900
ggctggagct gggcctactg ggagttctgc agcggcttcg gcgtgtacga cccgctgagg    960
aagcagtgga acaaggacct gctggaggcc ctgatcggcg cgacagcat cgagagcgag   1020 aaggacgagc tgtgagagct ca                                            1042
```

<210> SEQ ID NO 23
<211> LENGTH: 341
<212> TYPE: PRT
<213> ORGANISM: Artificial sequence
<220> FEATURE:
<223> OTHER INFORMATION: Synthetically generated polypeptide

<400> SEQUENCE: 23

```
Met Arg Val Leu Leu Val Ala Leu Ala Leu Ala Leu Ala Ala Ser
1               5                   10                  15

Ala Thr Ser Gly Val Asp Pro Phe Glu Arg Asn Lys Ile Leu Gly Arg
            20                  25                  30

Gly Ile Asn Ile Gly Asn Ala Leu Glu Ala Pro Asn Glu Gly Asp Trp
        35                  40                  45

Gly Val Val Ile Lys Asp Glu Tyr Phe Asp Ile Ile Lys Glu Ala Gly
    50                  55                  60

Phe Ser His Val Arg Ile Pro Ile Arg Trp Ser Thr His Ala Gln Ala
65                  70                  75                  80

Phe Pro Pro Tyr Lys Ile Glu Asp Ser Phe Phe Lys Arg Val Asp Glu
                85                  90                  95

Val Ile Asn Gly Ala Leu Lys Arg Gly Leu Ala Val Val Ile Asn Ile
            100                 105                 110

His His Tyr Glu Glu Leu Met Asn Asp Pro Glu Glu His Lys Glu Arg
        115                 120                 125

Phe Leu Ala Leu Trp Lys Gln Ile Ala Asp Arg Tyr Lys Asp Tyr Pro
    130                 135                 140

Glu Thr Leu Phe Phe Glu Ile Leu Asn Glu Pro His Gly Asn Leu Thr
145                 150                 155                 160

Pro Glu Lys Trp Asn Glu Leu Leu Glu Glu Ala Leu Lys Val Ile Arg
                165                 170                 175

Ser Ile Asp Lys Lys His Thr Val Ile Ile Gly Thr Ala Glu Trp Gly
            180                 185                 190

Gly Ile Ser Ala Leu Glu Lys Leu Arg Val Pro Lys Trp Glu Lys Asn
        195                 200                 205

Ala Ile Val Thr Ile His Tyr Tyr Asn Pro Phe Glu Phe Thr His Gln
    210                 215                 220

Gly Ala Glu Trp Val Pro Gly Ser Glu Lys Trp Leu Gly Arg Lys Trp
225                 230                 235                 240
```

-continued

```
Gly Ser Pro Asp Asp Gln Lys His Val Ile Glu Glu Phe Asn Phe Ile
                245                 250                 255

Glu Glu Trp Ser Lys Lys Asn Lys Arg Pro Ile Tyr Ile Gly Glu Phe
            260                 265                 270

Gly Ala Tyr Arg Lys Ala Asp Leu Glu Ser Arg Ile Lys Trp Thr Ser
            275                 280                 285

Phe Val Val Arg Glu Ala Glu Lys Arg Gly Trp Ser Trp Ala Tyr Trp
        290                 295                 300

Glu Phe Cys Ser Gly Phe Gly Val Tyr Asp Pro Leu Arg Lys Gln Trp
305                 310                 315                 320

Asn Lys Asp Leu Leu Glu Ala Leu Ile Gly Gly Asp Ser Ile Glu Ser
                325                 330                 335

Glu Lys Asp Glu Leu
            340

<210> SEQ ID NO 24
<211> LENGTH: 10
<212> TYPE: PRT
<213> ORGANISM: Artificial sequence
<220> FEATURE:
<223> OTHER INFORMATION: Synthetically generated polypeptide

<400> SEQUENCE: 24

Glu Ala Gly Val Asp Pro Phe Glu Arg Asn
                5                   10

<210> SEQ ID NO 25
<211> LENGTH: 11
<212> TYPE: DNA
<213> ORGANISM: Artificial sequence
<220> FEATURE:
<223> OTHER INFORMATION: Synthetically generated nucleic acid

<400> SEQUENCE: 25
aggatcccga t                                                              11

<210> SEQ ID NO 26
<211> LENGTH: 11
<212> TYPE: DNA
<213> ORGANISM: Artificial sequence
<220> FEATURE:
<223> OTHER INFORMATION: Synthetically generated nucleic acid

<400> SEQUENCE: 26
agaatcccga t                                                              11
```